(12) United States Patent
Butler et al.

(10) Patent No.: US 9,845,301 B2
(45) Date of Patent: Dec. 19, 2017

(54) 1,1,1-TRIFLUORO-3-HYDROXYPROPAN-2-YL CARBAMATE DERIVATIVES AND 1,1,1-TRIFLUORO-4-HYDROXYBUTAN-2-YL CARBAMATE DERIVATIVES AS MAGL INHIBITORS

(71) Applicant: PFIZER INC., New York, NY (US)

(72) Inventors: Christopher Ryan Butler, Canton, MA (US); Laura Ann McAllister, Arlington, MA (US); Elizabeth Mary Beck, Edinburgh (GB); Michael Aaron Brodney, Newton, MA (US); Adam Matthew Gilbert, Guilford, CT (US); Christopher John Helal, Mystic, CT (US); Douglas Scott Johnson, Concord, MA (US); Justin Ian Montgomery, Ledyard, CT (US); Steven Victor O'Neil, East Lyme, CT (US); Bruce Nelsen Rogers, Belmont, MA (US); Patrick Robert Verhoest, Newton, MA (US); Damien Webb, Brookline, MA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 15/221,658

(22) Filed: Jul. 28, 2016

(65) Prior Publication Data
US 2017/0029390 A1    Feb. 2, 2017

Related U.S. Application Data

(60) Provisional application No. 62/335,290, filed on May 12, 2016, provisional application No. 62/199,330, filed on Jul. 31, 2015.

(51) Int. Cl.

| | | |
|---|---|---|
| C07D 295/14 | (2006.01) |
| C07D 401/14 | (2006.01) |
| C07D 401/04 | (2006.01) |
| C07D 403/04 | (2006.01) |
| C07D 498/10 | (2006.01) |
| C07D 491/107 | (2006.01) |
| C07D 401/12 | (2006.01) |
| C07D 471/10 | (2006.01) |
| C07D 487/04 | (2006.01) |
| C07D 211/48 | (2006.01) |
| C07D 471/08 | (2006.01) |
| C07D 515/10 | (2006.01) |
| C07F 9/6561 | (2006.01) |
| C07D 405/14 | (2006.01) |

(Continued)

(52) U.S. Cl.
CPC .......... *C07D 295/14* (2013.01); *C07D 211/48* (2013.01); *C07D 401/04* (2013.01); *C07D 401/12* (2013.01); *C07D 401/14* (2013.01); *C07D 403/04* (2013.01); *C07D 405/12* (2013.01); *C07D 405/14* (2013.01); *C07D 413/14* (2013.01); *C07D 471/08* (2013.01); *C07D 471/10* (2013.01); *C07D 487/04* (2013.01); *C07D 491/107* (2013.01); *C07D 493/10* (2013.01); *C07D 498/10* (2013.01); *C07D 515/10* (2013.01); *C07F 9/6561* (2013.01)

(58) Field of Classification Search
CPC .. C07D 295/14; C07D 401/12; C07D 401/04; C07D 403/04; C07D 498/10; C07D 491/107; C07D 405/14; C07D 401/14; C07D 487/04; C07D 211/48; C07D 471/08; C07D 515/10; C07D 471/10; C07F 9/6561
See application file for complete search history.

(56) References Cited

U.S. PATENT DOCUMENTS

| 4,804,665 A | 2/1989 | Goto et al. |
| 5,854,268 A | 12/1998 | Baker et al. |

(Continued)

FOREIGN PATENT DOCUMENTS

| WO | 9111172 | 8/1991 |
| WO | 9402518 | 2/1994 |

(Continued)

OTHER PUBLICATIONS

Almarsson, O and M. J. Zaworotko, Chem. Commun. 2004, 17, 1889-1896.

(Continued)

*Primary Examiner* — Sudhakar Katakam
(74) *Attorney, Agent, or Firm* — Feng Shao

(57) ABSTRACT

The present invention provides, in part, compounds of Formula I:

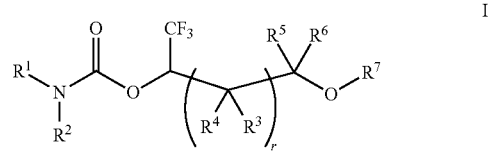

and pharmaceutically acceptable salts thereof; processes for the preparation of; intermediates used in the preparation of; and compositions containing such compounds or salts, and their uses for treating MAGL-mediated diseases and disorders including, e.g., pain, an inflammatory disorder, traumatic brain injury, depression, anxiety, Alzheimer's disease, a metabolic disorder, stroke, or cancer.

9 Claims, No Drawings

(51) Int. Cl.
  *C07D 413/14* (2006.01)
  *C07D 405/12* (2006.01)
  *C07D 493/10* (2006.01)

(56) References Cited

U.S. PATENT DOCUMENTS

| | | | |
|---|---|---|---|
| 6,106,864 | A | 8/2000 | Dolan et al. |
| 6,599,900 | B2 | 7/2003 | Cai et al. |
| 6,642,257 | B2 | 11/2003 | Yamamoto et al. |
| 6,696,443 | B2 | 2/2004 | Mavunkel et al. |
| 7,225,679 | B2 | 6/2007 | Miyagawa et al. |
| 7,241,770 | B2 | 7/2007 | Mentzel et al. |
| 7,786,046 | B2 | 8/2010 | Witschel et al. |
| 7,825,147 | B2 | 11/2010 | Palle et al. |
| 7,863,279 | B2 | 1/2011 | Even et al. |
| 7,879,761 | B2 | 2/2011 | Witschel et al. |
| 8,394,787 | B2 | 3/2013 | Abouabdellah et al. |
| 8,415,341 | B2 | 4/2013 | Chevalier et al. |
| 8,513,423 | B2 | 8/2013 | Connolly et al. |
| 8,748,417 | B2 | 6/2014 | Zhang et al. |
| 8,772,318 | B2 | 7/2014 | Cravatt et al. |
| 8,835,418 | B2 | 9/2014 | Bartsch et al. |
| 9,133,148 | B2 | 9/2015 | Cisar et al. |
| 2002/0151712 | A1 | 10/2002 | Lin et al. |
| 2007/0179167 | A1 | 8/2007 | Cottrell et al. |
| 2007/0249648 | A1 | 10/2007 | Bladh et al. |
| 2009/0048247 | A1 | 2/2009 | Palle et al. |
| 2010/0035909 | A1 | 2/2010 | Andres-Gil et al. |
| 2010/0063081 | A1 | 3/2010 | Bradly |
| 2010/0113417 | A1 | 5/2010 | Reich et al. |
| 2010/0190687 | A1 | 7/2010 | Boyle et al. |
| 2010/0324011 | A1 | 12/2010 | Bian et al. |
| 2011/0166165 | A1 | 7/2011 | Neelamkavil et al. |
| 2012/0077797 | A1 | 3/2012 | Connolly et al. |
| 2012/0264749 | A1 | 10/2012 | Hadida-Ruah et al. |
| 2014/0017698 | A1 | 1/2014 | Wang |

FOREIGN PATENT DOCUMENTS

| | | | |
|---|---|---|---|
| WO | 9855148 | 12/1998 | |
| WO | 0035298 | 6/2000 | |
| WO | 0111968 | 2/2001 | |
| WO | 2008/130581 | 10/2008 | |
| WO | WO 2008130581 A1 * | 10/2008 | ........... C07D 401/04 |
| WO | 2009060030 | 5/2009 | |
| WO | 2011142359 | 11/2011 | |
| WO | 2012173174 | 12/2012 | |
| WO | 2013/103973 | 7/2013 | |
| WO | 2013131010 | 9/2013 | |
| WO | 2014074715 | 5/2014 | |

OTHER PUBLICATIONS

Bridgeman and N. C. O. Tomkinson, Synlett 2006, 243-246.

Finnin and Morgan, J. Pharm. Sci. 1999, 88, 955-958.
Flack, Acta Cryst. 1983, A39, 867-881.
Freedman, T. B. et al., Absolute Configuration Determination of Chiral Molecules in the Solution State Using Vibrational Circular Dichroism. Chirality 2003, 15, 743-758.
Haleblian, J. K., J. Pharm. Sci. 1975, 64, 1269-1288.
Hooft, L. H. Strayer, and A. L. Spek, J. Appl. Cryst. 2008, 41, 96-103.
Mechoulam, R. et al., "Identification of an endogenous 2-monoglyceride, present in canine gut, that binds to cannabinoid receptors" Biochem. Pharmacol., 50 (1995), 83-90.
C. F. Macrae, P. R. Edington, P. McCabe, E. Pidcock, G. P. Shields, R. Taylor, M. Towler, and J. van de Streek, J. Appl. Cryst. 2006, 39, 453-457.
O. V. Dolomanov, L. J. Bourhis, R. J. Gildea, J. A. K. Howard, and H. Puschmann, J. Appl. Cryst. 2009, 42, 339-341.
Patel, J. Z. et al., "Loratadine analogues as MAGL inhibitors," Bioorg. Med. Chem. Lett., 2015, 25(7):1436-42.
A. L. Spek, J. Appl. Cryst. 2003, 36, 7-13.
Senczyszyn, J. et. al, "Spirocyclic Dihydropyridines by Electrophile-Induced Dearomatizing Cyclization of N-Alkenyl Pyridinecarboxamides"; Organic Letters (2013), 15(8), 1922-1925.
Sugiura, T. et al., "2-Arachidonoylglycerol: a possible endogenous cannabinoid receptor ligand in brain," Biochem. Biophys. Res. Commun., 215 (1995), 89-97.
Verma et al., Pharmaceutical Technology On-line, 25(2), 1-14 (2001).
Wang, Y. et al., "A Fluorescence-Based Assay for Monoacylglycerol Lipase Compatible with Inhibitor Screening," Assay and Drug Development Technologies, 2008, vol. 6 (3) pp. 387-393.
Bioreversible Carriers in Drug Design, Pergamon Press, 1987 (Ed. E. B. Roche, American Pharmaceutical Association).
Crystals and the Polarizing Microscope by N. H. Hartshorne and A. Stuart, 4th Edition (Edward Arnold, 1970).
Design of Prodrugs by H. Bundgaard (Elsevier, 1985).
Greene and P. G. M. Wuts, Protective Groups in Organic Synthesis, 3rd Ed., Wiley & Sons, Inc., New York (1999).
Handbook of Pharmaceutical Salts: Properties, Selection, and Use by Stahl and Wermuth (Wiley-VCH, 2002).
Prodrugs: Challenges and Reward, 2007 edition, edited by Valentino Stella, Ronald Borchardt, Michael Hageman, Reza Oliyai, Hans Maag, Jefferson Tilley, 125-176 (Springer, 2007).
Remington's Pharmaceutical Sciences, 19th Edition (Mack Publishing Company, 1995).
Stereochemistry of Organic Compounds by E. L. Eliel and S. H. Wilen (Wiley, New York, 1994).
Bringmann, G. et al., Atroposelective Synthesis of Axially Chiral Biaryl Compounds. Angew. Chem., Int. Ed. 2005, 44, 5384-5427.
Jae Won Chang et al: "Highly Selective Inhibitors of Monoacylglycerol Lipase Bearing a Reactive Group that Is Bioisosteric with Endocannabinoid Substrates", Chemistry & Biology, vol. 19, No. 5, May 1, 2012 (May 1, 2012), pp. 579-588.

* cited by examiner

1,1,1-TRIFLUORO-3-HYDROXYPROPAN-2-YL CARBAMATE DERIVATIVES AND 1,1,1-TRIFLUORO-4-HYDROXYBUTAN-2-YL CARBAMATE DERIVATIVES AS MAGL INHIBITORS

This application claims the benefit of priority to U.S. Provisional Patent Application Ser. No. 62/199,330 filed Jul. 31, 2015, and to U.S. Provisional Patent Application Ser. No. 62/335,290 filed May 12, 2016, the disclosure of each of which is hereby incorporated by reference in its entirety.

FIELD OF THE INVENTION

The present invention relates to novel 1,1,1-trifluoro-3-hydroxypropan-2-yl carbamate derivatives and 1,1,1-trifluoro-4-hydroxybutan-2-yl carbamate derivatives, which are monoacylglycerol lipase (MAGL) inhibitors, pharmaceutically compositions thereof, and uses thereof in the treatment of MAGL-mediated disorders such as pain, an inflammatory disorder, traumatic brain injury, depression, anxiety, Alzheimer's disease, a metabolic disorder, stroke, or cancer.

BACKGROUND OF THE INVENTION

MAGL is the principal enzyme responsible for the in vivo degradation of 2-arachidonoyl glycerol (2-AG), an endogenous ligand of the cannabinoid receptors (e.g., CB1 and CB2). See e.g., Patel, J. Z. et al., "Loratadine analogues as MAGL inhibitors," Bioorg. Med. Chem. Lett., 2015, 25(7): 1436-42; Mechoulam, R. et al., "Identification of an endogenous 2-monoglyceride, present in canine gut, that binds to cannabinoid receptors" Biochem. Pharmacol., 50 (1995), 83-90; Sugiura, T. et al., "2-Arachidonoylglycerol: a possible endogenous cannabinoid receptor ligand in brain," Biochem. Biophys. Res. Commun., 215 (1995), 89-97.

There continues to be a need for alternative MAGL inhibitors.

SUMMARY OF THE INVENTION

The present invention provides, in part, a novel compound of Formula I:

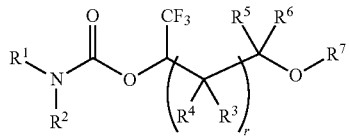

I or a pharmaceutically acceptable salt thereof, wherein:

each of $R^1$ and $R^2$ is independently $C_{1-6}$ alkyl that is optionally substituted with one or more substituents each independently selected from the group consisting of OH, halogen, $C_{1-4}$ alkoxy, $C_{1-4}$ haloalkoxy, and $C_{3-7}$ cycloalkyl, wherein the $C_{3-7}$ cycloalkyl is optionally substituted with one or more substituents each independently selected from the group consisting of OH, halogen, $C_{1-4}$ alkyl, $C_{1-4}$ haloalkyl, $C_{1-4}$ alkoxy, and $C_{1-4}$ haloalkoxy;

or $R^1$ and $R^2$, together with the N atom to which they are attached, form 4- to 14-membered heterocycloalkyl that is optionally substituted with $R^8$ and optionally substituted with one or more independently selected $R^9$ or $R^{30}$;

each of $R^3$ and $R^4$ is independently H, halogen, OH, $C_{1-6}$ alkyl, or $C_{3-7}$ cycloalkyl, wherein the $C_{1-6}$ alkyl of $R^3$ and $R^4$ is optionally substituted with one or more substituents each independently selected from the group consisting of OH, halogen, $C_{1-4}$ alkoxy, $C_{1-4}$ haloalkoxy, and $C_{3-6}$ cycloalkyl, and wherein the $C_{3-7}$ cycloalkyl of $R^3$ and $R^4$ is optionally substituted with one or more substituents each independently selected from the group consisting of OH, halogen, $C_{1-4}$ alkyl, $C_{1-4}$ haloalkyl, $C_{1-4}$ alkoxy, and $C_{1-4}$ haloalkoxy;

or $R^3$ and $R^4$, together with the C atom to which they are attached, form $C_{3-7}$ cycloalkyl that is optionally substituted with one or more substituents each independently selected from the group consisting of OH, halogen, $C_{1-4}$ alkyl, $C_{1-4}$ haloalkyl, $C_{1-4}$ alkoxy, and $C_{1-4}$ haloalkoxy;

each of $R^5$ and $R^6$ is independently H, $C_{1-6}$ alkyl, or $C_{3-7}$ cycloalkyl, wherein the $C_{1-6}$ alkyl of $R^5$ and $R^6$ is optionally substituted with one or more substituents each independently selected from the group consisting of OH, halogen, $C_{1-4}$ alkoxy, $C_{1-4}$ haloalkoxy, and $C_{3-6}$ cycloalkyl, and wherein the $C_{3-7}$ cycloalkyl of $R^5$ and $R^6$ is optionally substituted with one or more substituents each independently selected from the group consisting of OH, halogen, $C_{1-4}$ alkyl, $C_{1-4}$ haloalkyl, $C_{1-4}$ alkoxy, and $C_{1-4}$ haloalkoxy;

or $R^5$ and $R^6$, together with the C atom to which they are attached, form $C_{3-7}$ cycloalkyl that is optionally substituted with one or more substituents each independently selected from the group consisting of OH, halogen, $C_{1-4}$ alkyl, $C_{1-4}$ haloalkyl, $C_{1-4}$ alkoxy, and $C_{1-4}$ haloalkoxy;

$R^7$ is H, $C_{1-6}$ alkyl, $C_{3-7}$ cycloalkyl, or $R^{10}$, wherein the $C_{1-6}$ alkyl of $R^7$ is optionally substituted with one or more substituents each independently selected from the group consisting of OH, halogen, $C_{1-4}$ alkoxy, $C_{1-4}$ haloalkoxy, and $C_{3-6}$ cycloalkyl, and wherein the $C_{3-7}$ cycloalkyl of $R^7$ is optionally substituted with one or more substituents each independently selected from the group consisting of OH, halogen, $C_{1-4}$ alkyl, $C_{1-4}$ haloalkyl, $C_{1-4}$ alkoxy, and $C_{1-4}$ haloalkoxy;

or $R^7$ and $R^6$, together with the intervening moiety of "C($R^5$)—O" to which they are attached, form 4- to 7-membered heterocycloalkyl or 5- to 10-membered heteroaryl that is optionally substituted with one or more substituents each independently selected from the group consisting of OH, oxo, halogen, $C_{1-4}$ alkyl, $C_{1-4}$ haloalkyl, $C_{1-4}$ alkoxy, and $C_{1-4}$ haloalkoxy, and wherein each of the ring-forming atoms of the 4- to 7-membered heterocycloalkyl is independently C, N, O, S, or P and wherein each of the ring-forming atoms of the 5- to 10-membered heteroaryl is C, N, O, or S;

or $R^7$ and $R^3$, together with the intervening moiety of "C($R^4$)—C($R^5R^6$)—O" to which they are attached, form a 5- to 7-membered heterocycloalkyl or 5- to 10-membered heteroaryl that is optionally substituted with one or more substituents each independently selected from the group consisting of OH, oxo, halogen, $C_{1-4}$ alkyl, $C_{1-4}$ haloalkyl, $C_{1-4}$ alkoxy, and $C_{1-4}$ haloalkoxy, and wherein each of the ring-forming atoms of the 5- to 7-membered heterocycloalkyl is independently C, N, O, S, or P, and wherein each of the ring-forming atoms of the 5- to 10-membered heteroaryl is C, N, O, or S;

$R^8$ is -$L^1$-$R^{11}$, -$L^2$-$R^{12}$, -$L^3$-$R^{13}$, -$L^4$-$R^{14}$, —C($R^{15}$)($Cy^1$)($Cy^2$), —C($R^{15}$)($Cy^1$)[—$NR^{23}$—S(=O)$_2$-$Cy^2$], or -$L^5$-N(-$L^6$-$Cy^3$)(-$L^7$-$Cy^4$);

each $R^9$ is independently OH, oxo, halogen, optionally substituted $C_{1-4}$ alkyl, optionally substituted $C_{1-4}$ alkoxy, or optionally substituted $C_{3-6}$ cycloalkyl;

$R^{10}$ is —P(=O)($OR^{81}$)($OR^{82}$) or —S(=O)$_2OR^{90}$;

each of $L^1$, $L^2$, $L^3$, and $L^4$ is independently absent, —(C$R^{21}R^{22}$)$_m$—, —$NR^{23}$—, —O—, —C(=O)—, —S(=O)$_2$—, —S(=O)$_2$—(C$R^{21}R^{22}$)$_n$—, —C(=O)—(C$R^{21}R^{22}$)$_n$—, —S(=O)$_2$—$NR^{23}$—, —C(=O)—$NR^{23}$—, —(CR$^{21}$R$^{22}$)$_{n1}$—NR$^{23}$—(CR$^{21}$R$^{22}$)$_{n2}$—, —(CR$^{21}$R$^{22}$)$_{n1}$—O—(CR$^{21}$R$^{22}$)$_{n2}$—, —C(=O)—NR$^{23}$—(CR$^{21}$R$^{22}$)$_p$—, or —S(=O)$_2$—NR$^{23}$—(CR$^{21}$R$^{22}$)$_p$—;

L$^5$ is absent or —(CR$^{21}$R$^{22}$)—;

L$^6$ is absent or —(CR$^{21}$R$^{22}$)—;

L$^7$ is absent, —(CR$^{21}$R$^{22}$)—, or —S(=O)$_2$—;

R$^{11}$ is 5- to 10-membered heteroaryl optionally substituted with one or more independently selected R$^{31}$;

R$^{12}$ is 4- to 14-membered heterocycloalkyl optionally substituted with one or more independently selected R$^{32}$;

R$^{13}$ is C$_{6-10}$ aryl optionally substituted with one or more independently selected R$^{33}$;

R$^{14}$ is C$_{3-14}$ cycloalkyl optionally substituted with one or more independently selected R$^{34}$;

R$^{15}$ is H, OH, halogen, C$_{1-4}$ alkoxy, C$_{1-4}$ alkyl, or cyclopropyl;

each of R$^{21}$ and R$^{22}$ is independently H, OH, halogen, C$_{1-3}$ alkyl, or cyclopropyl, wherein the C$_{1-3}$ alkyl is optionally substituted with one or more substituents each independently selected from the group consisting of OH, halogen, C$_{1-3}$ alkoxy, C$_{1-3}$ haloalkoxy, and cyclopropyl;

R$^{23}$ is H, C$_{1-4}$ alkyl, or cyclopropyl;

each of R$^{30}$, R$^{31}$, R$^{32}$, R$^{33}$, and R$^{34}$ is independently selected from the group consisting of halogen, —N(R$^a$)(R$^b$), —N(R$^c$)(C(=O)R$^d$), —N(R$^c$)(S(=O)$_2$R$^d$), —C(=O)—N(R$^a$)(R$^b$), —C(=O)—R$^d$, —C(=O)—OR$^d$, —OC(=O)—R$^d$, —N(R$^c$)(S(=O)$_2$R$^d$), —S(=O)$_2$—N(R$^a$)(R$^b$), —SR$^d$, —S(=O)$_2$R$^d$, —SR$^d$, —S(=O)$_2$R$^d$, —OR$^d$, —OR$^{35}$, —CN, C$_{1-6}$ alkyl, C$_{2-6}$ alkenyl, C$_{2-6}$ alkynyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the C$_{1-6}$ alkyl, C$_{2-6}$ alkenyl, C$_{2-6}$ alkynyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with one or more independently selected R$^{36}$; and wherein each of the C$_{1-6}$ alkyl, C$_{3-10}$ cycloalkyl, 4- to 10-membered heterocycloalkyl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is further optionally substituted one or more oxo;

each R$^{35}$ is independently selected from the group consisting of H, C$_{1-6}$ alkyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the C$_{1-6}$ alkyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with one or more substituents independently selected from the group consisting of halogen, —CN, —C(=O)C$_{1-4}$ alkyl, —C(=O)OH, —C(=O)O—C$_{1-4}$ alkyl, —C(=O)NHC$_{1-4}$ alkyl, —C(=O)N(C$_{1-4}$ alkyl)$_2$, oxo, —OH, —OC(=O)—C$_{1-4}$ alkyl, —OC(=O)O—C$_{1-4}$ alkyl, —NH$_2$, —NH(C$_{1-4}$ alkyl), —N(C$_{1-4}$ alkyl)$_2$, —NHC(=O)C$_{1-4}$ alkyl, —NHC(=O)OC$_{1-4}$ alkyl, —NHC(=O)NHC$_{1-4}$ alkyl, and C$_{1-4}$ alkoxy;

each R$^{36}$ is independently selected from the group consisting of halogen, —OH, —NO$_2$, —CN, —SF$_5$, C$_{1-6}$ alkyl, C$_{1-6}$ haloalkyl, C$_{1-6}$ haloalkoxy, C$_{2-6}$ alkenyl, C$_{2-6}$ alkynyl, C$_{3-7}$ cycloalkyl, a 4- to 10-membered heterocycloalkyl, —N(R$^a$)(R$^b$), —N(R$^c$)(C(=O)R$^d$), —C(=O)—N(R$^a$)(R$^b$), —C(=O)—R$^d$, —C(=O)—OR$^d$, —OC(=O)—R$^d$, —N(R$^c$)(S(=O)$_2$R$^d$), —S(=O)$_2$—N(R$^a$)(R$^b$), —SR$^d$, —S(=O)$_2$R$^d$, and —OR$^d$, wherein each of the C$_{1-6}$ alkyl, C$_{3-7}$ cycloalkyl, and heterocycloalkyl is optionally substituted with one or more substituents each independently selected from the group consisting of halogen, —CN, —OH, C$_{1-4}$ alkyl, C$_{1-4}$ alkoxy, C$_{1-4}$ haloalkyl, C$_{1-4}$ haloalkoxy, C$_{3-6}$ cycloalkyl, —N(R$^a$)(R$^b$), —N(R$^c$)(C(=O)R$^d$), —C(=O)—OR$^d$, —C(=O)H, —C(=O)R$^d$, —C(=O)N(R$^a$)(R$^b$), —N(R$^c$)(S(=O)$_2$R$^d$), —S(=O)$_2$—N(R$^a$)(R$^b$), —SR$^d$, —S(=O)$_2$R$^d$, and —OR$^d$;

each of R$^{81}$, R$^{82}$, and R$^{90}$ is independently selected from the group consisting of H, C$_{1-6}$ alkyl, C$_{3-7}$ cycloalkyl, and (C$_{3-7}$ cycloalkyl)-C$_{1-4}$ alkyl-, wherein each of the C$_{1-6}$ alkyl, C$_{3-7}$ cycloalkyl, and (C$_{3-7}$ cycloalkyl)-C$_{1-4}$ alkyl- is optionally substituted with one or more substituents each independently selected from the group consisting of halogen, —CN, —OH, oxo, —NH$_2$, —NH(C$_{1-4}$ alkyl), —N(C$_{1-4}$ alkyl)$_2$, C$_{1-4}$ alkyl, C$_{1-4}$ alkoxy, C$_{1-4}$ haloalkyl, C$_{1-4}$ haloalkoxy, C$_{3-6}$ cycloalkyl;

or OR$^{81}$ and OR$^{82}$, together with the P(=O) to which they are attached, form 4- to 10-membered heterocycloalkyl that is further optionally substituted with one or more substituents each independently selected from the group consisting of halogen, —CN, —OH, oxo, —NH$_2$, —NH(C$_{1-4}$ alkyl), —N(C$_{1-4}$ alkyl)$_2$, C$_{1-4}$ alkyl, C$_{1-4}$ alkoxy, C$_{1-4}$ haloalkyl, C$_{1-4}$ haloalkoxy, C$_{3-6}$ cycloalkyl;

each of Cy$^1$, Cy$^2$, Cy$^3$, and Cy$^4$ is independently selected from the group consisting of R$^{11}$, R$^{12}$, R$^{13}$, and R$^{14}$;

each R$^a$ is independently H, C$_{1-4}$ alkyl, C$_{1-4}$ haloalkyl, C$_{3-7}$ cycloalkyl, or (C$_{3-7}$ cycloalkyl)-C$_{1-4}$ alkyl-;

each R$^b$ is independently H or selected from the group consisting of C$_{1-4}$ alkyl, C$_{1-4}$ haloalkyl, C$_{3-7}$ cycloalkyl, a 4- to 10-membered heterocycloalkyl, C$_{6-10}$ aryl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the selections from the group is optionally substituted with one or more substituents each independently selected from the group consisting of —OH, —CN, C$_{1-4}$ alkyl, C$_{3-7}$ cycloalkyl, C$_{1-4}$ hydroxylalkyl, —S—C$_{1-4}$ alkyl, —C(=O)H, —C(=O)—C$_{1-4}$ alkyl, —C(=O)—O—C$_{1-4}$ alkyl, —C(=O)—NH$_2$, —C(=O)—N(C$_{1-4}$ alkyl)$_2$, C$_{1-4}$ haloalkyl, C$_{1-4}$ alkoxy, and C$_{1-4}$ haloalkoxy;

or R$^a$ and R$^b$, together with the N atom to which they are attached, form a 4- to 10-membered heterocycloalkyl or a 5- to 10-membered heteroaryl, each optionally substituted with one or more substituents each independently selected from the group consisting of halogen, —OH, oxo, —C(=O)H, —C(=O)OH, —C(=O)—C$_{1-4}$ alkyl, —C(=O)—NH$_2$, —C(=O)—N(C$_{1-4}$ alkyl)$_2$, —CN, C$_{1-4}$ alkyl, C$_{3-6}$ cycloalkyl, (C$_{3-6}$ cycloalkyl)-C$_{1-2}$ alkyl-, C$_{1-4}$ alkoxy, C$_{1-4}$ hydroxylalkyl, C$_{1-4}$ haloalkyl, and C$_{1-4}$ haloalkoxy;

each R$^c$ is independently selected from the group consisting of H, C$_{1-4}$ alkyl, C$_{3-7}$ cycloalkyl, and (C$_{3-7}$ cycloalkyl)-C$_{1-4}$ alkyl-;

each R$^d$ is independently selected from the group consisting of C$_{1-6}$ alkyl, C$_{3-7}$ cycloalkyl, a 4- to 14-membered heterocycloalkyl, C$_{6-10}$ aryl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the selections from the group is optionally substituted with one or more substituents each independently selected from the group consisting of halogen, —CF$_3$, —CN, —OH, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy, and $C_{1-4}$ haloalkoxy;

each of f1 and f2 is independently 0, 1, or 2, provided that the sum of f1 and f2 is 1, 2, or 3;

m is 1, 2, or 3;
n is 1, 2, or 3;
p is 1, or 2; and
r is 0 or 1, provided that when r is 1 and each of $R^3$, $R^4$, $R^5$ and $R^6$ is H, then the moiety of "—N($R^1$)($R^2$)" is other than optionally substituted 4-oxo-3H-5,6,7,8-tetrahydropyrido[3,4-d]pyrimidin-7-yl.

In some embodiments, the compound of Formula I or pharmaceutically acceptable salt thereof is a compound of Formula I-1:

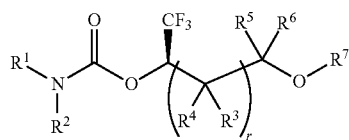

or pharmaceutically acceptable salt thereof.

In some embodiments, the compound of Formula I or pharmaceutically acceptable salt thereof is a compound of Formula I-a:

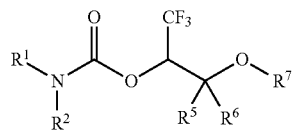

or pharmaceutically acceptable salt thereof.

In some embodiments, the compound of Formula I (or I-1 or I-a) or pharmaceutically acceptable salt thereof is a compound of Formula I-a1:

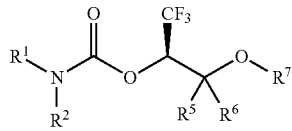

or pharmaceutically acceptable salt thereof.

In some embodiments, the compound of Formula I or pharmaceutically acceptable salt thereof is a compound of Formula I-b:

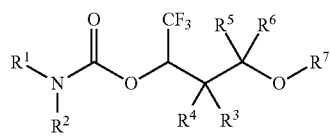

or pharmaceutically acceptable salt thereof.

In some embodiments, the compound of Formula I (or I-1 or I-b) or pharmaceutically acceptable salt thereof is a compound of Formula I-b1:

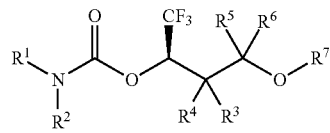

or pharmaceutically acceptable salt thereof.

Unless otherwise specified, the compound of Formula I or a salt thereof described in the following embodiments can be a compound of Formula I-1, I-a, I-a1, I-b, or I-b1, or a salt thereof.

In some embodiments, $R^1$ and $R^2$, together with the N atom to which they are attached, form 4- to 14-membered heterocycloalkyl that is optionally substituted with $R^8$ and optionally substituted with one or more independently selected $R^9$ or $R^{30}$.

In some embodiments, $R^1$ and $R^2$, together with the N atom to which they are attached, form 4- to 14-membered heterocycloalkyl that is optionally substituted with $R^8$ and optionally substituted with one or more independently selected $R^9$.

In some embodiments, $R^1$ and $R^2$, together with the N atom to which they are attached, form 4- to 14-membered heterocycloalkyl that is substituted with $R^8$ and optionally substituted with one or more independently selected $R^9$.

In some embodiments:
the moiety of "—N($R^1$)($R^2$)" is a moiety of Formula a-1, a-2, a-3, a-4, a-5, or a-6:

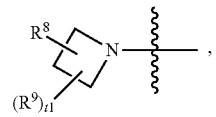

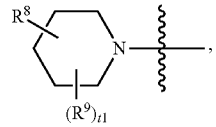

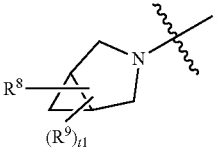

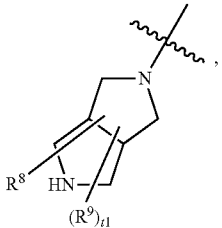

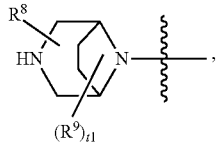

-continued a-6

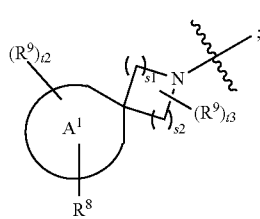

ring $A^1$ is 4- to 7-membered cycloalkyl or heterocycloalkyl;

t1 is 0, 1, 2, or 3;

t2 is 0, 1, 2, or 3;

t3 is 0, 1, 2, or 3;

s1 is 1 or 2; and s2 is 1 or 2.

In some embodiments:

the moiety of Formula a-6 is a moiety of Formula a-6-1 or a-6-2:

a-6-1

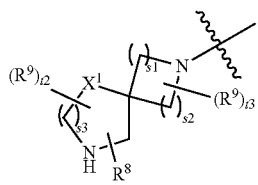

a-6-2

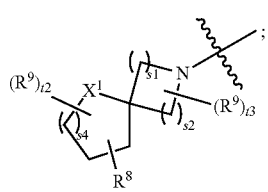

$X^1$ is O, $NR^{41}$, or $C(R^{42})_2$;

each of $R^{41}$ and $R^{42}$ is independently H or $R^9$;

s3 is 0, 1, or 2, provided that when s3 is 0, then $X^1$ is $C(R^{42})_2$; and s4 is 0, 1, or 2.

In some embodiments:

the moiety of "—$N(R^1)(R^2)$" is a moiety of Formula a-11, a-12, a-13, a-14, a-15, a-16-1, or a-16-2:

a-11

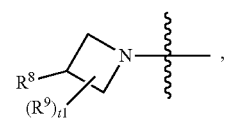

a-12

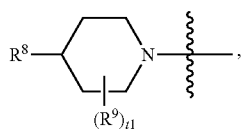

a-13

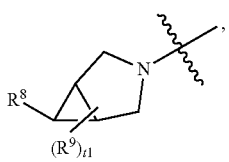

a-14

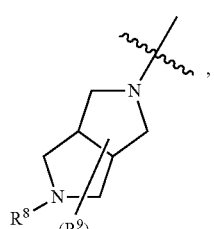

a-15

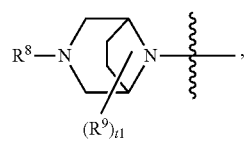

a-16-1

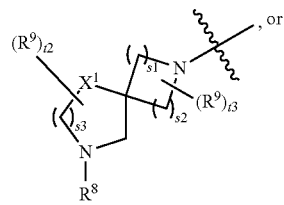

a-16-2

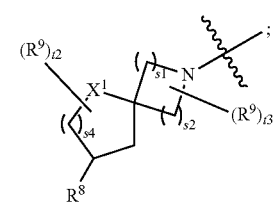

$X^1$ is O, $NR^{41}$, or $C(R^{42})_2$;

each of $R^{41}$ and $R^{42}$ is independently H or $R^9$;

t1 is 0, 1, 2, or 3;

t2 is 0, 1, 2, or 3;

t3, is 0, 1, 2, or 3;

s1 is 1 or 2;

s2 is 1 or 2;

s3 is 0, 1, or 2, provided that when s3 is 0, then $X^1$ is $C(R^{42})_2$; and s4 is 0, 1, or 2.

In some embodiments:

the moiety of Formula a-11 is a moiety of Formula a-11-1:

a-11-1

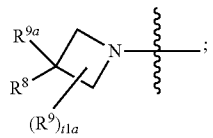

$R^{9a}$ is H, OH, optionally substituted $C_{1-4}$ alkoxy, $C_{1-4}$ alkyl, or cyclopropyl, or cyclobutyl; and t1a is 0, 1, or 2.

In some embodiments:

the moiety of Formula a-12 is a moiety of Formula a-12-1:

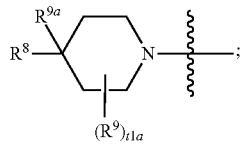

a-12-1

$R^{9a}$ is H, OH or optionally substituted $C_{1-4}$ alkoxy; and t1a is 0, 1, or 2.

In some embodiments:

the moiety of "—N(R$^1$)(R$^2$)" is a moiety of Formula a-26:

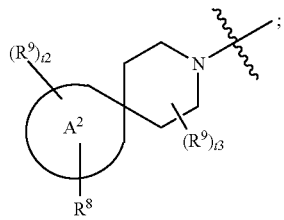

a-26 ring $A^2$ is 5- or 6-membered cycloalkyl or heterocycloalkyl;

t2 is 0, 1, 2, or 3; and t3 is 0, 1, 2, or 3.

In some embodiments, ring $A^2$ is 5- or 6-membered heterocycloalkyl and wherein at least one of the ring-forming atoms of ring $A^2$ is O.

In some embodiments:

the moiety of Formula a-26 is a moiety of Formula a-36:

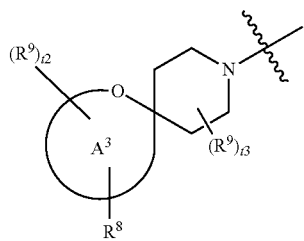

a-36 ring $A^3$ is 5- or 6-membered heterocycloalkyl (wherein the O atom shown in the ring is linked directly to the carbon bridge-head);

t2 is 0, 1, 2, or 3; and t3 is 0, 1, 2, or 3.

In some embodiments:

the moiety of Formula a-26 is a moiety of Formula a-46-1, a-46-2, a-46-3, or a-46-4, a-46-5, a-46-6, or a-46-7:

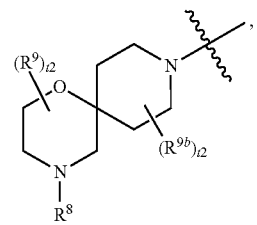

a-46-1

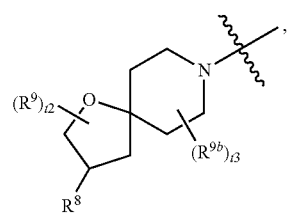

a-46-2

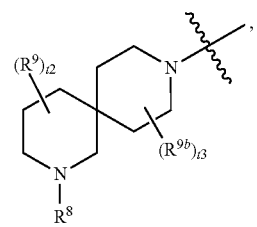

a-46-3

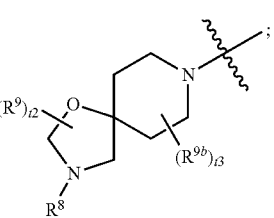

a-46-4

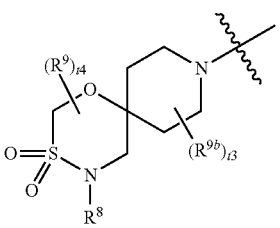

a-46-5

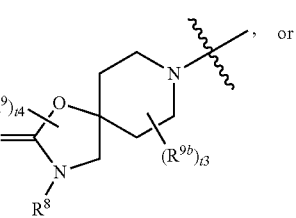

a-46-6, or

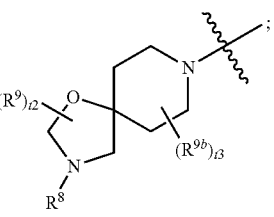

a-46-7 t2 is 0, 1, 2, or 3;

t3 is 0, 1, or 2;

t4 is 0, 1, or 2; and each $R^{9b}$ is independently F, Cl, methyl, or $C_1$ fluoroalkyl.

In some embodiments, the moiety of Formula a-26 is a moiety of Formula a-46-1 or a-46-2.

In some embodiments, the moiety of Formula a-26 is a moiety of Formula a-46-1.

In some embodiments, the moiety of Formula a-26 is a moiety of Formula a-46-2.

In some embodiments, the moiety of Formula a-26 is a moiety of Formula a-46-4.

In some embodiments, the moiety of Formula a-26 is a moiety of Formula a-46-6.

In some embodiments, the moiety of Formula a-26 is a moiety of Formula a-46-7.

In some embodiments:

the moiety of "—$N(R^1)(R^2)$" is a moiety of Formula b-6:

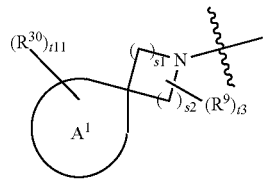

b-6 ring $A^1$ is 4- to 7-membered cycloalkyl or heterocycloalkyl;

t11 is 0, 1, 2, or 3;

t3 is 0, 1, 2, or 3;

s1 is 1 or 2; and s2 is 1 or 2.

In some embodiments:

the moiety of Formula b-6 is a moiety of Formula b-6-1 or b-6-2:

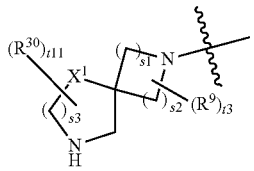

b-6-1

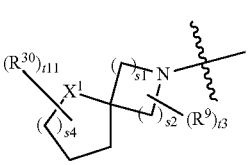

b-6-2

$X^1$ is O, $NR^{51}$, or $C(R^{52})_2$;

each of $R^{51}$ and $R^{52}$ is independently H or $R^{30}$;

s3 is 0, 1, or 2, provided that when s3 is 0, then $X^1$ is $C(R^{52})_2$; and s4 is 0, 1, or 2.

In some embodiments:

the moiety of "—$N(R^1)(R^2)$" is a moiety of Formula b-26:

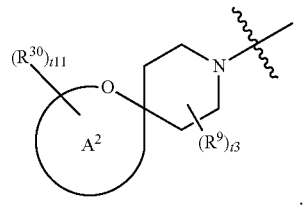

b-26

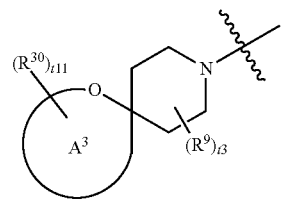

b-36 ring $A^2$ is 5- or 6-membered cycloalkyl or heterocycloalkyl;

ring $A^3$ is 5- or 6-membered heterocycloalkyl;

t11 is 0, 1, 2, or 3; and t3 is 0, 1, 2, or 3.

In some embodiments wherein the moiety of "—$N(R^1)(R^2)$" is a moiety of Formula b-26, ring $A^2$ is 5- or 6-membered heterocycloalkyl and at least one of the ring-forming atoms of ring $A^2$ is O.

In some embodiments wherein the moiety of "—$N(R^1)(R^2)$" is a moiety of Formula b-26:

the moiety of Formula b-26 is a moiety of Formula b-46-1, b-46-2, b-46-3, b-46-4, b-46-5, b-46-6, or b-47:

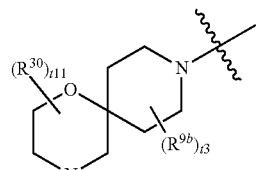

b-46-1

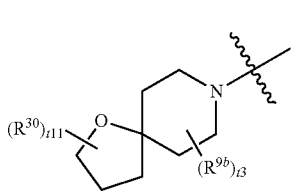

b-46-2

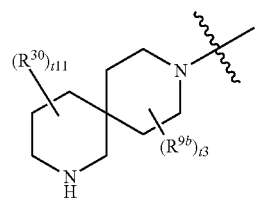

b-46-3

-continued b-46-4
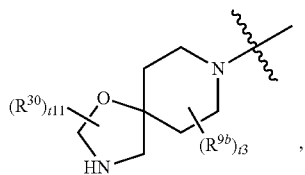

b-46-5
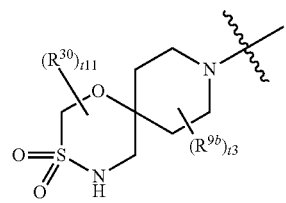

b-46-6
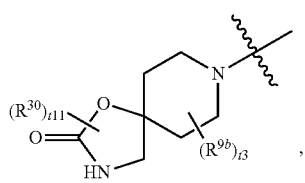

b-46-7
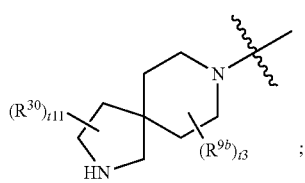

t11 is 0, 1, 2, or 3;

t3 is 0, 1, or 2; and each $R^{9b}$ is independently F, Cl, methyl, or $C_1$ fluoroalkyl.

In some embodiments wherein the moiety of "—N($R^1$)($R^2$)" is a moiety of Formula b-26, and the moiety of Formula b-26 is a moiety of Formula b-46-1, b-46-2, or b-46-7.

In some embodiments, the moiety of "—N($R^1$)($R^2$)" is a moiety of Formula b-46-1. In some further embodiments, the moiety of Formula b-46-1 is a moiety of Formula b-46-1a:

b-46-1a (R³⁰ᴬ)$_{t12}$ ... (R$^{9b}$)$_{t3}$ each $R^{30A}$ is independently halogen, $C_{1-4}$ alkyl, $C_{1-4}$ haloalkyl, $C_{1-4}$ alkoxy, or $C_{1-4}$ haloalkoxy; and t12 is 0, 1, or 2.

In some embodiments, the moiety of Formula b-46-1a is a moiety of Formula b-46-1a-1 or b-46-1a-2:

b-46-1a-1
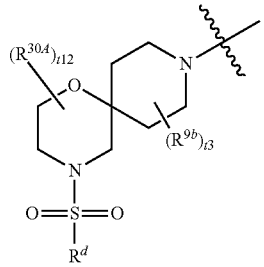

or b-46-1a-2
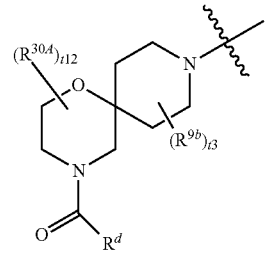

t12 is 0, 1, or 2; and each $R^{30A}$ is independently F, Cl, methyl, $C_1$ fluoroalkyl, methoxy, or $C_1$ fluoroalkoxy.

In some embodiments, the moiety of "—N($R^1$)($R^2$)" is a moiety of Formula b-46-1a-1.

In some embodiments, the moiety of "—N($R^1$)($R^2$)" is a moiety of Formula b-46-1a-2.

In some embodiments, the moiety of "—N($R^1$)($R^2$)" is a moiety of Formula b-46-2.

In some embodiments:

the moiety of "—N($R^1$)($R^2$)" is a moiety of Formula b-46-2;

the moiety of Formula b-46-2 is a moiety of Formula b-46-2a:

b-46-2a
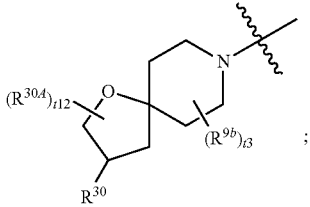

each $R^{30A}$ is independently halogen, $C_{1-4}$ alkyl, $C_{1-4}$ haloalkyl, $C_{1-4}$ alkoxy, or $C_{1-4}$ haloalkoxy; and t12 is 0, 1, or 2.

In some further embodiments, the moiety of Formula b-46-2a is a moiety of Formula b-46-2a-1, b-46-2a-2, or b-46-2a-3:

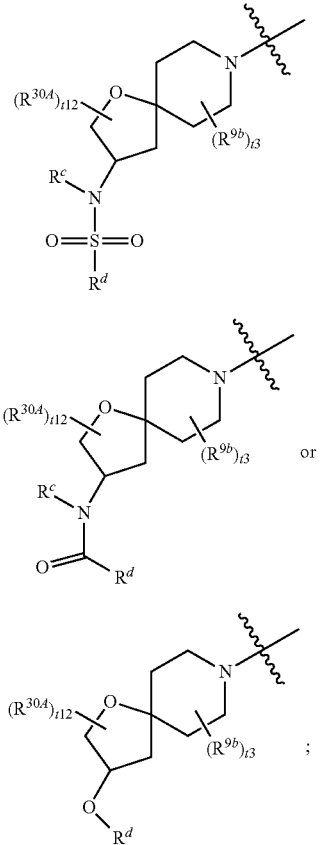

R$^c$ is C$_{1-3}$ alkyl or cyclopropyl;

t12 is 0, 1, or 2; and each R$^{30A}$ is independently F, Cl, methyl, C$_1$ fluoroalkyl, methoxy, or C$_1$ fluoroalkoxy. In some further embodiments, R$^c$ is C$_{1-3}$ alkyl. In some yet further embodiments, R$^c$ is methyl.

In some embodiments, the moiety of "—N(R$^1$)(R$^2$)" is a moiety of Formula b-46-2a-1; R$^c$ is C$_{1-3}$ alkyl; and each R$^{30A}$ is independently F, Cl, methyl, or C$_1$ fluoroalkyl. In some further embodiments, R$^c$ is methyl.

In some embodiments, the moiety of "—N(R$^1$)(R$^2$)" is a moiety of Formula b-46-2a-2; R$^c$ is C$_{1-3}$ alkyl; and each R$^{30A}$ is independently F, Cl, methyl, or C$_1$ fluoroalkyl. In some further embodiments, R$^c$ is methyl.

In some embodiments, the moiety of "—N(R$^1$)(R$^2$)" is a moiety of Formula b-46-2a-3.

In some embodiments, the moiety of "—N(R$^1$)(R$^2$)" is a moiety of Formula b-46-3.

In some embodiments, the moiety of "—N(R$^1$)(R$^2$)" is a moiety of Formula b-46-7. In some further embodiments, the moiety of Formula b-46-7 is a moiety of Formula b-46-7a:

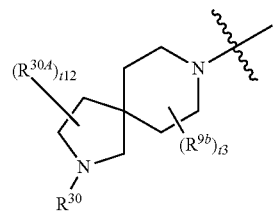

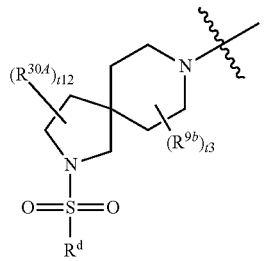

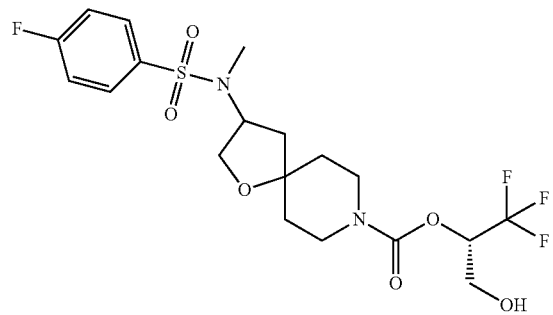

(2R)-1,1,1-trifluoro-3-hydroxypropan-2-yl 3-{[(4-fluorophenyl)sulfonyl](methyl)amino}-1-oxa-8-azaspiro[4.5]decane-8-carboxylate

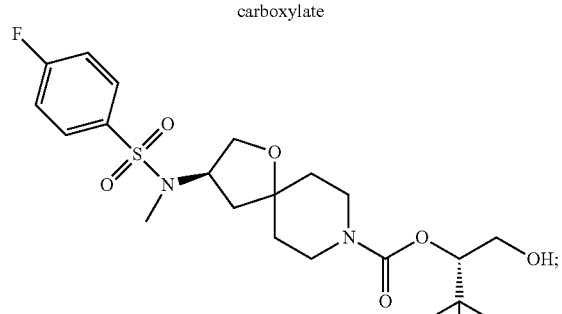

(2R)-1,1,1-trifluoro-3-hydroxypropan-2-yl (3R)-3-((4-fluoro-N-methylphenyl)sulfonamido)-1-oxa-8-azaspiro[4.5]decane-8-carboxylate each R$^{30A}$ is independently halogen, C$_{1-4}$ alkyl, C$_{1-4}$ haloalkyl, C$_{1-4}$ alkoxy, or C$_{1-4}$ haloalkoxy; and t12 is 0, 1, or 2.

In some embodiments, the moiety of "—N(R$^1$)(R$^2$)" is a moiety of Formula b-46-7a-1; and each R$^{30A}$ is independently F, Cl, methyl, or C$_1$ fluoroalkyl.

In some embodiments, the moiety of "—N(R$^1$)(R$^2$)" is a moiety of Formula b-46-7a-2; and each R$^{30A}$ is independently F, Cl, methyl, or C$_1$ fluoroalkyl. In some embodiments [e.g. wherein the moiety of "—N(R$^1$)(R$^2$)" is a moiety of Formula a-6, a-6-1, a-6-2, a-16-1, a-16-2, a-26, a-36, a-46-1, a-46-2, a-46-3, a-46-4, a-46-5, a-46-6, a-46-7, b-6, b-6-1, b-6-2, b-26, b-36, b-46-1, b-46-2, b-46-3, b-46-4, b-46-5, b-46-6, b-47, b-46-1a-1, b-46-1a-2, b-46-2a-1, b-46-2a-2, b-46-2a-3, b-46-7a-1, or b-46-7a-2], t3 is 0 or 1. In some further embodiments, t3 is 0.

In some embodiments [e.g. wherein the moiety of "—N($R^1$)($R^2$)" is a moiety of Formula a-6, a-6-1, a-6-2, a-16-1, a-16-2, a-26, a-36, a-46-1, a-46-2, a-46-3, a-46-6, or a-46-7], t3 is 0 or 1; and t2 is 0 or 1. In some further embodiments, t3 is 0.

In some embodiments [e.g. wherein the moiety of "—N($R^1$)($R^2$)" is a moiety of Formula b-6, b-6-1, b-6-2, b-26, b-36, b-46-1, b-46-2, b-46-3, b-46-4, b-46-5, b-46-6, or b-47], t3 is 0 or 1; and t11 is 0, 1, or 2. In some further embodiments, t3 is 0 and t11 is 1 or 2. In yet further embodiments, t11 is 1.

In some embodiments [e.g. wherein the moiety of "—N($R^1$)($R^2$)" is a moiety of Formula b-46-1a-1, b-46-1a-2, b-46-2a-1, b-46-2a-2, b-46-2a-3, b-46-7a-1, or b-46-7a-2], t3 is 0 or 1; and t12 is 0 or 1. In some further embodiments, t3 is 0. In yet further embodiments, t12 is 0.

In some embodiments wherein the moiety of "—N($R^1$)($R^2$)" is a moiety of Formula b-46-1a-1, b-46-1a-2, b-46-2a-1, b-46-2a-2, b-46-2a-3, b-46-7a-1, or b-46-7a-2; each $R^d$ is independently selected from the group consisting of $C_{1-6}$ alkyl, $C_{3-7}$ cycloalkyl, a 4- to 7-membered heterocycloalkyl, $C_{6-10}$ aryl, a 5- to 6-membered heteroaryl, ($C_{3-7}$ cycloalkyl)-$C_{1-4}$ alkyl-, (4- to 7-membered heterocycloalkyl)-$C_{1-4}$ alkyl-, ($C_{6-10}$ aryl)-$C_{1-4}$ alkyl-, and (5- to 6-membered heteroaryl)-$C_{1-4}$ alkyl-, wherein each of the selections from the group is optionally substituted with one or more substituents each independently selected from the group consisting of halogen, —$CF_3$, —CN, —OH, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy, and $C_{1-4}$ haloalkoxy.

In some embodiments, each of $R^3$ and $R^4$ is independently H, halogen, or methyl.

In some further embodiments, each of $R^3$ and $R^4$ is independently H or halogen (e.g., F).

In yet further embodiments, each of $R^3$ and $R^4$ is independently halogen (e.g., F).

In some other embodiments, each of $R^3$ and $R^4$ is independently H or methyl.

In some embodiments, each of $R^5$ and $R^6$ is independently H or $C_{1-4}$ alkyl (e.g., methyl or ethyl). In some further embodiments, each of $R^5$ and $R^6$ is independently H or methyl.

In some embodiments, each of $R^5$ and $R^6$ is H.

In some embodiments, $R^7$ is H or $R^{10}$; and $R^{10}$ is —P(=O)(O$R^{81}$)(O$R^{82}$).

In some embodiments, $R^7$ is H.

In some embodiments, $R^7$ is $R^{10}$; and $R^{10}$ is —P(=O)(O$R^{81}$)(O$R^{82}$).

In some embodiments, each of $R^{81}$ and $R^{82}$ is independently selected from the group consisting of H, $C_{1-6}$ alkyl, and ($C_{3-7}$ cycloalkyl)-$C_{1-4}$ alkyl-, wherein each of the $C_{1-6}$ alkyl and ($C_{3-7}$ cycloalkyl)-$C_{1-4}$ alkyl- is optionally substituted with one or more substituents each independently selected from the group consisting of halogen, —CN, —OH, oxo, —$NH_2$, —NH($C_{1-4}$ alkyl), —N($C_{1-4}$ alkyl)$_2$, $C_{1-4}$ alkyl, $C_{1-4}$ alkoxy, $C_{1-4}$ haloalkyl, $C_{1-4}$ haloalkoxy, and $C_{3-6}$ cycloalkyl. In some further embodiments, each $R^{81}$ and $R^{82}$ is independently H or $C_{1-4}$ alkyl. In some yet further embodiments, each $R^{81}$ and $R^{82}$ is H.

In some embodiments:
the moiety of "—N($R^1$)($R^2$)" is a moiety of Formula a-1, a-2, a-3, a-11, a-12, a-13, a-16-2, a-46-2, or a-46-7;

$R^8$ is -$L^1$-$R^{11}$, -$L^2$-$R^{12}$, -$L^3$-$R^{13}$, or -$L^4$-$R^{14}$;
each of $L^1$, $L^2$, $L^3$, and $L^4$ is independently absent, —O—, —S(=O)$_2$—, —(C$R^{21}R^{22}$)— [e.g. —(CH$_2$)—], —N$R^{23}$—, —O—(C$R^{21}R^{22}$)—, —(C$R^{21}R^{22}$)—O—(C$R^{21}R^{22}$)—, —(C$R^{21}R^{22}$)—S(=O)$_2$— [e.g., —(CH$_2$)—S(=O)$_2$—], —N$R^{23}$—S(=O)$_2$—, or —(C$R^{21}R^{22}$)—N$R^{23}$—S(=O)$_2$— [e.g. —(CH$_2$)—N$R^{23}$—S(=O)$_2$—];
each of $R^{21}$ and $R^{22}$ is independently H, OH, halogen, $C_{1-3}$ alkyl, cyclopropylmethyl, or $C_{1-3}$ haloalkyl;
$R^{23}$ is H or $C_{1-4}$ alkyl;
$R^{11}$ is 5- to 6-membered heteroaryl optionally substituted with one or more independently selected $R^{31}$;
$R^{12}$ is 5- to 6-membered heterocycloalkyl optionally substituted with one or more independently selected $R^{31}$;
$R^{13}$ is phenyl optionally substituted with one or more independently selected $R^{33}$; and
$R^{14}$ is $CO_{3-8}$ cycloalkyl optionally substituted with one or more independently selected $R^{34}$.

In some embodiments, the moiety of "—N($R^1$)($R^2$)" is a moiety of Formula a-12 or a-13; and $R^8$ is -$L^1$-$R^{11}$ or -$L^3$-$R^{13}$. In some further embodiments, $R^8$ is —$R^{11}$.

In some embodiments, the moiety of "—N($R^1$)($R^2$)" is a moiety of Formula a-12 (or Formula a-12-1) wherein $R^8$ is —$R^{11}$ or —$R^{13}$. In some further embodiments, $R^8$ is —$R^{11}$.

In some embodiments, the moiety of "—N($R^1$)($R^2$)" is a moiety of Formula a-13.

In some embodiments, the moiety of "—N($R^1$)($R^2$)" is a moiety of Formula a-13; and $R^8$ is -$L^1$-$R^{11}$ or -$L^3$-$R^{13}$. In some further embodiments, $R^8$ is —$R^{11}$ or —$R^{13}$. In yet further embodiments, $R^8$ is —$R^{11}$.

In some embodiments, the moiety of "—N($R^1$)($R^2$)" is a moiety of Formula a-46-2.

In some embodiments, the moiety of "—N($R^1$)($R^2$)" is a moiety of Formula a-46-2, $R^8$ is —N$R^{23}$—S(=O)$_2$—R, —N$R^{23}$—S(=O)$_2$—$R^{12}$, —N$R^{23}$—S(=O)$_2$—$R^{13}$, or —N$R^{23}$—S(=O)$_2$—$R^{14}$; and $R^{23}$ is $C_{1-3}$ alkyl. In some further embodiments, $R^{23}$ is methyl.

In some embodiments, the moiety of "—N($R^1$)($R^2$)" is a moiety of Formula a-46-2; $R^8$ is —N$R^{23}$—C(=O)—$R^{11}$, —N$R^{23}$—C(=O)—$R^{12}$, —N$R^{23}$—C(=O)—$R^{13}$, or —N$R^{23}$—C(=O)—$R^{14}$; and $R^{23}$ is $C_{1-3}$ alkyl. In some further embodiments, $R^{23}$ is methyl.

In some embodiments, the moiety of "—N($R^1$)($R^2$)" is a moiety of Formula a-46-2; and $R^8$ is —$R^{11}$, —$R^{12}$, —$R^{13}$, or —$R^{14}$. In some further embodiments, $R^8$ is —$R^{11}$ or —$R^{13}$. In some embodiments, the moiety of "—N($R^1$)($R^2$)" is a moiety of Formula a-46-2; and $R^8$ is -$L^1$-$R^{11}$ or -$L^3$-$R^{13}$. In some further embodiments, $R^8$ is —N$R^{23}$—S(=O)$_2$—$R^{11}$ or —N$R^{23}$—S(=O)$_2$—$R^{13}$. In some yet further embodiments, $R^{23}$ is H or $C_{1-4}$ alkyl (e.g., methyl). In still further embodiments, $R^{23}$ is $C_{1-4}$ alkyl (e.g., methyl).

In some embodiments, the moiety of "—N($R^1$)($R^2$)" is a moiety of Formula a-46-2; and $R^8$ is —O—$R^{11}$ or —O—$R^{13}$. In some embodiments, the moiety of "—N($R^1$)($R^2$)" is a moiety of Formula a-46-2; and $R^8$ is -$L^4$-$R^{14}$. In some further embodiments, $R^8$ is —$R^{14}$. In some embodiments:
the moiety of "—N($R^1$)($R^2$)" is a moiety of Formula a-14, a-15, a-16-1, a-36, a-46-1, a-46-3, a-46-4, a-46-5, or a-46-6;
$R^8$ is -$L^1$-$R^{11}$, -$L^2$-$R^{12}$, -$L^3$-$R^{13}$, or -$L^4$-$R^{14}$; (for example $R^8$ is -$L^1$-$R^{11}$, -$L^2$-$R^{12}$, or -$L^3$-$R^{13}$);
each of $L^1$, $L^2$, $L^3$, and $L^4$ is independently absent, —(C$R^{21}R^{22}$)— [e.g. —(CH$_2$)—], —C(=O)—, —S(=O)$_2$—, —S(=O)$_2$—N$R^{23}$—, —S(=O)$_2$—(C$R^{21}R^{22}$)—, —S(=O)$_2$—N$R^{23}$—(C$R^{21}R^{22}$)—, or —S(=O)$_2$—(C$R^{21}R^{22}$)$_2$—;

each of $R^{21}$ and $R^{22}$ is independently H, OH, halogen, $C_{1-3}$ alkyl, cyclopropylmethyl, or $C_{1-3}$ haloalkyl (for example, H, $C_{1-3}$ alkyl, or cyclopropyl);

$R^{11}$ is 5- to 6-membered heteroaryl optionally substituted with one or more independently selected $R^{31}$;

$R^{12}$ is 5- to 6-membered heterocycloalkyl optionally substituted with one or more independently selected $R^{31}$;

$R^{13}$ is phenyl optionally substituted with one or more independently selected $R^{33}$; and $R^{14}$ is $C_{3-8}$ cycloalkyl optionally substituted with one or more independently selected $R^{34}$. In some yet further embodiments, $R^{23}$ is H or $C_{1-4}$ alkyl (e.g., methyl).

In some embodiments, the moiety of "—N($R^1$)($R^2$)" is a moiety of Formula a-14 or a-15; and $R^8$ is -$L^1$-$R^{11}$ or -$L^3$-$R^{13}$.

In some embodiments, the moiety of "—N($R^1$)($R^2$)" is a moiety of Formula a-15; $R^8$ is -$L^1$-$R^{11}$ or -$L^3$-$R^{13}$. In some further embodiments, each of $L^1$ and $L^3$ is independently absent, —(C$R^{21}R^{22}$)—, —S(=O)$_2$—, —S(=O)$_2$—N$R^{23}$—, —S(=O)$_2$—N$R^{23}$—(C$R^{21}R^{22}$)—, —S(=O)$_2$—(C$R^{21}R^{22}$)—, or —S(=O)$_2$—(C$R^{21}R^{22}$)$_2$—; and each of $R^{21}$ and $R^{22}$ is independently H, $C_{1-3}$ alkyl, or cyclopropyl. In some yet further embodiments, each of $L^1$ and $L^3$ is independently —(C$R^{21}R^{22}$)— or —S(=O)$_2$—.

In some embodiments, the moiety of "—N($R^1$)($R^2$)" is a moiety of Formula a-16-1, a-46-1, a-46-3, a-46-4, or a-46-6; and $R^8$ is -$L^1$-$R^{11}$ or -$L^3$-$R^{13}$.

In some embodiments, the moiety of "—N($R^1$)($R^2$)" is a moiety of Formula a-46-1. In some further embodiments, $R^8$ is -$L^1$-$R^{11}$, -$L^2$-$R^{12}$, -$L^3$-$R^{13}$, or -$L^4$-$R^{14}$; and each of each of $L^1$, $L^2$, $L^3$, and $L^4$ is —S(=O)$_2$— or —C(=O)—. In some yet further embodiments, each of $L^1$, $L^2$, $L^3$, and $L^4$ is —S(=O)$_2$—.

In some embodiments, the moiety of "—N($R^1$)($R^2$)" is a moiety of Formula a-46-1; and $R^8$ is -$L^1$-$R^{11}$ or -$L^3$-$R^{13}$. In some further embodiments, each of $L^1$ and $L^3$ is independently absent, —(C$R^{21}R^{22}$)—, or —S(=O)$_2$—. In some yet further embodiments, each of $L^1$ and $L^3$ is independently, —(C$R^{21}R^{22}$)—, or —S(=O)$_2$—. In some still further embodiments, each of $L^1$ and $L^3$ is —S(=O)$_2$—.

In some embodiments, the moiety of "—N($R^1$)($R^2$)" is a moiety of Formula a-46-1; $R^8$ is -$L^1$-$R^{11}$; and $L^1$ is absent, —(C$R^{21}R^{22}$)—, or —S(=O)$_2$—. In some further embodiments, $L^1$ is absent or —S(=O)$_2$—. In some yet further embodiments, $L^1$ is —S(=O)$_2$—.

In some embodiments, the moiety of "—N($R^1$)($R^2$)" is a moiety of Formula a-46-1; $R^8$ is -$L^3$-$R^{13}$; and $L^3$ is absent, —(C$R^{21}R^{22}$)—, or —S(=O)$_2$—. In some further embodiments, $L^3$ is absent or —S(=O)$_2$—. In some yet further embodiments, $L^3$ is —S(=O)$_2$—.

In some embodiments, the moiety of "—N($R^1$)($R^2$)" is a moiety of Formula a-46-1; $R^8$ is -$L^1$-$R^{11}$ or -$L^3$-$R^{13}$; and each of $L^1$ and $L^3$ is —C(=O)— or —S(=O)$_2$—. In some further embodiments, each of $L^1$ and $L^3$ is —S(=O)$_2$—. In yet further embodiments, $R^8$ is —S(=O)$_2$—$R^{13}$; $R^{13}$ is phenyl optionally substituted with one or more independently selected $R^{33}$. In still further embodiments, each $R^{33}$ is independently selected from the group consisting of halogen (e.g. F or Cl), —CN, $C_{1-6}$ alkyl, $C_{1-6}$ haloalkyl, $C_{1-6}$ alkoxy, and $C_{1-6}$ haloalkoxy.

In some embodiments, the moiety of "—N($R^1$)($R^2$)" is a moiety of Formula a-46-2.

In some embodiments, the moiety of "—N($R^1$)($R^2$)" is a moiety of Formula a-46-2; and $R^8$ is -$L^1$-$R^{11}$ or -$L^3$-$R^{13}$. In some further embodiments, each of $L^1$ and $L^3$ is independently absent, —O—, —N$R^{23}$—, —S(=O)$_2$—(C$R^{21}R^{22}$)— [for example, $R^8$ is —(C$R^{21}R^{22}$)—S(=O)$_2$—$R^{11}$ or —(C$R^{21}R^{22}$)—S(=O)$_2$—$R^{13}$], —O—(C$R^{21}R^{22}$)— [for example, $R^8$ is —O—(C$R^{21}R^{22}$)—$R^{11}$ or —O—(C$R^{21}R^{22}$)—$R^{13}$], —S(=O)$_2$—N$R^{23}$— [for example, $R^8$ is —N$R^{23}$—S(=O)$_2$—$R^{11}$ or —N$R^{23}$—S(=O)$_2$—$R^{13}$], or —(C$R^{21}R^{22}$)—O—(C$R^{21}R^{22}$)—. In some yet further embodiments, $R^{23}$ is H or $C_{1-4}$ alkyl (e.g., methyl) and each of $R^{21}$ and $R^{22}$ is independently H, OH, halogen, $C_{1-3}$ alkyl, cyclopropylmethyl, or $C_{1-3}$ haloalkyl (for example, H, $C_{1-3}$ alkyl, or cyclopropyl).

In some embodiments, the moiety of "—N($R^1$)($R^2$)" is a moiety of Formula a-46-2; and $R^8$ is -$L^1$-$R^{11}$ or -$L^3$-$R^{13}$. In some further embodiments, each of $L^1$ and $L^3$ is independently —S(=O)$_2$—N$R^{23}$— [For example, $R^8$ is —N$R^{23}$—S(=O)$_2$—$R^{11}$ or —N$R^{23}$—S(=O)$_2$—$R^{13}$]. In some yet further embodiments, $R^{23}$ is H or $C_{1-4}$ alkyl (e.g., methyl). In some still further embodiments, $R^{23}$ is 01-4 alkyl (e.g., methyl).

In some embodiments, the moiety of "—N($R^1$)($R^2$)" is a moiety of Formula a-46-2; $R^8$ is -$L^1$-$R^{11}$ or -$L^3$-$R^{13}$; and each of $L^1$ and $L^3$ is independently —N$R^{23}$—. In some further embodiments, $R^{23}$ is H or $C_{1-4}$ alkyl (e.g., methyl).

In some embodiments, the moiety of "—N($R^1$)($R^2$)" is a moiety of Formula a-46-2; $R^8$ is -$L^1$-$R^{11}$ or -$L^3$-$R^{13}$; and each of $L^1$ and $L^3$ is —O—.

In some embodiments, the moiety of "—N($R^1$)($R^2$)" is a moiety of Formula a-46-2; $R^8$ is -$L^4$-$R^{14}$; and $L^4$ is —O—, —N$R^{23}$—, —S(=O)$_2$—(C$R^{21}R^{22}$)— [for example, $R^8$ is —(C$R^{21}R^{22}$)—S(=O)$_2$—$R^{11}$ or —(C$R^{21}R^{22}$)—S(=O)$_2$—$R^{13}$], or —S(=O)$_2$—N$R^{23}$— [for example, $R^8$ is —N$R^{23}$—S(=O)$_2$—$R^{11}$ or —N$R^{23}$—S(=O)$_2$—$R^{13}$]. In some further embodiments, $L^4$ is —S(=O)$_2$—N$R^{23}$— [For example, $R^8$ is —N$R^{23}$—S(=O)$_2$—$R^{14}$].

In some yet further embodiments, $R^{23}$ is H or $C_{1-4}$ alkyl (e.g., methyl).

In some embodiments, the moiety of "—N($R^1$)($R^2$)" is a moiety of Formula a-46-2; $R^8$ is —N$R^{23}$—C(=O)—$R^{11}$, —N$R^{23}$—C(=O)—$R^{12}$, —N$R^{23}$—C(=O)—$R^{13}$, or —N$R^{23}$—C(=O)—$R^{14}$; and $R^{23}$ is $C_{1-3}$ alkyl or cyclopropyl. In some further embodiments, $R^{23}$ is $C_{1-3}$ alkyl (e.g. methyl).

In some embodiments, the moiety of "—N($R^1$)($R^2$)" is a moiety of Formula a-46-2; and $R^8$ is —$R^{11}$ or —$R^{13}$.

In some embodiments, the moiety of "—N($R^1$)($R^2$)" is a moiety of Formula a-46-4 or a-46-6; and $R^8$ is -$L^1$-$R^{11}$ or -$L^3$-$R^{13}$. In some further embodiments, each of $L^1$ and $L^3$ is independently —(C$R^{21}R^{22}$)— or —S(=O)$_2$—. In some yet further embodiments, each of $L^1$ and $L^3$ is —(C$R^{21}R^{22}$)—.

In some embodiments, the moiety of "—N($R^1$)($R^2$)" is a moiety of Formula a-46-6; and $R^8$ is -$L^1$-$R^{11}$ or -$L^3$-$R^{13}$. In some further embodiments, each of $L^1$ and $L^3$ is independently —(C$R^{21}R^{22}$)— or —S(=O)$_2$—. In some yet further embodiments, each of $L^1$ and $L^3$ is —(C$R^{21}R^{22}$)—; and each of $R^{21}$ and $R^{22}$ is independently H or $C_{1-3}$ alkyl.

In some embodiments, the moiety of "—N($R^1$)($R^2$)" is a-46-7; $R^8$ is -$L^1$-$R^{11}$, -$L^2$-$R^{12}$, -$L^3$-$R^{13}$, or -$L^4$-$R^{14}$; and each of $L^1$, $L^2$, $L^3$, and $L^4$ is —C(=O)— or —S(=O)$_2$— [e.g. —C(=O)—]. In some embodiments, $R^8$ is -$L^1$-$R^{11}$ or -$L^3$-$R^{13}$; and each of $L^1$ and $L^3$ is —C(=O)—.

In some embodiments, each $R^9$ is independently OH, oxo, halogen, $C_{1-4}$ alkyl, $C_{1-4}$ haloalkyl, $C_{1-4}$ hydroxylalkyl, $C_{1-4}$ alkoxy, $C_{1-4}$ haloalkoxy, or cyclopropyl. In some further embodiments, each $R^9$ is independently OH, oxo, or methyl. In some yet further embodiments, each $R^9$ is independently OH or methyl. In some still further embodiments, each $R^9$ is OH.

In some embodiments of the compound of Formula I-a or a pharmaceutically acceptable salt thereof:

the moiety of "—N(R$^1$)(R$^2$)" is a moiety of Formula a-12 (or Formula a-12-1) wherein R$^8$ is —R$^{11}$ or —R$^{13}$;
  each of R$^5$ and R$^6$ is independently H or methyl;
  R$^7$ is H or —P(=O)(OR$^{81}$)(OR$^{82}$) [e.g., —P(=O)(OH)(OH)];
  R$^{11}$ is 5- to 6-membered heteroaryl optionally substituted with one or more independently selected R$^{31}$;
  R$^{13}$ is phenyl optionally substituted with one or more independently selected R$^{33}$;
  each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{2-6}$ alkenyl, C$_{2-6}$ alkynyl, C$_{3-10}$ cycloalkyl, 4- to 10-membered heterocycloalkyl, C$_6$10 aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the C$_{1-6}$ alkyl, C$_{2-6}$ alkenyl, C$_{2-6}$ alkynyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with one or more independently selected R$^{36}$;
  each R$^{36}$ is independently selected from the group consisting of halogen, —OH, C$_{1-6}$ alkoxy, C$_{1-6}$ haloalkoxy, —CN, C$_{1-6}$ alkyl, C$_{1-6}$ haloalkyl, C$_{2-6}$ alkenyl, C$_{2-6}$ alkynyl, and C$_{3-7}$ cycloalkyl. In some further embodiments, each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{1-6}$ hydroxylalkyl, C$_{1-6}$ cyanoalkyl, C$_{1-6}$ haloalkyl, and C$_{3-4}$ cycloalkyl.

In some embodiments of the compound of Formula I-a or a pharmaceutically acceptable salt thereof:
  the moiety of "—N(R$^1$)(R$^2$)" is a moiety of Formula a-13 wherein R$^8$ is —R$^{11}$ or —R$^{13}$;
  each of R$^5$ and R$^6$ is independently H or methyl;
  R$^7$ is H or —P(=O)(OR$^{81}$)(OR$^{82}$) [e.g., —P(=O)(OH)(OH)];
  R$^{11}$ is 5- to 6-membered heteroaryl optionally substituted with one or more independently selected R$^{31}$;
  R$^{13}$ is phenyl optionally substituted with one or more independently selected R$^{33}$;
  each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{2-6}$ alkenyl, C$_{2-6}$ alkynyl, C$_{3-10}$ cycloalkyl, 4- to 10-membered heterocycloalkyl, C$_6$10 aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the C$_{1-6}$ alkyl, C$_{2-6}$ alkenyl, C$_{2-6}$ alkynyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with one or more independently selected R$^{36}$;
  each R$^{36}$ is independently selected from the group consisting of halogen, —OH, C$_{1-6}$ alkoxy, C$_{1-6}$ haloalkoxy, —CN, C$_{1-6}$ alkyl, C$_{1-6}$ haloalkyl, C$_{2-6}$ alkenyl, C$_{2-6}$ alkynyl, and C$_{3-7}$ cycloalkyl. In some further embodiments, each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{1-6}$ hydroxylalkyl, C$_{1-6}$ cyanoalkyl, C$_{1-6}$ haloalkyl, and C$_{3-4}$ cycloalkyl. In some further embodiments, R$^8$ is —R$^{11}$.

In some embodiments of the compound of Formula I-a (including Formula I-a1) or a pharmaceutically acceptable salt thereof:
  the moiety of "—N(R$^1$)(R$^2$)" is a moiety of Formula a-15 wherein R$^8$ is -L$^1$-R$^{11}$ or -L$^3$-R$^{13}$;
  each of L$^1$ and L$^3$ is independently absent, —(CR$^{21}$R$^{22}$)—, —S(=O)$_2$—, —S(=O)$_2$—NR$^{23}$—, —S(=O)$_2$—NR$^{23}$—(CR$^{21}$R$^{22}$)—, —S(=O)$_2$—(CR$^{21}$R$^{22}$)—, or —S(=O)$_2$—(CR$^{21}$R$^{22}$)$_2$— [e.g., each of L$^1$ and L$^3$ is independently —(CR$^{21}$R$^{22}$)— or —S(=O)$_2$—)];
  each of R$^{21}$ and R$^{22}$ is independently H, C$_{1-3}$ alkyl, or cyclopropyl;
  each of R$^5$ and R$^6$ is independently H or methyl;
  R$^7$ is H or —P(=O)(OR$^{81}$)(OR$^{82}$) [e.g., —P(=O)(OH)(OH)];
  R$^{11}$ is 5- to 6-membered heteroaryl optionally substituted with one or more independently selected R$^{31}$;
  R$^{13}$ is phenyl optionally substituted with one or more independently selected R$^{33}$;
  each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{2-6}$ alkenyl, C$_{2-6}$ alkynyl, C$_{3-10}$ cycloalkyl, 4- to 10-membered heterocycloalkyl, C$_6$10 aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the C$_{1-6}$ alkyl, C$_{2-6}$ alkenyl, C$_{2-6}$ alkynyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with one or more independently selected R$^{36}$;
  each R$^{36}$ is independently selected from the group consisting of halogen, —OH, C$_{1-6}$ alkoxy, C$_{1-6}$ haloalkoxy, —CN, C$_{1-6}$ alkyl, C$_{1-6}$ haloalkyl, C$_{2-6}$ alkenyl, C$_{2-6}$ alkynyl, and C$_{3-7}$ cycloalkyl. In some further embodiments, each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{1-6}$ hydroxylalkyl, C$_{1-6}$ cyanoalkyl, C$_{1-6}$ haloalkyl, and C$_{3-4}$ cycloalkyl.

In some embodiments of the compound of Formula I-a (including Formula I-a1) or a pharmaceutically acceptable salt thereof:
  the moiety of "—N(R$^1$)(R$^2$)" is a moiety of Formula a-46-1 wherein R$^8$ is -L$^1$-R$^{11}$ or -L$^3$-R$^{13}$;
  each of L$^1$ and L$^3$ is independently absent, —(CR$^{21}$R$^{22}$)—, or —S(=O)$_2$— [e.g., each of L$^1$ and L$^3$ is —S(=O)$_2$—];
  each of R$^{21}$ and R$^{22}$ is independently H, C$_{1-3}$ alkyl, or cyclopropyl;
  each of R$^5$ and R$^6$ is independently H or methyl;
  R$^7$ is H or —P(=O)(OR$^{81}$)(OR$^{82}$) [e.g., —P(=O)(OH)(OH)];
  R$^{11}$ is 5- to 6-membered heteroaryl optionally substituted with one or more independently selected R$^{31}$;
  R$^{13}$ is phenyl optionally substituted with one or more independently selected R$^{33}$;
  each of R$^{31}$ and R$^{33}$ is independently selected from the group consisting of halogen, OH, C$_{1-6}$ alkoxy, C$_{1-6}$ haloalkoxy, —CN, C$_{1-6}$ alkyl, C$_{2-6}$ alkenyl, C$_{2-6}$ alkynyl, C$_{3-10}$ cycloalkyl, 4- to 10-membered heterocycloalkyl, C$_{6-10}$ aryl, 5- to 10-membered heteroaryl, (C$_{3-10}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the C$_{1-4}$ alkyl, C$_{2-6}$ alkenyl, C$_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected $R^{36}$;

each $R^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl.

In some embodiments of the compound of Formula I-a (including Formula I-a1) or a pharmaceutically acceptable salt thereof:

the moiety of "—N($R^1$)($R^2$)" is a moiety of Formula a-46-1 wherein $R^8$ is -$L^1$-$R^1$;

$L^1$ is independently absent, —($CR^{21}R^{22}$)—, or —$S(=O)_2$— [e.g., absent or —$S(=O)_2$];

each of $R^{21}$ and $R^{22}$ is independently H, $C_{1-3}$ alkyl, or cyclopropyl;

each of $R^5$ and $R^6$ is independently H or methyl;

$R^7$ is H or —$P(=O)(OR^{81})(OR^{82})$ [e.g., —$P(=O)(OH)(OH)$];

$R^{11}$ is 5- to 6-membered heteroaryl optionally substituted with one or more independently selected $R^{31}$;

each of $R^{31}$ is independently selected from the group consisting of halogen, OH, $C_{1-6}$ alkoxy, $C_{1-6}$ haloalkoxy, —CN, $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected $R^{36}$;

each $R^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl. In some further embodiments, $L^1$ is —$S(=O)_2$—.

In some embodiments of the compound of Formula I-a (including Formula I-a1) or a pharmaceutically acceptable salt thereof:

the moiety of "—N($R^1$)($R^2$)" is a moiety of Formula a-46-1 wherein $R^8$ is -$L^3$-$R^{13}$;

$L^3$ is absent, —($CR^{21}R^{22}$)— or —$S(=O)_2$— [e.g., $L^3$ is —$S(=O)_2$—];

each of $R^{21}$ and $R^{22}$ is independently H, $C_{1-3}$ alkyl, or cyclopropyl;

each of $R^5$ and $R^6$ is independently H or methyl;

$R^7$ is H or —$P(=O)(OR^{81})(OR^{82})$ [e.g., —$P(=O)(OH)(OH)$];

$R^{13}$ is phenyl optionally substituted with one or more independently selected $R^{33}$;

each $R^{33}$ is independently selected from the group consisting of halogen, OH, $C_{1-6}$ alkoxy, $C_{1-6}$ haloalkoxy, —CN, $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected $R^{36}$;

each $R^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, $R^{13}$ is phenyl optionally substituted with one or more substituents each independently selected from halogen, $C_{1-4}$ alkoxy, $C_{1-4}$ haloalkoxy, —CN, $C_{1-4}$ alkyl, $C_{1-4}$ haloalkyl, and $C_{3-4}$ cycloalkyl.

In some embodiments of the compound of Formula I-a (including Formula I-a1) or a pharmaceutically acceptable salt thereof:

the moiety of "—N($R^1$)($R^2$)" is a moiety of Formula a-46-1 wherein $R^8$ is -$L^3$-$R^{13}$;

$L^3$ is —$S(=O)_2$—;

each of $R^5$ and $R^6$ is independently H or methyl;

$R^7$ is H or —$P(=O)(OR^{81})(OR^{82})$ [e.g., —$P(=O)(OH)(OH)$];

$R^{13}$ is phenyl optionally substituted with one or more independently selected $R^{33}$;

each $R^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl. In some further embodiments, $R^{13}$ is phenyl optionally substituted with one or more substituents each independently selected from halogen, $C_{1-4}$ alkoxy, $C_{1-4}$ haloalkoxy, —CN, $C_{1-4}$ alkyl, $C_{1-4}$ haloalkyl, and $C_{3-4}$ cycloalkyl.

In some embodiments of the compound of Formula I-a (including Formula I-a1) or a pharmaceutically acceptable salt thereof:

the moiety of "—N($R^1$)($R^2$)" is a moiety of Formula b-26 (e.g. a moiety of Formula b-36);

each of $R^5$ and $R^6$ is independently H, methyl, or $C_1$ fluoroalkyl (e.g. H or methyl); and $R^7$ is H or —$P(=O)(OR^{81})(OR^{82})$ [e.g., —$P(=O)(OH)(OH)$]. In some further embodiments, each of $R^5$ and $R^6$ is independently H or methyl. In some yet further embodiments, the moiety of "—N($R^1$)($R^2$)" is a moiety of Formula b-36.

In some embodiments of the compound of Formula I-a (including Formula I-a1) or a pharmaceutically acceptable salt thereof:

the moiety of "—N($R^1$)($R^2$)" is a moiety of Formula b-46-1a (e.g. a moiety of Formula b-46-1a-1 or b-46-1a-2);

each of $R^5$ and $R^6$ is independently H, methyl, or $C_1$ fluoroalkyl (e.g. H or methyl); and $R^7$ is H or —$P(=O)(OR^{81})(OR^{82})$ [e.g., —$P(=O)(OH)(OH)$]. In some further embodiments, the moiety of "—N($R^1$)($R^2$)" is a moiety of Formula b-46-1a-1. In some yet further embodiments, each of $R^5$ and $R^6$ is independently H or methyl. In some embodiments of the compound of Formula I-a (including Formula I-a1) or a pharmaceutically acceptable salt thereof:

the moiety of "—N($R^1$)($R^2$)" is a moiety of Formula a-46-2 wherein $R^8$ is -$L^1$-$R^{11}$ or -$L^3$-$R^{13}$;

each of $L^1$ and $L^3$ is independently absent, —O—, —NR$^{23}$—, —S(=O)$_2$—(CR$^{21}$R$^{22}$)— [for example, R$^8$ is —(CR$^{21}$R$^{22}$)—S(=O)$_2$—R$^{11}$ or —(CR$^{21}$R$^{22}$)—S(=O)$_2$—R$^{13}$], or —S(=O)$_2$—NR$^{23}$— [for example, R$^8$ is —NR$^{23}$—S(=O)$_2$—R$^{11}$ or —NR$^{23}$—S(=O)$_2$—R$^{13}$];

each of $R^{21}$ and $R^{22}$ is independently H, OH, halogen, $C_{1-3}$ alkyl, cyclopropylmethyl, or $C_{1-3}$ haloalkyl (for example, H, $C_{1-3}$ alkyl, or cyclopropyl);

$R^{23}$ is H or $C_{1-4}$ alkyl (e.g., methyl);

each of $R^5$ and $R^6$ is independently H or methyl;

$R^7$ is H or —P(=O)(OR$^{81}$)(OR$^{82}$) [e.g., —P(=O)(OH)(OH)];

$R^{11}$ is 5- to 6-membered heteroaryl optionally substituted with one or more independently selected $R^{31}$;

$R^{13}$ is phenyl optionally substituted with one or more independently selected $R^{33}$;

each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected $R^{36}$;

each $R^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl.

In some embodiments of the compound of Formula I-a (including Formula I-a1) or a pharmaceutically acceptable salt thereof:

the moiety of "—N(R$^1$)(R$^2$)" is a moiety of Formula a-46-2 wherein R$^8$ is -L$^1$-R$^{11}$ or -L$^3$-R$^{13}$;

each of $L^1$ and $L^3$ is —S(=O)$_2$—NR$^{23}$— [for example, R$^8$ is —NR$^{23}$—S(=O)$_2$—R$^{11}$ or —NR$^{23}$—S(=O)$_2$—R$^{13}$];

$R^{23}$ is H or $C_{1-4}$ alkyl (e.g., methyl);

each of $R^5$ and $R^6$ is independently H or methyl;

$R^7$ is H or —P(=O)(OR$^{81}$)(OR$^{82}$) [e.g., —P(=O)(OH)(OH)];

$R^{11}$ is 5- to 6-membered heteroaryl optionally substituted with one or more independently selected $R^{31}$;

$R^{13}$ is phenyl optionally substituted with one or more independently selected $R^{33}$;

each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected $R^{36}$;

each $R^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl.

In some embodiments of the compound of Formula I-a (including Formula I-a1) or a pharmaceutically acceptable salt thereof:

the moiety of "—N(R$^1$)(R$^2$)" is a moiety of Formula a-46-2 wherein R$^8$ is -L$^1$-R$^{11}$ or -L$^3$-R$^{13}$;

each of $L^1$ and $L^3$ is —O— or —NR$^{23}$—;

$R^{23}$ is H or $C_{1-4}$ alkyl (e.g., methyl);

each of $R^5$ and $R^6$ is independently H or methyl;

$R^7$ is H or —P(=O)(OR$^{81}$)(OR$^{82}$) [e.g., —P(=O)(OH)(OH)];

$R^{11}$ is 5- to 6-membered heteroaryl optionally substituted with one or more independently selected $R^{31}$;

$R^{13}$ is phenyl optionally substituted with one or more independently selected $R^{33}$;

each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected $R^{36}$;

each $R^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, each of $R^{31}$ and $R^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl.

In some embodiments of the compound of Formula I-a (including Formula I-a1) or a pharmaceutically acceptable salt thereof:

the moiety of "—N(R$^1$)(R$^2$)" is a moiety of Formula b-46-2 (e.g. a moiety of Formula b-46-2a, Formula b-46-2a-1, b-46-2a-2, or b-46-2a-3);

each of $R^5$ and $R^6$ is independently H, methyl, or $C_1$ fluoroalkyl (e.g. H or methyl); and $R^7$ is H or —P(=O)(OR$^{81}$)(OR$^{82}$) [e.g., —P(=O)(OH)(OH)]. In some further embodiments, the moiety of "—N(R$^1$)(R$^2$)" is a moiety of Formula b-46-2a; and each of $R^5$ and $R^6$ is independently H or methyl.

In some embodiments of the compound of Formula I-a (including Formula I-a1) or a pharmaceutically acceptable salt thereof:

the moiety of "—N(R$^1$)(R$^2$)" is a moiety of Formula a-46-2;

$R^8$ is —NR$^{23}$—S(=O)$_2$—R, —NR$^{23}$—S(=O)$_2$—R$^{12}$, —NR$^{23}$—S(=O)$_2$—R$^{13}$, —NR$^{23}$—S(=O)$_2$—R$^{14}$, —NR$^{23}$—C(=O)—R$^{11}$, —NR$^{23}$—C(=O)—R$^{12}$, —NR$^{23}$—C(=O)—R$^{13}$, or —NR$^{23}$—C(=O)—R$^{14}$;

$R^{23}$ is $C_{1-3}$ alkyl (e.g. methyl);
each of $R^5$ and $R^6$ is independently H, methyl, or $C_1$ fluoroalkyl (e.g. H or methyl); and
$R^7$ is H or —P(=O)(OR$^{81}$)(OR$^{82}$) [e.g., —P(=O)(OH)(OH)]. In some further embodiments, $R^{23}$ is methyl; and each of $R^5$ and $R^6$ is independently H or methyl.

In some embodiments of the compound of Formula I-a (including Formula I-a1) or a pharmaceutically acceptable salt thereof:
the moiety of "—N(R$^1$)(R$^2$)" is a moiety of Formula a-46-2;
$R^8$ is —R$^{11}$, —R$^{12}$, —R$^{13}$, or —R$^{14}$ (e.g. $R^8$ is —R$^{11}$ or —R$^{13}$);
each of $R^5$ and $R^6$ is independently H, methyl, or $C_1$ fluoroalkyl (e.g. H or methyl); and
$R^7$ is H or —P(=O)(OR$^{81}$)(OR$^{82}$) [e.g., —P(=O)(OH)(OH)]. In some further embodiments, $R^{23}$ is —R$^{14}$; and each of $R^5$ and $R^6$ is independently H or methyl.

In some embodiments of the compound of Formula I-a (including Formula I-a1) or a pharmaceutically acceptable salt thereof:
the moiety of "—N(R$^1$)(R$^2$)" is a moiety of Formula a-46-7;
$R^8$ is -L$^1$-R$^{11}$, -L$^2$-R$^{12}$, -L$^3$-R$^{13}$, or -L$^4$-R$^{14}$;
each of L$^1$, L$^2$, L$^3$, and L$^4$ is —C(=O)— or —S(=O)$_2$— [e.g. —C(=O)—];
each of $R^5$ and $R^6$ is independently H, methyl, or $C_1$ fluoroalkyl (e.g. H or methyl); and
$R^7$ is H or —P(=O)(OR$^{81}$)(OR$^{82}$) [e.g., —P(=O)(OH)(OH)]. In some further embodiments, $R^8$ is -L$^1$-R$^{11}$ or -L$^3$-R$^{13}$; each of L$^1$ and L$^3$ is —C(=O)—; and each of $R^5$ and $R^6$ is independently H or methyl.

In some embodiments of the compound of Formula I-a (including Formula I-a1) or a pharmaceutically acceptable salt thereof:
the moiety of "—N(R$^1$)(R$^2$)" is a moiety of Formula b-46-7a (e.g. a moiety of Formula b-46-7a-1 or a moiety of Formula b-46-7a-2);
each of $R^5$ and $R^6$ is independently H, methyl, or $C_1$ fluoroalkyl (e.g. H or methyl); and $R^7$ is H or —P(=O)(OR$^{81}$)(OR$^{82}$) [e.g., —P(=O)(OH)(OH)]. In some further embodiments, the moiety of "—N(R$^1$)(R$^2$)" is a moiety of Formula b-46-7a-2; and each of $R^5$ and $R^6$ is independently H or methyl.

In some embodiments of the compound of Formula I-a (including Formula I-a1) or a pharmaceutically acceptable salt thereof:
the moiety of "—N(R$^1$)(R$^2$)" is a moiety of Formula a-46-4 or a-46-6 wherein $R^8$ is -L$^1$-R$^{11}$ or -L$^3$-R$^{13}$;
each of L$^1$ and L$^3$ is independently —(CR$^{21}$R$^{22}$)— or —S(=O)$_2$—;
each of R$^{21}$ and R$^{22}$ is independently H, $C_{1-3}$ alkyl, or cyclopropyl;
each of $R^5$ and $R^6$ is independently H or methyl;
$R^7$ is H or —P(=O)(OR$^{81}$)(OR$^{82}$) [e.g., —P(=O)(OH)(OH)];
R$^{11}$ is 5- to 6-membered heteroaryl optionally substituted with one or more independently selected R$^{31}$;
R$^{13}$ is phenyl optionally substituted with one or more independently selected R$^{33}$;
each of R$^{31}$ and R$^{33}$ is independently selected from the group consisting of halogen, OH, $C_{1-6}$ alkoxy, $C_{1-6}$ haloalkoxy, —CN, $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the $C_{1-6}$ alkyl, $C_{2-6}$ alkenyl, $C_{2-6}$ alkynyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with one or more independently selected R$^{36}$;
each R$^{36}$ is independently selected from the group consisting of halogen, —OH, $C_{1-6}$ alkoxy, $C_{1-6}$ haloalkoxy, —CN, $C_{1-6}$ alkyl, $C_{1-6}$ haloalkyl, $C_{2-6}$ alkenyl, $C_{2-6}$ alkynyl, and $C_{3-7}$ cycloalkyl. In some further embodiments, each of R$^{31}$ and R$^{33}$ is independently selected from the group consisting of halogen, OH, $C_{1-6}$ alkoxy, $C_{1-6}$ haloalkoxy, —CN, $C_{1-6}$ alkyl, $C_{1-6}$ hydroxylalkyl, $C_{1-6}$ cyanoalkyl, $C_{1-6}$ haloalkyl, and $C_{3-4}$ cycloalkyl.

In some embodiments, the present invention provides a compound selected from Examples 1 to 150 (e.g. Examples 1 to 91) in the EXAMPLES section or a pharmaceutically acceptable salt thereof (or the parent compound thereof where the exemplary compound, for example, is a salt) herein below.

In some embodiments, the present invention provides a compound selected from:
1,1,1-trifluoro-3-hydroxypropan-2-yl 6-[1-(5-methoxypyridin-2-yl)-1H-pyrazol-3-yl]-3-azabicyclo[3.1.0]hexane-3-carboxylate;
1,1,1-trifluoro-3-hydroxypropan-2-yl 6-[1-(4-fluorophenyl)-1H-pyrazol-3-yl]-3-azabicyclo[3.1.0]hexane-3-carboxylate;
1,1,1-trifluoro-3-hydroxypropan-2-yl (1α,5α,6α)-6-[1-(5-methoxypyridin-2-yl)-1H-pyrazol-3-yl]-3-azabicyclo[3.1.0]hexane-3-carboxylate;
1,1,1-trifluoro-3-hydroxypropan-2-yl (1α,5α,6α)-6-[1-(4-fluorophenyl)-1H-pyrazol-3-yl]-3-azabicyclo[3.1.0]hexane-3-carboxylate;
1,1,1-trifluoro-3-hydroxypropan-2-yl 4-[(4-fluorophenyl)sulfonyl]-1-oxa-4,9-diazaspiro[5.5]undecane-9-carboxylate;
1,1,1-trifluoro-3-hydroxypropan-2-yl 4-(phenylsulfonyl)-1-oxa-4,9-diazaspiro[5.5]undecane-9-carboxylate;
1,1,1-trifluoro-3-hydroxypropan-2-yl 3-[(phenylsulfonyl)amino]-1-oxa-8-azaspiro[4.5]decane-8-carboxylate;
1,1,1-trifluoro-3-hydroxypropan-2-yl 3-[(phenylsulfonyl)amino]-1-oxa-8-azaspiro[4.5]decane-8-carboxylate;
1,1,1-trifluoro-3-hydroxypropan-2-yl 4-[(3-fluorophenyl)sulfonyl]-1-oxa-4,9-diazaspiro[5.5]undecane-9-carboxylate;
1,1,1-trifluoro-3-hydroxypropan-2-yl 3-[methyl(phenylsulfonyl)amino]-1-oxa-8-azaspiro[4.5]decane-8-carboxylate;
1,1,1-trifluoro-3-hydroxypropan-2-yl 3-(4-fluorobenzyl)-3,8-diazabicyclo[3.2.1]octane-8-carboxylate;
1,1,1-trifluoro-3-hydroxypropan-2-yl 4-[(4-fluorophenyl)sulfonyl]-3-hydroxy-1-oxa-4,9-diazaspiro[5.5]undecane-9-carboxylate;
3,3,3-trifluoro-2-[({3-[methyl(phenylsulfonyl)amino]-1-oxa-8-azaspiro[4.5]dec-8-yl}carbonyl)oxy]propyl dihydrogen phosphate;
3,3,3-trifluoro-2-[({4-[(4-fluorophenyl)sulfonyl]-1-oxa-4,9-diazaspiro[5.5]undec-9-yl}carbonyl)oxy]propyl dihydrogen phosphate;
3,3,3-trifluoro-2-[({4-[(3-fluorophenyl)sulfonyl]-1-oxa-4,9-diazaspiro[5.5]undec-9-yl}carbonyl)oxy]propyl dihydrogen phosphate;
1,1,1-trifluoro-3-hydroxypropan-2-yl 4-[1-(tetrahydro-2H-pyran-4-yl)-1H-pyrazol-3-yl]piperidine-1-carboxylate;

1,1,1-trifluoro-3-hydroxypropan-2-yl 4-(4-fluorobenzyl)-1-oxa-4,9-diazaspiro[5.5]undecane-9-carboxylate;
1,1,1-trifluoro-3-hydroxypropan-2-yl 4-[(3,4-difluorophenyl)sulfonyl]-1-oxa-4,9-diazaspiro[5.5]undecane-9-carboxylate;
1,1,1-trifluoro-3-hydroxypropan-2-yl 4-[(4-ethynylphenyl)sulfonyl]-1-oxa-4,9-diazaspiro[5.5]undecane-9-carboxylate;
1,1,1-trifluoro-3-hydroxypropan-2-yl 3-(4-fluorobenzyl)-2-oxo-1-oxa-3,8-diazaspiro[4.5]decane-8-carboxylate;
3,3,3-trifluoro-2-({[4-(phenylsulfonyl)-1-oxa-4,9-diazaspiro[5.5]undec-9-yl]carbonyl}oxy)propyl dihydrogen phosphate;
1,1,1-trifluoro-3-hydroxypropan-2-yl 3-{[(4-fluorophenyl)sulfonyl](methyl)amino}-1-oxa-8-azaspiro[4.5]decane-8-carboxylate;
1,1,1-trifluoro-3-hydroxypropan-2-yl 3-[(cyclopropylsulfonyl)(methyl)amino]-1-oxa-8-azaspiro[4.5]decane-8-carboxylate;
1,1,1-trifluoro-3-hydroxypropan-2-yl 3-[benzoyl(methyl)amino]-1-oxa-8-azaspiro[4.5]decane-8-carboxylate;
1,1,1-trifluoro-3-hydroxypropan-2-yl 3-{[(cyclopropylmethyl)sulfonyl](methyl)amino}-1-oxa-8-azaspiro[4.5]decane-8-carboxylate;
1,1,1-trifluoro-3-hydroxypropan-2-yl 3-[3-(trifluoromethoxy)phenyl]-1-oxa-8-azaspiro[4.5]decane-8-carboxylate;
1,1,1-trifluoro-3-hydroxypropan-2-yl 2-(cyclopentylcarbonyl)-2,8-diazaspiro[4.5]decane-8-carboxylate;
1,1,1-trifluoro-3-hydroxypropan-2-yl 3-{methyl[(2,2,2-trifluoroethyl)sulfonyl]amino}-1-oxa-8-azaspiro[4.5]decane-8-carboxylate;
1,1,1-trifluoro-3-hydroxypropan-2-yl 3-{methyl[(2-methylpropyl)sulfonyl]amino}-1-oxa-8-azaspiro[4.5]decane-8-carboxylate; and
1,1,1-trifluoro-3-hydroxypropan-2-yl 3-[(cyclopropylacetyl)(methyl)amino]-1-oxa-8-azaspiro[4.5]decane-8-carboxylate,
or a pharmaceutically acceptable salt thereof;
or a pharmaceutically acceptable salt selected from:
3,3,3-trifluoro-2-[({3-[methyl(phenylsulfonyl)amino]-1-oxa-8-azaspiro[4.5]dec-8-yl}carbonyl)oxy]propyl phosphate, disodium salt;
3,3,3-trifluoro-2-[({4-[(4-fluorophenyl)sulfonyl]-1-oxa-4,9-diazaspiro[5.5]undec-9-yl}carbonyl)oxy]propyl phosphate, disodium salt;
3,3,3-trifluoro-2-[({4-[(4-fluorophenyl)sulfonyl]-1-oxa-4,9-diazaspiro[5.5]undec-9-yl}carbonyl)oxy]propyl phosphate, (bis)-L-lysine salt;
3,3,3-trifluoro-2-[({4-[(3-fluorophenyl)sulfonyl]-1-oxa-4,9-diazaspiro[5.5]undec-9-yl}carbonyl)oxy]propyl phosphate, disodium salt; and
3,3,3-trifluoro-2-({[4-(phenylsulfonyl)-1-oxa-4,9-diazaspiro[5.5]undec-9-yl]carbonyl}oxy)propyl phosphate, disodium salt.

The present invention includes any subset of any embodiment described herein.

The present invention includes combinations of two or more embodiments described hereinabove, or any subset thereof.

The present invention further provides the compound of Formula I or a pharmaceutically acceptable salt thereof (including all embodiments and combinations of two or more embodiments described herein or any subcombination thereof) for use in the treatment of a MAGL-mediated disease or disorder described herein.

The present invention further provides use of the compound of Formula I or a pharmaceutically acceptable salt thereof (including all embodiments and combinations of two or more embodiments described herein or any subcombination thereof) for treating a MAGL-mediated disease or disorder described herein.

The present invention further provides a method for treating a MAGL-mediated disease or disorder in a patient (e.g., a mammal such as a human) comprising administering to the patient a therapeutically effective amount of the compound of Formula I or a pharmaceutically acceptable salt thereof (including all embodiments and combinations of two or more embodiments described herein or any subcombination thereof).

The present invention further provides use of the compound of Formula I or a pharmaceutically acceptable salt thereof (including all embodiments and combinations of two or more embodiments described herein or any subcombination thereof) in the manufacture of a medicament for use in the treatment of a MAGL-mediated disease or disorder described herein.

The compound of Formula I or a pharmaceutically acceptable salt thereof of the present invention (or a metabolite thereof) is a MAGL inhibitor. Thus, the present invention further provides a method for inhibiting MAGL (i.e., an activity of MAGL either in vitro or in vivo), comprising contacting (including incubating) the MAGL with the compound of Formula I or a pharmaceutically acceptable salt thereof (such as one selected from Examples 1-91 herein) described herein.

The amount of the compound of Formula I or a pharmaceutically acceptable salt thereof used in any one of the methods (or uses) of the present invention is effective in inhibiting MAGL.

MAGL-mediated diseases or disorders include, for example, a metabolic disorder (e.g., obesity); a kidney disease (e.g. acute inflammatory kidney injury and diabetic nephropathy); vomiting or emesis (e.g. chemotherapy induced vomiting); nausea (e.g. refractory nausea or chemotherapy induced nausea); an eating disorder (e.g anorexia or bulimia); neuropathy (e.g., diabetic neuropathy, pellagric neuropathy, alcoholic neuropathy, Beriberi neuropathy); burning feet syndrome; a neurodegenerative disorder [multiple sclerosis (MS), Parkinson's disease (PD), Huntington's disease, dementia, Alzheimer's disease, amyotrophic lateral sclerosis (ALS), epilepsy, fronto-temporal lobe dementia, a sleep disorder, Creutzfeldt-Jakob disease (CJD), or prion disease]; a cardiovascular disease (e.g., hypertension, dyslipidemia, atherosclerosis, cardiac arrhythmias, or cardiac ischemia); osteoporosis; osteoarthritis; schizophrenia; depression; bipolar disease; tremor; dyskinesia; dystonia; spasticity; Tourette's syndrome; sleep apnea; hearing loss; an eye disease (e.g., glaucoma, ocular hypertension, macular degeneration, or a disease arising from elevated intraocular pressure); cachexia; insomnia; meningitis; sleeping sickness; progressive multifocal leukoencephalopathy; De Vivo disease; cerebral edema; cerebral palsy; withdrawal syndrome [alcohol withdrawal syndrome, antidepressant discontinuation syndrome, antipsychotic withdrawal syndrome, benzodiazepine withdrawal syndrome, cannabis withdrawal, neonatal withdrawal, nicotine withdrawal, or opioid withdrawal]; traumatic brain injury; non-traumatic brain injury; spinal cord injury; seizures; excitotoxin exposure; ischemia [stroke, hepatic ischemia or reperfusion, CNS ischemia or reperfusion]; liver fibrosis, iron overload, cirrhosis of the liver; a lung disorder [asthma, allergies, COPD, chronic bronchitis, emphysema, cystic fibrosis, pneumonia, tuberculosis, pulmonary edema, lung cancers, acute respiratory distress syndrome, interstitial lung disease (ILD), sarcoidosis, idiopathic pulmonary fibrosis, pulmonary embolism, pleural effusion, or mesothelioma]; a liver disorder [acute liver failure, Alagille syndrome, hepatitis, enlarged liver, Gilbert's syndrome, liver cysts, liver hemangioma, fatty liver disease, steatohepatitis, primary sclerosing cholangitis, fascioliasis, primary bilary cirrhosis, Budd-Chiari syndrome, hemochromatosis, Wilson's disease, or transthyretin-related hereditary amyloidosis], stroke [e.g., ischemic stroke; hemorrhagic stroke]; subarachnoid hemorrhage; intracerebral hemorrhage; vasospasm; AIDS wasting syndrome; renal ischemia; a disorder associated with abnormal cell growth or proliferation [e.g., a benign tumor or cancer such as benign skin tumor, brain tumor, papilloma, prostate tumor, cerebral tumor (glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, bladder cancer, brain cancer, glioblastoma (GBM), gastrointestinal cancer, leukemia or blood cancer]; an autoimmune disease [e.g., psoriasis, lupus erythematosus, Sjogren's syndrome, ankylosing spondylitis, undifferentiated spondylitis, Behcet's disease, hemolytic anemia, graft rejection]; an inflammatory disorder [e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, IBS, pelvic inflammatory disease, sarcoidosis, HIV encephalitis, rabies, brain abscess, neuroinflammation, inflammation in the central nervous system (CNS)]; a disorder of the immune system (e.g., transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); Asperger's syndrome; pain [e.g., acute pain; chronic pain; inflammatory pain; visceral pain; post-operative pain; migraine; lower back pain; joint pain; abdominal pain; chest pain; postmastectomy pain syndrome; menstrual pain; endometriosis pain; pain due to physical trauma; headache; sinus headache; tension headache arachnoiditis, herpes virus pain, diabetic pain; pain due to a disorder selected from: osteoarthritis, rheumatoid arthritis, osteoarthritis, spondylitis, gout, labor, musculoskeletal disease, skin disease, toothache, pyresis, burn, sunburn, snake bite, venomous snake bite, spider bite, insect sting, neurogenic bladder, interstitial cystitis, urinary tract infection (UTI), rhinitis, contact dermatitis/hypersensitivity, itch, eczema, pharyngitis, mucositis, enteritis, irritable bowel syndrome (IBS), cholecystitis, and pancreatitis; neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy from chemotherapeutic agent, or sciatica pain)]; a demyelinating disease [e.g., multiple sclerosis (MS), Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis]; and cognitive impairment [e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)].

The term "therapeutically effective amount" as used herein refers to that amount of the compound (including a pharmaceutically acceptable salt thereof) being administered which will relieve to some extent one or more of the symptoms of the disorder being treated. In reference to the treatment of a MAGL-mediated disease or disorder (e.g., Alzheimer's disease, inflammation, or pain), a therapeutically effective amount refers to that amount which has the effect of relieving to some extent (or, for example, eliminating) one or more symptoms associated with the MAGL-mediated disease or disorder (e.g., psychotic symptom of Alzheimer's disease).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

As used herein, the term "adjacent" in describing the relative positions of two substituent groups on a ring structure refers to two substituent groups that are respectively attached to two ring-forming atoms of the same ring, wherein the two ring-forming atoms are directly connected through a chemical bond. For example, in each of the following structures:

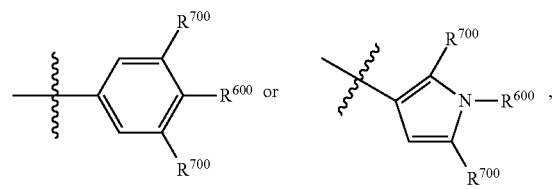

either of the two $R^{700}$ groups is an adjacent group of $R^{600}$.

As used herein, the term "n-membered", where n is an integer, typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). For yet another example, the term "$C_{1-4}$ alkyl" refers to linear or branched aliphatic hydrocarbon chains of 1 to 4 carbon atoms; the term "$C_{1-3}$ alkyl" refers to linear or branched aliphatic hydrocarbon chains of 1 to 3 carbon atoms; the term "$C_{1-2}$ alkyl" refers to methyl and/or ethyl; and the term "$C_1$ alkyl" refers to methyl. An alkyl group optionally can be substituted by one or more (e.g., 1 to 5) suitable substituents.

As used herein, the term "alkenyl" refers to aliphatic hydrocarbons having at least one carbon-carbon double bond, including straight chains and branched chains having at least one carbon-carbon double bond. In some embodiments, the alkenyl group has 2 to 20 carbon atoms, 2 to 10 carbon atoms, 2 to 6 carbon atoms, 3 to 6 carbon atoms, or 2 to 4 carbon atoms. For example, as used herein, the term "$C_{2-6}$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. When the compounds of Formula I contain an alkenyl group, the alkenyl group may exist as the pure E form, the pure Z form, or any mixture thereof.

As used herein, the term "alkynyl" refers to aliphatic hydrocarbons having at least one carbon-carbon triple bond, including straight chains and branched chains having at least one carbon-carbon triple bond. In some embodiments, the alkynyl group has 2 to 20, 2 to 10, 2 to 6, or 3 to 6 carbon atoms. For example, as used herein, the term "$C_{2-6}$ alkynyl" refers to straight or branched hydrocarbon chain alkynyl radicals as defined above, having 2 to 6 carbon atoms. An alkynyl group optionally can be substituted by one or more (e.g., 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.). The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_{3-14}$ cycloalkyl" refers to saturated or unsaturated, non-aromatic, monocyclic or polycyclic (such as bicyclic) hydrocarbon rings of 3 to 14 ring-forming carbon atoms (e.g., cyclopropyl, cyclobutyl, cyclopentyl, cyclohexyl, bicyclo[1.1.1]pentanyl, or cyclodecanyl); and the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, bicyclo[1.1.1]pentan-1-yl, or bicyclo[1.1.1]pentan-2-yl). For another example, the term "$C_{3-6}$ cycloalkyl" refers to saturated or unsaturated, non-aromatic, monocyclic or polycyclic (such as bicyclic) hydrocarbon rings of 3 to 6 ring-forming carbon atoms. For yet another example, the term "$C_{3-4}$ cycloalkyl" refers to cyclopropyl or cyclobutyl. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-indene-1-yl, or 1H-inden-2(3H)-one-1-yl). The cycloalkyl group optionally can be substituted by 1 or more (e.g., 1 to 5) suitable substituents.

As used herein, the term "aryl" refers to all-carbon monocyclic or fused-ring polycyclic aromatic groups having a conjugated pi-electron system. The aryl group has 6 or 10 carbon atoms in the ring(s). Most commonly, the aryl group has 6 carbon atoms in the ring. For example, as used herein, the term "$C_{6-10}$ aryl" means aromatic radicals containing from 6 to 10 carbon atoms such as phenyl or naphthyl. The aryl group optionally can be substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono (i.e., =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the monocyclic heteroaryl ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like. The heteroaryl group optionally can be substituted by 1 or more (e.g., 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 12-membered ring system, 5- to 10-membered ring system, 4- to 7-membered ring system, 4- to 6-membered ring system, or 5- to 6-membered ring system), including 1 to 14 ring-forming carbon atoms and 1 to 10 ring-forming heteroatoms each independently selected from O, S and N (and optionally P or B when present). The heterocycloalkyl group can also optionally contain one or more oxo (i.e., =O) or thiono (i.e., =S) groups. For example, the term "4- to 12-membered heterocycloalkyl" refers to a monocyclic or polycyclic, saturated or unsaturated, non-aromatic 4- to 12-membered ring system that comprises one or more ring-forming heteroatoms each independently selected from O, S and N; and the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N; and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. The heterocycloalkyl group optionally can be substituted by 1 or more (e.g., 1 to 5) suitable substituents.

Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g., 2-oxaspiro[3.3]hept-6-yl}, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g., tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-6}$ haloalkyl" refers to a $C_{1-6}$ alkyl group having one or more halogen substituents (up to perhaloalkyl, i.e., every hydrogen atom of the alkyl group has been replaced by a halogen atom). For another example, the term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom); the term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom); and the term "$C_{1-2}$ haloalkyl" refers to a $C_{1-2}$ alkyl group (i.e., methyl or ethyl) having one or more halogen substituents (up to perhaloalkyl, i.e., every hydrogen atom of the alkyl group has been replaced by a halogen atom). For yet another example, the term "$C_1$ haloalkyl" refers to a methyl group having one, two, or three halogen substituents. Examples of haloalkyl groups include $CF_3$, $C_2F_5$, $CHF_2$, $CH_2F$, $CH_2CF_3$, $CH_2Cl$ and the like.

As used herein, the term "alkoxy" or "alkyloxy" refers to an —O-alkyl group. For example, the term "$C_{1-6}$ alkoxy" or "$C_{1-6}$ alkyloxy" refers to an —O—($C_{1-6}$ alkyl) group; and the term "$C_{1-4}$ alkoxy" or "$C_{1-4}$ alkyloxy" refers to an —O—($C_{1-4}$ alkyl) group; For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

As used here, the term "haloalkoxy" refers to an —O-haloalkyl group. For example, the term "$C_{1-6}$ haloalkoxy" refers to an —O—($C_{1-6}$ haloalkyl) group. For another example, the term "$C_{1-4}$ haloalkoxy" refers to an —O—($C_{1-4}$ haloalkyl) group; and the term "$C_{1-2}$ haloalkoxy" refers to an —O—($C_{1-2}$ haloalkyl) group. For yet another example, the term "$C_1$ haloalkoxy" refers to a methoxy group having one, two, or three halogen substituents. An example of haloalkoxy is —$OCF_3$ or —$OCHF_2$.

As used herein, the term "fluoroalkyl" refers to an alkyl group having one or more fluorine substituents (up to perfluoroalkyl, i.e., every hydrogen atom of the alkyl group has been replaced by fluorine). For example, the term "$C_{1-2}$ fluoroalkyl" refers to a $C_{1-2}$ alkyl group having one or more fluorine substituents (up to perfluoroalkyl, i.e., every hydrogen atom of the $C_{1-2}$ alkyl group has been replaced by fluorine). For another example, the term "C fluoroalkyl" refers to a $C_1$ alkyl group (i.e., methyl) having 1, 2, or 3 fluorine substituents). Examples of fluoroalkyl groups include $CF_3$, $C_2F_5$, $CH_2CF_3$, $CHF_2$, $CH_2F$, and the like.

As used here, the term "fluoroalkoxy" refers to an —O-fluoroalkyl group. For example, the term "$C_{1-2}$ fluoroalkoxy" refers to an —O—$C_{1-2}$ fluoroalkyl group. For another example, the term "C fluoroalkoxy" refers to a methoxy group having one, two, or three fluorine substituents. An example of $C_1$ fluoroalkoxy is —$OCF_3$ or —$OCHF_2$.

As used herein, the term "hydroxylalkyl" or "hydroxyalkyl" refers to an alkyl group having one or more (e.g., 1, 2, or 3) OH substituents. The term "$C_{1-6}$ hydroxylalkyl" or "$C_{1-6}$ hydroxyalkyl" refers to a $C_{1-6}$ alkyl group having one or more (e.g., 1, 2, or 3) OH substituents.

The term "$C_{1-4}$ hydroxylalkyl" or "$C_{1-4}$ hydroxyalkyl" refers to a $C_{1-4}$ alkyl group having one or more (e.g., 1, 2, or 3) OH substituents; the term "$C_{1-3}$ hydroxylalkyl" or "$C_{1-3}$ hydroxyalkyl" refers to a $C_{1-3}$ alkyl group having one or more (e.g., 1, 2, or 3) OH substituents; and the term "$C_{1-2}$ hydroxylalkyl" or "$C_{1-2}$ hydroxyalkyl" refers to a $C_{1-2}$ alkyl group having one or more (e.g., 1, 2, or 3) OH substituents. An example of hydroxylalkyl is —$CH_2OH$ or —$CH_2CH_2OH$.

As used herein, the term "cyanoalkyl" refers to an alkyl group having one or more (e.g., 1, 2, or 3) —CN substituents. The term "$C_{1-6}$ cyanoalkyl" refers to a $C_{1-6}$ alkyl group having one or more (e.g., 1, 2, or 3) —CN substituents. For example, $C_1$ cyanoalkyl is $C_1$ alkyl (i.e., methyl) having one or more (e.g., one) —CN substituents. An example of cyanoalkyl is —$CH_2CN$ or —$CH_2CH_2CN$.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—$S(=O)_2$—].

As used herein, the term "thiono" refers to =S. When an thiono is substituted on a carbon atom, they together form moiety of [—C(=S)—].

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is optionally substituted, then up to 3 hydrogen atoms on the carbon atom can be replaced with substituent groups.

As used herein, the term "optionally substituted $C_{1-4}$ alkyl" refers to $C_{1-4}$ alkyl optionally substituted by one or more (e.g., 1 to 5) substituents each independently selected from the group consisting of —OH, halogen, —CN, —$NH_2$, —NH($C_{1-4}$ alkyl), —N($C_{1-4}$ alkyl)$_2$, $C_{1-4}$ alkoxy, and $C_{1-4}$ haloalkoxy.

As used herein, the term "optionally substituted $C_{3-6}$ cycloalkyl" refers to $C_{3-6}$ cycloalkyl optionally substituted by one or more (e.g., 1 to 5) substituents each independently selected from the group consisting of —OH, halogen, —CN, —$NH_2$, —NH($C_{1-4}$ alkyl), —N($C_{1-4}$ alkyl)$_2$, $C_{1-4}$ alkyl, $C_{1-4}$ haloalkyl, $C_{1-4}$ hydroxylalkyl, $C_{1-4}$ alkoxy, and $C_{1-4}$ haloalkoxy.

As used herein, the term "optionally substituted $C_{3-6}$ cycloalkyl-$C_{1-2}$ alkyl-" refers to $C_{3-6}$ cycloalkyl-$C_{1-2}$ alkyl- optionally substituted by one or more (e.g., 1 to 5) substituents each independently selected from the group consisting of —OH, halogen, —CN, —$NH_2$, —NH($C_{1-4}$ alkyl), —N($C_{1-4}$ alkyl)$_2$, $C_{1-4}$ alkyl, $C_{1-4}$ haloalkyl, $C_{1-4}$ hydroxylalkyl, $C_{1-4}$ alkoxy, and $C_{1-4}$ haloalkoxy.

As used herein, the term "optionally substituted $C_{1-4}$ alkoxy" refers to $C_{1-4}$ alkoxy optionally substituted by one or more (e.g., 1 to 5) substituents each independently selected from the group consisting of —OH, halogen, —CN, —$NH_2$, —NH($C_{1-4}$ alkyl), —N($C_{1-4}$ alkyl)$_2$, $C_{1-4}$ alkoxy, and $C_{1-4}$ haloalkoxy.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

As used herein, the point of attachment of a substituent can be specified to indicate the position where the substituent is attached to another moiety. For example, "—$C_{1-2}$ alkyl-($C_{3-4}$ cycloalkyl)" means the point of attachment occurs at the "$C_{1-2}$ alkyl" part of the "—$C_{1-2}$ alkyl-($C_{3-4}$ cycloalkyl)." For another example, "($C_{3-4}$ cycloalkyl)-$C_{1-2}$ alkyl-" also means the point of attachment occurs at the "$C_{1-2}$ alkyl" part of the "($C_{3-4}$ cycloalkyl)-$C_{1-2}$ alkyl-."

When a bond to a substituent is shown to cross a bond connecting two atoms in a ring, then such substituent may be bonded to any of the ring-forming atoms in that ring that are substitutable (i.e., bonded to one or more hydrogen atoms), unless otherwise specified or otherwise implicit from the context. For example, as shown in the structure of Formula a-6 below, $R^8$ may be bonded to any of the ring atoms of ring $A^1$, but not to the ring including the N atom as shown in Formula a-6. For another example, as shown in Formula a-5 below (when t1 is 1), the $R^9$ group can be bonded to any of the ring carbon atoms or the N atom (of the NH moiety) because the cross-bond is through both rings of the bicyclic structure; on the other hand, $R^8$ can only be bonded to the N atom (of the NH moiety) and the two carbon ring atoms that are directly connected to the N atom (of the NH moiety). $R^8$ cannot be bonded to either of the carbon atom of the moiety of "$CH_2CH_2$" (the H atoms are not shown) of the pyrrolidine ring of the bicyclic system of Formula a-5 because the bond does not cross the pyrrolidine ring.

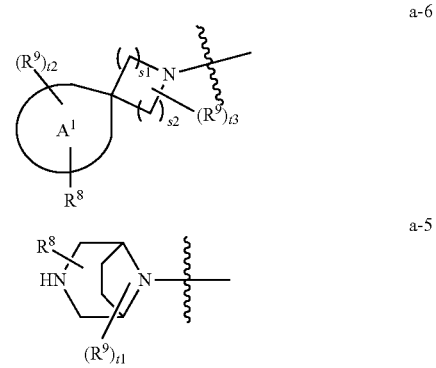

As used herein, unless otherwise specifically indicated, a linkage/linker—a moiety that links two other moieties—can be attached to the other two moieties in either direction, if the linkage/linker is asymmetric. For example, when $R^8$ is -$L^1$-$R^{11}$ and $L^1$ is —$S(=O)_2$—$NR^{23}$—, then $R^8$ can be either —$S(=O)_2$—$NR^{23}$—$R^{11}$ or —$NR^{23}$—$S(=O)_2$—$R^{11}$ (unless otherwise specifically indicated).

When a substituted or optionally substituted moiety is described without indicating the atom via which such moiety is bonded to a substituent, then the substituent may be bonded via any appropriate atom in such moiety. For example in a substituted arylalkyl, a substituent on the arylalkyl [e.g., $(C_{6-10}$ aryl)-$C_{1-4}$ alkyl-] can be bonded to any carbon atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/di hydrogen phosphate, pyroglutamate, saccharate, stearate, succinate, tannate, tartrate, tosylate, trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I" or "Formula I or a pharmaceutically acceptable salt thereof" are defined to include all forms of the compound of Formula I or pharmaceutically salt thereof, including hydrates, solvates, isomers (including for example rotational stereoisomers), crystalline and non-crystalline forms, isomorphs, polymorphs, metabolites, and prodrugs thereof.

As is known to the person skilled in the art, amine compounds (i.e., those comprising one or more nitrogen atoms), for example tertiary amines, can form N-oxides (also known as amine oxides or amine N-oxides). An N-oxide has the formula of $(R^{100})(R^{200})(R^{300})N^+$—$O^-$ wherein the parent amine $(R^{100})(R^{200})(R^{300})N$ can be, for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100})(R^{200})(R^{300})N$ together forms 1-alkylpiperidine, 1-alkylpyrrolidine, 1-benzylpyrrolidine, or pyridine]. For instance, an imine nitrogen, especially a heterocyclic or heteroaromatic imine nitrogen, or pyridine-type nitrogen

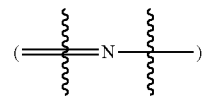 [SMILES: *N=*]

atom [such as a nitrogen atom in pyridine, pyridazine, or pyrazine], can be N-oxidized to form the N-oxide comprising the group

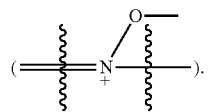

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

Compounds of Formula I and their salts described herein further include N-oxides thereof.

In the description herein below, unless otherwise specified, compounds of Formula I (or compounds of the invention) include salts of the compounds and the N-oxides of the compounds or the salts.

As is also known to the person skilled in the art, tertiary amine compounds (i.e., those comprising one or more tertiary amine nitrogen atoms) can form quaternary ammonium salts. In the description herein below, unless otherwise specified, compounds of Formula I (or compounds of the invention) further include their quaternary ammonium salts.

Compounds of Formula I may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components, which may be in stoichiometric or non-stoichiometric amounts. The resulting complexes may be ionized, partially ionized, or non-ionized. Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of Formula I may themselves act as prodrugs of other compounds of Formula I.

Also included within the scope of the invention are metabolites of compounds of Formula I, that is, compounds formed in vivo upon administration of the drug.

The compounds of Formula I include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I (including salts thereof) may have asymmetric carbon atoms. The carbon-carbon bonds of the compounds of Formula I may be depicted herein using a solid line (-), a wavy line ( ~~~~ ), a solid wedge ( ▬ ), or a dotted wedge ( ·······IIIII ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. The use of a wavy line to depict bonds to asymmetric carbon atoms is meant to indicate that the stereochemistry is unknown (unless otherwise specified). It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of different types are possible. One type is the racemic compound (true racemate) wherein one homogeneous form of crystal is produced containing both enantiomers in equimolar amounts. Another type is a racemic mixture or conglomerate wherein two forms of crystal are produced in equal or different molar amounts each comprising a single enantiomer.

The compounds of Formula I may exhibit the phenomena of tautomerism and structural isomerism. For example, the compounds of Formula I may exist in several tautomeric forms, including the enol and imine form, the amide and imidic acid form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I. For example, when one of the following two tautomers (wherein R can be, for example, phenyl that is further substituted) is disclosed, those skilled in the art would readily recognize the other tautomer.

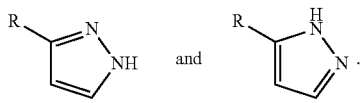

The present invention includes all pharmaceutically acceptable isotopically labelled compounds of Formula I or salts thereof wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically labelled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron-emitting isotopes, such as $^{11}$C, $^{18}$F, $^{15}$O and $^{13}$N, can be useful in Positron Emission Topography (PET) studies for examining substrate receptor occupancy.

Isotopically labeled compounds of Formula I can generally be prepared by conventional techniques known to those skilled in the art or by processes analogous to those described in the accompanying Examples and Preparations using an appropriate isotopically labeled reagent in place of the non-labeled reagent previously employed.

The present invention also provides compositions (e.g., pharmaceutical compositions) comprising a novel compound of Formula I. Accordingly, in one embodiment, the invention provides a pharmaceutical composition comprising (a therapeutically effective amount of) a novel compound of Formula I or a pharmaceutically acceptable salt thereof and optionally comprising a pharmaceutically acceptable carrier. In one further embodiment, the invention provides a pharmaceutical composition comprising (a therapeutically effective amount of) a compound of Formula I or a pharmaceutically acceptable salt thereof, optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I or salt thereof and a pharmaceutically acceptable carrier.

Compounds of Formula I (including salts thereof) are MAGL inhibitors. In some embodiments, the $IC_{50}$ of a compound of Formula I (or its metabolite) is less than about 10 µM, 5 µM, 2 µM, 1 µM, 500 nM, 200 nM, 100 nM, 50, 40, 30, 20, 10, 5, 2, or 1 nM as determined by the method in Example AA described herein below.

Administration of the compounds of Formula I (including salts thereof) may be effected by any method that enables delivery of the compounds to the site of action. These methods include, for example, enteral routes (e.g., oral routes, buccal routes, sublabial routes, sublingual routes), oral routes, intranasal routes, inhaled routes, intraduodenal routes, parenteral injection (including intravenous, subcutaneous, intramuscular, intravascular or infusion), intrathecal routes, epidural routes, intracerebral routes, intracerebroventricular routes, topical, and rectal administration.

In one embodiment of the present invention, the compounds of Formula I may be administered/effected by parenteral injection routes (e.g., intravenous injection route).

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with an at least one additional pharmaceutical or medicinal agent (e.g., an anti-schizophrenia agent), either sequentially or simultaneously.

The present invention includes the use of a combination of a compound of Formula I (including a salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including a pharmaceutically acceptable salt thereof); (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-β (or fragments thereof), such as $Aβ_{1-15}$ conjugated to pan HLA DR-binding epitope (PADRE) and ACC-001 (Elan/Wyeth);

(iii) antibodies to amyloid-β (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 subtype) agonists such as bethanechol chloride (DUVOID, URECHOLINE);

(xxvi) neuroprotective drugs such as 2,3,4,9-tetrahydro-1H-carbazol-3-one oxime;

(xxvii) nicotinic receptor agonists such as epibatidine;

(xxviii) norepinephrine (noradrenaline) reuptake inhibitors such as atomoxetine (STRATTERA);

(xxix) phosphodiesterase (PDE) inhibitors, for example, PDE9 inhibitors such as BAY 73-6691 (Bayer AG) and PDE 10 (e.g., PDE1A) inhibitors such as papaverine;
(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));
(xxxi) quinolines such as quinine (including its hydrochloride, dihydrochloride, sulfate, bisulfate and gluconate salts);
(xxxii) β-secretase inhibitors such as WY-25105;
(i) γ-secretase inhibitors such as LY-411575 (Lilly);
(xxxiv) serotonin (5-hydroxytryptamine) 1A (5-$HT_{1A}$) receptor antagonists such as spiperone;
(xxxv) serotonin (5-hydroxytryptamine) 4 (5-$HT_4$) receptor agonists such as PRX-03140 (Epix);
(xxxvi) serotonin (5-hydroxytryptamine) 6 (5-$HT_6$) receptor antagonists such as mianserin (TORVOL, BOLVIDON, NORVAL);
(xxxvii) serotonin (5-HT) reuptake inhibitors such as alaproclate, citalopram (CELEXA, CIPRAMIL);
(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;
(xxxix) antihemorrhagic (i.e., hemostatic) agents such as rivaroxaban or apixaban; and the like.

The compound of Formula I (including a salt thereof) is optionally used in combination with another active agent. Such an active agent may be, for example, an atypical antipsychotic or an anti-Parkinson's disease agent or an anti-Alzheimer's agent. Accordingly, another embodiment of the invention provides methods of treating a MAGL-mediated disease or disorder in a mammal, comprising administering to the mammal an effective amount of a compound of Formula I (including a pharmaceutically acceptable salt thereof) and further comprising administering another active agent.

As used herein, the term "another active agent" refers to any therapeutic agent, other than the compound of Formula I (including or a pharmaceutically acceptable salt thereof) that is useful for the treatment of a subject disorder. Examples of additional therapeutic agents include antidepressants, antipsychotics (such as anti-schizophrenia), anti-pain, anti-Parkinson's disease agents, anti-LID (levodopa-induced dyskinesia), anti-Alzheimer's, anti-anxiety, and antihemorrhagic agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (i), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical antidepressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NOR- PRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional "another active agent" examples include rivastigmine (Exelon), Clozapine, Levodopa, Rotigotine, Aricept, Methylphenidate, memantine. milnacipran, guanfacine, bupropion, and atomoxetine. Examples of antihemorrhagic agents (including, e.g., coagulation factors, activators, or stabilizers) include Factor Xa inhibitors (e.g., rivaroxaban or apixaban) and recombinant Coagulation Factor VIIa (e.g., NovoSeven®).

As noted above, the compounds of Formula I or salts thereof may be used in combination with one or more additional anti-Alzheimer's agents which are described herein. When a combination therapy is used, the one or more additional anti-Alzheimer's agents may be administered sequentially or simultaneously with the compound of the invention. In one embodiment, the additional anti-Alzheimer's agent(s) is(are) administered to a mammal (e.g., a human) prior to administration of the compound of the invention. In another embodiment, the additional anti-Alzheimer's agent(s) is(are) administered to the mammal after administration of the compound of the invention. In another embodiment, the additional anti-Alzheimer's agent(s) is(are) administered to the mammal (e.g., a human) simultaneously with the administration of the compound of the invention (or a pharmaceutically acceptable salt thereof).

The invention also provides a pharmaceutical composition for the treatment of an inflammatory disorder (e.g., neuroinflammation) in a mammal, including a human, which comprises an amount of a compound of Formula I (including a salt thereof), as defined above (including hydrates, solvates and polymorphs of said compound or pharmaceutically acceptable salts thereof), in combination with one or more (for example one to three) anti-inflammation agents, wherein the amounts of the active agent and the combination when taken as a whole are therapeutically effective for treating the inflammatory disorder.

The invention also provides a pharmaceutical composition for treating a MAGL-mediated disease or disorder in a mammal, including a human, which comprises an amount of a compound of Formula I (including a salt thereof), as defined above (including hydrates, solvates and polymorphs of said compound or a salt thereof), in combination with one or more (for example one to three) other agents for treating the MAGL-mediated disease or disorder, wherein the amount of the active agents and the combination when taken as a whole are therapeutically effective for treating the MAGL-mediated disease or disorder.

It will be understood that the compounds of Formula I depicted above are not limited to a particular stereoisomer (e.g., enantiomer or diastereoisomer) shown, but also include all stereoisomers and mixtures thereof.

DETAILED DESCRIPTION OF THE INVENTION

Compounds of the invention, including salts of the compounds, can be prepared using known organic synthesis techniques and can be synthesized according to any of numerous possible synthetic routes. The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^3$, $R^4$, $R^5$, $R^6$, $R^7$, r and structural Formula I (including I-a) in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1 refers to the synthesis of compounds of Formula I. Referring to Scheme 1, a compound of Formula 1-3 [wherein Pg$^1$ is an alcohol protecting group such as tert-butyldimethyl silyl (TBDMS) or p-methoxbenzyl] can be prepared by reacting an amine of Formula 1-1 with a compound of Formula 1-2 using standard methods of carbamate formation well known to those skilled in the art [for example, in the presence of phosgene, triphosgene, or a suitably activated carbonate reagent such as bis(pentafluorophenyl)carbonate or N,N'-disuccinimidyl carbonate]. Amines of Formula 1-1 may be obtained commercially, synthesized by methods described herein, or made by other methods well known to those skilled in the art. Carbamate formation may be accomplished in the presence of a base (such as triethylamine or hunigs base). A compound of Formula 1-4 may be obtained by deprotecting the compounds of Formula 1-3, using appropriate conditions depending on the selection of the Pg$^1$ group. For example, where Pg$^1$ is TBDMS, treatment with an acid such as trifluoroacetic acid in aprotic solvent such as dichloromethane may be employed. The compound of Formula 1-4 (which is a compound of Formula I wherein R$^7$ is H) may optionally be converted to a compound of Formula I wherein R$^7$ is other than H. For example, an alkylation reaction of the compound of Formula 1-4 with a halide compound (alkyl halide or cycloalkyl halide) can provide a compound of Formula I wherein $R^7$ is $C_{1-6}$ alkyl, $C_{3-7}$ cycloalkyl. As another example, reaction of the alcohol of Formula 1-4 with diphosphoryl tetrachloride in a suitable solvent such as acetonitrile affords compounds of Formula I where $R^7$ is —P(=O)(OH)$_2$ or a salt thereof. For yet another example, reaction of the alcohol of Formula 1-4 with a sulfating agent [e.g. SO$_3$, sulfamic acid H$_2$N—S(=O)$_2$(OH), chlorosulfonic acid HO—S(=O)$_2$(Cl)] under suitable conditions can afford a compound of Formula I wherein $R^7$ is —S(=O)$_2$(OH) or a salt thereof.

Scheme 3 refers to the preparation of compounds of Formula 3-4 [wherein $Pg^1$ is an alcohol protecting group such TBDMS or p-methoxbenzyl], which can be used as a compound of Formula 1-2 in Scheme 1 [wherein r is 1; and both $R^5$ and $R^6$ are H]. Referring to Scheme 3, a compound of Formula 3-3 may be prepared by treatment of compound 3-1 with a base (such as n-butyllithium) followed by addition to formaldehyde 3-2 (or its equivalent such as para-

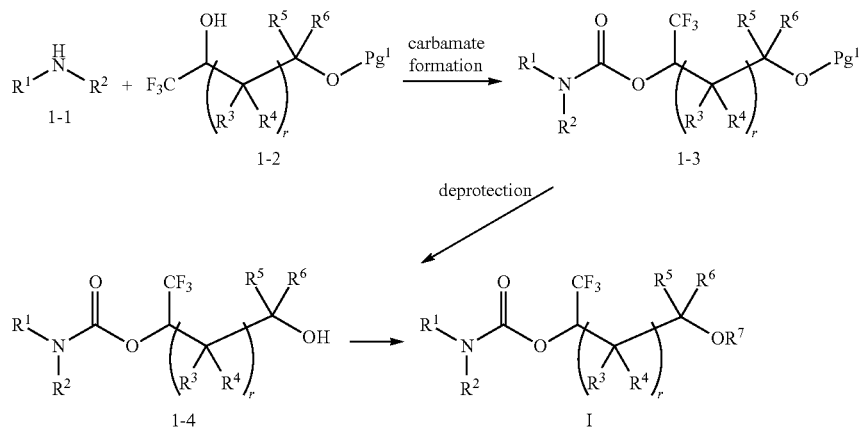

Scheme 1 formaldehyde) in the presence of a reducing agent such as sodium borohydride. Protection of the alcohol moiety in the compound of Formula 3-3 may be achieved by methods known to those skilled in the art. For example, where the $Pg^1$ is TBDMS, the protection can be achieved by treatment of the compound of Formula 3-3 with an activated silyl reagent [such as tert-butyl(dimethyl)silyl chloride] in the presence of a base (such as 1H-imidazole) in a suitable non-protic solvent (such as THF or DMF) at a suitable temperature (e.g., ambient temperature).

Scheme 2 refers to synthesis of compounds of Formula I-a. An amine of Formula 1-1 may be reacted with a compound of Formula 2-2 [where $Pg^1$ is a suitable alcohol protecting group, such as TBDMS or p-methoxybenzyl], using methods analogous to those described in Scheme 1, to form a carbamate of Formula 2-3. The compound of Formula 2-3 may be deprotected using appropriate conditions depending of the selection of $Pg^1$ to give a compound of Formula 2-4. Similar to the discussions in Scheme 1, the compound of Formula 2-4 (which is a compound of Formula I-a wherein $R^7$ is H) may optionally be converted to a compound of Formula I-a wherein $R^7$ is other than H.

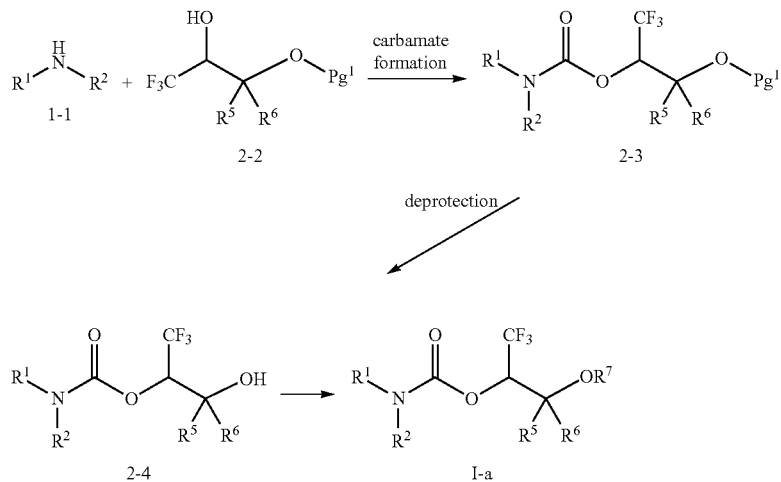

Scheme 2

Scheme 3

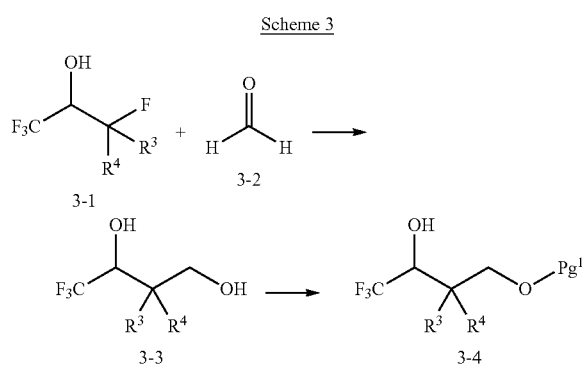

Scheme 4 refers to a synthesis of compounds of Formula 4-3 [wherein $Pg^2$ is an alcohol protecting group such p-methoxbenzyl], which can be used as a compound of Formula 1-2 in Scheme 1 [wherein r is 0]. Referring to Scheme 4, reaction of an epoxide of Formula 4-1 with an alcohol of Formula 4-2, in the presence of a base [e.g., $NaN(TMS)_2$] in a in non-protic solvent (e.g., THF or DMF), affords a compound of Formula 4-3.

Scheme 4

Scheme 4A refers to a synthesis of a compound of Formula 4A-5 or a salt thereof [i.e., a compound of Formula I-a or salt thereof, wherein $R^7$ is —P(=O)(OH)$_2$]. Referring to Scheme 4A, reaction of an epoxide of Formula 4A-1 with a phosphorus compound of Formula 4A-2 [wherein each of $Pg^{2A}$ is a hydroxyl protecting group such as benzyl], optionally in the presence of a base [e.g., $NaN(TMS)_2$] in a in non-protic solvent (e.g., THF or DMF), affords a compound of Formula 4A-3. Similar to the carbamate formation reaction described in Schemes 1 and 2, reaction of the compound of Formula 4A-3 and an amine of Formula 1-1 affords a compound of Formula 4A-4. Depending on the choice of the $Pg^{2A}$ groups, removal of the protecting $Pg^{2A}$ groups under suitable conditions will afford a compound of Formula 4A-5 or a salt thereof.

Scheme 4A

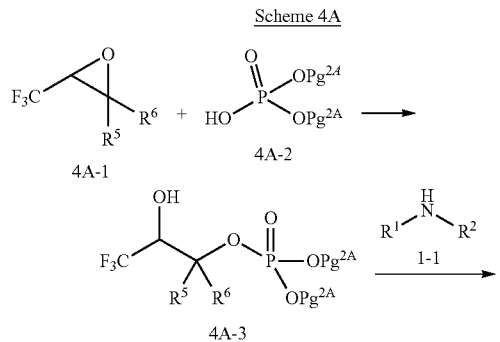

-continued 4A-4

4A-5

Scheme 5 refers to the preparation of amines of Formula 5-8 (wherein $R^{31}$ is aryl or heteroaryl that are optionally substituted), which can be used as a specific type of amine of Formula 1-1 for the preparation of compounds of Formula I or I-a in Schemes 1 and 2. The Weinreb amide of Formula 5-2 [where $Pg^3$ is an amine protecting group such as tert-butoxycarbonyl (BOC)] can be prepared by coupling N-methoxymethanamine with a carboxylic acid of Formula 5-1 using a suitable coupling agent [e.g., O-(7-azabenzotriazol-1-yl)-N,N,N',N'-tetramethyluronium hexafluorophosphate (HATU)]. Addition of a Grignard reagent (e.g., methylmagnesium bromide) to the Weinreb amide of Formula 5-2 results in a ketone of Formula 5-3. Treatment of the ketone of Formula 5-3 with N,N-dimethylformamide dimethyl acetal at elevated temperatures results in an enamine of Formula 5-4. Subsequent treatment with hydrazine (or its equivalent) in a protic solvent such as ethanol affords a pyrazole of Formula 5-5. A compound of Formula 5-7 can be obtained by reacting the pyrazole of Formula 5-5 with a (hetero)aryl boronic acid of Formula 5-6 in the presence of a catalyst (such as copper acetate) and a base (e.g., pyridine) in a suitable solvent (such as dichloromethane). Alternatively, the pyrazole of Formula 5-5 can be transformed into the compound of Formula 5-7 by palladium-catalyzed coupling with a suitable (hetero)aryl halide of Formula 5-9 wherein X is a suitable halide such are Cl, Br or I. Coupling can be achieved by reaction of the pyrazole of Formula 5-5 and (hetero)aryl halide of Formula 5-9 in the presence of a palladium catalyst such as [1,1'-bis(diphenylphosphino)ferrocene]dichloropalladium(II) [Pd(dppf)Cl$_2$] together with a base such as potassium acetate at an elevated temperature in a non-protic solvent such as toluene. A compound of Formula 5-8 can be prepared by removal of the protecting group $Pg^3$. For example, wherein the $Pg^3$ is tert-butoxycarbonyl (BOC), cleavage can be achieved under acidic conditions by treatment with, for example, trifluoroacetic acid.

Scheme 5

5-1

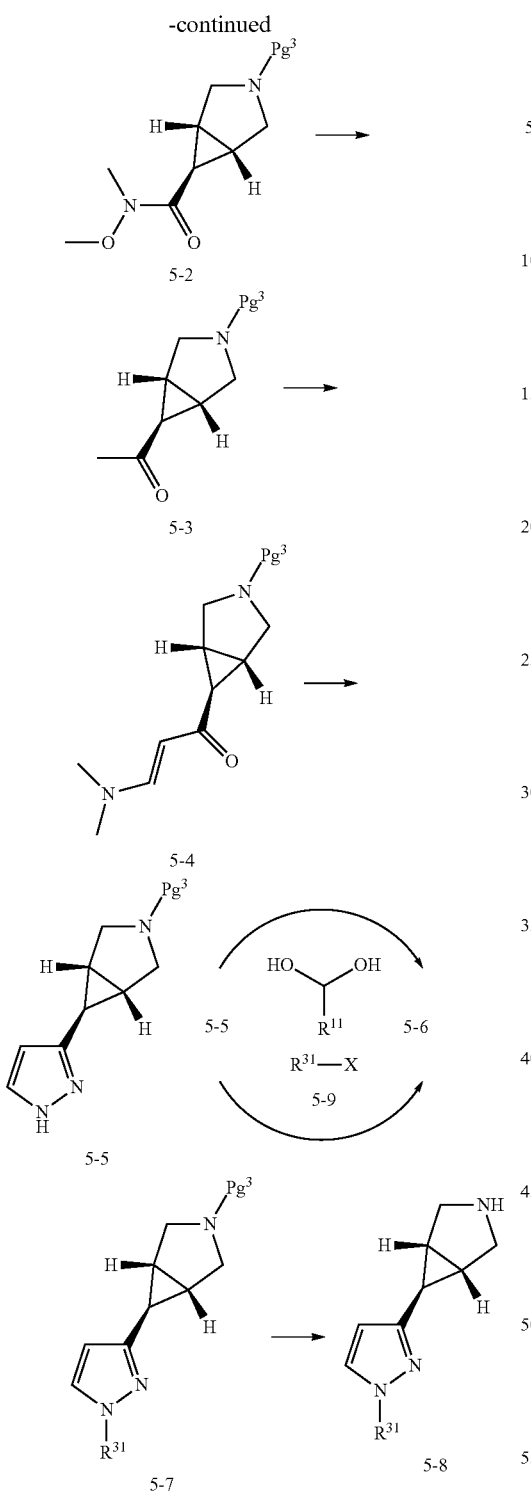

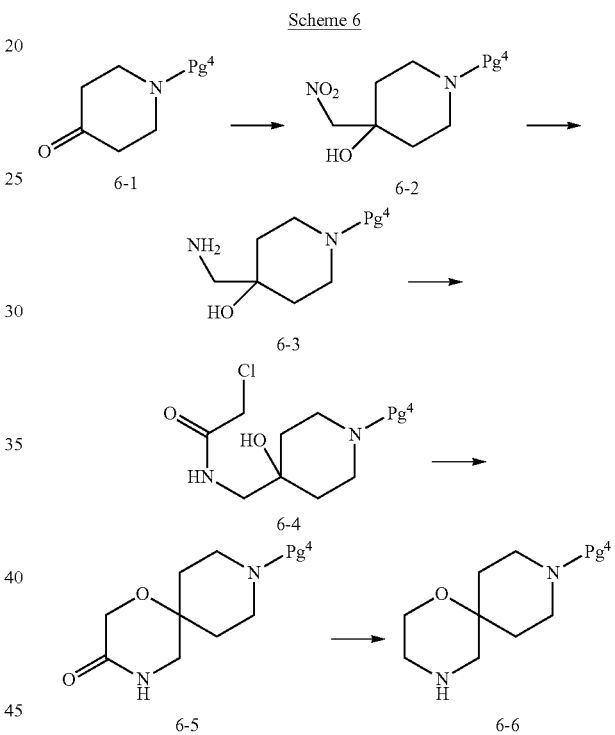

Formula 6-3 can be achieved by using methods such as palladium-catalyzed hydrogenation, for example utilizing 10% palladium on carbon in an alcoholic solvent under an atmosphere of hydrogen. Acetylation of the compound of Formula 6-3 can be achieved by treatment with chloroacetyl chloride in the presence of a suitable base such as potassium carbonate. Ring closure of the chloride compound of Formula 6-4 can be achieved by treatment with a suitable base (e.g., potassium tert-butoxide) in a non-protic solvent (e.g., THF) under reflux conditions to furnish a compound of Formula 6-5. A spiromorpholine compound of Formula 6-6 may be obtained by reduction of the amide functionality in the compound of Formula 6-5 using a suitable reducing agent (e.g. borane-dimethyl sulfide complex in THF).

Scheme 6 refers to a synthesis of a spiromorpholine of Formula 6-6 (wherein $Pg^4$ is a suitable amine protecting group such as BOC), which can be used as a starting material in Scheme 7. Referring to Scheme 6, reaction of a suitably protected piperidine of Formula 6-1 with nitromethane in the presence of a mild base such as triethylamine affords a compound of Formula 6-2. Reduction of the nitro moiety of the compound of Formula 6-2 to obtain an aminoalcohol of Scheme 7 refers to the synthesis of compounds of Formula 7-4, 7-7, 7-10, or 7-13 from an amine of Formula 6-6. A compound of Formula 7-3 [wherein $R^{70}$ can be, for example, $R^{11}$, $R^{12}$, $R^{13}$, or $R^{14}$] can be prepared by reacting the amine of Formula 6-6 with an aldehyde of Formula 7-2 using reductive amination conditions well known to those skilled in the art. For example, treatment with titanium(IV) isopropoxide and a reducing agent such as sodium borohydride can be employed. Reaction of an amine of Formula 6-6 with sulfonyl chlorides of Formula 7-5 [wherein $R^{70}$ can be, for example, $R^{11}$, $R^{12}$, $R^{13}$, or $R^{14}$] in the presence of a suitable base (such as pyridine or sodium bicarbonate) results in a sulfonamide of Formula 7-6. An amine 6-6 can be treated with a suitably activated compound of Formula 7-8 (wherein $Lg^1$ is a leaving group such as Cl) to give a compound of Formula 7-9 [wherein $R^{71}$ can be, for example, $R^{23}$; and $R^{72}$ can be, for example, $R^{11}$, $R^{12}$, $R^{13}$, $R^{14}$, —$(CR^{21}R^{22})_p$—$R^{11}$, —$(CR^{21}R^{22})_p$—$R^{12}$, —$(CR^{21}R^{22})_p$—

$R^{13}$, or —$(CR^{21}R^{22})_p$—$R^{14}$; or $R^{71}$ and $R^{72}$, together with the N atom to which they are attached, form 4- to 14-membered heterocycloalkyl optionally substituted with $R^8$ and one or more independently selected $R^9$]. A compound of Formula 7-12 [wherein $R^{73}$ can be, for example, $R^{11}$ or $R^{12}$] can be prepared by metal-catalyzed coupling of compounds of Formula 6-6 with a compound of Formula 7-11 (wherein X is a halogen atom such as Cl or Br). A compound of Formula 7-3, 7-6, 7-9, or 7-12 can be converted to a compound of Formula 7-4, 7-7, 7-10, or 7-13, respectively, by appropriate deprotection. For example, when $Pg^4$ is BOC, the deprotection can be achieved by treatment with an acid such as trifluoroacetic acid. A compound of Formula 7-4, 7-7, 7-10, or 7-13 can each be used as starting material [as a specific amine of Formula 1-1] for synthesis of compounds of Formula I (e.g., Formula I-a or I-b) as described in Schemes 1 and 2.

Scheme 8 refers to a synthesis of compounds of Formula 8-6 [where each t2a is independently 0 or 1; and $R^{8,4}$ can be, for example, $R^{11}$, $R^{12}$, $R^{13}$, or $R^{14}$]. A compound of Formula 8-3 can be prepared by treatment of the aminoalcohol of Formula 8-1 (which can be prepared using the method as described in Scheme 6 for the aminoalcohol of Formula 6-3) with a sulfonyl chloride of Formula 8-2 in the presence of a suitable base (e.g., pyridine). Reaction of the compound of Formula 8-3 with a compound of Formula 8-4 (wherein each X is independently a suitable leaving group such as Br or Cl), in the presence of a base such as potassium carbonate in a polar aprotic solvent such as DMF, results in a compound of Formula 8-5. Removal of the protecting group results in a compound of Formula 8-6, which can be used as starting material [as a specific amine of Formula 1-1] in Schemes 1 and 2 for the preparation of compounds of Formula I (including compounds of Formula I-a or I-b).

Scheme 7

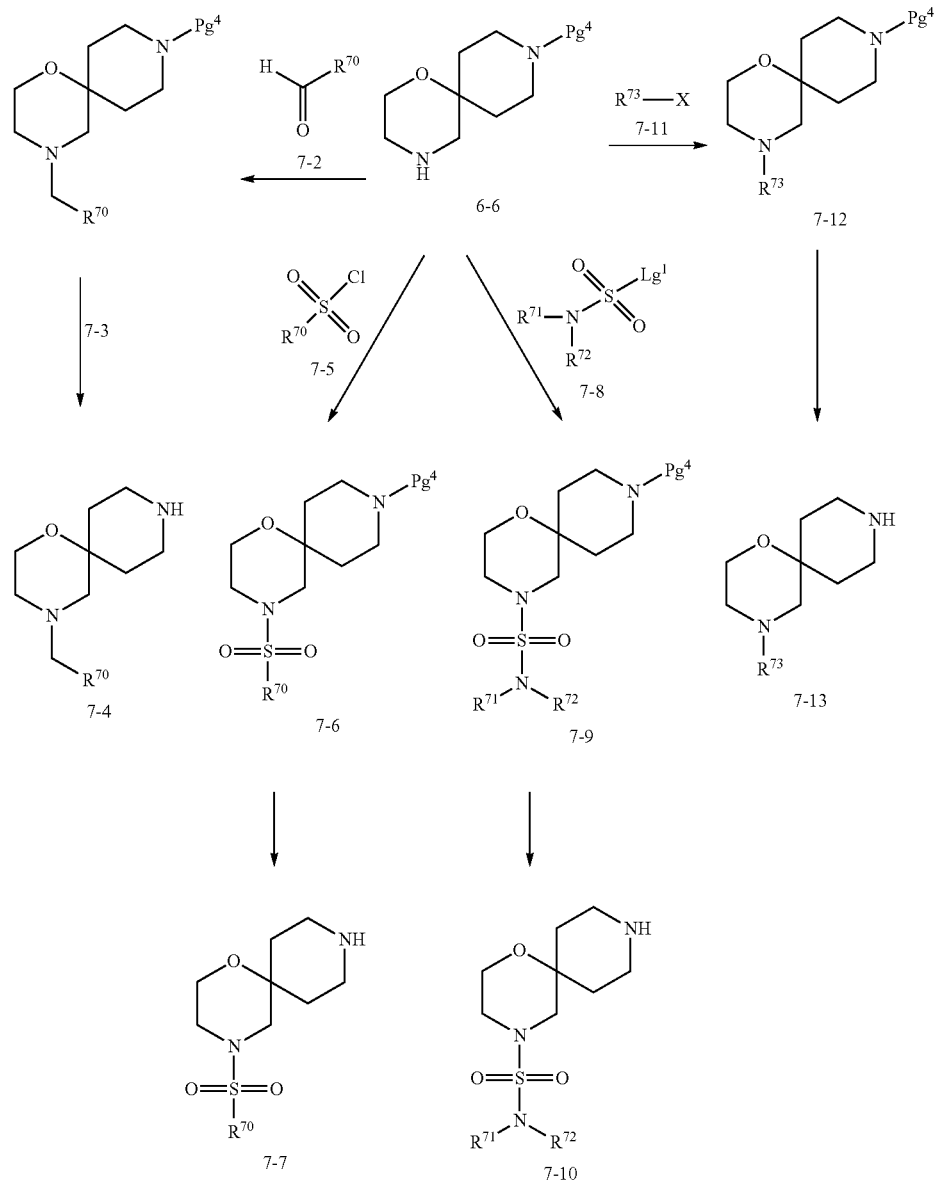

Scheme 8

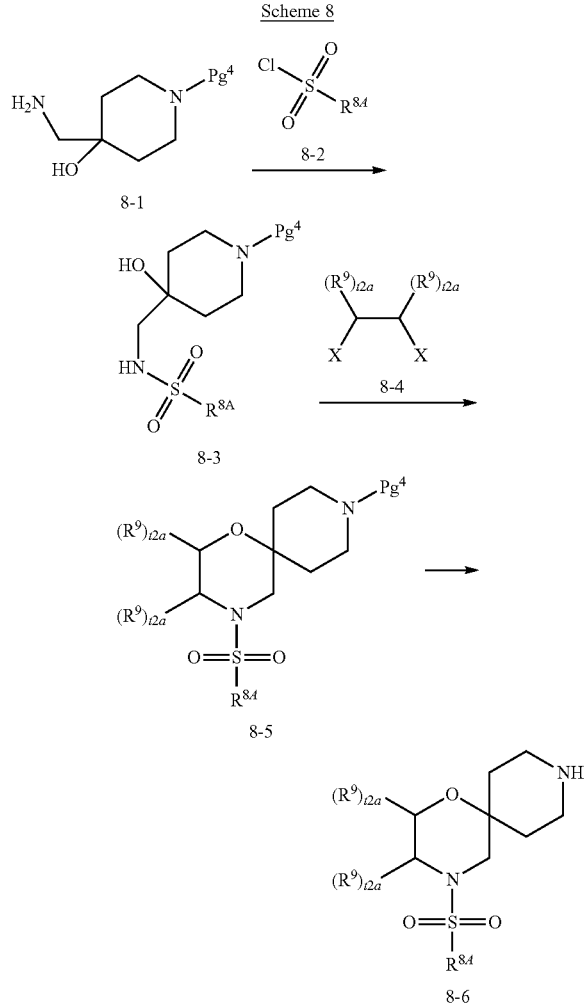

Scheme 9 refers to a preparation of compounds of Formula 9-3 [where $R^{8A}$ can be, for example, $R^{11}$, $R^{12}$, $R^{13}$, or $R^{14}$]. A compound of formula 9-1 [where $Pg^4$ is an amine protecting group (e.g., BOC)] can be obtained commercially or be readily synthesized by methods well known to those skilled in the art. A compound of Formula 9-2 can be obtained by reaction of a compound of Formula 9-1 with sulfonyl chlorides of Formula 8-2 in a suitable solvent (e.g., dichloromethane) in the presence of a suitable base (e.g., sodium bicarbonate). Deprotection of compounds of Formula 9-2 using appropriate conditions well known to those skilled in the art provides a compound of Formula 9-3. The compound of Formula 9-3 can be used as starting material [as a specific amine of Formula 1-1] in Schemes 1 and 2 for the preparation of compounds of Formula I (including compounds of Formula I-a or I-b).

Scheme 9

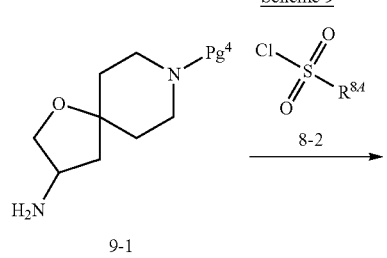

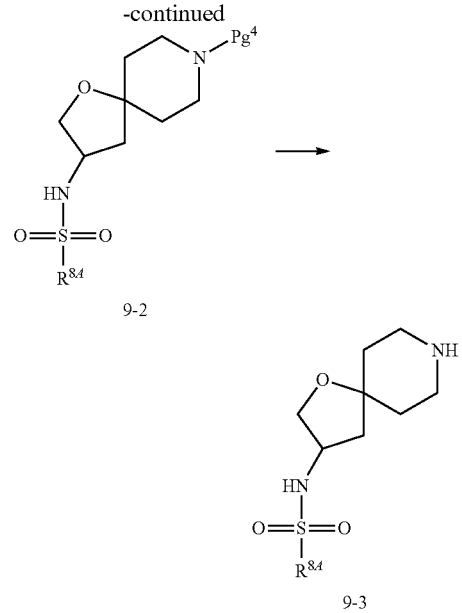

Additional starting materials and intermediates useful for making the compounds of the present invention can be obtained from chemical vendors such as Sigma-Aldrich or can be made according to methods described in the chemical art.

Those skilled in the art can recognize that in all of the schemes described herein, if there are functional (reactive) groups present on a part of the compound structure such as a substituent group, for example $R^1$, $R^2$, $R^3$, $R^4$, $R^5$, $R^6$, $R^7$, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion ($CN^-$). For another example, an —S— can be oxidized to —S($=$O)— and/or —S($=$O)$_2$—. For yet another example, an unsaturated bond such as C$=$C or C$\equiv$C can be reduced to a saturated bond by hydrogenation. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^1$, $R^2$, $R^3$, $R^4$, $R^5$, $R^6$, $R^7$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Cbz) or BOC group; conversion back to the $NH_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., Stereochemistry of Organic Compounds by E. L. Eliel and S. H. Wilen (Wiley, New York, 1994), the disclosure of which is incorporated herein by reference in its entirety. Suitable stereoselective techniques are well known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula I-a or I-b) may be prepared by, e.g., one or more of three methods:
(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention (including pharmaceutically acceptable salts thereof) may be administered orally. Oral administration may involve swallowing, so that the compound enters the gastrointestinal tract, and/or buccal, lingual, or sublingual administration by which the compound enters the bloodstream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast-dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxides thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (including pharmaceutically acceptable salts thereof) may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methyl cellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 μL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 μg to 200 mg, which may be administered in a single dose or, more usually, as divided doses throughout the day.

The compounds of the invention (including pharmaceutically acceptable salts thereof) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof, or a salt of such compound or prodrug; and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen on which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "µmol" means micromoles, "eq." means equivalent, "° C." means degrees Celsius, "MHz" means megahertz, "HPLC" means high-performance liquid chromatography.

EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers or diastereomers of certain compounds of the invention (in some examples, the separated enantiomers are designated as ENT-1 and ENT-2, or the separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate R$_f$s or retention times.

For clarity purposes, the stereochemistry of the substituents on the 3-azabicyclo[3.1.0]hexyl skeleton in Examples and intermediates herein is indicated by using Chemical Abstracts nomenclature. The stereochemistry of the other compounds in the Examples and intermediates herein is indicated by using IUPAC nomenclature.

ABBREVIATIONS

BOC—tert-butoxycarbonyl

HPLC—high-performance liquid chromatography

NADP—nicotinamide adenine dinucleotide phosphate

PMB—para-methoxybenzyl (or 4-methoxybenzyl)

p-TsOH—para-toluenesulfonic acid, 4-methylbenzenesulfonic acid psi—pounds per square inch

Example 1

(2R)-1,1,1-Trifluoro-3-hydroxypropan-2-yl (1α,5α, 6α)-6-[1-(5-methoxypyridin-2-yl)-1H-pyrazol-3-yl]-3-azabicyclo[3.1.0]hexane-3-carboxylate (1)

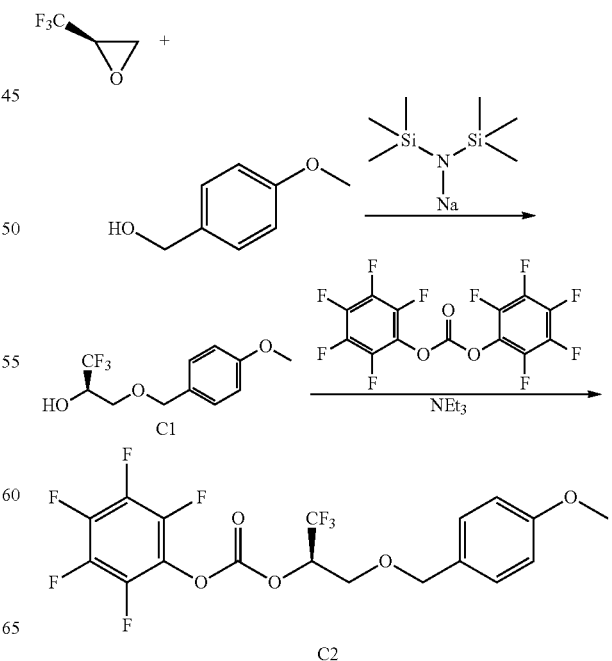

71
-continued
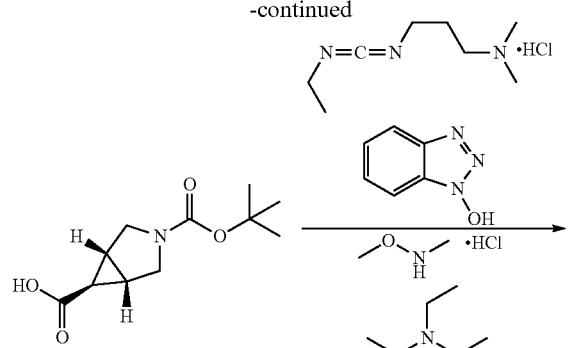
C3
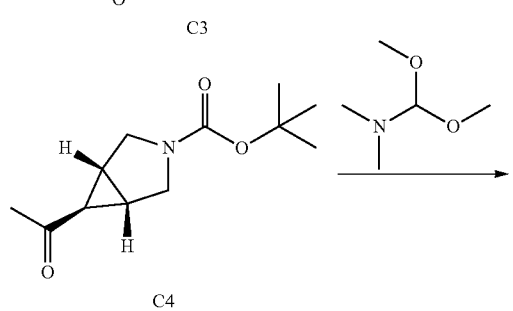
C4
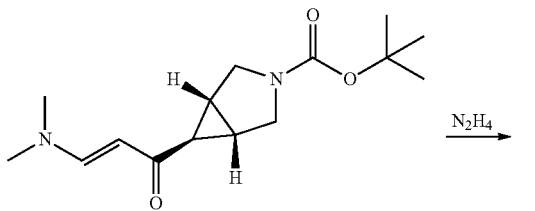
C5
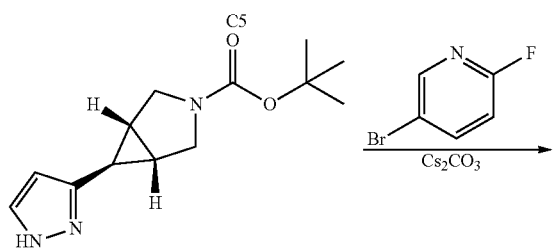
C6
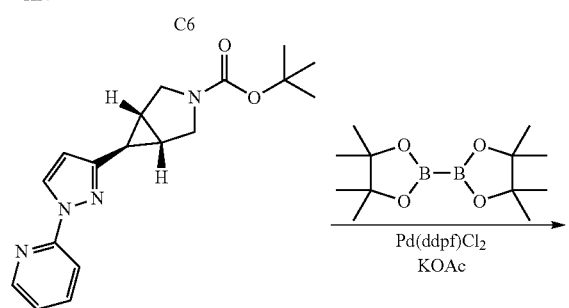
C7
72
-continued
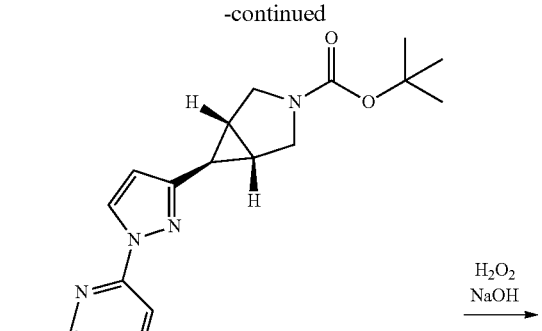
C8
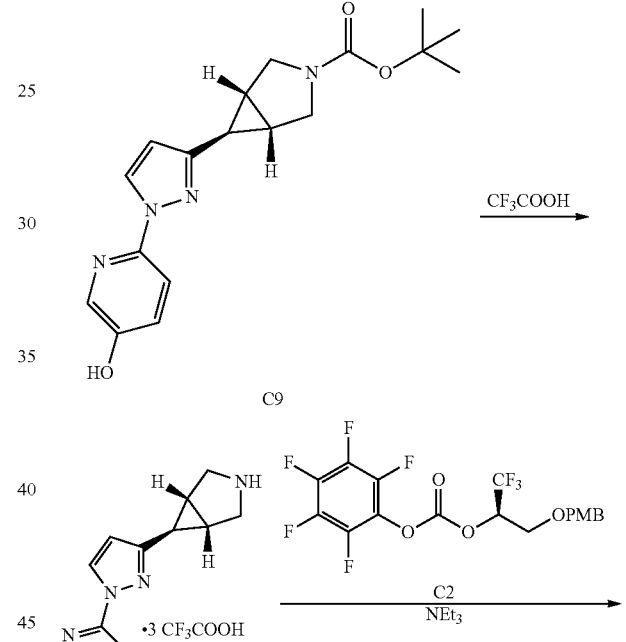
C9
C10
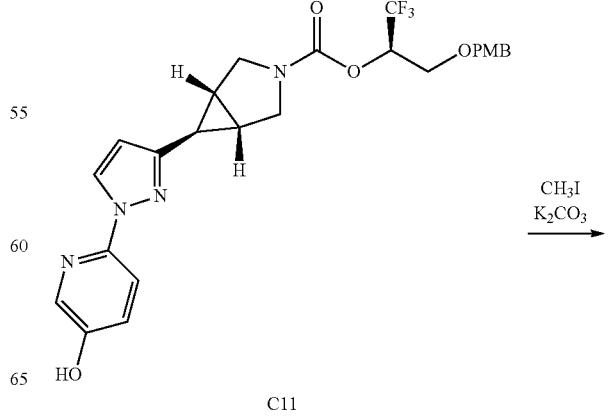
C11

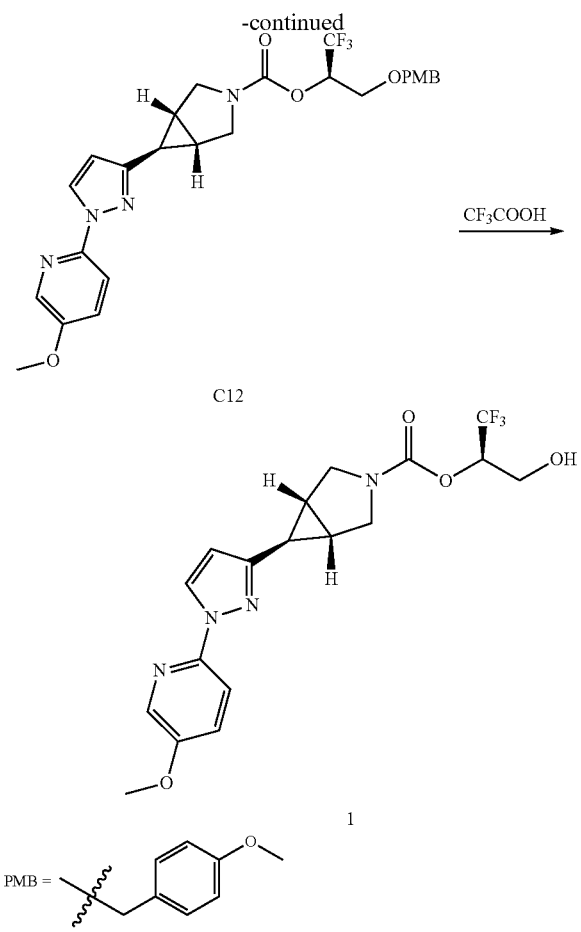

Step 1. Synthesis of (2R)-1,1,1-trifluoro-3-[(4-methoxybenzyl)oxy]propan-2-ol (C1)

(4-Methoxyphenyl)methanol (98%, 1.14 mL, 8.96 mmol) was slowly added to a 0° C. solution of sodium bis(trimethylsilyl)amide in tetrahydrofuran (1.0 M, 8.9 mL, 8.9 mmol) in a microwave vial. After the reaction mixture had stirred at 0° C. for 45 minutes, (2R)-2-(trifluoromethyl) oxirane (500 mg, 4.46 mmol) in tetrahydrofuran (2 mL) was added via syringe, and the vial was sealed and heated at 100° C. for 18 hours. The reaction mixture was then cooled to room temperature and diluted with water; the mixture was extracted twice with tert-butyl methyl ether and the combined organic layers were washed with saturated aqueous sodium chloride solution, dried over sodium sulfate, filtered, and concentrated in vacuo. Purification via chromatography on silica gel (Gradient: 0% to 60% ethyl acetate in heptane) afforded the product as a pale yellow oil. Yield: 1.09 g, 4.36 mmol, 98%. GCMS m/z 250.1 [M]. $^1$H NMR (400 MHz, DMSO-$d_6$) δ 7.26 (d, J=8.5 Hz, 2H), 6.91 (d, J=8.5 Hz, 2H), 6.36 (d, J=6.7 Hz, 1H), 4.46 (s, 2H), 4.21-4.09 (m, 1H), 3.74 (s, 3H), 3.58 (dd, half of ABX pattern, J=10.6, 4.5 Hz, 1H), 3.48 (dd, half of ABX pattern, J=10.5, 6.3 Hz, 1H).

Step 2. Synthesis of pentafluorophenyl (2R)-1,1,1-trifluoro-3-[(4-methoxybenzyl)oxy]propan-2-yl carbonate (C2)

Bis(pentafluorophenyl) carbonate (1.33 g, 3.37 mmol) was added to a 0° C. solution of C1 (929 mg, 3.71 mmol) in acetonitrile (30 mL). Triethylamine (1.71 g, 16.9 mmol) was added in a drop-wise manner, and the reaction was warmed to 25° C. and stirred for 2 hours. The resulting solution of C2 was used directly in Step 11. For subsequent syntheses described herein that utilize C2, this material was generated at the appropriate scale, and the reaction solution of C2 was used directly in the coupling reaction.

Step 3. Synthesis of tert-butyl (1α,5α,6α)-6-[methoxy(methyl)carbamoyl]-3-azabicyclo[3.1.0]hexane-3-carboxylate (C3)

1-[3-(Dimethylamino)propyl]-3-ethylcarbodiimide hydrochloride (10.1 g, 52.7 mmol) and 1H-benzotriazol-1-ol (7.13 g, 52.8 mmol) were added to a 0° C. solution of (1α,5α,6α)-3-(tert-butoxycarbonyl)-3-azabicyclo[3.1.0]hexane-6-carboxylic acid (8.00 g, 35 mmol) in dichloromethane (80 mL), and the reaction mixture was stirred at 0° C. for 30 minutes. A solution of N-methoxymethanamine hydrochloride (6.87 g, 70.4 mmol) and N,N-diisopropylethylamine (13.6 g, 105 mmol) in dichloromethane (50 mL) was then added drop-wise over a period of 10 minutes, and the reaction mixture was stirred at room temperature (25° C.) for 2 hours. After addition of water (100 mL), the mixture was extracted with dichloromethane (3×100 mL), and the combined organic layers were washed with water (50 mL) and with saturated aqueous sodium chloride solution (50 mL), dried over sodium sulfate, filtered, and concentrated in vacuo to provide the product as a light yellow oil. Yield: 9.46 g, 35.0 mmol, 100%. $^1$H NMR (400 MHz, CDCl$_3$) δ 3.72 (s, 3H), 3.64 (d, half of AB quartet, J=11.2 Hz, 1H), 3.55 (d, half of AB quartet, J=11.0 Hz, 1H), 3.49-3.39 (m, 2H), 3.18 (s, 3H), 2.11-1.99 (m, 2H), 1.99-1.91 (br s, 1H), 1.43 (s, 9H).

Step 4. Synthesis of tert-butyl (1α,5α,6α)-6-acetyl-3-azabicyclo[3.1.0]hexane-3-carboxylate (C4)

Methylmagnesium bromide (3.0 M solution in tetrahydrofuran; 23.3 mL, 69.9 mmol) was added in a drop-wise manner to a 0° C. solution of C3 (9.46 g, 35.0 mmol) in tetrahydrofuran (100 mL). The reaction mixture was stirred at room temperature (25° C.) for 1 hour, whereupon it was quenched with saturated aqueous ammonium chloride solution (200 mL) and extracted with ethyl acetate (3×100 mL). The combined organic layers were washed sequentially with water (100 mL) and with saturated aqueous sodium chloride solution (100 mL), dried over sodium sulfate, filtered, and concentrated in vacuo to provide the product as a red solid. Yield: 7.82 g, 34.7 mmol, 99%. $^1$H NMR (400 MHz, CDCl$_3$) δ 3.62 (d, half of AB quartet, J=11.3 Hz, 1H), 3.53 (d, half of AB quartet, J=11.3 Hz, 1H), 3.41-3.32 (m, 2H), 2.21 (s, 3H), 2.05-2.01 (m, 2H), 1.77 (dd, J=3.0, 2.9 Hz, 1H), 1.39 (s, 9H).

Step 5. Synthesis of tert-butyl (1α,5α,6α)-6-[(2E)-3-(dimethylamino)prop-2-enoyl]-3-azabicyclo[3.1.0]hexane-3-carboxylate (C5)

To a solution of C4 (7.82 g, 34.7 mmol) in N,N-dimethylformamide (50 mL) was added N,N-dimethylformamide dimethyl acetal (12.4 g, 104 mmol), and the reaction mixture was stirred at 110° C. for 16 hours. It was then cooled, treated with water (100 mL), and extracted with ethyl acetate (3×100 mL). The combined organic layers were washed sequentially with water (3×100 mL) and with saturated aqueous sodium chloride solution (90 mL), dried over sodium sulfate, filtered, and concentrated under reduced pressure to afford the product as a red solid. Yield: 9.20 g, 32.8 mmol, 94%. $^1$H NMR (400 MHz, CDCl$_3$) δ 7.51 (d, J=12.7 Hz, 1H), 5.13 (d, J=12.7 Hz, 1H), 3.63 (d, half of AB quartet, J=11.2 Hz, 1H), 3.54 (d, half of AB quartet, J=11.0 Hz, 1H), 3.44-3.36 (m, 2H), 3.15-2.93 (br s, 3H), 2.93-2.70 (br s, 3H), 2.10-1.97 (m, 2H), 1.60 (dd, J=2.9, 2.9 Hz, 1H), 1.42 (s, 9H).

Step 6. Synthesis of tert-butyl (1α,5α,6α)-6-(1H-pyrazol-3-yl)-3-azabicyclo[3.1.0]hexane-3-carboxylate (C6)

Hydrazine hydrate (1.97 g, 39.4 mmol) was added to a solution of C5 (9.20 g, 32.8 mmol) in ethanol (100 mL), and the reaction mixture was stirred at 80° C. for 16 hours. After concentration in vacuo, the residue was purified by chromatography on silica gel (Eluents: 9%, then 17%, then 50% ethyl acetate in diethyl ether) to afford the product as a white solid. Yield: 7.00 g, 28.1 mmol, 86%. LCMS m/z 193.8 [(M−2-methylprop-1-ene)+H]$^+$. $^1$H NMR (400 MHz, CDCl$_3$) δ 7.47 (d, J=2.0 Hz, 1H), 6.01 (br d, J=1.8 Hz, 1H), 3.78 (d, J=10.9 Hz, 1H), 3.69 (d, J=11.0 Hz, 1H), 3.51-3.41 (m, 2H), 1.90-1.83 (m, 2H), 1.80 (dd, J=3.4, 3.4 Hz, 1H), 1.46 (s, 9H).

Step 7. Synthesis of tert-butyl (1α,5α,6α)-6-[1-(5-bromopyridin-2-yl)-1H-pyrazol-3-yl]-3-azabicyclo[3.1.0]hexane-3-carboxylate (C7)

A mixture of C6 (500 mg, 2.01 mmol), 5-bromo-2-fluoropyridine (529 mg, 3.01 mmol) and cesium carbonate (1.96 g, 6.02 mmol) in N,N-dimethylformamide (20 mL) was stirred in a microwave reactor at 160° C. for 1 hour. The reaction mixture was then combined with two similar reactions carried out on C6 (500 mg, 2.01 mmol, and 350 mg, 1.40 mmol), diluted with water (100 mL), and extracted with ethyl acetate (3×50 mL); the combined organic layers were dried over sodium sulfate, filtered, and concentrated in vacuo. Purification via silica gel chromatography (Gradient: 0% to 20% ethyl acetate in petroleum ether) afforded the product as a white solid. Yield: 1.25 g, 3.08 mmol, 57%. $^1$H NMR (400 MHz, CDCl$_3$) δ 8.41 (dd, J=2.4, 0.6 Hz, 1H), 8.37 (d, J=2.6 Hz, 1H), 7.87 (dd, half of ABX pattern, J=8.7, 2.3 Hz, 1H), 7.80 (dd, half of ABX pattern, J=8.7, 0.7 Hz, 1H), 6.16 (d, J=2.6 Hz, 1H), 3.80 (d, J=11.0 Hz, 1H), 3.72 (d, J=11.0 Hz, 1H), 3.52-3.42 (m, 2H), 1.99-1.91 (m, 2H), 1.85 (dd, J=3.5, 3.4 Hz, 1H), 1.47 (s, 9H).

Step 8. Synthesis of tert-butyl (1α,5α,6α)-6-{1-[5-(4, 4, 5, 5-tetramethyl-1,3, 2-dioxaborolan-2-yl)pyridin-2-yl]-1H-pyrazol-3-yl}-3-azabicyclo[3.1.0]hexane-3-carboxylate (C8)

To a suspension of C7 (1.00 g, 2.47 mmol) in toluene (20 mL) were added 4,4,4',4',5,5,5',5'-octamethyl-2,2'-bi-1,3,2-dioxaborolane (940 mg, 3.70 mmol), [1,1'-bis(diphenylphosphino)ferrocene]dichloropalladium(II) (181 mg, 0.247 mmol), and potassium acetate (726 mg, 7.40 mmol), and the mixture was degassed with nitrogen for 5 minutes. The reaction mixture was stirred for 18 hours at 120° C., whereupon it was concentrated in vacuo and purified by chromatography on silica gel (Gradient: 0% to 20% ethyl acetate in petroleum ether) to afford the product as a white solid. Yield: 1.02 g, 2.25 mmol, 91%. LCMS m/z 453.3 [M+H]$^+$. $^1$H NMR (400 MHz, CDCl$_3$) δ 8.73-8.69 (m, 1H), 8.48 (d, J=2.5 Hz, 1H), 8.14 (dd, J=8.2, 1.8 Hz, 1H), 7.86 (br d, J=8.2 Hz, 1H), 6.16 (d, J=2.5 Hz, 1H), 3.81 (d, J=11 Hz, 1H), 3.73 (d, J=11 Hz, 1H), 3.53-3.42 (m, 2H), 2.01-1.93 (m, 2H), 1.87 (dd, J=3.3, 3.3 Hz, 1H), 1.47 (s, 9H), 1.37 (s, 12H).

Step 9. Synthesis of tert-butyl (1α,5α,6α)-6-[1-(5-hydroxypyridin-2-yl)-1H-pyrazol-3-yl]-3-azabicyclo[3.1.0]hexane-3-carboxylate (C9)

To a 0° C. mixture of C8 (1.02 g, 2.25 mmol) in tetrahydrofuran and water (1:1 mixture, 80 mL) was added aqueous sodium hydroxide solution (6 M, 1 mL, 6 mmol), followed by hydrogen peroxide (30% solution in water, 0.77 g, 6.8 mmol). The reaction mixture was allowed to warm to 25° C., and was stirred for 12 hours, whereupon it was quenched with aqueous sodium thiosulfate solution, acidified to pH 6 with aqueous hydrochloric acid, and extracted with dichloromethane (3×30 mL). The combined organic layers were concentrated under reduced pressure and purified via chromatography on silica gel (Gradient: 0% to 10% methanol in dichloromethane) to provide the product as a white solid. Yield: 742 mg, 2.17 mmol, 96%. LCMS m/z 343.1 [M+H]$^+$. $^1$H NMR (400 MHz, CD$_3$OD) δ 8.26 (d, J=2.6 Hz, 1H), 7.93 (dd, J=2.9, 0.5 Hz, 1H), 7.67 (dd, J=8.8, 0.5 Hz, 1H), 7.32 (dd, J=8.8, 2.9 Hz, 1H), 6.21 (d, J=2.5 Hz, 1H), 3.69 (d, J=10.9 Hz, 2H), 3.52-3.42 (m, 2H), 2.02-1.94 (m, 2H), 1.75 (dd, J=3.5, 3.4 Hz, 1H), 1.47 (s, 9H).

Step 10. Synthesis of 6-{3-[(1α,5α,6α)-3-azabicyclo[3.1.0]hex-6-yl]-1H-pyrazol-1-yl}pyridin-3-ol, tris(trifluoroacetic acid) salt (C10)

A solution of C9 (742 mg, 2.17 mmol) in dichloromethane (5 mL) was cooled in an ice bath, and then treated with trifluoroacetic acid (3 mL). The reaction mixture was stirred for 30 minutes at 25° C., whereupon it was concentrated in vacuo, affording the product (1.27 g) as a yellow gum. LCMS m/z 243.0 [M+H]$^+$.

Step 11. Synthesis of (2R)-1,1,1-trifluoro-3-[(4-methoxybenzyl)oxy]propan-2-yl (1α,5α,6α)-6-[1-(5-hydroxypyridin-2-yl)-1H-pyrazol-3-yl]-3-azabicyclo[3.1.0]hexane-3-carboxylate (C11)

Triethylamine (1.10 g, 10.9 mmol) was slowly added to a 0° C. solution of C10 (from the previous step, 1.27 g, ≤2.17 mmol) in acetonitrile (20 mL), whereupon the mixture was stirred for 1 hour. Compound C2 [from step 2, as the crude reaction mixture in acetonitrile (30 mL); ~1.6 g, 3.4 mmol] was added to the 0° C. reaction mixture, which was then stirred at 28° C. for 18 hours. It was then cooled in an ice-water bath and slowly treated with a second batch of C2 (~0.74 g, 1.6 mmol). After stirring for 18 hours at 25° C., the reaction mixture was concentrated in vacuo; the residue was purified via chromatography on silica gel (Gradient: 0% to 30% ethyl acetate in petroleum ether) to provide the product as a white solid. By $^1$H NMR analysis, this was judged to be a mixture of rotamers. Yield: 430 mg, 0.83 mmol, 38% over two steps. LCMS m/z 519.1 [M+H]$^+$. $^1$H NMR (400 MHz, CD$_3$OD) δ 8.29-8.25 (m, 1H), 7.93 (d, J=2.9 Hz, 1H), [7.69 (d, J=8.8 Hz) and 7.68 (d, J=8.9 Hz), total 1H], 7.32 (dd, J=8.8, 2.9 Hz, 1H), 7.29-7.23 (m, 2H), 6.95-6.88 (m, 2H), [6.24 (d, J=2.5 Hz) and 6.20 (d, J=2.5 Hz), total 1H], 5.53-5.40 (m, 1H), [4.56 (d, half of AB quartet, J=11.4 Hz) and 4.54 (d, half of AB quartet, J=11.5 Hz), total 1H], 4.46 (d, half of AB quartet, J=11.5 Hz, 1H), 3.84-3.68 (m, 4H),

[3.79 (s) and 3.73 (s), total 3H], 3.60-3.53 (m, 2H), 2.07-1.99 (m, 2H), [1.77 (dd, J=3.5, 3.4 Hz) and 1.74 (dd, J=3.5, 3.3 Hz), total 1H].

Step 12. Synthesis of (2R)-1,1,1-trifluoro-3-[(4-methoxybenzyl)oxy]propan-2-yl (1α,5α,6α)-6-[1-(5-methoxypyridin-2-yl)-1H-pyrazol-3-yl]-3-azabicyclo[3.1.0]hexane-3-carboxylate (C12)

To a 0° C. solution of C11 (90.0 mg, 0.174 mmol) in N,N-dimethylformamide (1 mL) were added potassium carbonate (36 mg, 0.26 mmol) and iodomethane (25.9 mg, 0.182 mmol). The reaction mixture was stirred at 28° C. for 2 hours, whereupon it was concentrated in vacuo and purified by silica gel chromatography (Gradient: 0% to 30% ethyl acetate in petroleum ether) to afford the product as a colorless gum. By $^1$H NMR analysis, this was judged to be a mixture of rotamers. Yield: 86 mg, 0.16 mmol, 92%. LCMS m/z 533.3 [M+H]$^+$. $^1$H NMR (400 MHz, CDCl$_3$) δ 8.33 (d, J=2.4 Hz, 1H), 8.05 (d, J=2.8 Hz, 1H), 7.82 (d, J=8.9 Hz, 1H), 7.32 (dd, J=9.0, 2.9 Hz, 1H), 7.30-7.23 (m, 2H), 6.94-6.86 (m, 2H), [6.14 (d, J=2.3 Hz) and 6.13 (d, J=2.4 Hz), total 1H], 5.54-5.43 (m, 1H), [4.57 (d, half of AB quartet, J=11.7 Hz) and 4.56 (d, half of AB quartet, J=11.7 Hz), total 1H], 4.48 (d, half of AB quartet, J=11.7 Hz, 1H), 3.92-3.65 (m, 4H), 3.87 (s, 3H), [3.81 (s) and 3.78 (s), total 3H], 3.64-3.53 (m, 2H), 2.06-1.97 (m, 2H), 1.89-1.82 (m, 1H).

Step 13. Synthesis of (2R)-1,1,1-trifluoro-3-hydroxypropan-2-yl (1α,5α,6α)-6-[1-(5-methoxypyridin-2-yl)-1H-pyrazol-3-yl]-3-azabicyclo[3.1.0]hexane-3-carboxylate (1)

Trifluoroacetic acid (1 mL) was slowly added to a 0° C. solution of C12 (114 mg, 0.214 mmol) in dichloromethane (2 mL). The reaction mixture was stirred at 26° C. for 30 minutes, whereupon it was cooled in an ice bath and slowly treated with saturated aqueous sodium bicarbonate solution (20 mL). The mixture was extracted with dichloromethane (3×20 mL), and the combined organic layers were dried over sodium sulfate, filtered, and concentrated in vacuo. Preparative thin layer chromatography on silica gel (Eluent: 1:1 petroleum ether: ethyl acetate) provided the product as a white solid. By $^1$H NMR analysis, this was judged to be a mixture of rotamers. Yield: 65 mg, 0.16 mmol, 75%. LCMS m/z 413.1 [M+H]$^+$. $^1$H NMR (400 MHz, CD$_3$OD) δ 8.32 (d, J=2.5 Hz, 1H), 8.07 (d, J=2.9 Hz, 1H), 7.80-7.76 (m, 1H), 7.51 (dd, J=9.0, 3.0 Hz, 1H), [6.26 (d, J=2.6 Hz) and 6.25 (d, J=2.8 Hz), total 1H], 5.34-5.24 (m, 1H), 3.94-3.74 (m, 4H), 3.90 (s, 3H), 3.70-3.57 (m, 2H), 2.11-2.02 (m, 2H), [1.86 (dd, J=3.6, 3.5 Hz) and 1.79 (dd, J=3.5, 3.4 Hz), total 1H].

Example 2

(2R)-1,1,1-Trifluoro-3-hydroxypropan-2-yl 4-[1-(4-fluorophenyl)-1H-pyrazol-3-yl]piperidine-1-carboxylate (2)

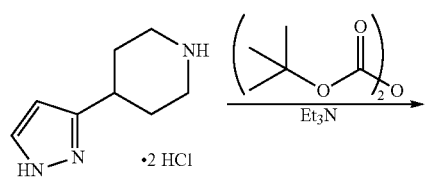

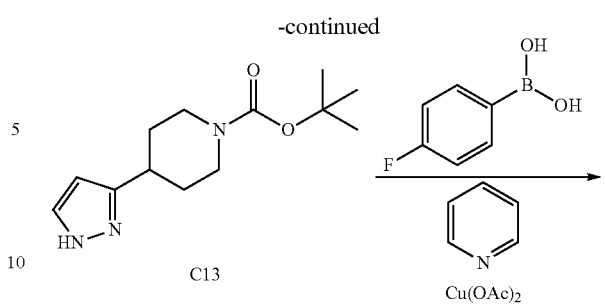

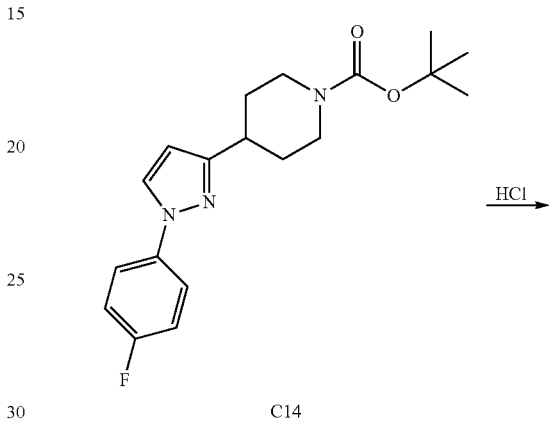

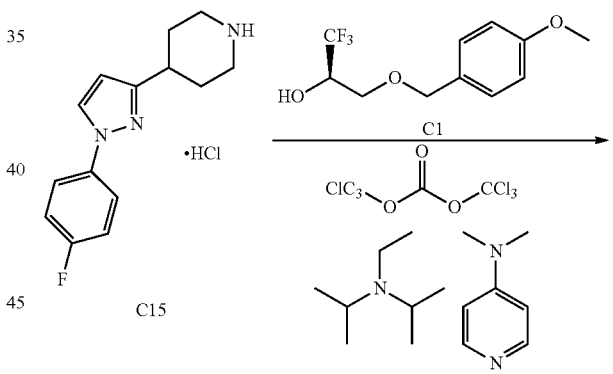

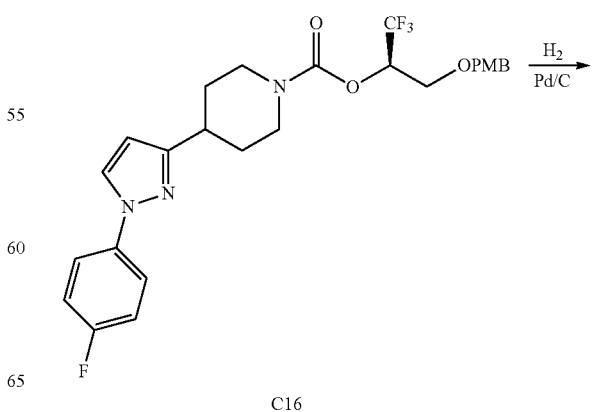

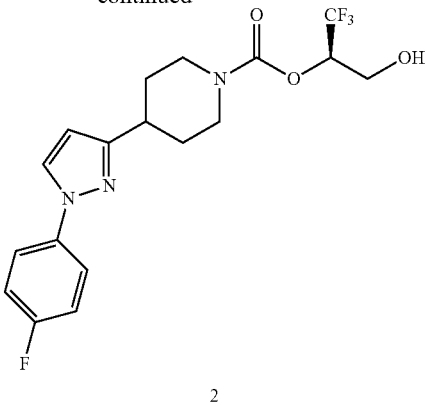

2

Step 1. Synthesis of tert-butyl 4-(1H-pyrazol-3-yl) piperidine-1-carboxylate (C13)

To a 0° C. mixture of 4-(1H-pyrazol-3-yl)piperidine, dihydrochloride salt (11.3 g, 50.4 mmol) and triethylamine (20.4 g, 202 mmol) in dichloromethane (250 mL) was slowly added di-tert-butyl dicarbonate (11.0 g, 50.4 mmol), and the reaction mixture was allowed to stir at room temperature overnight. It was then concentrated under reduced pressure and purified using silica gel chromatography (Gradient: 17% to 80% ethyl acetate in petroleum ether), providing the product as a light yellow gum. Yield: 9.50 g, 37.8 mmol, 75%. LCMS m/z 195.8 [(M−2-methylprop-1-ene)+H]$^+$. $^1$H NMR (400 MHz, CDCl$_3$) δ 7.50 (br s, 1H), 6.12 (br s, 1H), 4.30-4.03 (br s, 2H), 2.96-2.73 (m, 3H), 2.04-1.86 (m, 2H), 1.73-1.55 (m, 2H), 1.48 (s, 9H).

Step 2. Synthesis of tert-butyl 4-[1-(4-fluorophenyl)-1H-pyrazol-3-yl]piperidine-1-carboxylate (C14)

To a mixture of C13 (700 mg, 2.78 mmol), (4-fluorophenyl)boronic acid (429 mg, 3.07 mmol), and 4 Å molecular sieves (1.0 g) in dry dichloromethane (40 mL) were added pyridine (441 mg, 5.58 mmol) and copper(II) acetate (759 mg, 4.18 mmol). The reaction mixture was stirred for 48 hours at room temperature, while open to the air, and was then filtered. The filtrate was poured into water and extracted with dichloromethane (3×50 mL); the combined organic layers were washed sequentially with water (100 mL) and with saturated aqueous sodium chloride solution (100 mL), dried over sodium sulfate, filtered, and concentrated in vacuo. Purification via chromatography on silica gel (Eluent: 25% ethyl acetate in petroleum ether) afforded the product as a white solid. Yield: 700 mg, 2.0 mmol, 72%. $^1$H NMR (400 MHz, CD$_3$OD) δ 8.05 (br d, J=2.5 Hz, 1H), 7.74-7.68 (m, 2H), 7.24-7.17 (m, 2H), 6.37 (br d, J=2.5 Hz, 1H), 4.19-4.10 (m, 2H), 3.02-2.85 (m, 3H), 2.02-1.92 (m, 2H), 1.71-1.58 (m, 2H), 1.48 (s, 9H).

Step 3. Synthesis of 4-[1-(4-fluorophenyl)-1H-pyrazol-3-yl]piperidine, hydrochloride salt (C15)

A solution of hydrogen chloride in ethyl acetate (4 M, 10 mL, 40 mmol) was added to a 0° C. solution of C$_{1-4}$ (700 mg, 2.0 mmol) in ethyl acetate (10 mL). After the reaction mixture had been stirred for 1.5 hours at room temperature (18° C.), it was concentrated in vacuo to provide the product as a white solid. This material was used without further purification. Yield: 560 mg, assumed quantitative. $^1$H NMR (400 MHz, CD$_3$OD) δ 8.13-8.10 (m, 1H), 7.77-7.70 (m, 2H), 7.26-7.19 (m, 2H), 6.44-6.42 (m, 1H), 3.49 (ddd, J=13, 4, 4 Hz, 2H), 3.22-3.07 (m, 3H), 2.31-2.22 (m, 2H), 2.06-1.93 (m, 2H).

Step 4. Synthesis of (2R)-1,1,1-trifluoro-3-[(4-methoxybenzyl)oxy]propan-2-yl 4-[1-(4-fluorophenyl)-1H-pyrazol-3-yl]piperidine-1-carboxylate (C16)

To a 0° C. solution of bis(trichloromethyl) carbonate (27.2 mg, 91.6 μmol) in dichloromethane (5 mL) was added C1 (69.4 mg, 0.277 mmol), followed by N,N-diisopropylethylamine (36 mg, 0.28 mmol) and 4-(dimethylamino)pyridine (2.0 mg, 16 μmol). After the reaction mixture had stirred at room temperature (15° C.) for 7 hours, it was cooled to 0° C. and treated with a solution of C15 (100 mg, 0.408 mmol) and N,N-diisopropylethylamine (72 mg, 0.56 mmol) in dichloromethane (5 mL). The reaction mixture was then stirred at 15° C. for 16 hours, whereupon it was diluted with dichloromethane (10 mL) and washed sequentially with water (3×20 mL) and with saturated aqueous sodium chloride solution (2×20 mL), dried over sodium sulfate, filtered, and concentrated in vacuo. Silica gel chromatography (Eluent: 20% ethyl acetate in petroleum ether) provided the product as a colorless oil, which was not pure via $^1$H NMR analysis. Yield: 90 mg, ≤60%. $^1$H NMR (400 MHz, CD$_3$OD), characteristic peaks: δ 8.04 (d, J=2.5 Hz, 1H), 7.74-7.68 (m, 2H), 7.20 (br dd, J=8.8, 8.8 Hz, 2H), 3.79 (s, 3H), 3.15-2.92 (m, 3H), 2.06-1.95 (m, 2H), 1.75-1.61 (m, 2H).

Step 5. Synthesis of (2R)-1,1,1-trifluoro-3-hydroxypropan-2-yl 4-[1-(4-fluorophenyl)-1H-pyrazol-3-yl]piperidine-1-carboxylate (2)

To a solution of C16 (50 mg, 96 μmol) in ethanol (50 mL) was added palladium on carbon (30 mg), and the reaction mixture was stirred at 20° C. under hydrogen (40 psi) for 6 hours. It was then filtered through a pad of diatomaceous earth, and the filtrate was concentrated in vacuo; purification via preparative thin layer chromatography on silica gel (Eluent: 25% ethyl acetate in petroleum ether) afforded the product as a white solid. Yield: 15 mg, 37 μmol, 38%. LCMS m/z 402.0 [M+H]$^+$. $^1$H NMR (400 MHz, CD$_3$OD) δ 8.06 (d, J=2.5 Hz, 1H), 7.74-7.68 (m, 2H), 7.21 (br dd, J=9.0, 8.4 Hz, 2H), 6.38 (d, J=2.5 Hz, 1H), 5.32 (dqd, J=7, 7, 4 Hz, 1H), 4.29-4.16 (br m, 2H), 3.89 (br dd, half of ABX pattern, J=12.5, 4 Hz, 1H), 3.79 (br dd, half of ABX pattern, J=12.4, 6.9 Hz, 1H), 3.19-3.0 (m, 2H), 2.98 (tt, J=11.5, 4 Hz, 1H), 2.08-1.96 (m, 2H), 1.85-1.61 (br m, 2H).

Example 3

(2R)-1,1,1-Trifluoro-3-hydroxypropan-2-yl (1α,5α, 6α)-6-[1-(4-fluorophenyl)-1H-pyrazol-3-yl]-3-azabicyclo[3.1.0]hexane-3-carboxylate (3)

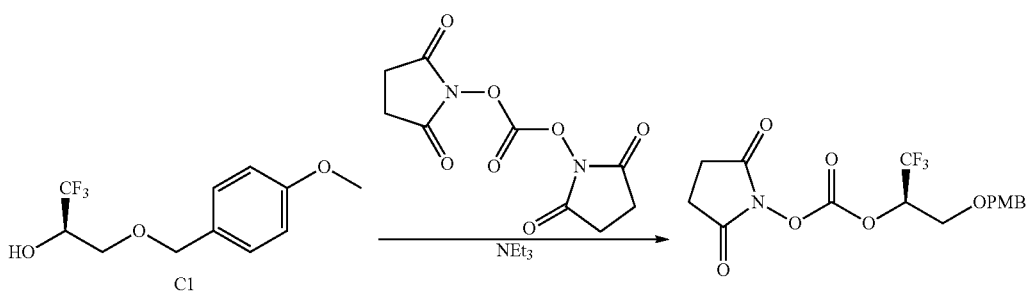

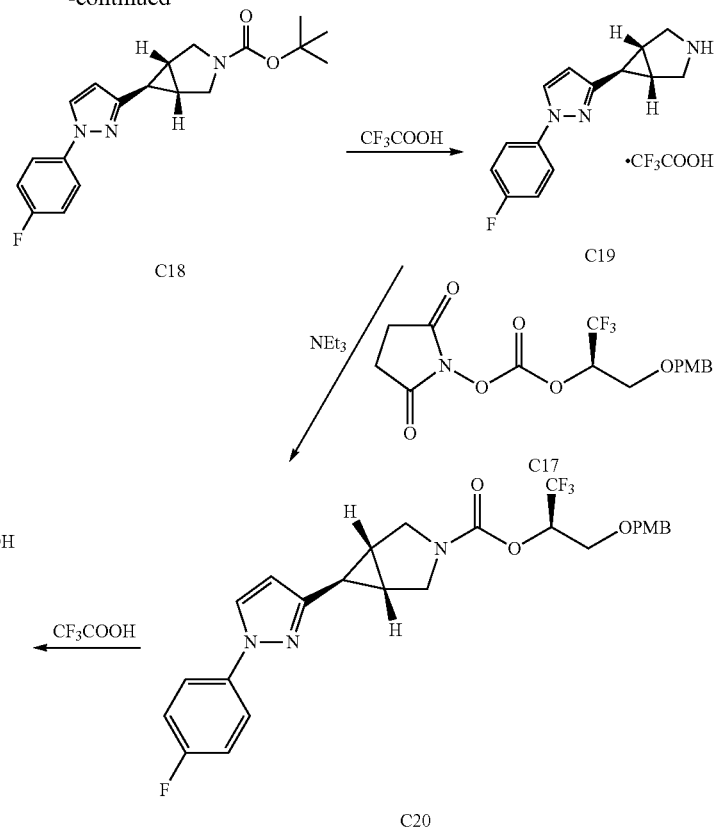

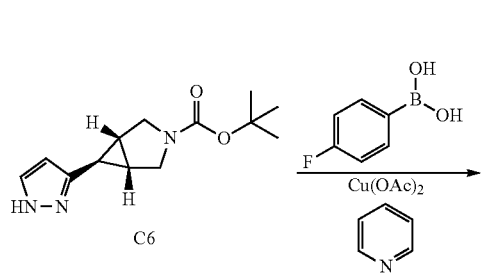

Step 1. Synthesis of 1-{[({(2R)-1,1,1-trifluoro-3-[(4-methoxybenzyl)oxy]propan-2-yl}oxy) carbonyl]oxy}pyrrolidine-2, 5-dione (C17)

To a solution of C1 (701 mg, 2.80 mmol) in dichloromethane (20 mL) were added triethylamine (850 mg, 8.40 mmol) and 1,1'-[carbonylbis(oxy)]dipyrrolidine-2,5-dione (717 mg, 2.80 mmol). The reaction mixture was stirred for 18 hours at 25° C., then used directly in Step 4. For subsequent syntheses described herein that utilize C17, this material was generated at the appropriate scale, and the reaction solution of C17 was used directly in the coupling reaction.

Step 2. Synthesis of tert-butyl (1α,5α,6α)-6-[1-(4-fluorophenyl)-1H-pyrazol-3-yl]-3-azabicyclo[3.1.0]hexane-3-carboxylate (C18)

To a 15° C. solution of C6 (4.0 g, 16 mmol) in dichloromethane (300 mL) were added (4-fluorophenyl)boronic acid (2.92 g, 20.9 mmol), copper(II) acetate (4.37 g, 24.1 mmol), pyridine (3.81 g, 48.2 mmol), and 4 Å molecular sieves (0.5 g). The reaction mixture was stirred for 18 hours at 30° C., whereupon it was washed with aqueous ammonium hydroxide solution (100 mL). This aqueous layer was extracted with dichloromethane (2×100 mL), and the combined organic layers were washed with saturated aqueous sodium chloride solution (150 mL), dried over sodium sulfate, filtered, and concentrated in vacuo. Silica gel chromatography (Gradient: 0% to 25% ethyl acetate in petroleum ether) provided the product as a white solid. Yield: 3.3 g, 9.6 mmol, 60%. LCMS m/z 287.8 [(M−2-methylprop-1-ene)+H]$^+$. $^1$H NMR (400 MHz, CDCl$_3$) δ 7.73 (d, J=2.5 Hz, 1H), 7.62-7.56 (m, 2H), 7.12 (br dd, J=8.9, 8.4 Hz, 2H), 6.16 (d, J=2.4 Hz, 1H), 3.80 (d, half of AB quartet, J=11.0 Hz, 1H), 3.71 (d, half of AB quartet, J=10.9 Hz, 1H), 3.52-3.42 (m, 2H), 1.99-1.90 (m, 2H), 1.85 (dd, J=3.4, 3.4 Hz, 1H), 1.47 (s, 9H).

Step 3. Synthesis of (1α,5α,6α)-6-[1-(4-fluorophenyl)-1H-pyrazol-3-yl]-3-azabicyclo[3.1.0]hexane, trifluoroacetate salt (C19)

A mixture of C18 (1.0 g, 2.9 mmol) in trifluoroacetic acid (10 mL) was stirred for 30 minutes at 15° C., whereupon it was concentrated in vacuo. The residue was triturated with tert-butyl methyl ether (10 mL) to provide the product as a white solid, which was used directly in the following step. LCMS m/z 243.9 [M+H]$^+$.

Step 4. Synthesis of (2R)-1,1,1-trifluoro-3-[(4-methoxybenzyl)oxy]propan-2-yl (1α,5α,6α)-6-[1-(4-fluorophenyl)-1H-pyrazol-3-yl]-3-azabicyclo [3.1.0]hexane-3-carboxylate (C20)

To a 15° C. solution of C17 [the reaction mixture from Step 1; ≤2.80 mmol in dichloromethane (20 mL)] was added a solution of C19 (from the previous step, ≤2.9 mmol) and triethylamine (566 mg, 5.59 mmol) in dichloromethane (10 mL). The reaction mixture was stirred overnight at 18° C., whereupon it was concentrated in vacuo. Purification using silica gel chromatography (Gradient: 0% to 25% ethyl acetate in petroleum ether) provided the product as a gum. By $^1$H NMR analysis, this was judged to be a mixture of rotamers. Yield: 900 mg, 1.7 mmol, 61% over two steps. $^1$H NMR (400 MHz, CDCl$_3$) δ 7.74 (d, J=2.4 Hz, 1H), 7.62-7.57 (m, 2H), 7.29-7.24 (m, 2H), 7.13 (br dd, J=8.9, 8.3 Hz, 2H), 6.93-6.88 (m, 2H), [6.19 (d, J=2.4 Hz) and 6.16 (d, J=2.4 Hz), total 1H], 5.53-5.43 (m, 1H), 4.60-4.54 (m, 1H), 4.48 (d, half of AB quartet, J=11.7 Hz, 1H), 3.90-3.84 (m, 1H), 3.84-3.73 (m, 2H), [3.82 (s) and 3.79 (s), total 3H], 3.73-3.65 (m, 1H), 3.65-3.54 (m, 2H), 2.04-2.00 (m, 2H), 1.87-1.82 (m, 1H).

Step 5. Synthesis of (2R)-1,1,1-trifluoro-3-hydroxy-propan-2-yl (1α,5α,6α)-6-[1-(4-fluorophenyl)-1H-pyrazol-3-yl]-3-azabicyclo[3.1.0]hexane-3-carboxylate (3)

Trifluoroacetic acid (10 mL) was added to a solution of C20 (890 mg, 1.7 mmol) in dichloromethane (30 mL), and the reaction mixture was stirred for 4 hours at 15° C. It was then slowly poured into saturated aqueous sodium bicarbonate solution, and the resulting mixture was extracted with dichloromethane (3×50 mL). The combined organic layers were dried over sodium sulfate, filtered, and concentrated in vacuo; purification via chromatography on silica gel (Gradient: 0% to 50% ethyl acetate in petroleum ether) afforded the product as a white solid. Yield: 440 mg, 1.1 mmol, 65%. LCMS m/z 399.9 [M+H]$^+$. $^1$H NMR (400 MHz, CDCl$_3$) δ 7.74 (d, J=2.4 Hz, 1H), 7.63-7.56 (m, 2H), 7.13 (dd, J=8.7, 8.5 Hz, 2H), 6.21-6.17 (m, 1H), 5.31-5.21 (m, 1H), 4.06-3.96 (m, 1H), 3.93-3.80 (m, 3H), 3.67-3.58 (m, 2H), 2.38-2.27 (br m, 1H), 2.08-2.01 (m, 2H), 1.90-1.84 (m, 1H).

Examples 4 and 5

(2R)-1,1,1-Trifluoro-3-hydroxypropan-2-yl 4-(tetrahydro-2H-pyran-3-ylmethyl)-1-oxa-4,9-diazaspiro[5.5]undecane-9-carboxylate [from C25, DIAST-1] (4) and (2R)-1,1,1-Trifluoro-3-hydroxypropan-2-yl 4-(tetrahydro-2H-pyran-3-ylmethyl)-1-oxa-4,9-diazaspiro[5.5]undecane-9-carboxylate [from C26, DIAST-2] (5)

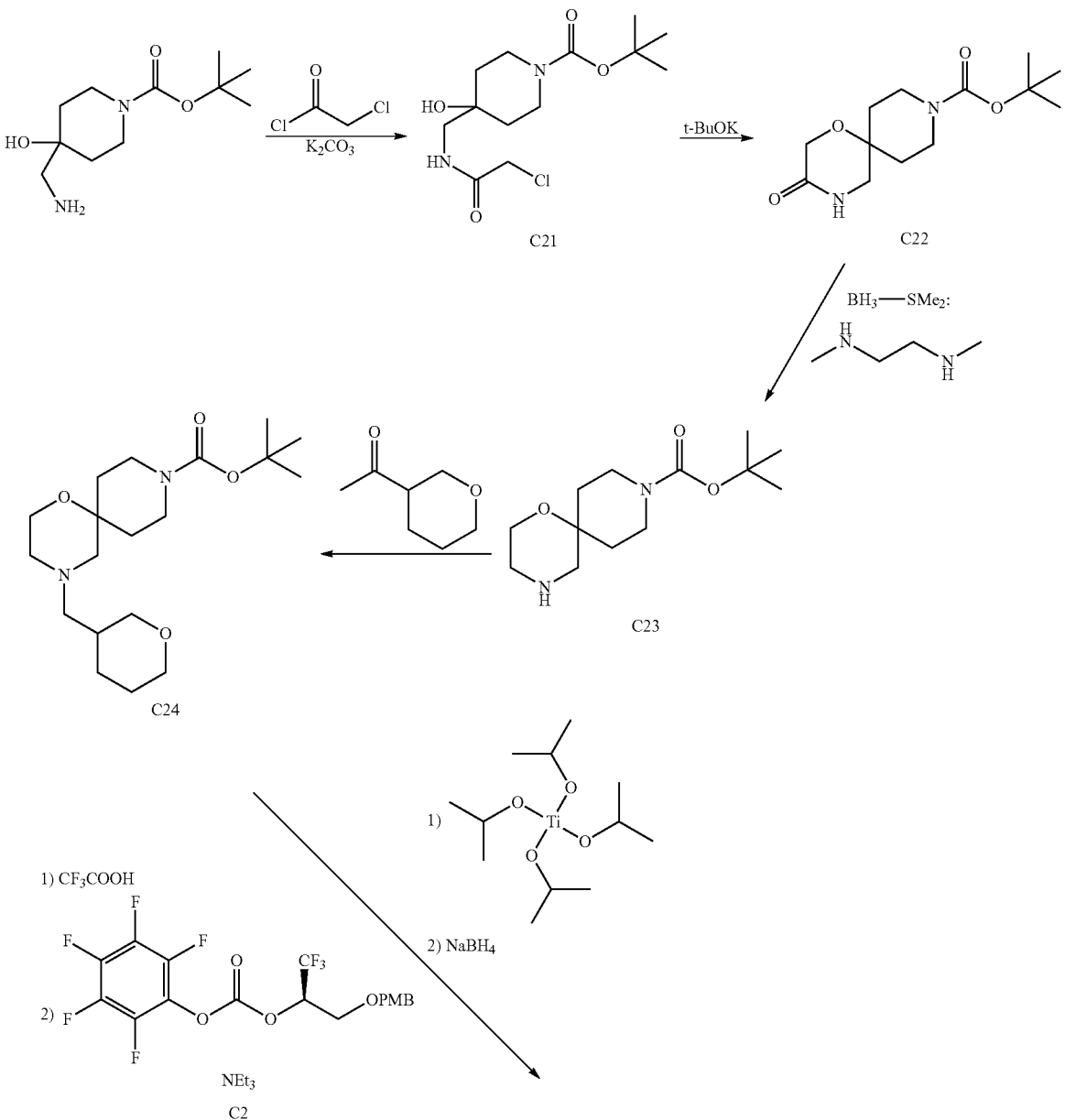

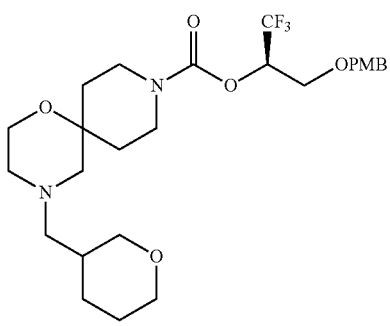

DIAST-1
C25

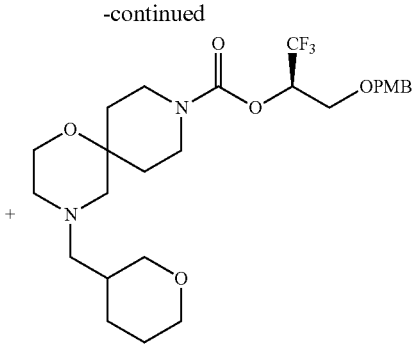

DIAST-2
C26

| CF₃COOH

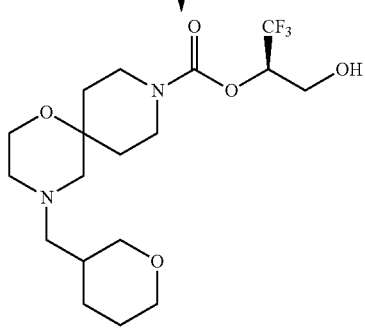

[From C25, DIAST-1]
4

| CF₃COOH

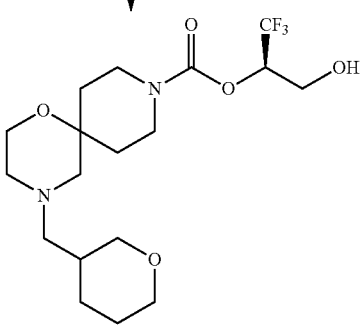

[From C26, DIAST-2]
5

Step 1. Synthesis of tert-butyl 4-{[(chloroacetyl)amino]methyl}-4-hydroxypiperidine-1-carboxylate (C21)

A solution of potassium carbonate (1.32 kg, 9.55 mol) in water (11 L) was added to a solution of tert-butyl 4-(aminomethyl)-4-hydroxypiperidine-1-carboxylate (1.10 kg, 4.78 mol) in ethyl acetate (11 L). The mixture was cooled to 0° C., and then treated in a drop-wise manner with chloroacetyl chloride (595 g, 5.27 mol). After completion of the addition, the reaction mixture was warmed to 25° C. and allowed to stir for 16 hours. The aqueous layer was extracted with ethyl acetate (3×10 L), and the combined organic layers were dried over sodium sulfate, filtered, and concentrated in vacuo; trituration of the residue with tert-butyl methyl ether (10 L) afforded the product (1040 g). The filtrate from the trituration was concentrated and triturated with a mixture of tert-butyl methyl ether and petroleum ether (1:1; 300 mL) to provide additional product (123 g) as a white solid. Combined yield: 1.16 kg, 3.78 mol, 79%. ¹H NMR (400 MHz, CDCl₃) δ 7.02 (br t, J=5 Hz, 1H), 4.09 (s, 2H), 3.88-3.70 (br m, 2H), 3.43-3.28 (br s, 2H), 3.20 (br dd, J=11, 11 Hz, 2H), 2.71 (s, 1H), 1.62-1.46 (m, 4H), 1.45 (s, 9H).

Step 2. Synthesis of tert-butyl 3-oxo-1-oxa-4,9-diazaspiro[5.5]undecane-9-carboxylate (C22)

This reaction was carried out in two similar batches. To a solution of C21 (540 g, 1.76 mol) in 2-propanol (20 L) was added potassium tert-butoxide (1.98 kg, 17.6 mol) at 25° C., and the reaction mixture was stirred at 25° C. for 16 hours. After removal of solvent in vacuo, the residue was partitioned between ethyl acetate (15 L) and water (20 L). The aqueous layer was extracted with ethyl acetate (2×15 L), and the combined organic layers were washed with saturated aqueous sodium chloride solution (15 L), dried over sodium sulfate, filtered, and concentrated under reduced pressure. The residue was triturated with tert-butyl methyl ether (2 L) at 25° C. for 3 hours to afford the product as a white solid. Combined yield from the two batches: 540 g, 2.00 mmol, 57%. ¹H NMR (400 MHz, CDCl₃) δ 6.78-6.59 (br m, 1H), 4.16 (s, 2H), 3.96-3.74 (br s, 2H), 3.24 (d, J=2.6 Hz, 2H), 3.11 (br dd, J=12, 12 Hz, 2H), 1.89 (br d, J=13 Hz, 2H), 1.58-1.48 (m, 2H), 1.46 (s, 9H).

Step 3. Synthesis of tert-butyl 1-oxa-4,9-diazaspiro[5.5]undecane-9-carboxylate (C23)

This reaction was carried out in 12 batches, as follows. Borane-dimethyl sulfide complex (10 M in dimethyl sulfide, 75 mL, 750 mmol) was added in a drop-wise manner to a solution of C22 (50 g, 180 mmol) in tetrahydrofuran (1.5 L). The reaction mixture was heated at reflux (70° C.) for 6 hours and subsequently allowed to stir at 25° C. for 10 hours. It was then quenched with methanol (500 mL), stirred for 30 minutes at 25° C., and concentrated under reduced pressure. The resulting white solid was dissolved in methanol (1 L), treated with N,N'-dimethylethane-1,2-diamine (65 g, 740 mmol), and heated at reflux (70° C.) for 16 hours. The 12 reaction mixtures were combined and concentrated in vacuo to provide a light yellow oil; this was dissolved in dichloromethane (4 L), washed with aqueous ammonium chloride solution (4×2 L), dried over sodium sulfate, filtered, and concentrated under reduced pressure. The residue was triturated with petroleum ether (500 mL) at 25° C. for 30 minutes to provide the product (304 g) as a white solid. The filtrate from the trituration was concentrated in vacuo, and the residue was triturated with petroleum ether (200 mL) at 25° C. for 36 hours, affording additional product (135 g) as a white solid. Combined yield: 439 g, 1.71 mol, 77%. LCMS m/z 257.2 [M+H]$^+$. $^1$H NMR (400 MHz, CDCl$_3$) δ 3.85-3.59 (m, 4H), 3.14 (br dd, J=11, 11 Hz, 2H), 2.84 (dd, J=4.9, 4.6 Hz, 2H), 2.68 (s, 2H), 2.02-1.84 (br m, 2H), 1.47-1.33 (m, 2H), 1.45 (s, 9H).

Step 4. Synthesis of tert-butyl 4-(tetrahydro-2H-pyran-3-ylmethyl)-1-oxa-4,9-diazaspiro[5.5]undecane-9-carboxylate (C24)

Titanium(IV) isopropoxide (998 mg, 3.51 mmol) was added to a mixture of C23 (300 mg, 1.17 mmol) and tetrahydro-2H-pyran-3-carbaldehyde (160 mg, 1.40 mmol) in ethanol (10 mL) at 27° C., and the reaction mixture was stirred at 27° C. for 15 hours. It was then cooled to 0° C., treated with sodium borohydride (88.6 mg, 2.34 mmol), and allowed to stir at 25° C. for 4 hours. Water (10 mL) was added slowly, and the resulting mixture was stirred at 25° C. for 30 minutes. After combination with a mixture derived from a smaller-scale reaction carried out on C23 (50 mg, 0.20 mmol), this was extracted with ethyl acetate (3×30 mL). The combined organic layers were dried, filtered, and concentrated in vacuo; purification via chromatography on silica gel (Gradient: 0% to 5% methanol in dichloromethane) provided the product as a colorless oil. Starting material C23 (200 mg) was also recovered, as a yellow gum. Yield: 106 mg, 0.299 mmol, 22% (51% based on recovered starting material). LCMS m/z 355.3 [M+H]$^+$. $^1$H NMR (400 MHz, CDCl$_3$) δ 3.96-3.88 (m, 1H), 3.88-3.80 (m, 1H), 3.79-3.58 (m, 4H), 3.42-3.33 (m, 1H), 3.19-3.04 (m, 3H), 2.42-2.33 (m, 1H), 2.33-2.26 (m, 1H), 2.26-2.19 (m, 1H), 2.15-2.01 (m, 3H), 1.98-1.73 (m, 5H), 1.64-1.53 (m, 2H), 1.44 (s, 9H), 1.44-1.34 (m, 2H).

Step 5. Synthesis of (2R)-1,1,1-trifluoro-3-[(4-methoxybenzyl)oxy]propan-2-yl 4-(tetrahydro-2H-pyran-3-ylmethyl)-1-oxa-4,9-diazaspiro[5.5]undecane-9-carboxylate, DIAST 1 (C25) and (2R)-1,1,1-trifluoro-3-[(4-methoxybenzyl)oxy]propan-2-yl 4-(tetrahydro-2H-pyran-3-ylmethyl)-1-oxa-4,9-diazaspiro[5.5]undecane-9-carboxylate, DIAST 2 (C26)

A solution of C24 (106 mg, 0.299 mmol) in dichloromethane (2 mL) was cooled to 0° C. and treated with trifluoroacetic acid (0.5 mL). The reaction mixture was stirred at 25° C. for 50 minutes, whereupon it was concentrated in vacuo to provide 4-(tetrahydro-2H-pyran-3-ylmethyl)-1-oxa-4,9-diazaspiro[5.5]undecane, bis-trifluoroacetic acid salt as a yellow oil (100 mg). This material was taken up in acetonitrile (5 mL) and cooled to 0° C. Triethylamine (151 mg, 1.49 mmol) was added, and the reaction mixture was allowed to stir at 0° C. for a few minutes, whereupon C2 (reaction solution in acetonitrile, containing 0.49 mmol) was added drop-wise. The resulting solution was stirred at 0° C. for a few minutes, and then allowed to stir at 25° C. for 15 hours. The reaction mixture was cooled to 0° C. and treated in a drop-wise manner with additional C2 (reaction solution in acetonitrile, containing 0.22 mmol). The reaction mixture was again stirred for a few minutes at 0° C., before being allowed to stir at 25° C. for another 15 hours. It was then concentrated in vacuo, and the residue was subjected to preparative thin layer chromatography on silica gel (Eluent: 1:1 petroleum ether/ethyl acetate) to afford a mixture of diastereomeric products (100 mg). The diastereomers were separated via supercritical fluid chromatography (Column: Chiral Technologies Chiralpak AD, 5 μm; Mobile phase: 1:3 ethanol/carbon dioxide). The first-eluting compound was C25, obtained as a light yellow gum. Yield: 50 mg, 94 μmol, 31%. LCMS m/z 531.1 [M+H]$^+$. $^1$H NMR (400 MHz, CDCl$_3$), characteristic peaks: δ 7.28-7.23 (m, 2H, assumed; partially obscured by solvent peak), 6.89 (d, J=8.8 Hz, 2H), 5.53-5.44 (m, 1H), 4.51 (AB quartet, downfield doublet is broadened, $J_{AB}$=11.7 Hz, $\Delta v_{AB}$=28 Hz, 2H), 3.97-3.90 (m, 1H), 3.90-3.82 (m, 2H), 3.82 (s, 3H), 3.45-3.36 (m, 1H), 3.28-3.16 (m, 2H), 3.15-3.07 (m, 1H), 2.45-2.36 (m, 1H), 2.36-2.27 (m, 1H), 2.13-2.06 (m, 2H), 2.05-1.93 (m, 2H), 1.87-1.76 (m, 2H), 1.47-1.35 (m, 2H).

The second-eluting diastereomer was C26, also obtained as a light yellow gum. Yield: 50 mg, 94 μmol, 31%. LCMS m/z 531.2 [M+H]$^+$. $^1$H NMR (400 MHz, CDCl$_3$), characteristic peaks: δ 7.28-7.22 (m, 2H, assumed; partially obscured by solvent peak), 6.89 (d, J=8.8 Hz, 2H), 5.54-5.43 (m, 1H), 4.51 (AB quartet, $J_{AB}$=12 Hz, $\Delta v_{AB}$=26 Hz, 2H), 3.97-3.90 (m, 1H), 3.90-3.82 (m, 2H), 3.82 (s, 3H), 3.45-3.35 (m, 1H), 3.29-3.16 (m, 2H), 3.16-3.07 (m, 1H), 2.45-2.36 (m, 1H), 2.36-2.28 (m, 1H), 2.14-2.03 (m, 2H), 2.03-1.92 (m, 2H), 1.86-1.75 (m, 2H), 1.46-1.34 (m, 2H).

Step 6. Synthesis of (2R)-1,1,1-trifluoro-3-hydroxypropan-2-yl 4-(tetrahydro-2H-pyran-3-ylmethyl)-1-oxa-4,9-diazaspiro[5.5]undecane-9-carboxylate [from C25, DIAST-1] (4)

Trifluoroacetic acid (1 mL) was added in a drop-wise manner to a 0° C. solution of C25 (50 mg, 94 μmol) in dichloromethane (4 mL), and the reaction mixture was allowed to stir at 0° C. for 1 hour. Saturated aqueous sodium bicarbonate solution (20 mL) was added, and the mixture was extracted with dichloromethane (3×15 mL). The combined organic layers were dried over sodium sulfate, filtered, and concentrated in vacuo; preparative thin layer chromatography on silica gel (Eluent: 1:1 ethyl acetate/petroleum ether) provided the product as a light yellow gum. Yield: 34.5 mg, 84.0 μmol, 89%. LCMS m/z 411.2 [M+H]$^+$. $^1$H NMR (400 MHz, CDCl$_3$) δ 5.31-5.18 (br m, 1H), 4.04-3.76 (m, 6H), 3.76-3.66 (m, 2H), 3.44-3.35 (m, 1H), 3.32-3.15 (m, 2H), 3.11 (br dd, J=10, 10 Hz, 1H), 2.68-2.46 (br m, 1H), 2.47-2.28 (m, 2H), 2.28-2.21 (m, 1H), 2.20-1.93 (m, 5H), 1.89-1.75 (m, 2H), 1.65-1.54 (m, 2H), 1.51-1.35 (m, 2H).

Step 7. Synthesis of (2R)-1,1,1-trifluoro-3-hydroxypropan-2-yl 4-(tetrahydro-2H-pyran-3-ylmethyl)-1-oxa-4,9-diazaspiro[5.5]undecane-9-carboxylate [from C26, DIAST-2] (5)

Compound C26 was converted to the product using the method described for synthesis of 4 from C25. The product was isolated as a yellow gum. Yield: 34.0 mg, 82.8 μmol, 88%. LCMS m/z 411.1 [M+H]$^+$. $^1$H NMR (400 MHz, CDCl$_3$) δ 5.30-5.19 (br m, 1H), 4.05-3.77 (m, 6H), 3.77-3.65 (m, 2H), 3.44-3.35 (m, 1H), 3.32-3.17 (m, 2H), 3.12 (br dd, J=10, 10 Hz, 1H), 2.61-2.20 (m, 4H), 2.20-1.94 (m, 5H), 1.90-1.75 (m, 2H), 1.64-1.53 (m, 2H, assumed; partially obscured by water peak), 1.51-1.38 (m, 2H).

Example 6

(2R)-1,1,1-Trifluoro-3-hydroxypropan-2-yl 4-[(4-fluorophenyl)sulfonyl]-1-oxa-4,9-diazaspiro[5.5]undecane-9-carboxylate (6)

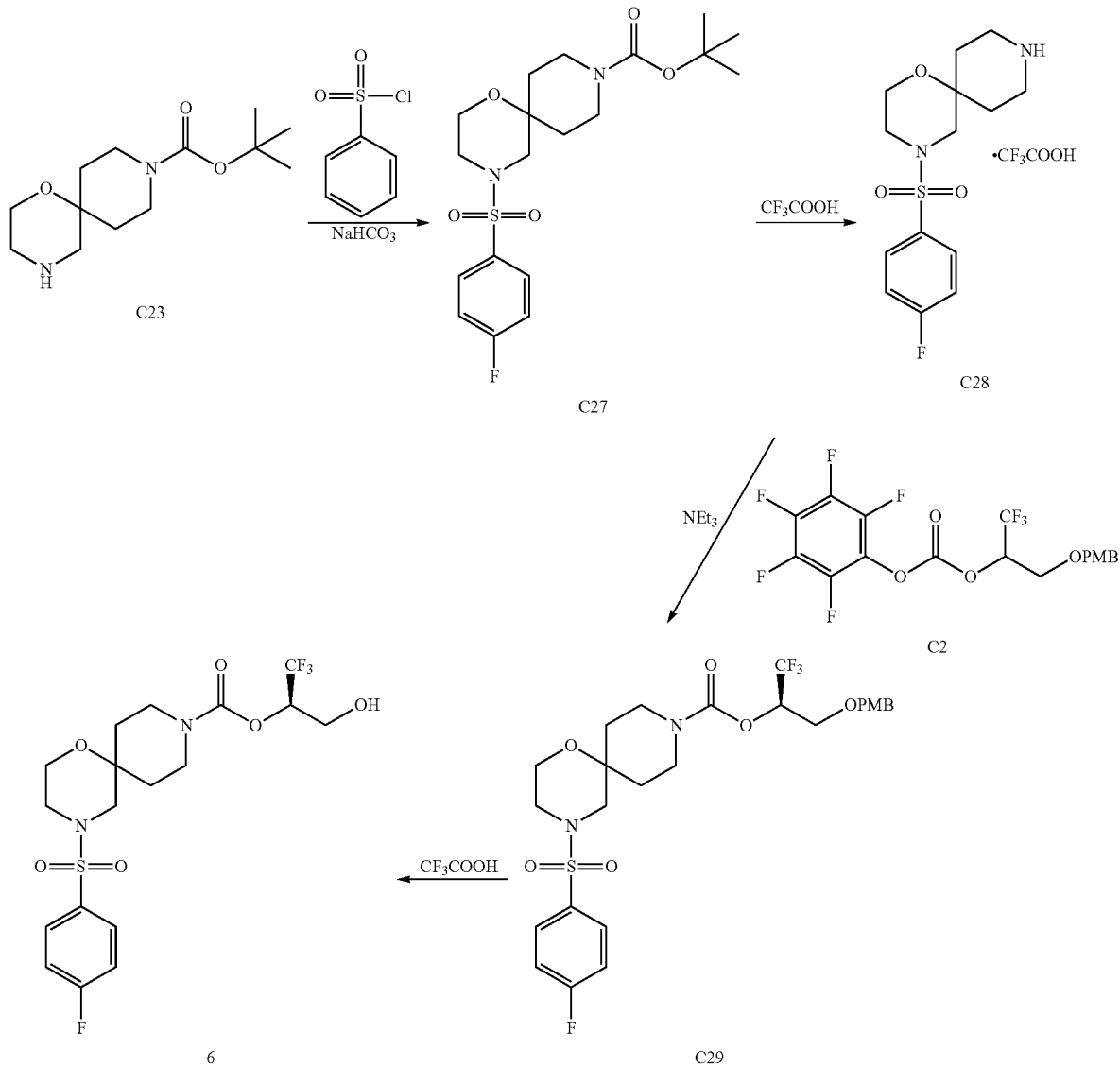

Step 1. Synthesis of tert-butyl 4-[(4-fluorophenyl)sulfony]-1-oxa-4,9-diazaspiro[5.5]undecane-9-carboxylate (C27)

4-Fluorobenzenesulfonyl chloride (4.18 g, 21.5 mmol) was added portion-wise to a mixture of C23 (5.0 g, 20 mmol), saturated aqueous sodium bicarbonate solution (55 mL), and dichloromethane (195 mL). The reaction mixture was stirred at room temperature overnight, whereupon the aqueous layer was extracted twice with dichloromethane, and the combined organic layers were dried over magnesium sulfate, filtered, and concentrated in vacuo. Silica gel chromatography (Gradient: 0% to 10% methanol in dichloromethane) afforded the product as a white foam. Yield: 8.4 g, 20 mmol, quantitative. $^1$H NMR (400 MHz, CDCl$_3$) δ 7.79-7.73 (m, 2H), 7.28-7.22 (m, 2H, assumed; partially obscured by solvent peak), 3.8-3.66 (m, 2H), 3.79 (dd, J=5.0, 5.0 Hz, 2H), 3.19-3.08 (m, 2H), 3.08-2.89 (m, 2H), 2.89-2.67 (m, 2H), 1.96-1.82 (m, 2H), 1.54-1.48 (m, 2H), 1.47 (s, 9H).

Step 2. Synthesis of 4-[(4-fluorophenyl)sulfonyl]-1-oxa-4,9-diazaspiro[5.5]undecane, trifluoroacetic acid salt (C28)

Trifluoroacetic acid (15 mL) was slowly added to a solution of C27 (3.16 g, 7.62 mmol) and dichloromethane (38 mL). After the reaction mixture had stirred at room temperature for 2 hours, it was concentrated in vacuo to afford the product, which was used in the next step without further purification. LCMS m/z 315.4 [M+H]$^+$. $^1$H NMR (400 MHz, CDCl$_3$) δ 7.81-7.75 (m, 2H), 7.31-7.24 (m, 2H, assumed; partially obscured by solvent peak), 3.81 (br dd, J=5.1, 4.7 Hz, 2H), 3.43-3.34 (m, 2H), 3.33-3.21 (m, 2H), 3.04 (br dd, J=4.9, 4.7 Hz, 2H), 2.86 (s, 2H), 2.24 (br d, J=14.4 Hz, 2H), 1.82 (ddd, J=14.8, 13.3, 4.5 Hz, 2H).

Step 3. Synthesis of (2R)-1,1,1-trifluoro-3-[(4-methoxybenzyl)oxy]propan-2-yl 4-[(4-fluorophenyl)sulfonyl]-1-oxa-4,9-diazaspiro[5.5]undecane-9-carboxylate (C29)

Triethylamine (5.3 mL, 38 mmol) was added to a 0° C. solution of C28 (from the previous step, ≤7.62 mmol) in acetonitrile (40 mL). The reaction mixture was allowed to stir at 0° C. for a few minutes, whereupon C2 (reaction solution in acetonitrile, containing 9.9 mmol) was added drop-wise. The temperature was maintained at 0° C. for a few minutes, and then the reaction mixture was allowed to stir at room temperature for 3 days. Solvents were removed in vacuo, and the residue was purified using silica gel chromatography (Gradient: 0% to 50% ethyl acetate in heptane) to afford the product as a white foam. Yield: 3.9 g, 6.6 mmol, 87% over 2 steps. LCMS m/z 635.5 [(M+HCOOH)-H$^+$]. $^1$H NMR (400 MHz, CDCl$_3$) δ 7.79-7.73 (m, 2H), 7.29-7.22 (m, 4H, assumed; partially obscured by solvent peak), 6.96-6.85 (m, 2H), 5.54-5.43 (m, 1H), 4.51 (AB quartet, downfield doublet is broadened, J$_{AB}$=11.7 Hz, Δν$_{AB}$=28 Hz, 2H), 3.95-3.64 (m, 9H), 3.26-3.13 (m, 2H), 3.08-2.89 (m, 2H), 2.85-2.65 (m, 2H), 2.00-1.87 (m, 2H), 1.55-1.38 (m, 2H).

Step 4. Synthesis of (2R)-1,1,1-trifluoro-3-hydroxy-propan-2-yl 4-[(4-fluorophenyl)sulfonyl]-1-oxa-4,9-diazaspiro[5.5]undecane-9-carboxylate (6)

Trifluoroacetic acid (25 mL) was added drop-wise to a 0° C. solution of C29 (3.9 g, 6.6 mmol) in dichloromethane (100 mL), and the reaction mixture was allowed to warm to room temperature and stir for 2 hours. It was then concentrated in vacuo; the residue was dissolved in ethyl acetate, washed sequentially with saturated aqueous sodium bicarbonate solution and with saturated aqueous sodium chloride solution, dried over magnesium sulfate, filtered, and concentrated under reduced pressure. Silica gel chromatography (Gradient: 0% to 100% ethyl acetate in heptane) provided the product as a white foam. Yield: 2.6 g, 5.5 mmol, 83%. LCMS m/z 471.5 [M+H]$^+$. $^1$H NMR (400 MHz, DMSO-d$_6$) δ 7.85-7.78 (m, 2H), 7.51 (br dd, J=8.9, 8.8 Hz, 2H), 5.30-5.16 (m, 2H), 3.78-3.60 (m, 6H), 3.20-3.02 (m, 2H), 2.94-2.82 (m, 2H), 2.81-2.69 (m, 2H), 1.89-1.75 (m, 2H), 1.57-1.38 (m, 2H).

Crystallization of 6 (1 g) was carried out using ethyl acetate (10 mL) and hexanes (20 mL), providing the product as a white solid, melting point 132° C.; this material was determined to be crystalline via powder X-ray diffraction. Yield for crystallization: 826 mg, 83%. LCMS m/z 471.4 [M+H]$^+$. $^1$H NMR (400 MHz, DMSO-d$_6$) δ 7.85-7.78 (m, 2H), 7.51 (br dd, J=8.8, 8.7 Hz, 2H), 5.30-5.16 (m, 2H), 3.78-3.60 (m, 6H), 3.21-3.01 (m, 2H), 2.95-2.82 (m, 2H), 2.81-2.69 (m, 2H), 1.89-1.75 (m, 2H), 1.58-1.38 (m, 2H).

Example 7

(2R)-1,1,1-Trifluoro-3-hydroxypropan-2-yl 4-(phenylsulfonyl)-1-oxa-4,9-diazaspiro[5.5]undecane-9-carboxylate (7)

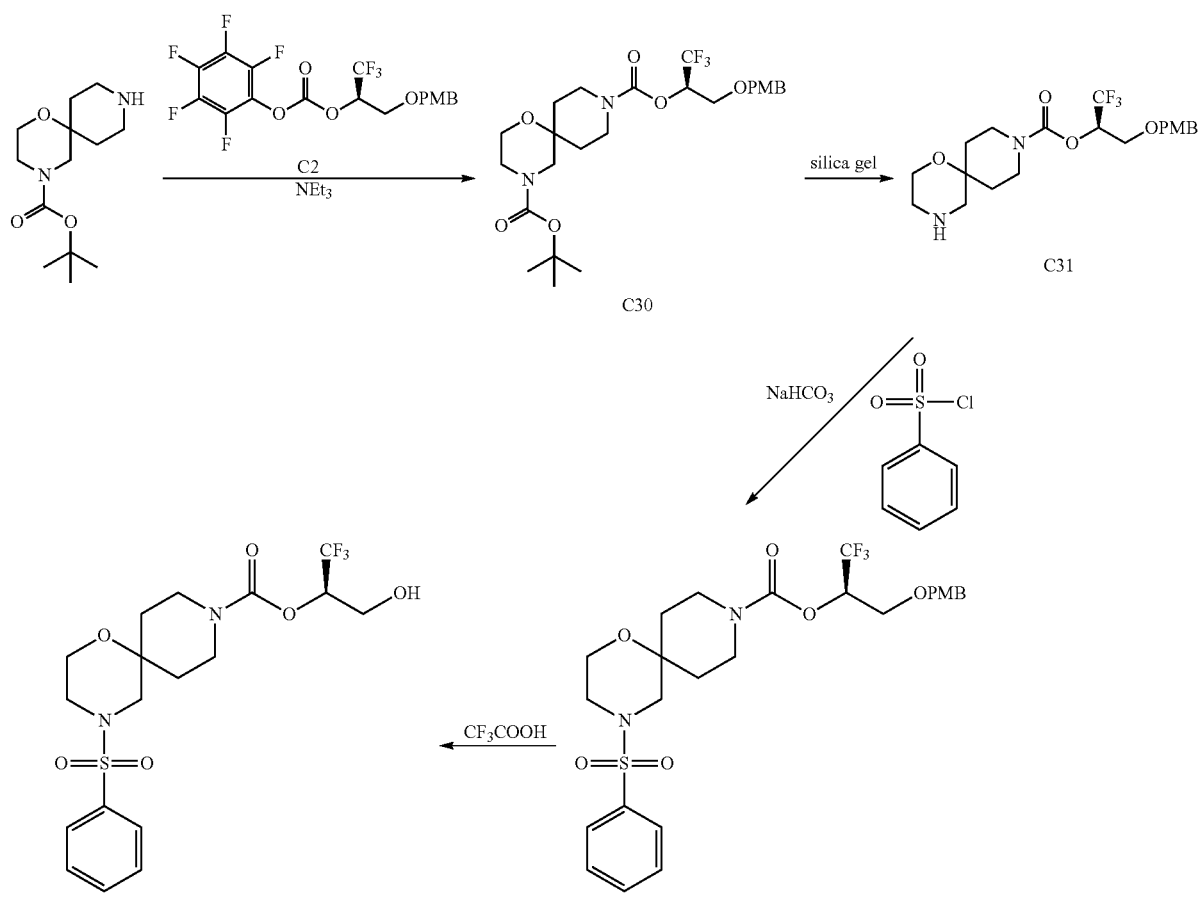

Step 1. Synthesis of 4-tert-butyl 9-{(2R)-1,1,1-trifluoro-3-[(4-methoxybenzyl)oxy]propan-2-yl} 1-oxa-4,9-diazaspiro[5.5]undecane-4,9-dicarboxylate (C30)

Triethylamine (9.28 g, 91.7 mmol) was added to a 0° C. solution of tert-butyl 1-oxa-4,9-diazaspiro[5.5]undecane-4-carboxylate (4.70 g, 18.3 mmol) in acetonitrile (60 mL); C2 (reaction solution in acetonitrile, containing 27.5 mmol) was then added drop-wise, and the reaction mixture was stirred at 0° C. few minutes. It was then allowed to warm to 25° C. and stir for 15 hours, whereupon it was concentrated in vacuo and purified via silica gel chromatography (Gradient: 0% to 100% dichloromethane in petroleum ether). The product (11.2 g) was isolated as a yellow oil, which by LCMS analysis was impure; this material was used without additional purification. LCMS m/z 555.1 [M+Na$^+$].

Step 2. Synthesis of (2R)-1,1,1-trifluoro-3-[(4-methoxybenzyl)oxy]propan-2-yl 1-oxa-4,9-diazaspiro[5.5]undecane-9-carboxylate (C31)

A mixture of C30 (from the previous step, 4.5 g, ≤7.4 mmol) and silica gel (5.0 g) was stirred at 150° C. for 3.5 hours, whereupon it was combined with a similar reaction carried out on C30 (4.5 g, ≤7.4 mmol) and purified via silica gel chromatography (Gradient: 0% to 8% methanol in dichloromethane). The product was obtained as a brown oil. Yield: 2.53 g, 5.85 mmol, 40% over 2 steps. LCMS m/z 433.2 [M+H]$^+$. $^1$H NMR (400 MHz, CDCl$_3$) δ 7.25 (br d, J=8.4 Hz, 2H), 6.88 (br d, J=8.5 Hz, 2H), 5.54-5.43 (br m, 1H), 4.51 (AB quartet, J$_{AB}$=11.7 Hz, Δv$_{AB}$=270.5 Hz, 2H), 3.95-3.79 (m, 2H), 3.81 (s, 3H), 3.79-3.63 (m, 4H), 3.30-3.14 (m, 2H), 2.86 (dd, J=4.8, 4.5 Hz, 2H), 2.73-2.62 (m, 2H), 2.10-1.91 (m, 2H), 1.50-1.29 (m, 2H).

Step 3. Synthesis of (2R)-1,1,1-trifluoro-3-[(4-methoxybenzyl)oxy]propan-2-yl 4-(phenylsulfonyl)-1-oxa-4,9-diazaspiro[5.5]undecane-9-carboxylate (C32)

Benzenesulfonyl chloride (61.3 mg, 0.347 mmol) was added to a 5° C. solution of C31 (100 mg, 0.23 mmol) in saturated aqueous sodium bicarbonate solution (2 mL) and dichloromethane (5 mL), and the reaction mixture was stirred at 5° C. for 16 hours. The aqueous layer was extracted with dichloromethane, and the combined organic layers were dried over sodium sulfate, filtered, and concentrated in vacuo. Preparative thin layer chromatography on silica gel (Eluent: 3:1 petroleum ether/ethyl acetate) provided the product as a colorless gum. Yield: 116 mg, 0.203 mmol, 88%. LCMS m/z 594.9 [M+Na$^+$].

Step 4. Synthesis of (2R)-1,1,1-trifluoro-3-hydroxypropan-2-yl 4-(phenylsulfonyl)-1-oxa-4,9-diazaspiro[5.5]undecane-9-carboxylate (7)

To a solution of C32 (203 mg, 0.354 mmol) in dichloromethane (10 mL) was added trifluoroacetic acid (2 mL, 30 mmol) and the reaction mixture was stirred at 25° C. for 10 minutes. The reaction was quenched via addition of saturated aqueous sodium bicarbonate solution to a pH of ~8, and the resulting mixture was extracted with dichloromethane (2×20 mL). The combined organic layers were dried over sodium sulfate, filtered, and concentrated in vacuo. Purification via reversed phase HPLC (Column: Phenomenex Luna C18; Mobile phase A: 0.225% formic acid in water; Mobile phase B: acetonitrile; Gradient: 40% to 60% B) afforded the product as a white solid. Yield: 101 mg, 0.224 mmol, 63%. LCMS m/z 452.9 [M+H]$^+$. $^1$H NMR (400 MHz, CDCl$_3$) δ 7.78-7.72 (m, 2H), 7.68-7.62 (m, 1H), 7.61-7.55 (m, 2H), 5.32-5.20 (br m, 1H), 4.05-3.95 (br m, 1H), 3.95-3.8 (m, 3H), 3.79 (dd, J=5.1, 4.8 Hz, 2H), 3.32-3.13 (m, 2H), 3.10-2.92 (br m, 2H), 2.90-2.72 (m, 2H), 2.34-2.22 (br m, 1H), 2.04-1.90 (m, 2H), 1.6-1.44 (m, 2H, assumed; partially obscured by water peak).

Example 8 and 9

(2R)-1,1,1-Trifluoro-3-hydroxypropan-2-yl (3S)-3-[(phenylsulfonyl)amino]-1-oxa-8-azaspiro[4.5]decane-8-carboxylate (8) and (2R)-1,1,1-Trifluoro-3-hydroxypropan-2-yl (3R)-3-[(phenylsulfonyl)amino]-1-oxa-8-azaspiro[4.5]decane-8-carboxylate (9)

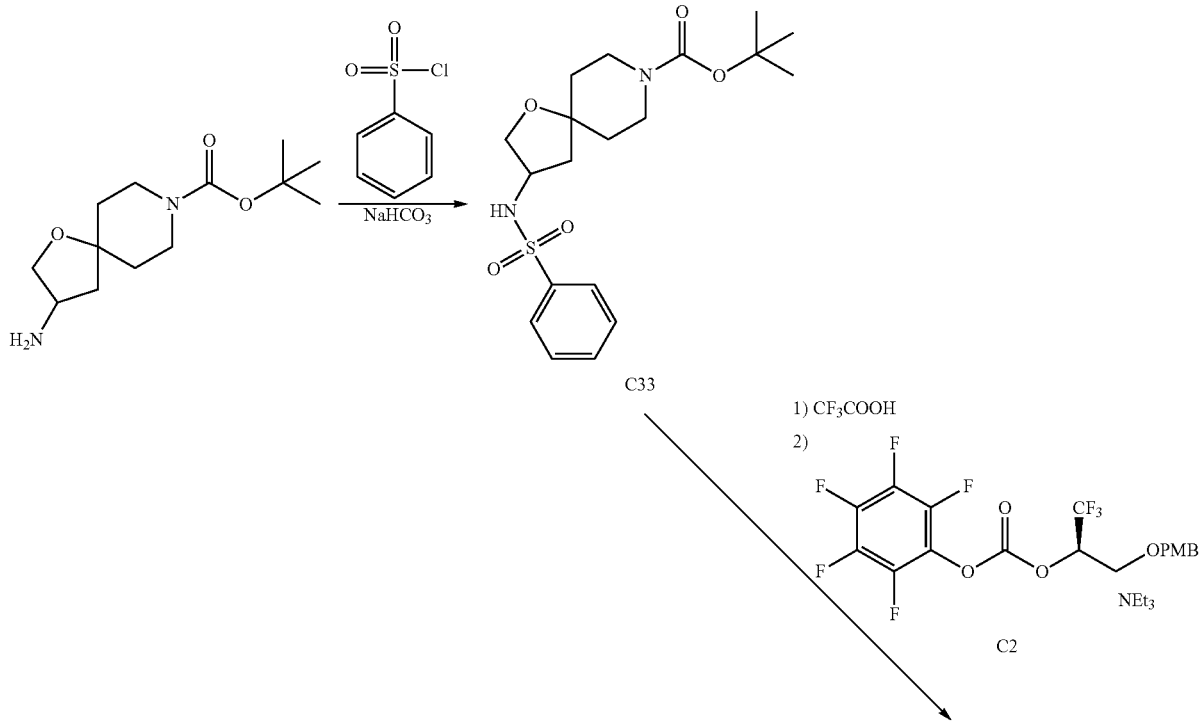

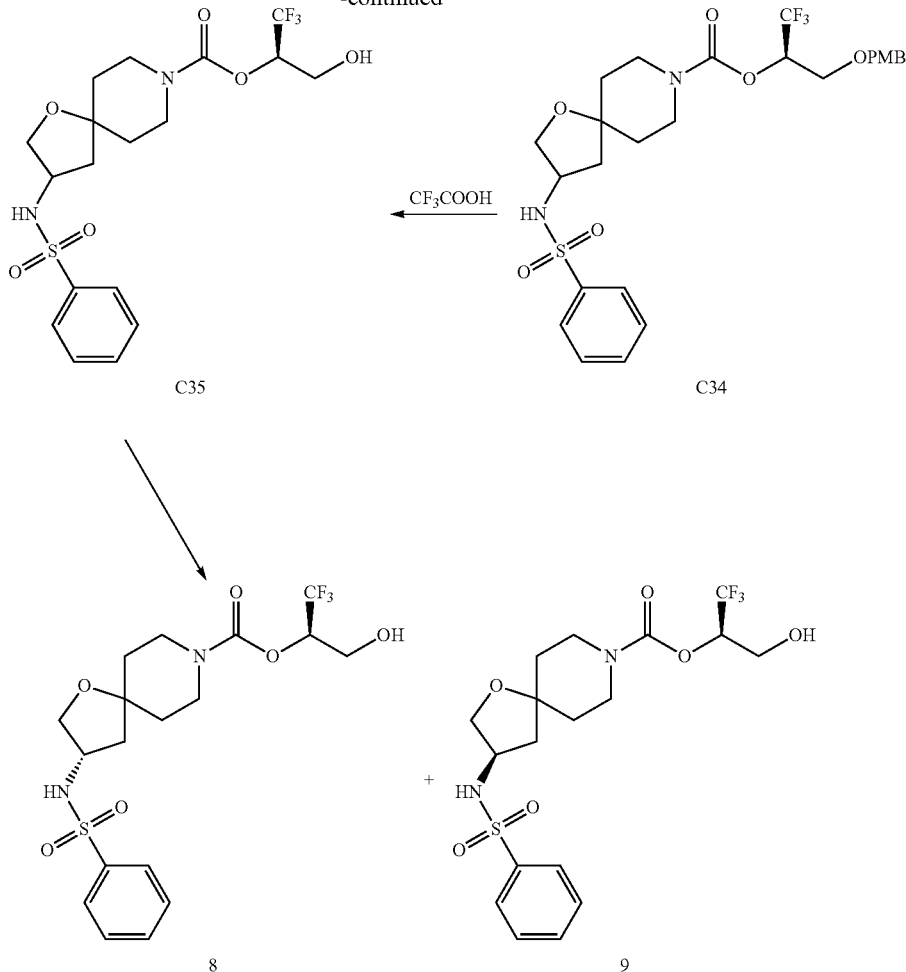

Step 1. Synthesis of tert-butyl 3-[(phenylsulfonyl)amino]-1-oxa-8-azaspiro[4.5]decane-8-carboxylate (C33)

tert-Butyl 3-amino-1-oxa-8-azaspiro[4.5]decane-8-carboxylate was converted to the product using the method described for synthesis of C32 from C31 in Example 7. The product was isolated as a colorless gum. Yield: 200 mg, 0.504 mmol, 65%. LCMS m/z 296.8 [(M-BOC)+H]$^+$. $^1$H NMR (400 MHz, CDCl$_3$) δ 7.91-7.85 (m, 2H), 7.65-7.58 (m, 1H), 7.58-7.51 (m, 2H), 4.82 (br d, J=8 Hz, 1H), 4.00-3.90 (m, 1H), 3.82 (dd, J=9.6, 5.7 Hz, 1H), 3.60-3.48 (m, 3H), 3.31-3.19 (m, 2H), 1.97 (dd, J=13.3, 7.6 Hz, 1H), 1.63-1.48 (m, 5H, assumed; partially obscured by water peak), 1.44 (s, 9H).

Step 2. Synthesis of (2R)-1,1,1-trifluoro-3-[(4-methoxybenzyl)oxy]propan-2-yl 3-[(phenylsulfonyl)amino]-1-oxa-8-azaspiro[4.5]decane-8-carboxylate (C34)

Trifluoroacetic acid (2 mL) was added to a solution of C33 (200 mg, 0.504 mmol) in dichloromethane (5 mL), and the reaction mixture was stirred at 25° C. for 1 hour. Removal of solvents in vacuo provided N-(1-oxa-8-azaspiro[4.5]dec-3-yl)benzenesulfonamide, trifluoroacetic acid salt, as a colorless gum, LCMS m/z 297.0 [M+H]$^+$. This material was dissolved in acetonitrile (5 mL), cooled to 0° C., and treated with triethylamine (153 mg, 1.51 mmol). After this solution had stirred at 0° C. for a few minutes, C2 (reaction solution in acetonitrile containing 0.755 mmol) was added drop-wise, and stirring was continued at 0° C. for 30 minutes. The reaction mixture was then allowed to warm to 25° C. and stir for 18 hours, whereupon it was concentrated under reduced pressure. Silica gel chromatography (Gradient: 1% to 34% ethyl acetate in petroleum) afforded the product as a colorless gum. Yield: 180 mg, 0.314 mmol, 62%. LCMS m/z 595.1 [M+Na$^+$]. $^1$H NMR (400 MHz, CDCl$_3$) δ 7.88 (br d, J=7 Hz, 2H), 7.65-7.60 (m, 1H), 7.59-7.52 (m, 2H), 7.23 (br d, J=8 Hz, 2H), 6.88 (br d, J=8 Hz, 2H), 5.52-5.40 (m, 1H), 4.64-4.58 (m, 1H), 4.50 (AB quartet, J$_{AB}$=11.3 Hz, Δv$_{AB}$=28 Hz, 2H), 4.01-3.91 (m, 1H), 3.82 (s, 3H), 3.88-3.78 (m, 1H), 3.78-3.62 (m, 4H), 3.59-3.47 (m, 1H), 3.36-3.21 (m, 2H), 2.02-1.91 (m, 1H), 1.72-1.38 (m, 5H, assumed; partially obscured by water peak).

Step 3. Synthesis of (2R)-1,1,1-trifluoro-3-hydroxypropan-2-yl 3-[(phenylsulfonyl)amino]-1-oxa-8-azaspiro[4.5]decane-8-carboxylate (C35)

Trifluoroacetic acid (2 mL) was added to a 0° C. solution of C34 (180 mg, 0.314 mmol) in dichloromethane (8 mL) and the reaction mixture was stirred at 0° C. for 30 minutes, whereupon it was treated with saturated aqueous sodium bicarbonate solution until the pH was above 7. The aqueous layer was extracted with ethyl acetate (5×5 mL), and the combined organic layers were dried over sodium sulfate, filtered, and concentrated in vacuo. Preparative thin layer chromatography on silica gel (Eluent: 1:1 petroleum ether/ethyl acetate) provided a diastereomeric mixture of the product as a colorless oil. Yield: 130 mg, 0.287 mmol, 91%.

Step 4. Isolation of (2R)-1,1,1-trifluoro-3-hydroxypropan-2-yl (3S)-3-[(phenylsulfonyl)amino]-1-oxa-8-azaspiro[4.5]decane-8-carboxylate (8) and (2R)-1,1,1-trifluoro-3-hydroxypropan-2-yl (3R)-3-[(phenylsulfonyl)amino]-1-oxa-8-azaspiro[4.5]decane-8-carboxylate (9)

Compound C35 (130 mg, 0.287 mmol) was separated into its component diastereomers via supercritical fluid chromatography (Column: Chiral Technologies Chiralpak AD, 5 μm; Mobile phase: 3:7 2-propanol/carbon dioxide). The first-eluting diastereomer was further purified by preparative thin layer chromatography on silica gel (Eluent: 1:1 petroleum ether/ethyl acetate) to afford 8 as a colorless gum. Yield for the separation: 62.0 mg, 0.137 mmol, 48%. LCMS m/z 474.8 [M+Na$^+$]. $^1$H NMR (400 MHz, CDCl$_3$) δ 7.91-7.85 (m, 2H), 7.66-7.59 (m, 1H), 7.59-7.52 (m, 2H), 5.30-5.18 (br m, 1H), 4.89-4.77 (br m, 1H), 4.03-3.90 (m, 2H), 3.90-3.64 (m, 4H), 3.58-3.50 (m, 1H), 3.39-3.19 (m, 2H), 1.99 (dd, J=13.6, 7.6 Hz, 1H), 1.75-1.44 (m, 5H, assumed; partially obscured by water peak).

The second-eluting diastereomer was 9, also isolated as a colorless gum. Yield for the separation: 67.0 mg, 0.148 mmol, 52%. LCMS m/z 475.1 [M+Na$^+$]. $^1$H NMR (400 MHz, CDCl$_3$) δ 7.91-7.85 (m, 2H), 7.66-7.59 (m, 1H), 7.59-7.52 (m, 2H), 5.29-5.18 (m, 1H), 4.87-4.79 (m, 1H), 4.04-3.90 (m, 2H), 3.90-3.79 (m, 2H), 3.79-3.66 (m, 2H), 3.58-3.50 (m, 1H), 3.41-3.21 (m, 2H), 2.05-1.93 (m, 1H), 1.75-1.39 (m, 5H, assumed; partially obscured by water peak).

The absolute configurations indicated for 8 and 9 were established by relation to the X-ray crystal structure determination of C48 (see Example 15) in the following manner: C48 and its enantiomer C49 were converted to samples of the general structure of 8 and 9 using the methods described in this Example. Supercritical fluid chromatography (Column: Chiral Technologies Chiralpak AD, 5 um; Mobile phase A: carbon dioxide; Mobile phase B: 2-propanol; Gradient: 5% to 60% B) provided a clear correlation between the material derived from C48 and 9 (retention times 7.44 and 7.45 minutes). Likewise, the material derived from C49 exhibited a very similar retention time to that of 8 (6.86 and 6.87 minutes).

Example 10

(2R)-1,1,1-Trifluoro-3-hydroxypropan-2-yl 4-[(5-cyclopropylpyridin-2-yl)oxy]piperidine-1-carboxylate (10)

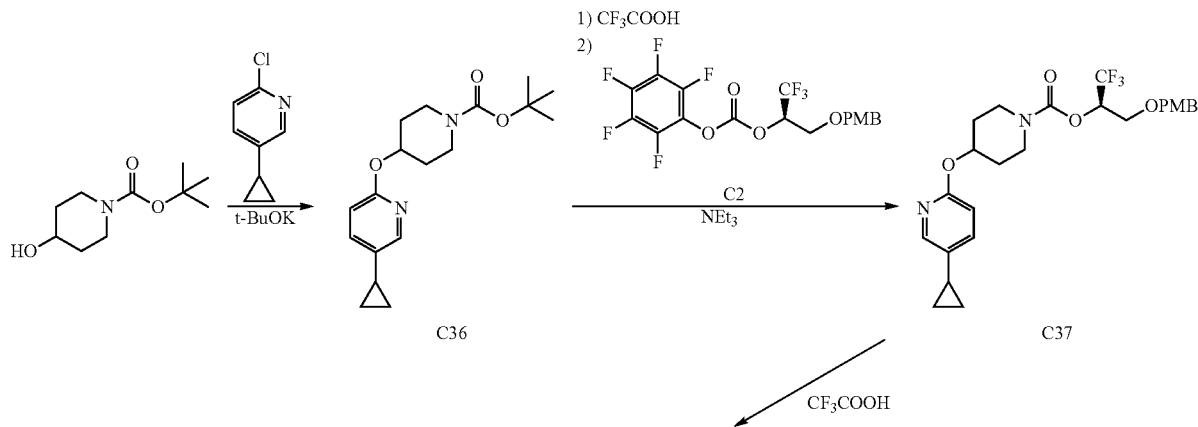

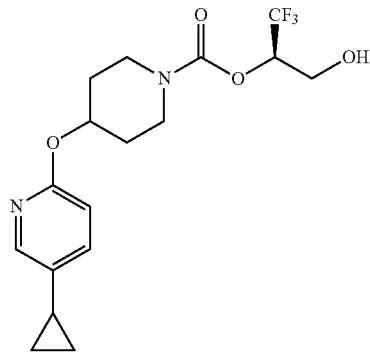

10

Step 1. Synthesis of tert-butyl 4-[(5-cyclopropylpyridin-2-yl)oxy]piperidine-1-carboxylate (C36)

Potassium tert-butoxide (913 mg, 8.14 mmol) was added to a solution of tert-butyl 4-hydroxypiperidine-1-carboxylate (983 mg, 4.88 mmol) in N,N-dimethylformamide (30 mL) and the reaction mixture was heated at 50° C. for 2 hours. 2-Chloro-5-cyclopropylpyridine (250 mg, 1.63 mmol) was then added, and the reaction mixture was stirred at 100° C. for 18 hours. After solvent had been removed in vacuo, the residue was diluted with water (50 mL) and extracted with ethyl acetate (3×50 mL); the combined organic layers were concentrated under reduced pressure. Chromatography on silica gel (Gradient: 0% to 10% ethyl acetate in petroleum ether) afforded the product as a white solid. Yield: 120 mg, 0.377 mmol, 23%. $^1$H NMR (400 MHz, CDCl$_3$) δ 7.97-7.93 (m, 1H), 7.3-7.21 (m, 1H, assumed; partially obscured by solvent peak), 6.62 (d, J=8.4 Hz, 1H), 5.22-5.13 (m, 1H), 3.82-3.72 (m, 2H), 3.34-3.24 (m, 2H), 2.02-1.92 (m, 2H), 1.88-1.78 (m, 1H), 1.77-1.65 (m, 2H), 1.48 (s, 9H), 0.97-0.90 (m, 2H), 0.65-0.59 (m, 2H).

Step 2. Synthesis of (2R)-1,1,1-trifluoro-3-[(4-methoxybenzyl)oxy]propan-2-yl 4-[(5-cyclopropylpyridin-2-yl)oxy]piperidine-1-carboxylate (C37)

Conversion of C36 to C37 was carried out using the method described for synthesis of C34 from C33 in Examples 8 and 9. The product was isolated as a colorless gum. Yield: 120 mg, 0.243 mmol, 64%.

$^1$H NMR (400 MHz, CDCl$_3$) of intermediate 5-cyclopropyl-2-(piperidin-4-yloxy)pyridine, trifluoroacetic acid salt, characteristic peaks: δ 8.07-8.03 (m, 1H), 7.79 (br d, J=8 Hz, 1H), 7.07 (d, J=9 Hz, 1H), 3.60-3.45 (m, 2H), 3.43-3.32 (m, 2H), 2.46-2.34 (m, 2H), 2.24-2.13 (m, 2H), 2.01-1.91 (m, 1H), 1.17-1.09 (m, 2H), 0.79-0.72 (m, 2H).

Compound C37: LCMS m/z 517.0 [M+Na$^+$]. $^1$H NMR (400 MHz, CDCl$_3$) δ 7.97-7.92 (m, 1H), 7.30-7.22 (m, 3H, assumed; partially obscured by solvent peak), 6.89 (d, J=8.5 Hz, 2H), 6.64 (d, J=8.4 Hz, 1H), 5.55-5.44 (m, 1H), 5.24-5.15 (m, 1H), 4.52 (AB quartet, J$_{AB}$=11.5 Hz, Δv$_{AB}$=260.5 Hz, 2H), 3.82 (s, 3H), 3.8-3.66 (m, 4H), 3.52-3.39 (m, 2H), 2.06-1.90 (m, 2H), 1.89-1.70 (m, 3H), 0.98-0.91 (m, 2H), 0.66-0.59 (m, 2H).

Step 3. Synthesis of (2R)-1,1,1-trifluoro-3-hydroxypropan-2-yl 4-[(5-cyclopropylpyridin-2-yl)oxy]piperidine-1-carboxylate (10)

Trifluoroacetic acid (5 mL) was added drop-wise to a solution of C37 (120 mg, 0.243 mmol) in dichloromethane (15 mL), and the reaction mixture was stirred at 30° C. for 2 hours, whereupon it was concentrated in vacuo and diluted with ethyl acetate (20 mL). The resulting mixture was poured into saturated aqueous sodium bicarbonate solution (20 mL) and extracted with ethyl acetate (3×20 mL); the combined organic layers were concentrated under reduced pressure. Preparative thin layer chromatography on silica gel (Eluent: 1:1 petroleum ether:ethyl acetate) provided the product as a colorless gum. Yield: 70 mg, 0.19 mmol, 78%. LCMS m/z 375.0 [M+H]$^+$. $^1$H NMR (400 MHz, CDCl$_3$) δ 7.94 (d, J=2.1 Hz, 1H), 7.25 (dd, J=8.5, 2.4 Hz, 1H), 6.63 (d, J=8.5 Hz, 1H), 5.32-5.19 (m, 2H), 4.01 (br d, half of AB quartet, J=12 Hz, 1H), 3.88 (dd, half of ABX pattern, J=12, 7 Hz, 1H), 3.87-3.70 (m, 2H), 3.57-3.40 (m, 2H), 2.52-2.40 (br s, 1H), 2.07-1.93 (m, 2H), 1.89-1.74 (m, 3H), 0.98-0.91 (m, 2H), 0.66-0.59 (m, 2H).

Example 11

(2R)-1,1,1-Trifluoro-3-hydroxypropan-2-yl 4-[(3-fluorophenyl)sulfonyl]-1-oxa-4,9-diazaspiro[5.5]undecane-9-carboxylate (11)

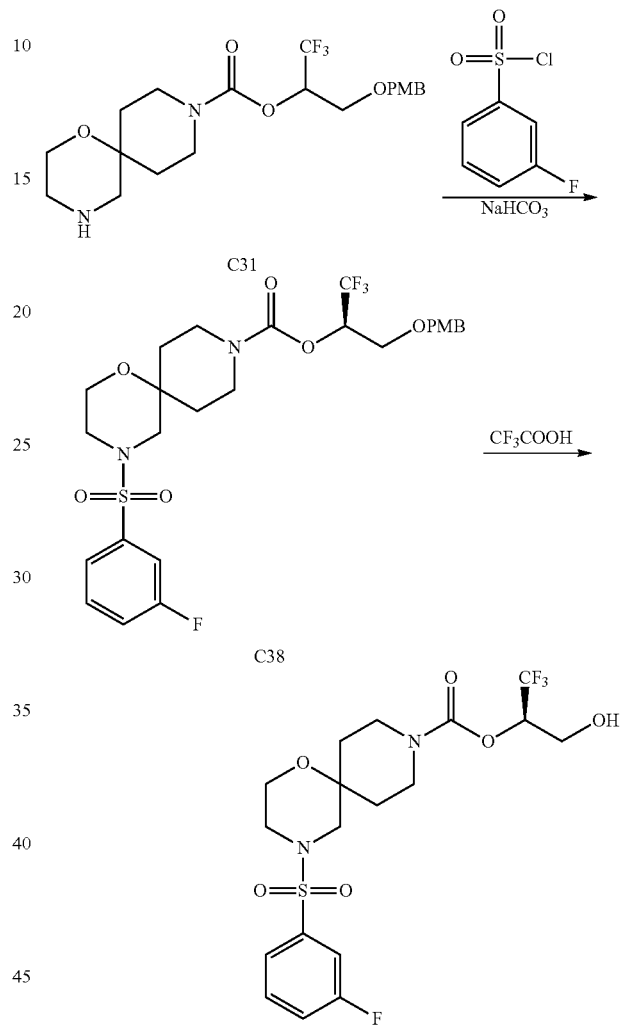

Step 1. Synthesis of (2R)-1,1,1-trifluoro-3-[(4-methoxybenzyl)oxy]propan-2-yl 4-[(3-fluorophenyl)sulfonyl]-1-oxa-4,9-diazaspiro[5.5]undecane-9-carboxylate (C38)

Conversion of C31 to the product was carried out using the method described for synthesis of C32 from C31 in Example 7, providing C38 as a colorless gum. Yield: 130 mg, 0.220 mmol, 79%. LCMS m/z 612.9 [M+Na$^+$].

Step 2. Synthesis of (2R)-1,1,1-trifluoro-3-hydroxypropan-2-yl 4-[(3-fluorophenyl)sulfonyl]-1-oxa-4,9-diazaspiro[5.5]undecane-9-carboxylate (11)

Trifluoroacetic acid (2 mL, 30 mmol) was added to a solution of C38 (190 mg, 0.322 mmol) in dichloromethane (10 mL) and the reaction mixture was stirred at 25° C. for 10 minutes, whereupon it was treated with saturated aqueous sodium bicarbonate solution to a pH of ~8. The mixture was extracted with dichloromethane (2×20 mL), and the combined organic layers were dried over sodium sulfate, filtered, and concentrated in vacuo. Purification via reversed phase HPLC (Column: Phenomenex Luna C18; Mobile phase A: 0.225% formic acid in water; Mobile phase B: acetonitrile; Gradient: 43% to 63% B) afforded the product as a white solid. Yield: 93.4 mg, 0.198 mmol, 61%. LCMS m/z 470.9 [M+H]$^+$. $^1$H NMR (400 MHz, CDCl$_3$) δ 7.61-7.52 (m, 2H), 7.48-7.43 (m, 1H), 7.39-7.32 (m, 1H), 5.31-5.20 (m, 1H), 4.06-3.96 (m, 1H), 3.95-3.83 (m, 3H), 3.80 (dd, J=5.0, 4.9 Hz, 2H), 3.32-3.14 (m, 2H), 3.11-2.95 (m, 2H), 2.91-2.75 (m, 2H), 2.33-2.23 (m, 1H), 2.05-1.92 (m, 2H), 1.6-1.45 (m, 2H, assumed; partially obscured by water peak).

Example 12

(2R)-1,1,1-Trifluoro-3-hydroxypropan-2-yl 2-[(4-fluorophenyl)sulfonyl]-2,9-diazaspiro[5.5]undecane-9-carboxylate (12)

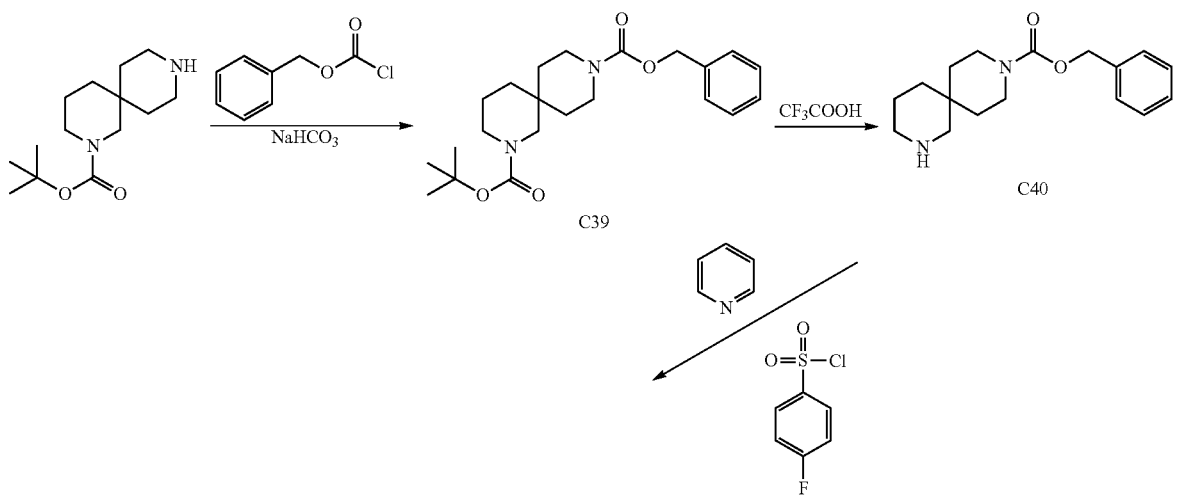

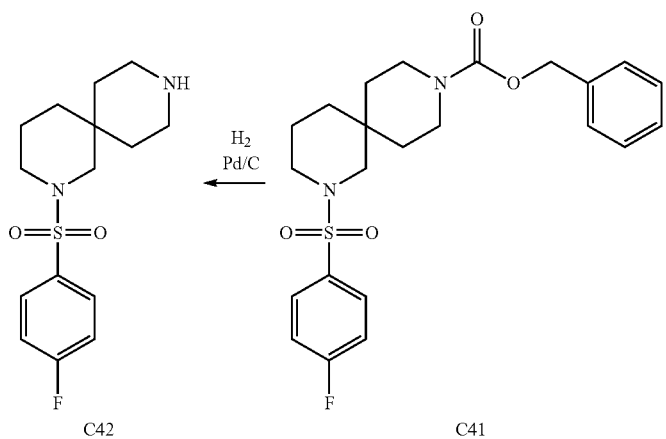

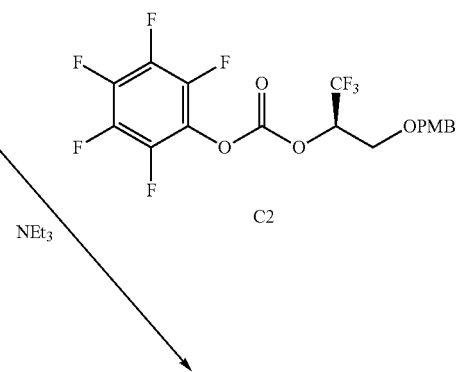

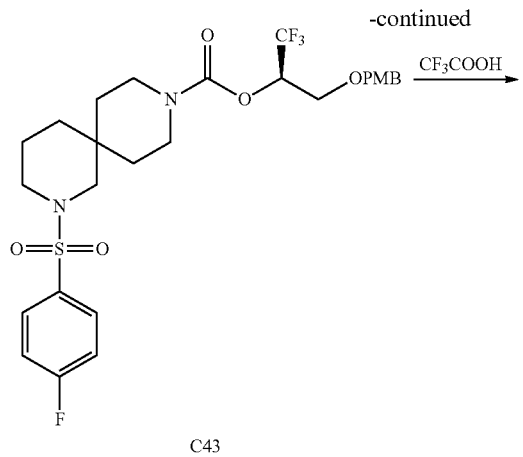
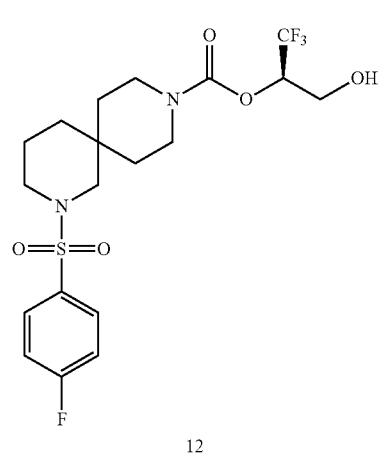

Step 1. Synthesis of 9-benzyl 2-tert-butyl 2,9-diazaspiro[5.5]undecane-2,9-dicarboxylate (C39)

Saturated aqueous sodium bicarbonate solution (5 mL) and benzyl chloroformate (161 mg, 0.944 mmol) were added to a 0° C. solution of tert-butyl 2,9-diazaspiro[5.5]undecane-2-carboxylate (200 mg, 0.786 mmol) in ethyl acetate (5 mL), and the reaction mixture was stirred for 18 hours at 30° C. The aqueous layer was extracted with ethyl acetate (2×5 mL), and the combined organic layers were dried over sodium sulfate, filtered, and concentrated in vacuo; silica gel chromatography (Gradient: 0% to 20% ethyl acetate in petroleum ether) provided the product as an oil. Yield: 235 mg, 0.605 mmol, 77%. $^1$H NMR (400 MHz, CDCl$_3$) δ 7.41-7.29 (m, 5H), 5.13 (s, 2H), 3.73-3.60 (m, 2H), 3.48-3.19 (m, 6H), 1.60-1.50 (m, 2H), 1.50-1.28 (m, 6H), 1.45 (m, 9H).

Step 2. Synthesis of benzyl 2,9-diazaspiro[5.5]undecane-9-carboxylate (C40)

Trifluoroacetic acid (3 mL) was added to a solution of C39 (235 mg, 0.605 mmol) in dichloromethane (5 mL) and the reaction mixture was stirred for 30 minutes at room temperature. After removal of solvents in vacuo, the residue was taken up in aqueous sodium bicarbonate solution (20 mL) and extracted with dichloromethane (3×20 mL). The combined organic layers were dried over sodium sulfate, filtered, and concentrated in vacuo to afford the product as a gum. Yield: 116 mg, 0.402 mmol, 66%. LCMS m/z 289.1 [M+H]$^+$.

Step 3. Synthesis of benzyl 2-[(4-fluorophenyl)sulfonyl]-2,9-diazaspiro[5.5]undecane-9-carboxylate (C41)

4-Fluorobenzenesulfonyl chloride (117 mg, 0.601 mmol) was added to a solution of C40 (116 mg, 0.402 mmol) in pyridine (2 mL) and the reaction mixture was stirred for 18 hours at 30° C., whereupon it was concentrated in vacuo. The residue was partitioned between dichloromethane (20 mL) and saturated aqueous sodium bicarbonate solution (20 mL), and the organic layer was concentrated under reduced pressure. Silica gel chromatography (Gradient: 0% to 25% ethyl acetate in petroleum ether) provided the product as a gum. Yield: 140 mg, 0.314 mmol, 78%. LCMS m/z 446.9 [M+H]$^+$. $^1$H NMR (400 MHz, CDCl$_3$) δ 7.81-7.73 (m, 2H), 7.41-7.29 (m, 5H), 7.22 (dd, J=8.8, 8.4 Hz, 2H), 5.14 (s, 2H), 3.64-3.54 (m, 2H), 3.44-3.32 (m, 2H), 3.22-3.04 (m, 1H), 3.04-2.80 (m, 2H), 2.80-2.60 (m, 1H), 1.77-1.65 (m, 2H), 1.65-1.5 (m, 2H, assumed; obscured by water peak), 1.44 (ddd, J=14, 9, 4 Hz, 2H), 1.39-1.29 (m, 2H).

Step 4. Synthesis of 2-[(4-fluorophenyl)sulfonyl]-2,9-diazaspiro[5.5]undecane (C42)

To a solution of C41 (60.0 mg, 0.134 mmol) in tetrahydrofuran (10 mL) was added 10% palladium on carbon (14.3 mg, 13.4 μmol), and the mixture was stirred under a hydrogen atmosphere (45 psi) for 18 hours at 50° C. After filtration of the reaction mixture, the filter cake was washed with methanol (20 mL); the combined filtrates were concentrated in vacuo to afford the product as a colorless gum. Yield: 42.0 mg, 0.134 mmol, 100%. LCMS m/z 312.9 [M+H]$^+$.

Step 5. Synthesis of (2R)-1,1,1-trifluoro-3-[(4-methoxybenzyl)oxy]propan-2-yl 2-[(4-fluorophenyl)sulfonyl]-2,9-diazaspiro[5.5]undecane-9-carboxylate (C43)

Conversion of C42 to the product was effected using the method described for synthesis of C30 in Example 7. In this case, purification was carried out via preparative thin layer chromatography on silica gel (Eluent: 3:1 petroleum ether/ethyl acetate) to afford the product as a gum. Yield: 55 mg, 93 μmol, 35%. LCMS m/z 611.0 [M+Na]$^+$.

Step 6. Synthesis of (2R)-1,1,1-trifluoro-3-hydroxypropan-2-yl 2-[(4-fluorophenyl)sulfonyl]-2,9-diazaspiro[5.5]undecane-9-carboxylate (12)

Conversion of C43 to the product was carried out using the method described for synthesis of 11 from C38 in Example 11, except that the reaction was carried out at 0° C. Purification was effected via preparative thin layer chromatography on silica gel (Eluent: 9:1 dichloromethane/methanol) to provide the product as a white solid. Yield: 13 mg, 28 μmol, 30%. LCMS m/z 491.1 [M+Na]$^+$. $^1$H NMR (400 MHz, CDCl$_3$) δ 7.77 (br dd, J=8.5, 5.0 Hz, 2H), 7.23 (dd, J=8.5, 8.3 Hz, 2H), 5.32-5.20 (m, 1H), 4.05-3.95 (m, 1H), 3.92-3.81 (m, 1H), 3.69-3.53 (m, 2H), 3.50-3.31 (m, 2H), 3.16-3.02 (m, 1H), 3.01-2.84 (m, 2H), 2.81-2.69 (m, 1H), 1.80-1.54 (m, 5H), 1.54-1.42 (m, 2H), 1.41-1.31 (m, 2H).

Example 13

(2R)-1,1,1-Trifluoro-3-hydroxypropan-2-yl (3aR,6aS)-5-[(3,4-difluorophenyl)sulfonyl]hexahydropyrrolo[3,4-c]pyrrole-2(1H)-carboxylate (13)

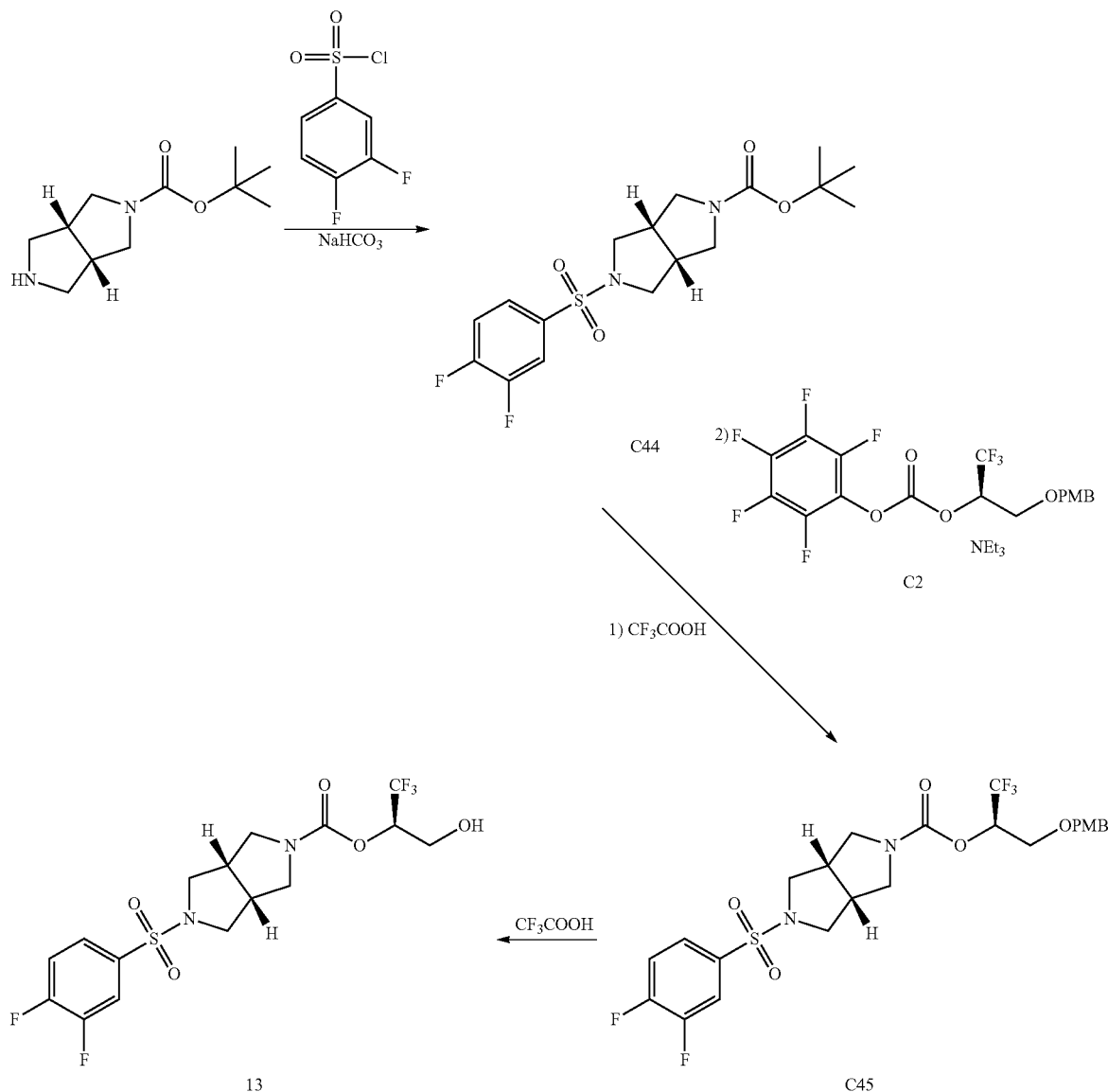

Step 1. Synthesis of tert-butyl (3aR,6aS)-5-[(3,4-difluorophenyl)sulfonyl]hexahydropyrrolo[3,4-c]pyrrole-2(1H)-carboxylate (C44)

tert-Butyl (3aR,6aS)-hexahydropyrrolo[3,4-c]pyrrole-2(1H)-carboxylate was converted to C44 using the method described for synthesis of C32 from C31 in Example 7. The product was obtained as a white solid. Yield: 100 mg, 0.257 mmol, 68%. LCMS m/z 410.9 [M+Na+]. $^1$H NMR (400 MHz, CDCl$_3$) δ 7.68 (ddd, J=9, 7, 2 Hz, 1H), 7.64-7.59 (m, 1H), 7.36 (ddd, J=9, 9, 7 Hz, 1H), 3.57-3.48 (m, 2H), 3.48-3.39 (m, 2H), 3.20-2.98 (m, 4H), 2.89-2.80 (m, 2H), 1.44 (s, 9H).

Step 2. Synthesis of (2R)-1,1,1-trifluoro-3-[(4-methoxybenzyl)oxy]propan-2-yl (3aR,6aS)-5-[(3,4-difluorophenyl)sulfonyl]hexahydropyrrolo[3,4-c]pyrrole-2(1H)-carboxylate (C45)

Conversion of C44 to C45 was effected using the method described for synthesis of C34 from C33 in Examples 8 and 9. $^1$H NMR (400 MHz, CD$_3$OD) of intermediate (3aR,6aS)-2-[(3,4-difluorophenyl)sulfonyl]octahydropyrrolo[3,4-c]pyrrole, trifluoroacetic acid salt, δ 7.80 (ddd, J=9.7, 7.3, 2.2 Hz, 1H), 7.72-7.67 (m, 1H), 7.58 (ddd, J=10.0, 8.7, 7.5 Hz, 1H), 3.60-3.53 (m, 2H), 3.38-3.33 (m, 2H), 3.13-3.07 (m, 2H), 3.07-2.96 (m, 4H). In this case, purification was carried out via preparative thin layer chromatography on silica gel (Eluent: 2:1 petroleum ether/ethyl acetate) to afford C45 as a colorless gum. By ¹H NMR analysis, this was judged to be a mixture of rotamers. Yield: 100 mg, 0.18 mmol, 69%. LCMS m/z 587.0 [M+Na⁺]. ¹H NMR (400 MHz, CDCl₃) δ 7.71-7.64 (m, 1H), 7.64-7.57 (m, 1H), 7.39-7.31 (m, 1H), 7.28-7.20 (m, 2H, assumed; partially obscured by solvent peak), 6.94-6.85 (m, 2H), 5.47-5.37 (m, 1H), 4.58-4.41 (m, 2H), [3.83 (s) and 3.81 (s), total 3H], 3.77-3.55 (m, 4H), 3.55-3.35 (m, 2H), 3.29-3.05 (m, 4H), 2.95-2.84 (m, 2H).

Step 3. Synthesis of (2R)-1,1,1-trifluoro-3-hydroxypropan-2-yl (3aR,6aS)-5-[(3,4-difluorophenyl)sulfonyl]hexahydropyrrolo[3,4-c]pyrrole-2(1H)-carboxylate (13)

Conversion of C45 to 13 was carried out using the method described for synthesis of C35 from C34 in Examples 8 and 9. The product was isolated as a colorless oil. Yield: 40 mg, 90 μmol, 50%. LCMS m/z 445.0 [M+H]⁺. ¹H NMR (400 MHz, CDCl₃) δ 7.68 (br dd, J=9.0, 7.3 Hz, 1H), 7.64-7.58 (m, 1H), 7.42-7.31 (m, 1H), 5.29-5.18 (m, 1H), 4.03-3.93 (m, 1H), 3.90-3.79 (m, 1H), 3.74-3.58 (m, 2H), 3.52-3.42 (m, 1H), 3.42-3.07 (m, 5H), 2.99-2.84 (m, 2H).

Example 14

(2R)-1,1,1-Trifluoro-3-hydroxypropan-2-yl 4-(5-fluoropyridin-2-yl)-1-oxa-4,9-diazaspiro[5.5]undecane-9-carboxylate (14)

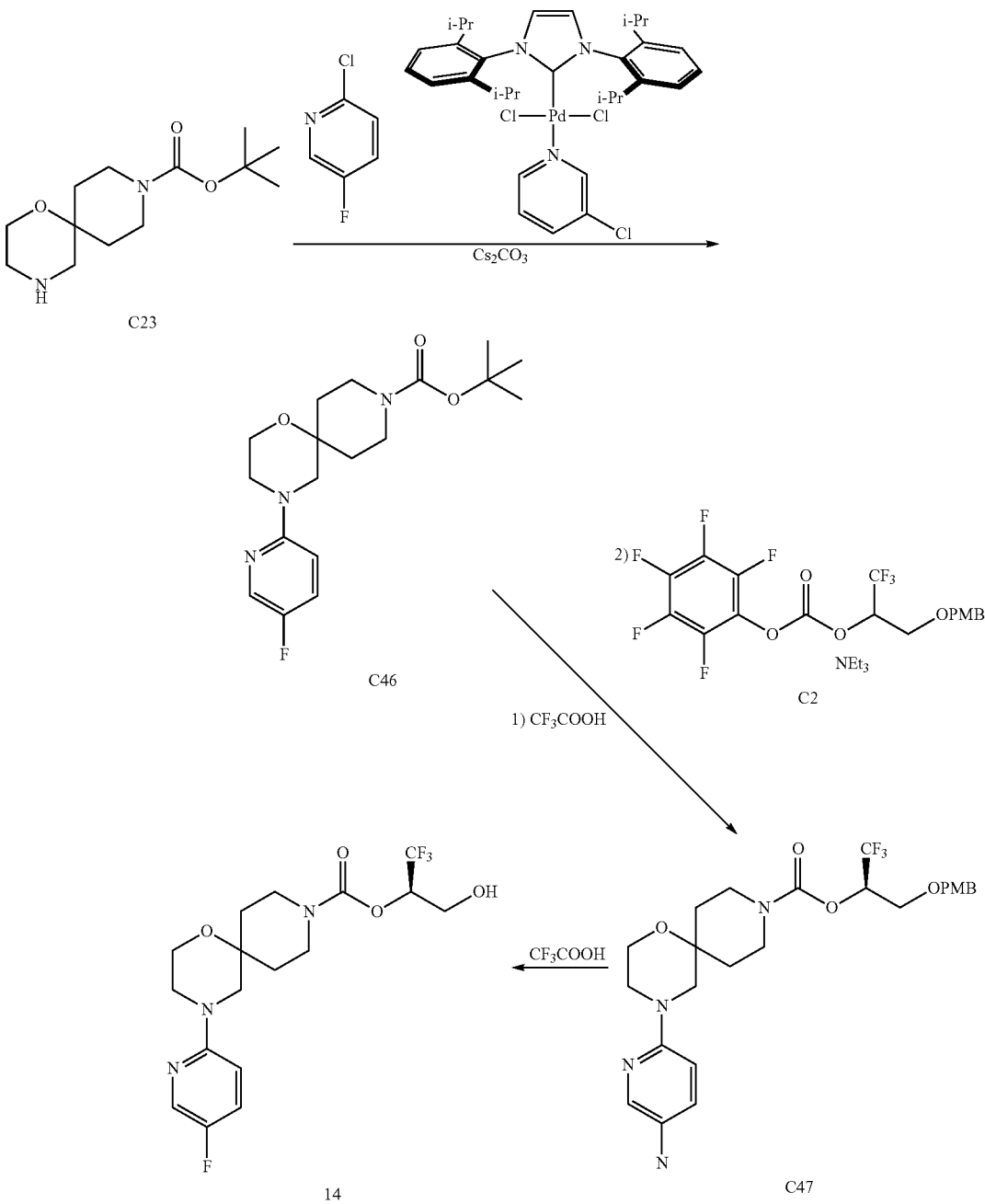

Step 1. Synthesis of tert-butyl 4-(5-fluoropyridin-2-yl)-1-oxa-4,9-diazaspiro[5.5]undecane-9-carboxylate (C46)

A mixture of C23 (100 mg, 0.39 mmol), 2-chloro-5-fluoropyridine (103 mg, 0.783 mmol), [1,3-bis(2,6-diisopropylphenyl)imidazol-2-ylidene](3-chloropyridyl)palladium(II) dichloride (26.6 mg, 39.1 μmol), and cesium carbonate (381 mg, 1.17 mmol) in toluene (10 mL) was heated at 120° C. for 3 days. The reaction mixture was then filtered and the filtrate was concentrated in vacuo; silica gel chromatography (Gradient: 0% to 10% methanol in dichloromethane) afforded the product as a brown gum. Yield: 135 mg, 0.384 mmol, 98%. LCMS m/z 352.3 [M+H]$^+$. $^1$H NMR (400 MHz, CDCl$_3$) δ 8.03 (d, J=3.0 Hz, 1H), 7.26 (ddd, J=9.2, 7.7, 3.1 Hz, 1H), 6.57 (dd, J=9.3, 3.3 Hz, 1H), 3.83 (dd, J=6.0, 4.1 Hz, 2H), 3.8-3.65 (m, 2H), 3.42 (dd, J=5.4, 4.8 Hz, 2H), 3.33 (s, 2H), 3.19 (br dd, J=12, 12 Hz, 2H), 1.91 (br d, J=13 Hz, 2H), 1.56-1.45 (m, 2H), 1.46 (s, 9H).

Step 2. Synthesis of (2R)-1,1,1-trifluoro-3-[(4-methoxybenzyl)oxy]propan-2-yl 4-(5-fluoropyridin-2-yl)-1-oxa-4,9-diazaspiro[5.5]undecane-9-carboxylate (C47)

Conversion of C46 to C47 was carried out using the method described for synthesis of C34 from C33 in Examples 8 and 9. LCMS of intermediate 4-(5-fluoropyridin-2-yl)-1-oxa-4,9-diazaspiro[5.5]undecane, bis(trifluoroacetic acid) salt, m/z 252.1 [M+H]$^+$. In this case, purification was carried out using preparative thin layer chromatography (Eluent: 3:1 petroleum ether/ethyl acetate) to afford C47 as a light yellow gum. Yield: 70 mg, 0.13 mmol, 68%. LCMS m/z 528.2 [M+H]$^+$.

Step 3. Synthesis of (2R)-1,1,1-trifluoro-3-hydroxypropan-2-yl 4-(5-fluoropyridin-2-yl)-1-oxa-4,9-diazaspiro[5.5]undecane-9-carboxylate (14)

Trifluoroacetic acid (1 mL) was added to a 0° C. solution of C47 (70 mg, 0.13 mmol) in dichloromethane (5 mL), and the reaction mixture was stirred at 25° C. for 1 hour. Solvents were removed in vacuo, and the residue was subjected to preparative thin layer chromatography on silica gel (Eluent: 2:3 petroleum ether/ethyl acetate). Further purification using reversed phase HPLC (Column: Agela Durashell C18, 5 μm; Mobile phase A: 0.225% formic acid in water; Mobile phase B: 0.225% formic acid in acetonitrile; Gradient: 38% to 58% B) provided the product as a colorless gum. Yield: 33.4 mg, 82.0 μmol, 63%. LCMS m/z 408.1 [M+H]$^+$. $^1$H NMR (400 MHz, CDCl$_3$) δ 8.04 (d, J=2.8 Hz, 1H), 7.31-7.23 (m, 1H, assumed; partially obscured by solvent peak), 6.59 (dd, J=9.2, 3.1 Hz, 1H), 5.32-5.20 (m, 1H), 4.06-3.77 (m, 6H), 3.49-3.39 (m, 2H), 3.39-3.19 (m, 4H), 2.68-2.38 (br s, 1H), 2.08-1.92 (m, 2H), 1.62-1.48 (m, 2H).

Example 15

(2R)-1,1,1-Trifluoro-3-hydroxypropan-2-yl (3R)-3-[methyl(phenylsulfonyl)amino]-1-oxa-8-azaspiro[4.5]decane-8-carboxylate (15)

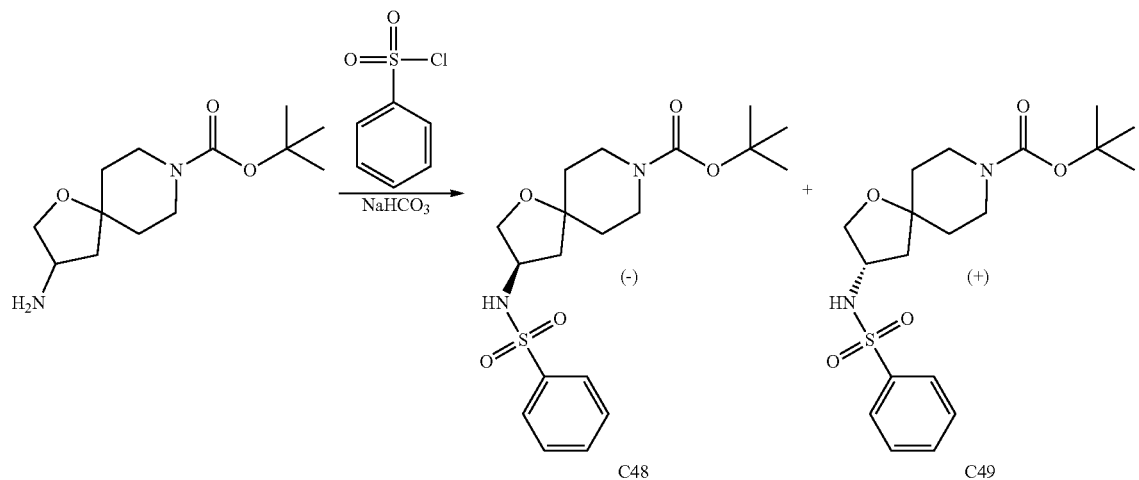

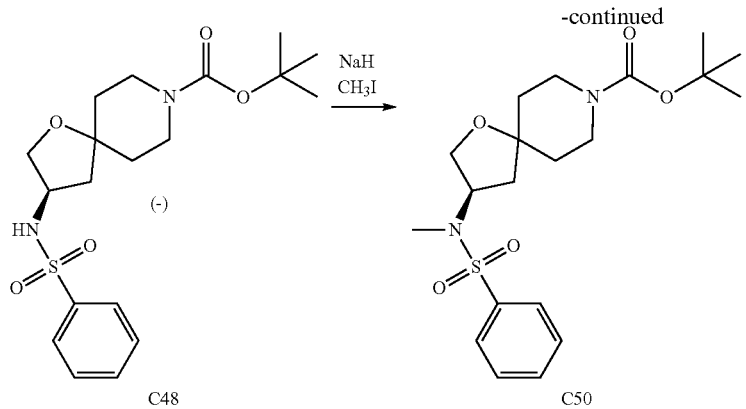

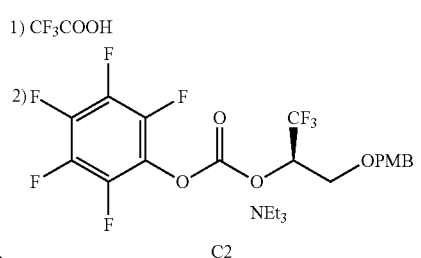

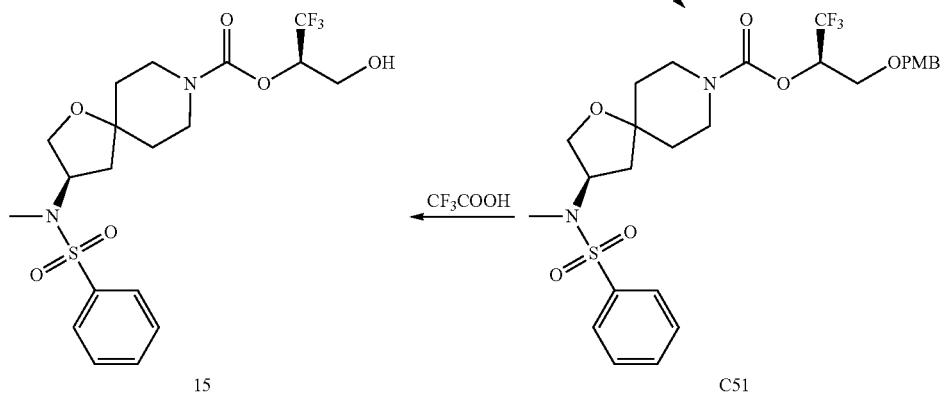

Step 1. Synthesis of tert-butyl (3R)-3-[(phenylsulfonyl)amino]-1-oxa-8-azaspiro[4.5]decane-8-carboxylate (C48) and tert-butyl (3S)-3-[(phenylsulfonyl)amino]-1-oxa-8-azaspiro[4.5]decane-8-carboxylate (C49)

Reaction of tert-butyl 3-amino-1-oxa-8-azaspiro[4.5]decane-8-carboxylate with benzenesulfonyl chloride was carried out as described for synthesis of C32 from C31 in Example 7. The racemic product was purified using silica gel chromatography (Gradient: 20% to 50% ethyl acetate in heptane) to afford a white solid (2.88 g), which was then separated into its component enantiomers via supercritical fluid chromatography [Column: Phenomenex Lux Cellulose-3, 5 µm; Eluent: 7.5% (1:1 methanol/acetonitrile) in carbon dioxide]. The first-eluting product, obtained as a tacky white solid that exhibited a negative (−) rotation, was designated as C48. Yield: 1.35 g, 3.40 mmol, 45%. LCMS m/z 395.5 [M−H+]. $^1$H NMR (400 MHz, CDCl$_3$) δ 7.90-7.86 (m, 2H), 7.64-7.59 (m, 1H), 7.57-7.52 (m, 2H), 4.81 (d, J=7.9 Hz, 1H), 4.00-3.91 (m, 1H), 3.81 (dd, J=9.7, 5.7 Hz, 1H), 3.59-3.48 (m, 3H), 3.30-3.19 (m, 2H), 1.97 (dd, J=13.4, 7.7 Hz, 1H), 1.67-1.49 (m, 4H), 1.48-1.38 (m, 1H), 1.44 (s, 9H).

The second-eluting product, obtained as a tacky white solid that exhibited a positive (+) rotation, was designated as C49. Yield: 1.15 g, 2.90 mmol, 38%. LCMS m/z 395.5 [M−H+]. $^1$H NMR (400 MHz, CDCl$_3$) δ 7.90-7.86 (m, 2H), 7.64-7.59 (m, 1H), 7.57-7.52 (m, 2H), 4.79 (d, J=8.0 Hz, 1H), 4.00-3.91 (m, 1H), 3.81 (dd, J=9.7, 5.7 Hz, 1H), 3.59-3.48 (m, 3H), 3.30-3.19 (m, 2H), 1.97 (dd, J=13.4, 7.7 Hz, 1H), 1.67-1.49 (m, 4H), 1.47-1.38 (m, 1H), 1.44 (s, 9H).

The absolute configurations shown were established as follows: a portion of this batch of C48 was recrystallized from dichloromethane/tert-butyl methyl ether, and its absolute configuration was determined via single crystal X-ray structure determination:

Single-Crystal X-Ray Structural Determination of C48

Data collection was performed on a Bruker APEX diffractometer at room temperature. Data collection consisted of omega and phi scans.

The structure was solved by direct methods using SHELX software suite in the space group $P2_12_12_1$. The structure was subsequently refined by the full-matrix least squares method. All non-hydrogen atoms were found and refined using anisotropic displacement parameters.

The hydrogen atom located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2010). The results indicate that the absolute structure has been correctly assigned. The method calculates that the probability that the structure is correct is 100.0. The Hooft parameter is reported as 0.015 with an esd of 0.09.

The final R-index was 4.2%. A final difference Fourier revealed no missing or misplaced electron density.

Pertinent crystal, data collection and refinement information is summarized in Table 1. Atomic coordinates, bond lengths, bond angles, and displacement parameters are listed in Tables 2-5.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE 1

Crystal data and structure refinement for C48.

| | |
|---|---|
| Empirical formula | $C_{19}H_{28}N_2O_5S$ |
| Formula weight | 396.50 |
| Temperature | 276(2) K |
| Wavelength | 1.54178 Å |
| Crystal system | Orthorhombic |
| Space group | $P2_12_12_1$ |
| Unit cell dimensions | a = 9.79150(10) Å   α = 90° |
| | b = 11.11580(10) Å   β = 90° |
| | c = 18.6694(2) Å   γ = 90° |
| Volume | 2031.98(4) Å³ |
| Z | 4 |
| Density (calculated) | 1.296 Mg/m³ |
| Absorption coefficient | 1.686 mm⁻¹ |
| F(000) | 848 |
| Crystal size | 0.260 × 0.180 × 0.140 mm³ |
| Theta range for data collection | 4.630 to 68.568° |
| Index ranges | −11 <= h <= 11, −13 <= k <= 13, −20 <= l <= 22 |
| Reflections collected | 9404 |
| Independent reflections | 3633 [R(int) = 0.0247] |
| Completeness to theta = 70.31° | 99.3% |
| Absorption correction | None |
| Refinement method | Full-matrix least-squares on $F^2$ |
| Data/restraints/parameters | 3633/1/251 |
| Goodness-of-fit on $F^2$ | 1.067 |
| Final R indices [I > 2sigma(I)] | R1 = 0.0418, wR2 = 0.1074 |
| R indices (all data) | R1 = 0.0441, wR2 = 0.1098 |
| Absolute structure parameter | 0.017(9) |
| Extinction coefficient | n/a |
| Largest diff. peak and hole | 0.428 and −0.457 e.Å⁻³ |

TABLE 2

Atomic coordinates (×10⁴) and equivalent isotropic displacement parameters (Å² × 10³) for C48. U(eq) is defined as one-third of the trace of the orthogonalized $U^{ij}$ tensor.

| | x | y | z | U(eq) |
|---|---|---|---|---|
| S(1) | −3733(1) | 10920(1) | 849(1) | 53(1) |
| N(1) | −3045(3) | 9602(2) | 839(2) | 59(1) |
| N(2) | 3033(2) | 7292(2) | 1366(2) | 52(1) |
| O(1) | −5113(3) | 10761(2) | 1075(1) | 74(1) |
| O(2) | −2848(3) | 11724(2) | 1218(1) | 68(1) |
| O(3) | 29(3) | 8787(2) | 1780(1) | 68(1) |
| O(4) | 5295(2) | 7383(2) | 1100(1) | 53(1) |
| O(5) | 4386(2) | 5806(2) | 1709(1) | 55(1) |
| C(1) | −4868(3) | 11071(3) | −483(2) | 63(1) |
| C(2) | −4920(4) | 11465(4) | −1195(2) | 76(1) |
| C(3) | −3910(5) | 12188(4) | −1452(2) | 77(1) |
| C(4) | −2853(5) | 12532(4) | −1029(2) | 80(1) |
| C(5) | −2775(3) | 12136(3) | −315(2) | 64(1) |
| C(6) | −3796(3) | 11406(2) | −54(2) | 49(1) |
| C(7) | −1575(3) | 9468(3) | 927(2) | 49(1) |
| C(8) | −1069(4) | 9583(4) | 1697(2) | 77(1) |
| C(9) | 248(3) | 8100(3) | 1135(2) | 48(1) |
| C(10) | −1087(3) | 8216(3) | 724(2) | 51(1) |
| C(11) | 601(3) | 6821(3) | 1356(2) | 62(1) |
| C(12) | 1914(4) | 6735(3) | 1772(2) | 67(1) |
| C(13) | 2776(3) | 8526(3) | 1137(2) | 55(1) |
| C(14) | 1463(3) | 8609(3) | 722(2) | 49(1) |
| C(15) | 4329(3) | 6873(2) | 1372(2) | 46(1) |
| C(16) | 5650(3) | 5100(3) | 1749(2) | 50(1) |
| C(17) | 6713(4) | 5783(4) | 2169(2) | 69(1) |
| C(18) | 6126(5) | 4758(4) | 1005(2) | 82(1) |
| C(19) | 5191(4) | 3991(3) | 2158(2) | 62(1) |

TABLE 3

Bond lengths [Å] and angles [°] for C48.

| | |
|---|---|
| S(1)—O(2) | 1.423(3) |
| S(1)—O(1) | 1.426(2) |
| S(1)—N(1) | 1.613(2) |
| S(1)—C(6) | 1.772(3) |
| N(1)—C(7) | 1.456(4) |
| N(2)—C(15) | 1.353(4) |
| N(2)—C(13) | 1.459(4) |
| N(2)—C(12) | 1.468(4) |
| O(3)—C(8) | 1.400(4) |
| O(3)—C(9) | 1.441(4) |
| O(4)—C(15) | 1.214(4) |
| O(5)—C(15) | 1.344(3) |
| O(5)—C(16) | 1.467(3) |
| C(1)—C(6) | 1.372(5) |
| C(1)—C(2) | 1.400(5) |
| C(2)—C(3) | 1.362(6) |
| C(3)—C(4) | 1.358(6) |
| C(4)—C(5) | 1.405(5) |
| C(5)—C(6) | 1.376(4) |
| C(7)—C(10) | 1.520(4) |
| C(7)—C(8) | 1.525(5) |
| C(9)—C(11) | 1.520(4) |
| C(9)—C(10) | 1.521(4) |
| C(9)—C(14) | 1.526(4) |
| C(11)—C(12) | 1.506(5) |
| C(13)—C(14) | 1.503(4) |
| C(16)—C(17) | 1.508(5) |
| C(16)—C(18) | 1.514(5) |
| C(16)—C(19) | 1.518(4) |
| O(2)—S(1)—O(1) | 120.73(17) |
| O(2)—S(1)—N(1) | 108.79(15) |
| O(1)—S(1)—N(1) | 106.64(15) |
| O(2)—S(1)—C(6) | 106.86(14) |
| O(1)—S(1)—C(6) | 106.70(15) |
| N(1)—S(1)—C(6) | 106.29(15) |
| C(7)—N(1)—S(1) | 120.3(2) |
| C(15)—N(2)—C(13) | 119.2(2) |
| C(15)—N(2)—C(12) | 123.4(2) |
| C(13)—N(2)—C(12) | 114.8(3) |

TABLE 3-continued

Bond lengths [Å] and angles [°] for C48.

| | |
|---|---|
| C(8)—O(3)—C(9) | 110.9(2) |
| C(15)—O(5)—C(16) | 122.1(2) |
| C(6)—C(1)—C(2) | 119.8(3) |
| C(3)—C(2)—C(1) | 119.6(4) |
| C(4)—C(3)—C(2) | 120.9(4) |
| C(3)—C(4)—C(5) | 120.4(4) |
| C(6)—C(5)—C(4) | 118.7(3) |
| C(1)—C(6)—C(5) | 120.6(3) |
| C(1)—C(6)—S(1) | 119.9(2) |
| C(5)—C(6)—S(1) | 119.4(3) |
| N(1)—C(7)—C(10) | 112.1(3) |
| N(1)—C(7)—C(8) | 114.8(3) |
| C(10)—C(7)—C(8) | 102.1(3) |
| O(3)—C(8)—C(7) | 107.5(3) |
| O(3)—C(9)—C(11) | 107.7(3) |
| O(3)—C(9)—C(10) | 104.4(2) |
| C(11)—C(9)—C(10) | 114.3(3) |
| O(3)—C(9)—C(14) | 109.9(3) |
| C(11)—C(9)—C(14) | 107.9(2) |
| C(10)—C(9)—C(14) | 112.6(2) |
| C(7)—C(10)—C(9) | 102.8(2) |
| C(12)—C(11)—C(9) | 113.1(3) |
| N(2)—C(12)—C(11) | 110.1(3) |
| N(2)—C(13)—C(14) | 110.9(3) |
| C(13)—C(14)—C(9) | 112.6(2) |
| O(4)—C(15)—O(5) | 125.2(3) |
| O(4)—C(15)—N(2) | 124.5(3) |
| O(5)—C(15)—N(2) | 110.3(2) |
| O(5)—C(16)—C(17) | 109.8(3) |
| O(5)—C(16)—C(18) | 110.3(3) |
| C(17)—C(16)—C(18) | 113.0(3) |
| O(5)—C(16)—C(19) | 102.1(2) |
| C(17)—C(16)—C(19) | 110.6(3) |
| C(18)—C(16)—C(19) | 110.4(3) |

Symmetry transformations used to generate equivalent atoms.

TABLE 4

Anisotropic displacement parameters (Å$^2$ × 10$^3$) for C48.
The anisotropic displacement factor exponent takes the form:
$-2\pi^2[h^2 a^{*2}U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| S(1) | 48(1) | 42(1) | 69(1) | 2(1) | 10(1) | 8(1) |
| N(1) | 44(1) | 42(1) | 91(2) | 9(1) | 4(1) | 3(1) |
| N(2) | 41(1) | 49(1) | 67(2) | 17(1) | 2(1) | 2(1) |
| O(1) | 57(1) | 69(1) | 95(2) | 19(1) | 28(1) | 18(1) |
| O(2) | 80(2) | 52(1) | 70(2) | −7(1) | −6(1) | 9(1) |
| O(3) | 66(2) | 88(2) | 49(1) | −8(1) | −5(1) | 24(1) |
| O(4) | 43(1) | 49(1) | 68(1) | 7(1) | 4(1) | 0(1) |
| O(5) | 46(1) | 46(1) | 73(1) | 16(1) | 1(1) | 4(1) |
| C(1) | 45(2) | 51(2) | 92(2) | 0(2) | −4(2) | −4(1) |
| C(2) | 66(2) | 78(2) | 84(2) | −6(2) | −20(2) | 2(2) |
| C(3) | 85(3) | 77(2) | 69(2) | 6(2) | −1(2) | 2(2) |
| C(4) | 77(2) | 83(3) | 81(2) | 12(2) | 15(2) | −22(2) |
| C(5) | 53(2) | 65(2) | 75(2) | 1(2) | 2(2) | −18(2) |
| C(6) | 40(1) | 36(1) | 70(2) | −2(1) | 5(1) | 4(1) |
| C(7) | 42(2) | 44(1) | 60(2) | 2(1) | 4(1) | 4(1) |
| C(8) | 78(2) | 83(2) | 70(2) | −22(2) | −9(2) | 27(2) |
| C(9) | 47(2) | 49(2) | 48(2) | −1(1) | 3(1) | 6(1) |
| C(10) | 46(1) | 49(1) | 57(2) | −5(2) | 1(1) | 7(1) |
| C(11) | 44(2) | 54(2) | 91(2) | 21(2) | 9(2) | 1(1) |
| C(12) | 50(2) | 69(2) | 83(2) | 35(2) | 10(2) | 9(2) |
| C(13) | 48(2) | 48(2) | 68(2) | 10(2) | −2(1) | 0(1) |
| C(14) | 51(2) | 45(1) | 51(2) | 5(2) | 1(1) | 5(1) |
| C(15) | 44(2) | 43(1) | 50(1) | 2(1) | −1(1) | 2(1) |
| C(16) | 51(2) | 51(2) | 48(2) | 5(1) | 1(1) | 13(1) |
| C(17) | 56(2) | 80(2) | 70(2) | 17(2) | −7(2) | −6(2) |
| C(18) | 120(4) | 71(2) | 56(2) | 4(2) | 14(2) | 37(2) |
| C(19) | 71(2) | 51(2) | 64(2) | 12(1) | −4(2) | 10(2) |

TABLE 5

Hydrogen coordinates (×10$^4$) and isotropic displacement parameters (Å$^2$ × 10$^3$) for C48.

| | x | y | z | U(eq) |
|---|---|---|---|---|
| H(1X) | −3660(30) | 8980(20) | 932(17) | 57(9) |
| H(1) | −5558 | 10584 | −302 | 75 |
| H(2) | −5639 | 11234 | −1490 | 91 |
| H(3) | −3946 | 12450 | −1925 | 92 |
| H(4) | −2177 | 13033 | −1212 | 96 |
| H(5) | −2047 | 12362 | −25 | 77 |
| H(7) | −1107 | 10063 | 628 | 59 |
| H(8A) | −776 | 10401 | 1791 | 92 |
| H(8B) | −1794 | 9380 | 2029 | 92 |
| H(10A) | −938 | 8151 | 212 | 61 |
| H(10B) | −1738 | 7606 | 872 | 61 |
| H(11A) | −137 | 6501 | 1645 | 75 |
| H(11B) | 674 | 6326 | 929 | 75 |
| H(12A) | 1811 | 7141 | 2229 | 81 |
| H(12B) | 2127 | 5898 | 1865 | 81 |
| H(13A) | 3526 | 8801 | 840 | 66 |
| H(13B) | 2726 | 9045 | 1554 | 66 |
| H(14A) | 1562 | 8173 | 275 | 59 |
| H(14B) | 1285 | 9446 | 607 | 59 |
| H(17A) | 7038 | 6448 | 1888 | 103 |
| H(17B) | 7462 | 5258 | 2281 | 103 |
| H(17C) | 6316 | 6080 | 2605 | 103 |
| H(18A) | 5376 | 4423 | 741 | 124 |
| H(18B) | 6844 | 4173 | 1040 | 124 |
| H(18C) | 6460 | 5461 | 763 | 124 |
| H(19A) | 4803 | 4229 | 2609 | 93 |
| H(19B) | 5962 | 3476 | 2242 | 93 |
| H(19C) | 4519 | 3565 | 1883 | 93 |

Step 2. Synthesis of tert-butyl (3R)-3-[methyl(phenylsulfonyl)amino]-1-oxa-8-azaspiro[4.5]decane-8-carboxylate (C50)

To a solution of C48 (1.5 g, 3.8 mmol) in N,N-dimethylformamide at 0° C. was added sodium hydride (60% dispersion in mineral oil; 227 mg, 5.67 mmol). The reaction mixture was stirred at room temperature for 30 minutes, whereupon iodomethane (1.61 g, 11.3 mmol) was added, and stirring was continued for 1 hour. Saturated aqueous ammonium chloride solution was added, and the aqueous layer was extracted three times with ethyl acetate. The combined organic layers were dried over magnesium sulfate, filtered, and concentrated in vacuo to provide the product. Yield: 1.53 g, 3.73 mmol, 98%. $^1$H NMR (400 MHz, CDCl$_3$) δ 7.80-7.76 (m, 2H), 7.63-7.58 (m, 1H), 7.56-7.50 (m, 2H), 4.73-4.64 (m, 1H), 3.78 (dd, J=10.2, 7.4 Hz, 1H), 3.64-3.51 (m, 2H), 3.55 (dd, J=10.2, 4.9 Hz, 1H), 3.27-3.13 (m, 2H), 2.76 (s, 3H), 1.87 (dd, J=13.5, 9.1 Hz, 1H), 1.63-1.54 (m, 3H), 1.44 (dd, J=13.5, 6.8 Hz, 1H), 1.43 (s, 9H), 1.37 (br ddd, J=13, 10, 4 Hz, 1H).

Step 3. Synthesis of (2R)-1,1,1-trifluoro-3-[(4-methoxybenzyl)oxy]propan-2-yl (3R)-3-[methyl(phenylsulfonyl)amino]-1-oxa-8-azaspiro[4.5]decane-8-carboxylate (C51)

Conversion of C50 to C51 was carried out using the method described for synthesis of C34 from C33 in Examples 8 and 9. Purification in this case was effected via silica gel chromatography (Gradient: 0% to 60% ethyl acetate in heptane) to afford the product as a colorless oil. Yield: 1.7 g, 2.9 mmol, 77%. LCMS m/z 609.4 [M+Na$^+$]. $^1$H NMR (400 MHz, CDCl$_3$) δ 7.82-7.78 (m, 2H), 7.64-7.59 (m, 1H), 7.57-7.52 (m, 2H), 7.23 (br d, J=8.7 Hz, 2H), 6.87 (br d, J=8.6 Hz, 2H), 5.52-5.40 (m, 1H), 4.75-4.63 (m, 1H), 4.49 (AB quartet, upfield doublet is broadened, J$_{AB}$=11.7 Hz, Δv$_{AB}$=28.4 Hz, 2H), 3.85-3.62 (m, 5H), 3.81 (s, 3H), 3.62-3.52 (m, 1H), 3.34-3.17 (m, 2H), 2.77 (s, 3H), 1.85 (dd, J=13.5, 9.1 Hz, 1H), 1.71-1.53 (m, 3H), 1.46 (dd, J=13.5, 6.9 Hz, 1H), 1.38 (ddd, J=13.5, 11.2, 4.4 Hz, 1H).

Step 4. Synthesis of (2R)-1,1,1-trifluoro-3-hydroxypropan-2-yl (3R)-3-[methyl(phenylsulfonyl)amino]-1-oxa-8-azaspiro[4.5]decane-8-carboxylate (15)

Trifluoroacetic acid (10.8 mL) was added drop-wise to a 0° C. solution of C51 (1.7 g, 2.9 mmol) in dichloromethane (30 mL) and the reaction mixture was stirred for 1.5 hours at room temperature. After removal of solvents in vacuo, the residue was dissolved in ethyl acetate and washed with saturated aqueous sodium bicarbonate solution. The aqueous layer was extracted with ethyl acetate, and the combined organic layers were dried over magnesium sulfate, filtered, and concentrated under reduced pressure. Silica gel chromatography (Gradient: 0% to 80% ethyl acetate in heptane) provided the product as a white solid. Yield: 1.06 g, 2.27 mmol, 78%. LCMS m/z 467.4 [M+H]$^+$. $^1$H NMR (400 MHz, CDCl$_3$) δ 7.81-7.77 (m, 2H), 7.64-7.59 (m, 1H), 7.57-7.51 (m, 2H), 5.28-5.18 (m, 1H), 4.74-4.65 (m, 1H), 3.98 (dd, half of ABX pattern, J=12.5, 3.3 Hz, 1H), 3.89-3.69 (m, 3H), 3.80 (dd, J=10.3, 7.4 Hz, 1H), 3.62-3.54 (m, 1H), 3.38-3.19 (m, 2H), 2.77 (s, 3H), 2.4-2.0 (v br s, 1H), 1.94-1.81 (m, 1H), 1.72-1.59 (m, 3H), 1.48 (br dd, J=13, 6 Hz, 1H), 1.45-1.34 (m, 1H).

Example 16

(2R)-1,1,1-Trifluoro-3-hydroxypropan-2-yl 4-hydroxy-4-{[(phenylsulfonyl)amino]methyl}piperidine-1-carboxylate (16)

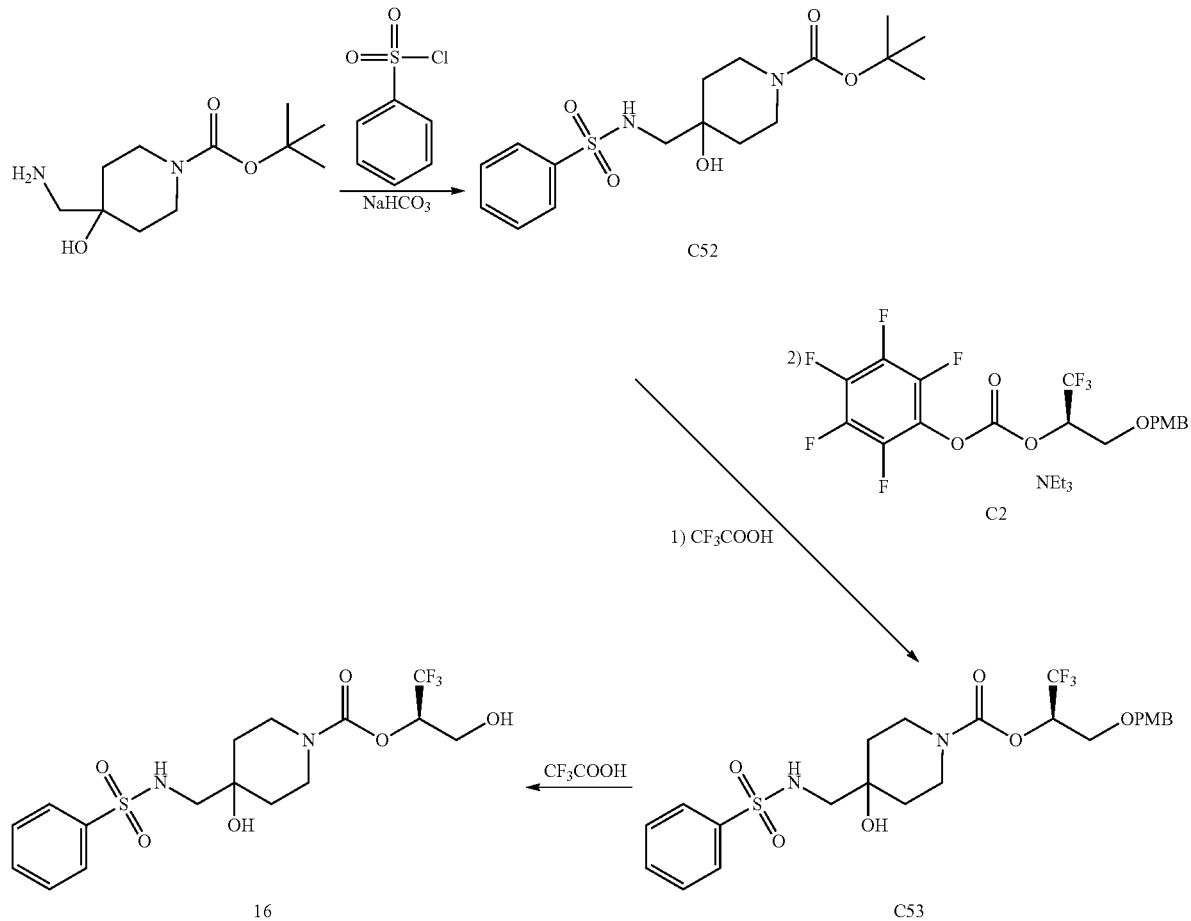

Step 1. Synthesis of tert-butyl/4-hydroxy-4-{[(phenylsulfonyl)amino]methyl/}piperidine-1-carboxylate (C52)

tert-Butyl 4-(aminomethyl)-4-hydroxypiperidine-1-carboxylate was converted to C52 using the method described for synthesis of C32 from C31 in Example 7. Purification via preparative thin layer chromatography (Eluent: 10:1 dichloromethane/methanol) afforded the product as a colorless gum. Yield: 127 mg, 0.343 mmol, 79%. LCMS m/z 393.0 [M+Na$^+$]. $^1$H NMR (400 MHz, CDCl$_3$) δ 7.90-7.84 (m, 2H), 7.64-7.58 (m, 1H), 7.57-7.51 (m, 2H), 5.10 (br t, J=6.6 Hz, 1H), 3.83-3.70 (m, 2H), 3.17 (br dd, J=12, 11 Hz, 2H), 2.92 (br d, J=6 Hz, 2H), 2.16 (br s, 1H), 1.63-1.54 (m, 2H), 1.53-1.45 (m, 2H), 1.45 (s, 9H).

Step 2. Synthesis of (2R)-1,1,1-trifluoro-3-[(4-methoxybenzyl)oxy]propan-2-yl 4-hydroxy-4-{[(phenylsulfonyl)amino]methyl/}piperidine-1-carboxylate (C53)

Conversion of C52 to C53 was carried out using the method described for synthesis of C34 from C33 in Examples 8 and 9. Purification in this case was effected via preparative thin layer chromatography on silica gel (Eluent:

1:1 ethyl acetate/petroleum ether) to afford the product as a colorless gum. Yield: 60 mg, 0.11 mmol, 58% over 3 steps. LCMS m/z 569.1 [M+Na$^+$].

Step 3. Synthesis of (2R)-1,1,1-trifluoro-3-hydroxypropan-2-yl 4-hydroxy-4-{[(phenylsulfonyl)amino]methyl/}piperidine-1-carboxylate (16)

Conversion of C53 to 16 was carried out using the method described for synthesis of 1 from C12 in Example 1. Purification via reversed phase HPLC (Column: Agela Durashell C18, 5 μm; Mobile phase A: 0.1% aqueous hydrochloric acid; Mobile phase B: acetonitrile; Gradient: 28% to 48% B) afforded the product as a white solid. Yield: 23 mg, 54 μmol, 49%. LCMS m/z 449.0 [M+Na$^+$]. $^1$H NMR (400 MHz, CDCl$_3$), characteristic peaks: δ 7.85 (br d, J=7 Hz, 2H), 7.59 (br dd, half of ABX pattern, J=7, 7 Hz, 1H), 7.53 (br dd, half of ABX pattern, J=7, 7 Hz, 2H), 5.87-5.69 (m, 1H), 5.33-5.20 (m, 1H), 4.02-3.91 (m, 1H), 3.92-3.74 (m, 3H), 3.39-3.16 (m, 2H), 1.74-1.38 (m, 4H).

Example 17

(2R)-1,1,1-Trifluoro-3-hydroxypropan-2-yl 4-(4-fluorobenzyl)-3-oxo-1-oxa-4,9-diazaspiro[5.5]undecane-9-carboxylate (17)

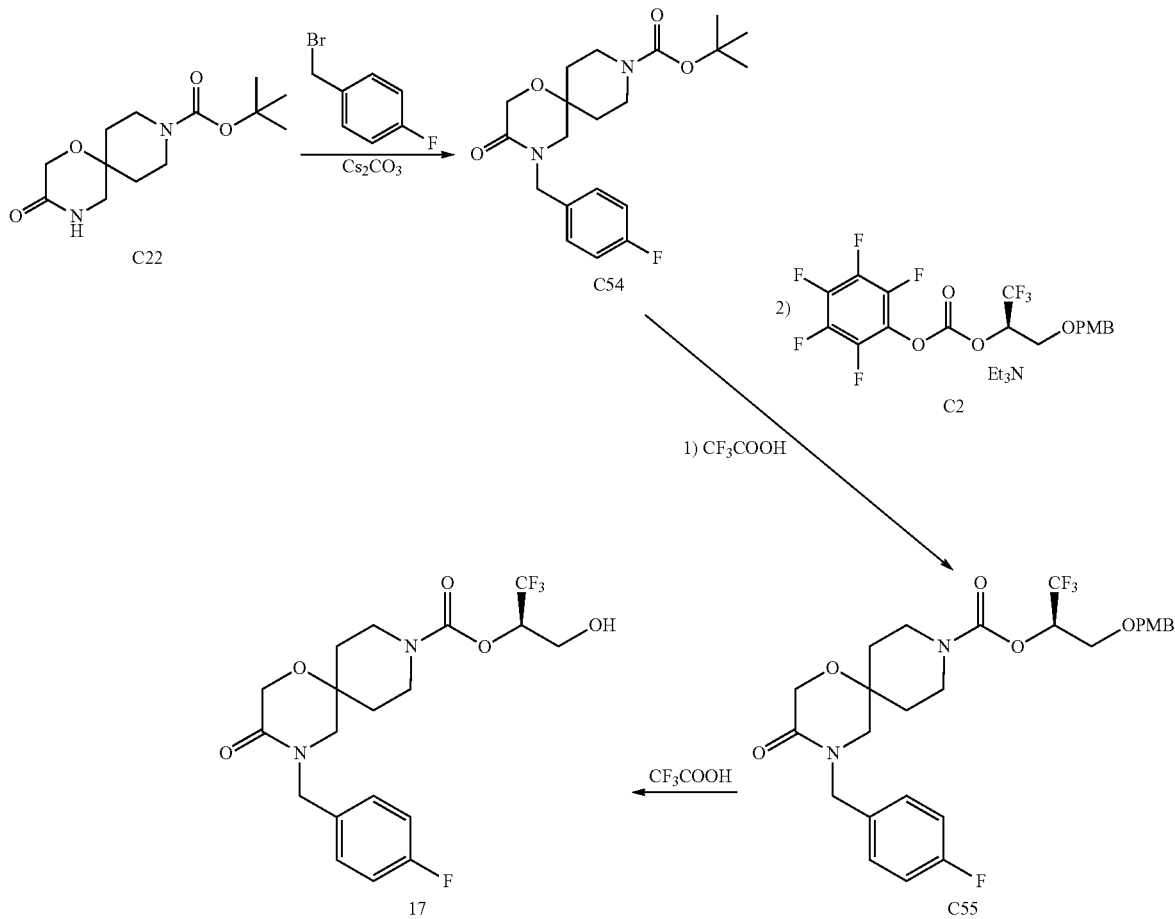

Step 1. Synthesis of tert-butyl 4-(4-fluorobenzyl)-3-oxo-1-oxa-4,9-diazaspiro[5.5]undecane-9-carboxylate (C54)

A mixture of C22 (100 mg, 0.370 mmol), 1-(bromomethyl)-4-fluorobenzene (119 mg, 0.629 mmol), and cesium carbonate (241 mg, 0.740 mmol) in N,N-dimethylformamide (2 mL) was stirred at 100° C. for 64 hours. The reaction mixture was then filtered and concentrated in vacuo; the residue was purified by preparative thin layer chromatography on silica gel (Eluent: 1:1 petroleum ether/ethyl acetate), affording the product as a colorless gum. Yield: 42 mg, 0.11 mmol, 30%. $^1$H NMR (400 MHz, CDCl$_3$) δ 7.28-7.21 (m, 2H, assumed; partially obscured by solvent peak), 7.04 (br dd, J=8.7, 8.5 Hz, 2H), 4.57 (s, 2H), 4.23 (s, 2H), 3.82-3.67 (m, 2H), 3.14-3.03 (m, 2H), 3.07 (s, 2H), 1.84-1.74 (m, 2H), 1.44 (s, 9H), 1.42-1.32 (m, 2H).

Step 2. Synthesis of (2R)-1,1,1-trifluoro-3-[(4-methoxybenzyl)oxy]propan-2-yl 4-(4-fluorobenzyl)-3-oxo-1-oxa-4,9-diazaspiro[5.5]undecane-9-carboxylate (C55)

Conversion of C54 to C55 was carried out using the method described for synthesis of C34 from C33 in Examples 8 and 9. Purification was effected via preparative thin layer chromatography on silica gel (Eluent: 1:1 ethyl acetate/petroleum ether) to provide the product as a colorless gum. Yield: 48 mg, 87 μmol, 78% over 2 steps. LCMS m/z 577.3 [M+Na$^+$]. $^1$H NMR (400 MHz, CDCl$_3$) δ 7.27-7.19 (m, 4H, assumed; partially obscured by solvent peak), 7.04 (br dd, J=8.7, 8.4 Hz, 2H), 6.92-6.82 (m, 2H), 5.50-5.40 (m, 1H), 4.64-4.40 (m, 4H), 4.22 (s, 2H), 3.96-3.78 (m, 2H), 3.81 (s, 3H), 3.78-3.63 (m, 2H), 3.24-2.97 (m, 4H), 1.91-1.73 (m, 2H), 1.44-1.28 (m, 2H).

Step 3. Synthesis of (2R)-1,1,1-trifluoro-3-hydroxypropan-2-yl 4-(4-fluorobenzyl)-3-oxo-1-oxa-4,9-diazaspiro[5.5]undecane-9-carboxylate (17)

Conversion of C55 to 17 was carried out using the method described for synthesis of C35 from C34 in Examples 8 and 9. Purification via reversed phase HPLC (Column: Agela Durashell C18, 5 μm; Mobile phase A: 0.225% formic acid in water; Mobile phase B: 0.225% formic acid in acetonitrile; Gradient: 30% to 50% B) afforded the product as a colorless gum. Yield: 15.4 mg, 35.4 μmol, 41%. LCMS m/z 435.0 [M+H]$^+$. $^1$H NMR (400 MHz, CDCl$_3$) δ 7.28-7.21 (m, 2H, assumed; partially obscured by solvent peak), 7.05 (br dd, J=8.5, 8.5 Hz, 2H), 5.29-5.18 (m, 1H), 4.66-4.49 (m, 2H), 4.23 (s, 2H), 4.02-3.95 (m, 1H), 3.93-3.79 (m, 3H), 3.28-3.11 (m, 2H), 3.09 (s, 2H), 1.93-1.80 (m, 2H), 1.46-1.35 (m, 2H).

Example 18

(2R)-1,1,1-Trifluoro-3-hydroxypropan-2-yl 2-ethyl-4-[(4-fluorophenyl)sulfonyl]-1-oxa-4,9-diazaspiro[5.5]undecane-9-carboxylate (18)

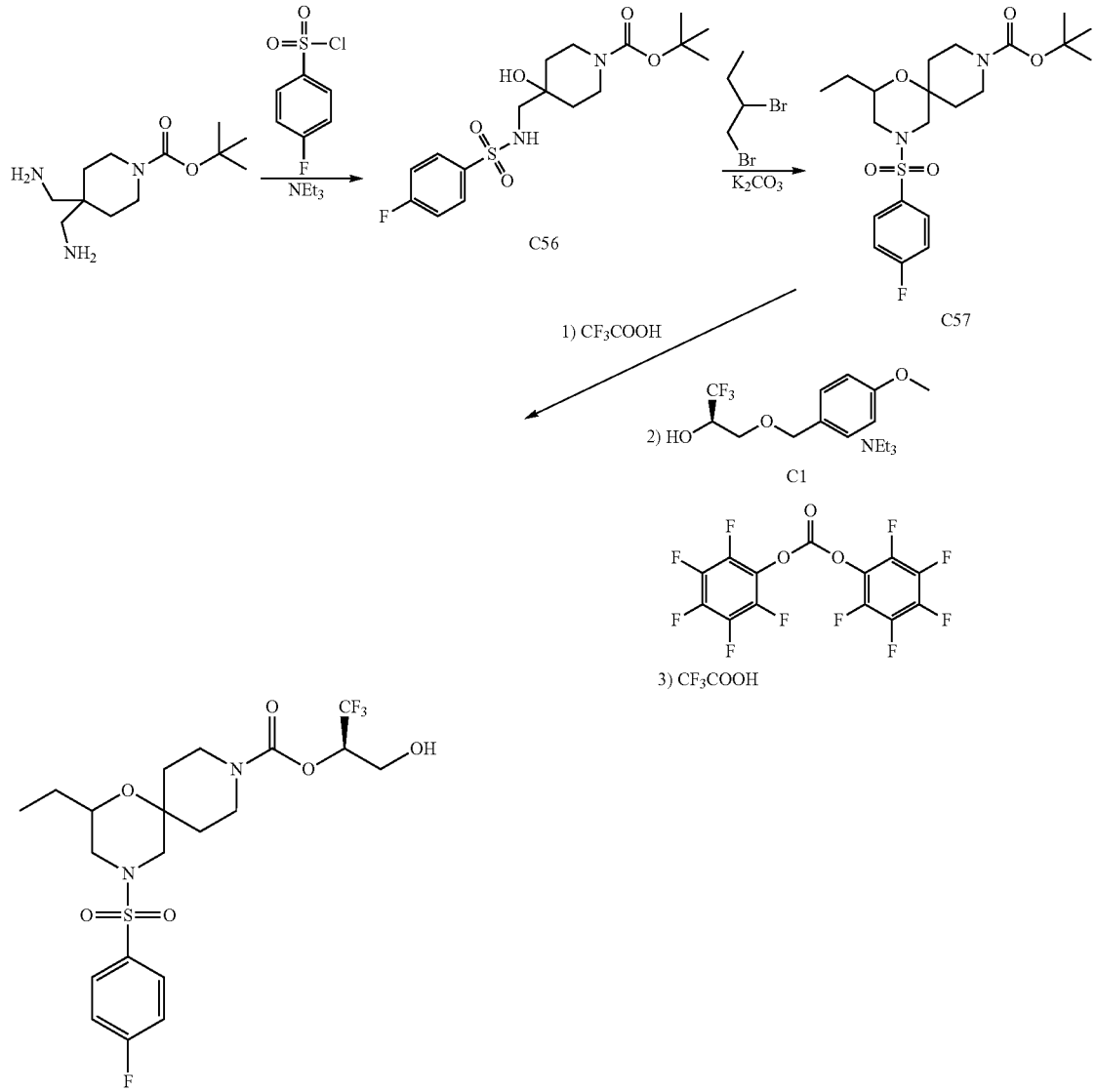

Step 1. Synthesis of tert-butyl 4-({[(4-fluorophenyl)sulfonyl]amino}methyl)-4-hydroxypiperidine-1-carboxylate (C56)

4-Fluorobenzenesulfonyl chloride (2.21 g, 11.4 mmol) was added portion-wise to a 0° C. solution of tert-butyl 4-(aminomethyl)-4-hydroxypiperidine-1-carboxylate (2.95 g, 12.8 mmol) and triethylamine (4.7 mL, 33.7 mmol) in dichloromethane (150 mL) and the reaction mixture was allowed to warm to room temperature and stir for 1 hour. It was then diluted with dichloromethane (100 mL) and washed sequentially with water (200 mL) and with saturated aqueous sodium chloride solution (200 mL), dried over sodium sulfate, filtered, and concentrated in vacuo. The residue was dissolved in ethyl acetate (20 mL); addition of heptane (100 mL) caused a solid to precipitate. Solvents were evaporated off to afford the product as a white solid. Yield: 4.3 g, 11.1 mmol, 97%. LCMS m/z 387.4 [M−H+].
$^1$H NMR (500 MHz, CDCl$_3$) δ 7.91-7.86 (m, 2H), 7.22 (br dd, J=8.6, 8.5 Hz, 2H), 5.2-4.9 (v br s, 1H), 3.87-3.67 (m, 2H), 3.24-3.09 (m, 2H), 2.92 (s, 2H), 2.12-1.94 (br s, 1H), 1.63-1.55 (m, 2H), 1.53-1.45 (m, 2H), 1.45 (s, 9H).

Step 2. Synthesis of tert-butyl 2-ethyl-4-[(4-fluorophenyl)sulfonyl]-1-oxa-4,9-diazaspiro[5.5]undecane-9-carboxylate (C57)

1,2-Dibromobutane (0.14 mL, 1.2 mmol) was added to a solution of C56 (150 mg, 0.386 mmol) in N,N-dimethylformamide (2 mL). Potassium carbonate (330 mg, 2.4 mmol) was added, and the reaction mixture was heated at 100° C. for 1 hour. It was then cooled to room temperature and treated with additional 1,2-dibromobutane (0.14 mL, 1.2 mmol), followed by potassium carbonate (330 mg, 2.4 mmol). The reaction temperature was increased to 110° C. for 1 hour, whereupon the reaction mixture was partitioned between ethyl acetate (50 mL) and water (50 mL). The organic layer was washed sequentially with water (50 mL) and with saturated aqueous sodium chloride solution (50 mL), dried over sodium sulfate, filtered, and concentrated in vacuo. Silica gel chromatography (Gradient: 0% to 60% ethyl acetate in heptane) provided the product as a colorless, viscous oil. Yield: 115 mg, 0.260 mmol, 67%. LCMS m/z 465.5 [M+Na+].

Step 3. Synthesis of (2R)-1,1,1-trifluoro-3-hydroxypropan-2-yl 2-ethyl-4-[(4-fluorophenyl) sulfonyl]-1-oxa-4,9-diazaspiro[5.5]undecane-9-carboxylate (18)

Trifluoroacetic acid (0.40 mL, 5.2 mmol) was added to a solution of C57 (115 mg, 0.260 mmol in dichloromethane (5 mL) and the reaction mixture was allowed to stir for 1 hour at room temperature, whereupon it was concentrated in vacuo and mixed with dichloromethane (5 mL) and triethylamine (1.5 mL, 11 mmol). In a separate flask, a solution of C1 (65.0 mg, 0.260 mmol) in tetrahydrofuran (2 mL) was treated sequentially with bis(pentafluorophenyl) carbonate (102 mg, 0.259 mmol) and triethylamine (1.8 mL, 13 mmol), and this reaction was allowed to stir at room temperature for 1 hour. The solution containing the deprotected C57 was added to the carbonate reaction mixture, and stirring was continued for 2 hours at room temperature. The reaction mixture was then partitioned between ethyl acetate (100 mL) and saturated aqueous sodium bicarbonate solution (60 mL), and the organic layer was washed with aqueous sodium hydrogen sulfate solution (1 M, 60 mL), dried over sodium sulfate, filtered, and concentrated under reduced pressure. The resulting viscous oil was taken up in dichloromethane (5 mL); trifluoroacetic acid (2 mL) was added at room temperature while the reaction mixture was stirred. The reaction mixture was allowed to stir for an additional 30 minutes, whereupon it was concentrated in vacuo; the residue was dissolved in dichloromethane (5 mL) and concentrated once more. Purification was carried out via reversed phase HPLC (Column: Waters Sunfire C18, 5 µm; Mobile phase A: 0.05% trifluoroacetic acid in water (v/v); Mobile phase B: 0.05% trifluoroacetic acid in acetonitrile (v/v); Gradient: 35% to 55% B) to provide the product. Yield: 12.3 mg, 24.7 µmol, 10%. LCMS m/z 499.2 [M+H]+. Retention time: 2.79 minutes [Analytical HPLC column: Waters Atlantis dC18, 4.6× 50 mm, 5 µm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute].

Examples 19, 20 and 21

1,1,1,3,3-Pentafluoro-4-hydroxybutan-2-yl 4-[(4-fluorophenyl)sulfonyl]-1-oxa-4,9-diazaspiro[5.5]undecane-9-carboxylate (19); 1,1,1,3,3-Pentafluoro-4-hydroxybutan-2-yl 4-[(4-fluorophenyl)sulfonyl]-1-oxa-4,9-diazaspiro[5.5]undecane-9-carboxylate, ENT-1 (20); and 1,1,1,3,3-Pentafluoro-4-hydroxybutan-2-yl 4-[(4-fluorophenyl)sulfonyl]-1-oxa-4,9-diazaspiro[5.5]undecane-9-carboxylate, ENT-2 (21)

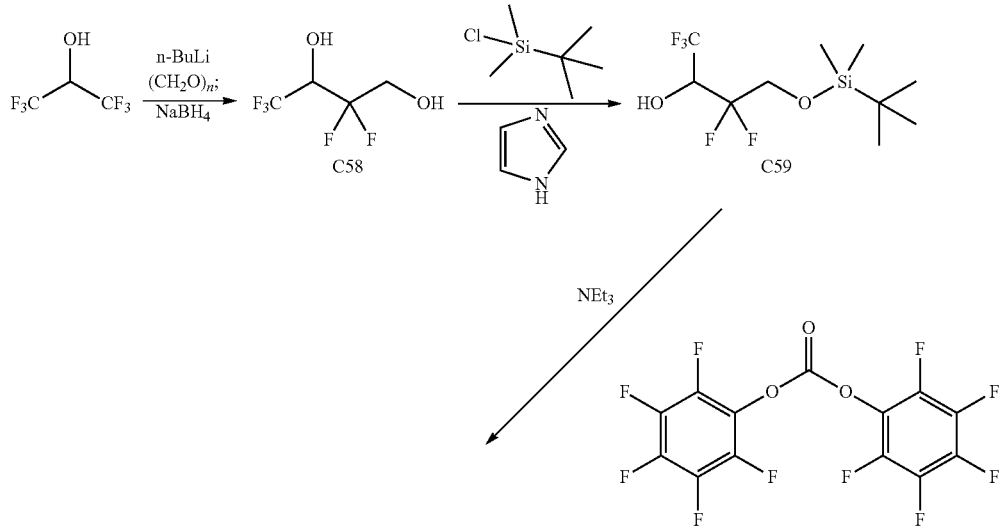

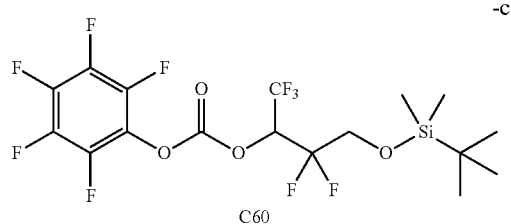
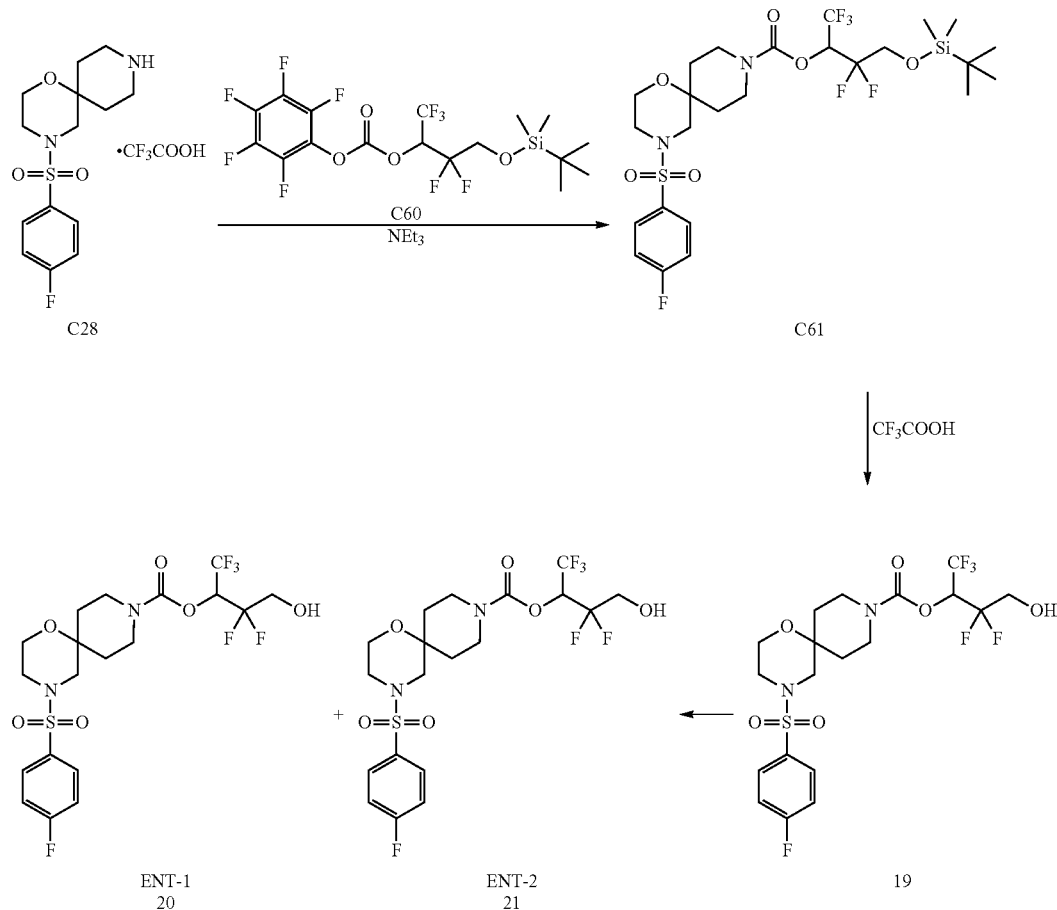

Step 1. Synthesis of 2,2,4,4,4-pentafluorobutane-1,3-diol (C58)

n-Butyllithium (2.5 M solution in hexanes; 23.9 mL, 59.8 mmol) was added drop-wise to a −78° C. solution of 1,1,1,3,3,3-hexafluoropropan-2-ol (4.90 g, 29.2 mmol) in tetrahydrofuran (40 mL). The reaction mixture was stirred for 10 minutes at −78° C., then allowed to warm to 0° C. and stir for 1 hour. Paraformaldehyde (8.7 g, 0.29 mol) was added in a portion-wise manner, and the reaction mixture was stirred at room temperature overnight. Water (50 mL) was added, followed by sodium borohydride (3.7 g, 98 mmol) {Caution: exothermic reaction, accompanied by gas evolution!}; in the course of the addition, the reaction mixture was cooled in an ice bath to control the reaction. Upon completion of the addition, stirring was continued overnight at room temperature, whereupon the reaction was quenched via addition of 1 M aqueous hydrochloric acid {Caution: gas evolution}. The resulting mixture was extracted with ethyl acetate, and the combined organic layers were dried over sodium sulfate, filtered, and concentrated in vacuo to afford the product as a yellow-brown oil. Yield: 4.5 g, 25 mmol, 86%. $^1$H NMR (400 MHz, CDCl$_3$) δ 4.50-4.38 (m, 1H), 4.14-4.02 (m, 1H), 4.00-3.89 (m, 1H).

Step 2. Synthesis of 4-{[tert-butyl(dimethyl)silyl]oxy}-1,1,1,3,3-pentafluorobutan-2-ol (C59)

N,N-Dimethylformamide (5 mL) was added to a 0° C. solution of C58 (6.30 g, 35.0 mmol) and 1H-imidazole (2.62 g, 38.5 mmol) in dichloromethane (60 mL). tert-Butyl (dimethyl)silyl chloride (5.27 g, 35.0 mmol) was then introduced portion-wise, and the reaction mixture was allowed to warm to room temperature and stir for 4 days. Saturated aqueous ammonium chloride solution (100 mL) was added, and the aqueous layer was extracted with dichloromethane (2×30 mL). The combined organic layers were dried over sodium sulfate, filtered, and concentrated in vacuo; silica gel chromatography (Eluent: 5% ethyl acetate in petroleum ether) afforded the product as a yellow oil. Yield: 3.0 g, 10 mmol, 29%. $^1$H NMR (400 MHz, CDCl$_3$) δ 4.44-4.31 (m, 1H), 4.13-4.01 (m, 1H), 3.95-3.85 (m, 1H), 3.57-3.46 (m, 1H), 0.92 (s, 9H), 0.13 (s, 6H).

Step 3. Synthesis of 4-{[tert-butyl(dimethyl)silyl]oxy}-1,1,1,3,3-pentafluorobutan-2-yl pentafluorophenyl carbonate (C60)

Bis(pentafluorophenyl) carbonate (158 mg, 0.401 mmol) was added to a 0° C. solution of C59 (118 mg, 0.401 mmol) in acetonitrile (4 mL). Triethylamine (122 mg, 1.20 mmol) was added drop-wise to the reaction mixture, which was stirred briefly in the ice bath, and then allowed to warm to 25° C. and stir for 2 hours. The reaction solution of C60 was used directly in the following step.

Step 4. Synthesis of 4-{[tert-butyl(dimethyl)silyl]oxy}-1,1,1,3,3-pentafluorobutan-2-yl 4-[(4-fluorophenyl) sulfonyl]-1-oxa-4,9-diazaspiro[5.5]undecane-9-carboxylate (C61)

Triethylamine (118 mg, 1.17 mmol) was added to a 0° C. solution of C28 (100 mg, 0.233 mmol) in acetonitrile (5 mL). After a few minutes, C60 (reaction solution from the previous step; 0.401 mmol) was added drop-wise to the 0° C. mixture, which was stirred in the ice bath for several minutes, stirred at 28° C. for 20 hours, and then cooled to 0° C. A second batch of C60 (using the same scale and method as step 3 above; 0.401 mmol) was prepared and added to the 0° C. reaction mixture, which was allowed to warm to room temperature and stir overnight.

After removal of volatiles in vacuo, the residue was purified using preparative thin layer chromatography on silica gel (Eluent: 3:1 petroleum ether/ethyl acetate) to afford the product as a white solid. Yield: 120 mg, 0.189 mmol, 81%. By $^1$H NMR analysis, this material was judged to be a mixture of rotamers. $^1$H NMR (400 MHz, CD$_3$OD) δ 7.87-7.80 (m, 2H), 7.36 (br dd, J=8.7, 8.7 Hz, 2H), 5.84-5.70 (m, 1H), 4.63-4.54 (m, 1H), 3.97-3.77 (m, 5H), 3.3-3.15 (m, 2H, assumed; partially obscured by solvent peak), 3.02-2.95 (m, 2H), 2.86-2.78 (m, 2H), 2.06-1.94 (m, 2H), 1.61-1.45 (m, 2H), [0.93 (s) and 0.90 (s), total 9H], [0.12 (s), 0.10 (s), and 0.08 (s), total 6H].

Step 5. Synthesis of 1,1,1,3,3-pentafluoro-4-hydroxybutan-2-yl 4-[(4-fluorophenyl)sulfonyl]-1-oxa-4,9-diazaspiro[5.5]undecane-9-carboxylate (19)

Trifluoroacetic acid (4 mL) and water (1 mL) were added drop-wise to a 0° C. solution of C61 (120 mg, 0.189 mmol) in dichloromethane (6 mL) and the reaction mixture was stirred at 28° C. for 3 hours. It was then concentrated in vacuo and partitioned between ethyl acetate (50 mL) and saturated aqueous sodium bicarbonate solution (50 mL); the organic layer was washed with saturated aqueous sodium bicarbonate solution (3×20 mL), dried over sodium sulfate, filtered, and concentrated in vacuo. Preparative thin layer chromatography on silica gel (Eluent: 1:1 petroleum ether/ethyl acetate) provided the product as a colorless gum. Yield: 73 mg, 0.14 mmol, 74%. LCMS m/z 521.1 [M+H]$^+$. $^1$H NMR (400 MHz, CD$_3$OD) δ 7.84 (br dd, J=8.8, 5.0 Hz, 2H), 7.37 (br dd, J=8.8, 8.7 Hz, 2H), 5.86-5.73 (m, 1H), 3.91-3.72 (m, 6H), 3.3-3.17 (m, 2H, assumed; partially obscured by solvent peak), 3.01-2.94 (m, 2H), 2.86-2.76 (m, 2H), 2.02-1.92 (m, 2H), 1.60-1.47 (m, 2H).

Step 6. Isolation of 1, 1,1,3,3-pentafluoro-4-hydroxybutan-2-yl 4-[(4-fluorophenyl)sulfonyl]-1-oxa-4,9-diazaspiro[5.5]undecane-9-carboxylate, ENT-1 (20), and 1,1,1,3,3-pentafluoro-4-hydroxybutan-2-yl 4-[(4-fluorophenyl)sulfonyl]-1-oxa-4,9-diazaspiro[5.5]undecane-9-carboxylate, ENT-2 (21)

The racemate 19 was separated into its component enantiomers via supercritical fluid chromatography [Column: Chiral Technologies Chiralcel OD, 3 μm; Gradient: 5% to 40% (2-propanol containing 0.05% diethylamine) in carbon dioxide]. The first-eluting enantiomer was 20, obtained as a colorless gum. Yield: 19.9 mg, 38.2 μmol, 27% for the separation. LCMS m/z 521.2 [M+H]$^+$. $^1$H NMR (400 MHz, CD$_3$OD) δ 7.84 (br dd, J=8.7, 5.1 Hz, 2H), 7.37 (br dd, J=8.8, 8.7 Hz, 2H), 5.86-5.73 (m, 1H), 3.91-3.72 (m, 6H), 3.3-3.17 (m, 2H, assumed; partially obscured by solvent peak), 3.01-2.94 (m, 2H), 2.86-2.76 (m, 2H), 2.03-1.92 (m, 2H), 1.61-1.47 (m, 2H). Retention time via supercritical fluid chromatography: 3.97 minutes (Column: Chiral Technologies Chiralcel OD-3, 4.6 mm×150 mm I.D., 3 μm; Mobile phase A: carbon dioxide; Mobile phase B: 2-propanol containing 0.05% diethylamine; Gradient: 5% to 40% B; Flow rate: 2.5 mL/minute).

The second-eluting enantiomer was 21, also isolated as a colorless gum. Yield: 19.6 mg, 37.6 μmol, 27% for the separation. LCMS m/z 521.2 [M+H]$^+$. $^1$H NMR (400 MHz, CD$_3$OD) δ 7.87-7.81 (m, 2H), 7.41-7.33 (m, 2H), 5.85-5.73 (m, 1H), 3.91-3.72 (m, 6H), 3.3-3.17 (m, 2H, assumed; partially obscured by solvent peak), 3.01-2.94 (m, 2H), 2.86-2.76 (m, 2H), 2.03-1.92 (m, 2H), 1.60-1.47 (m, 2H). Retention time via supercritical fluid chromatography: 4.38 min (Same analytical conditions as those described for 20).

Example 22

(2R)-1,1,1-Trifluoro-3-hydroxypropan-2-yl 4-(morpholin-4-ylsulfonyl)-1-oxa-4,9-diazaspiro[5.5]undecane-9-carboxylate (22)

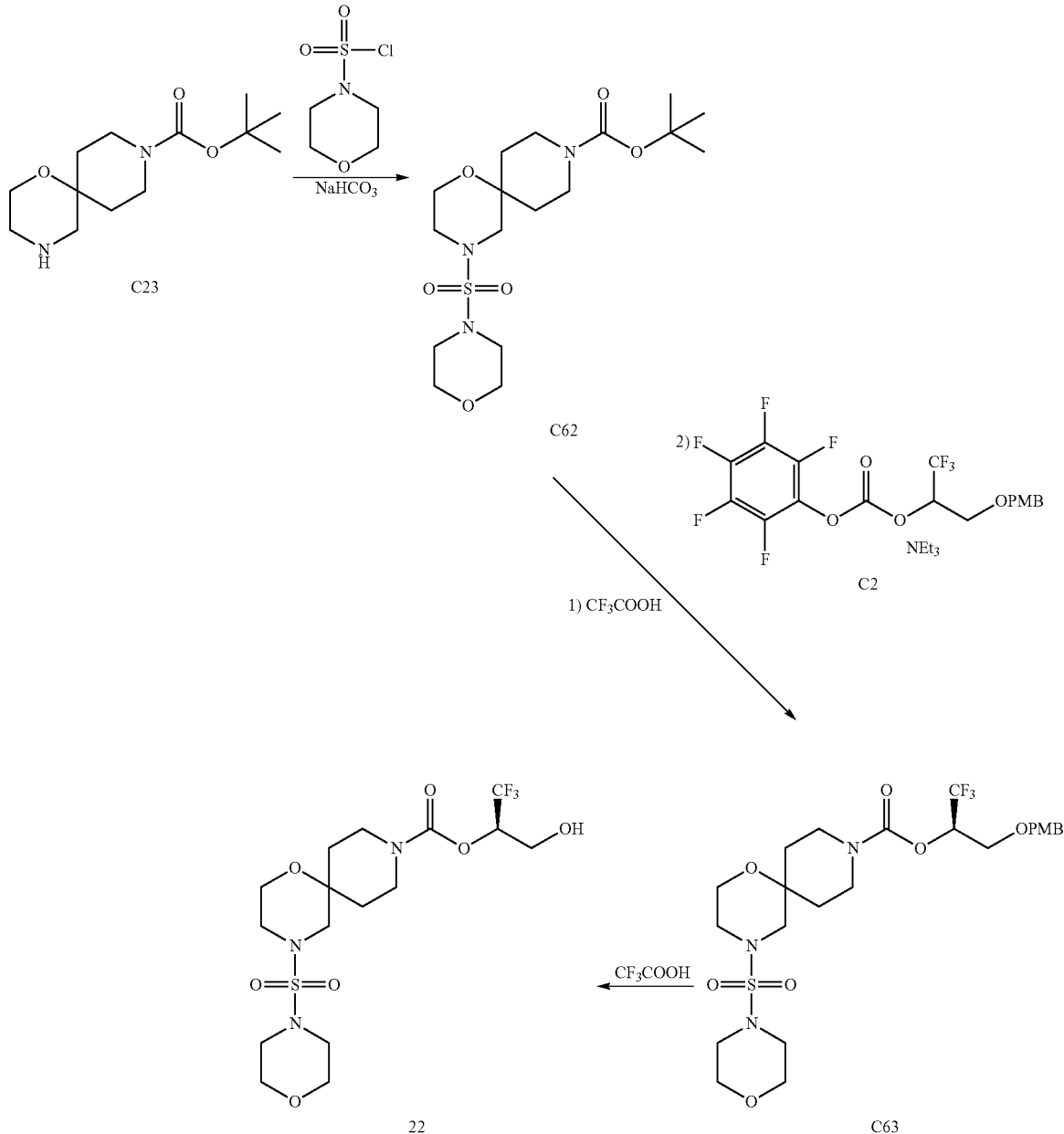

Step 1. Synthesis of tert-butyl 4-(morpholin-4-ylsulfonyl)-1-oxa-4,9-diazaspiro[5.5]undecane-9-carboxylate (C62)

Reaction of C23 with morpholine-4-sulfonyl chloride was carried out using the method described for synthesis of C32 from C31 in Example 7, providing the product as a colorless gum. Yield: 100 mg, 0.247 mmol, 63%. LCMS m/z 428.2 [M+Na$^+$]. $^1$H NMR (400 MHz, CDCl$_3$) δ 3.81-3.70 (m, 8H), 3.29-3.21 (m, 6H), 3.15 (br dd, J=12, 12 Hz, 2H), 3.06 (s, 2H), 1.95-1.86 (m, 2H), 1.52-1.41 (m, 2H), 1.46 (s, 9H).

Step 2. Synthesis of (2R)-1,1,1-trifluoro-3-[(4-methoxybenzyl)oxy]propan-2-yl 4-(morpholin-4-ylsulfonyl)-1-oxa-4,9-diazaspiro[5.5]undecane-9-carboxylate (C63)

Conversion of C62 to C63 was carried out using the method described for synthesis of C34 from C33 in Examples 8 and 9. LCMS of intermediate 4-(morpholin-4-ylsulfonyl)-1-oxa-4,9-diazaspiro[5.5]undecane, trifluoroacetic acid salt: m/z 306.0 [M+H]$^+$. In this case, purification was carried out using preparative thin layer chromatography (Eluent: 1:1 petroleum ether/ethyl acetate) to afford C63 as a colorless gum. Yield: 90.0 mg, 0.155 mmol, 65%. LCMS m/z 603.9 [M+Na$^+$]. $^1$H NMR (400 MHz, CDCl$_3$) δ 7.23 (d, J=8.5 Hz, 2H), 6.87 (d, J=8.4 Hz, 2H), 5.52-5.41 (m, 1H), 4.50 (AB quartet, J$_{AB}$=11.7 Hz, Δv$_{AB}$=28.2 Hz, 2H), 3.95-3.80 (m, 2H), 3.80 (s, 3H), 3.78-3.64 (m, 8H), 3.28-3.16 (m, 8H), 3.07-3.00 (m, 2H), 1.99-1.90 (m, 2H), 1.50-1.40 (m, 2H).

Step 3. Synthesis of (2R)-1,1,1-trifluoro-3-hydroxy-propan-2-yl 4-(morpholin-4-ylsulfonyl)-1-oxa-4,9-diazaspiro[5.5]undecane-9-carboxylate (22)

Conversion of C63 to 22 was carried out using the method described for synthesis of C35 from C34 in Examples 8 and 9. Purification via reversed phase HPLC (Column: Agela Durashell C18, 5 μm; Mobile phase A: 0.225% formic acid in water; Mobile phase B: 0.225% formic acid in acetonitrile; Gradient: 25% to 45% B) afforded the product as a colorless gum. Yield: 33.4 mg, 72.3 μmol, 47%. LCMS m/z 462.1 [M+H]$^+$. $^1$H NMR (400 MHz, CDCl$_3$) δ 5.32-5.21 (m, 1H), 4.06-3.96 (m, 1H), 3.96-3.82 (m, 3H), 3.82-3.69 (m, 6H), 3.34-3.18 (m, 8H), 3.07 (s, 2H), 2.34-2.21 (m, 1H), 2.06-1.95 (m, 2H), 1.6-1.42 (m, 2H, assumed; partially obscured by water peak).

Example 23

(2R)-1,1,1-Trifluoro-3-hydroxypropan-2-yl 3-(4-fluorobenzyl)-3,8-diazabicyclo[3.2.1]octane-8-carboxylate (23)

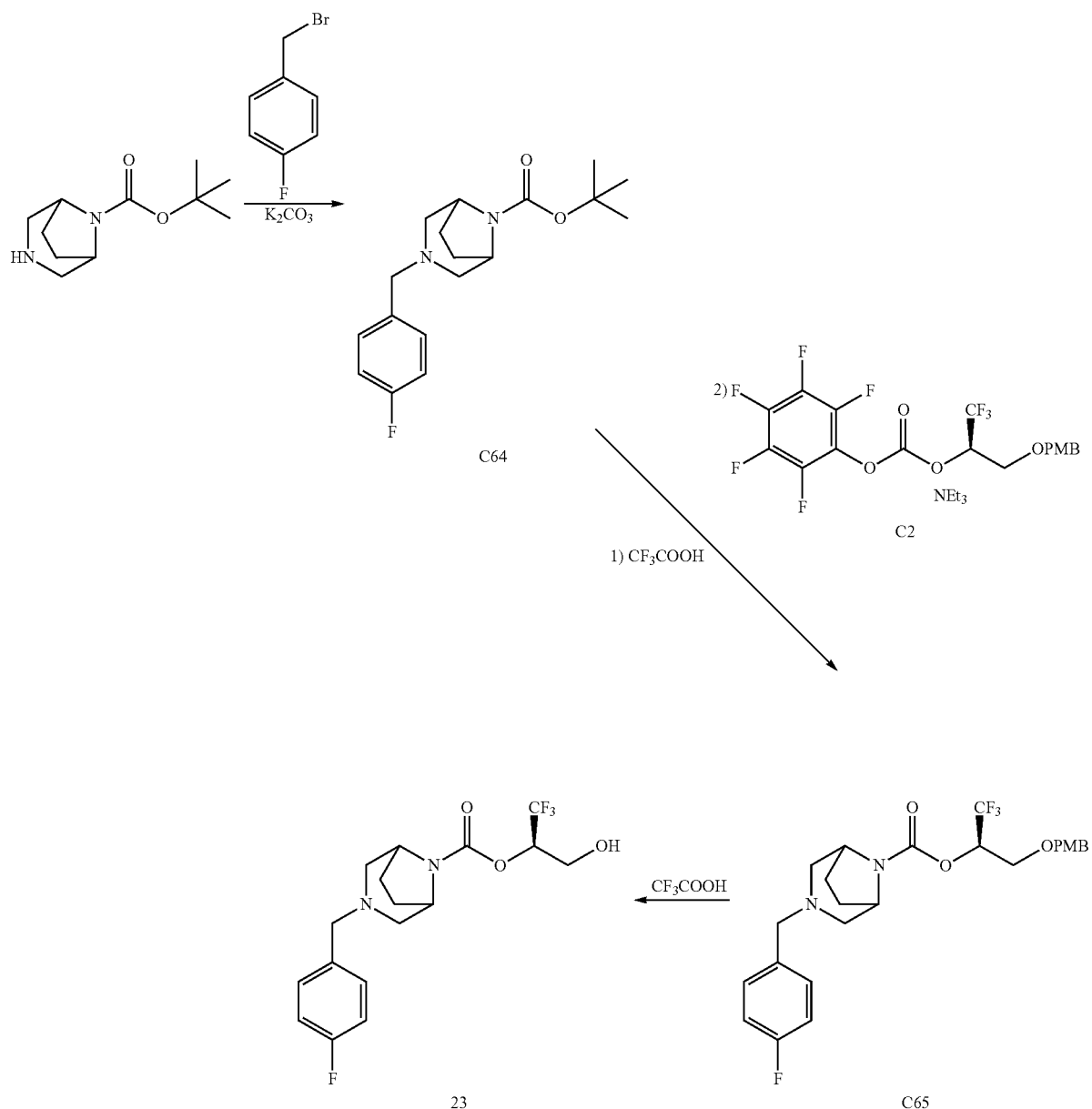

Step 1. Synthesis of tert-butyl 3-(4-fluorobenzyl)-3,8-diazabicyclo[3.2.1]octane-8-carboxylate (C64)

A solution of 1-(bromomethyl)-4-fluorobenzene (134 mg, 0.709 mmol) in acetonitrile (3 mL) was slowly added to a room temperature mixture of tert-butyl 3,8-diazabicyclo[3.2.1]octane-8-carboxylate (150 mg, 0.706 mmol) and potassium carbonate (293 mg, 2.12 mmol) in acetonitrile (12 mL) and the reaction mixture was stirred at 25° C. for 16 hours. It was then filtered, and the filtrate was concentrated in vacuo; silica gel chromatography (Gradient: 0% to 20% ethyl acetate in petroleum ether) afforded the product as a colorless gum. Yield: 226 mg, 0.705 mmol, quantitative. $^1$H NMR (400 MHz, CDCl$_3$) δ 7.30-7.24 (m, 2H), 6.99 (br dd, J=8.8, 8.7 Hz, 2H), 4.26-4.03 (m, 2H), 3.43 (s, 2H), 2.58 (dd, J=10.7, 2.3 Hz, 2H), 2.36-2.16 (m, 2H), 1.93-1.78 (m, 4H), 1.47 (s, 9H).

Step 2. Synthesis of (2R)-1,1,1-trifluoro-3-[(4-methoxybenzyl)oxy]propan-2-yl 3-(4-fluorobenzyl)-3,8-diazabicyclo[3.2.1]octane-8-carboxylate (C65)

Conversion of C64 to C65 was carried out using the method described for synthesis of C34 from C33 in Examples 8 and 9. LCMS of intermediate 3-(4-fluorobenzyl)-3,8-diazabicyclo[3.2.1]octane, bis(trifluoroacetic acid) salt: m/z 221.1 [M+H]$^+$. In this case, purification was carried out via silica gel chromatography (Gradient: 0% to 5% methanol in dichloromethane) to afford C65 as a colorless gum. Yield: 150 mg, 0.302 mmol, 88% over 2 steps. LCMS m/z 497.2 [M+H]$^+$.

Step 3. Synthesis of (2R)-1,1,1-trifluoro-3-hydroxypropan-2-yl 3-(4-fluorobenzyl)-3,8-diazabicyclo[3.2.1]octane-8-carboxylate (23)

Conversion of C65 to 23 was carried out using the method described for synthesis of 7 from C32 in Example 7. In this case, purification was effected via reversed phase HPLC (Column: Agela Durashell C18, 5 μm; Mobile phase A: 0.225% formic acid in water; Mobile phase B: 0.225% formic acid in acetonitrile; Gradient: 10% to 30% B) to provide the product as a colorless gum. Yield: 75 mg, 0.199 mmol, 66%. LCMS m/z 377.0 [M+H]$^+$. $^1$H NMR (400 MHz, CDCl$_3$) δ 7.31-7.23 (m, 2H, assumed; partially obscured by solvent peak), 7.01 (br dd, J=8.8, 8.7 Hz, 2H), 5.33-5.22 (m, 1H), 4.31-4.21 (m, 2H), 4.06-3.96 (m, 1H), 3.93-3.83 (m, 1H), 3.49-3.43 (m, 2H), 2.69-2.61 (m, 2H), 2.38-2.20 (m, 3H), 2.00-1.84 (m, 4H).

Example 24

(2R)-1,1,1-Trifluoro-3-hydroxypropan-2-yl 4-hydroxy-4-{[methyl(phenylsulfonyl)amino]methyl}piperidine-1-carboxylate (24)

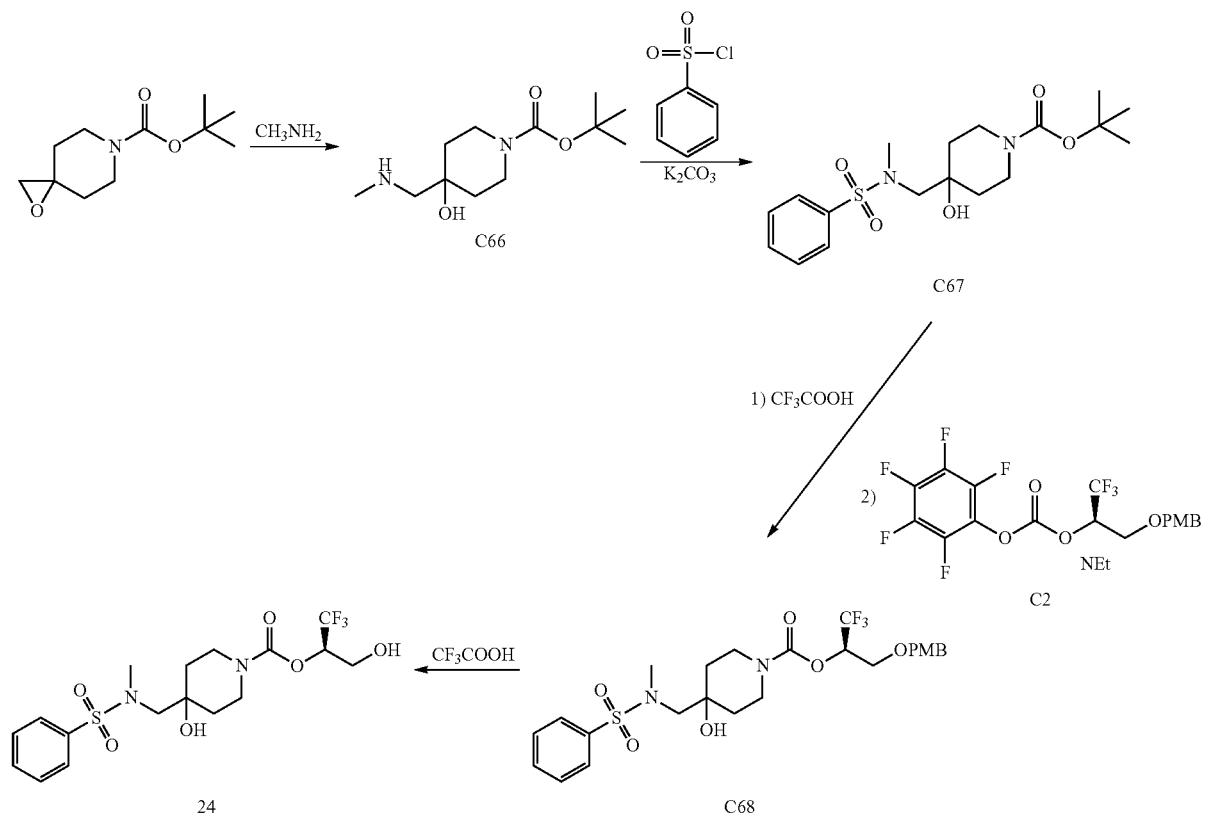

Step 1. Synthesis of tert-butyl 4-hydroxy-4-[(methylamino)methyl]piperidine-1-carboxylate (C66)

Methylamine (2 M solution in tetrahydrofuran; 0.245 mL, 0.490 mmol) was added to a solution of tert-butyl 1-oxa-6-azaspiro[2.5]octane-6-carboxylate (95 mg, 0.44 mmol) in ethanol (2 mL) and the reaction mixture was heated to 80°

C. for 20 hours. Concentration in vacuo provided the product as an oil (105 mg); this material was used in the following step without additional purification.

Step 2. Synthesis of tert-butyl 4-hydroxy-4-{[methyl(phenylsulfonyl)amino]methyl}piperidine-1-carboxylate (C67)

To a solution of C66 (from the previous step; 105 mg, ≤0.44 mmol) in acetonitrile (2 mL) were added benzenesulfonyl chloride (0.110 mL, 0.862 mmol) and potassium carbonate (119 mg, 0.861 mmol). The reaction mixture was stirred at 25° C. for 3 hours, whereupon it was concentrated in vacuo; silica gel chromatography (Eluent: ethyl acetate) afforded the product as a gum. Yield: 115 mg, 0.299 mmol, 68% over 2 steps. $^1$H NMR (400 MHz, CDCl$_3$) δ 7.82-7.77 (m, 2H), 7.65-7.59 (m, 1H), 7.58-7.52 (m, 2H), 3.95-3.81 (m, 2H), 3.24-3.10 (m, 2H), 3.04-2.91 (m, 2H), 2.90 (s, 3H), 1.70-1.61 (m, 2H), 1.56-1.46 (m, 2H), 1.45 (s, 9H).

Step 3. Synthesis of (2R)-1,1,1-trifluoro-3-[(4-methoxybenzyl)oxy]propan-2-yl 4-hydroxy-4-{[methyl(phenylsulfonyl)amino]methyl}piperidine-1-carboxylate (C68)

Conversion of C67 to C68 was carried out using the method described for synthesis of C34 from C33 in Examples 8 and 9. LCMS of intermediate N-[(4-hydroxypiperidin-4-yl)methyl]-N-methylbenzenesulfonamide, trifluoroacetic acid salt: m/z 285.0 [M+H]$^+$. In this case, purification was carried out via silica gel chromatography (Gradient: 40% to 60% ethyl acetate in petroleum ether), affording C68 as a colorless gum. By $^1$H NMR analysis, this was judged to be a mixture of diastereomers. Yield: 130 mg, 0.232 mmol, 78% over 2 steps. LCMS m/z 583.1 [M+Na$^+$]. $^1$H NMR (400 MHz, CDCl$_3$) δ 7.81 (br d, J=8 Hz, 2H), 7.67-7.62 (m, 1H), 7.61-7.54 (m, 2H), 7.25 (d, J=8.5 Hz, 2H), 6.92-6.84 (m, 2H), 5.55-5.43 (m, 1H), 4.51 (AB quartet, upfield doublet is broadened, J$_{AB}$=11.7 Hz, Δv$_{AB}$=29 Hz, 2H), 4.07-3.90 (m, 2H), 3.85-3.65 (m, 2H), [3.82 (s) and 3.77 (s), total 3H], 3.37-3.22 (m, 2H), 3.01-2.79 (m, 2H), [2.91 (s) and 2.87 (s), total 3H], 1.75-1.64 (m, 2H), 1.55-1.43 (m, 2H).

Step 4. Synthesis of (2R)-1,1,1-trifluoro-3-hydroxypropan-2-yl 4-hydroxy-4-{[methyl(phenylsulfonyl)amino]methyl}piperidine-1-carboxylate (24)

Trifluoroacetic acid (1.2 mL, 16 mmol) was added dropwise to a 0° C. solution of C68 (130 mg, 0.232 mmol) in acetonitrile (5 mL). The reaction mixture was stirred at room temperature for 30 minutes, whereupon saturated aqueous sodium bicarbonate solution was added until the mixture reached a pH of approximately 8. The organic layer was dried over sodium sulfate, filtered, and concentrated in vacuo to provide an off-white solid; purification via reversed phase HPLC (Column: Agela Durashell C18, 5 μm; Mobile phase A: 0.225% formic acid in water; Mobile phase B: acetonitrile; Gradient: 30% to 50% B) afforded the product. Yield: 51.6 mg, 0.117 mmol, 50%. LCMS m/z 463.1 [M+Na$^+$]. $^1$H NMR (400 MHz, CDCl$_3$) δ 7.83-7.77 (m, 2H), 7.67-7.61 (m, 1H), 7.60-7.53 (m, 2H), 5.31-5.21 (m, 1H), 4.05-3.92 (m, 3H), 3.90-3.81 (m, 1H), 3.41-3.22 (m, 2H), 3.04-2.93 (m, 2H), 2.90 (s, 3H), 2.84-2.74 (br s, 1H), 1.77-1.67 (m, 2H), 1.64-1.46 (m, 2H).

Example 25

(2R)-1,1,1-Trifluoro-3-hydroxypropan-2-yl 4-(4-fluorobenzyl)piperazine-1-carboxylate (25)

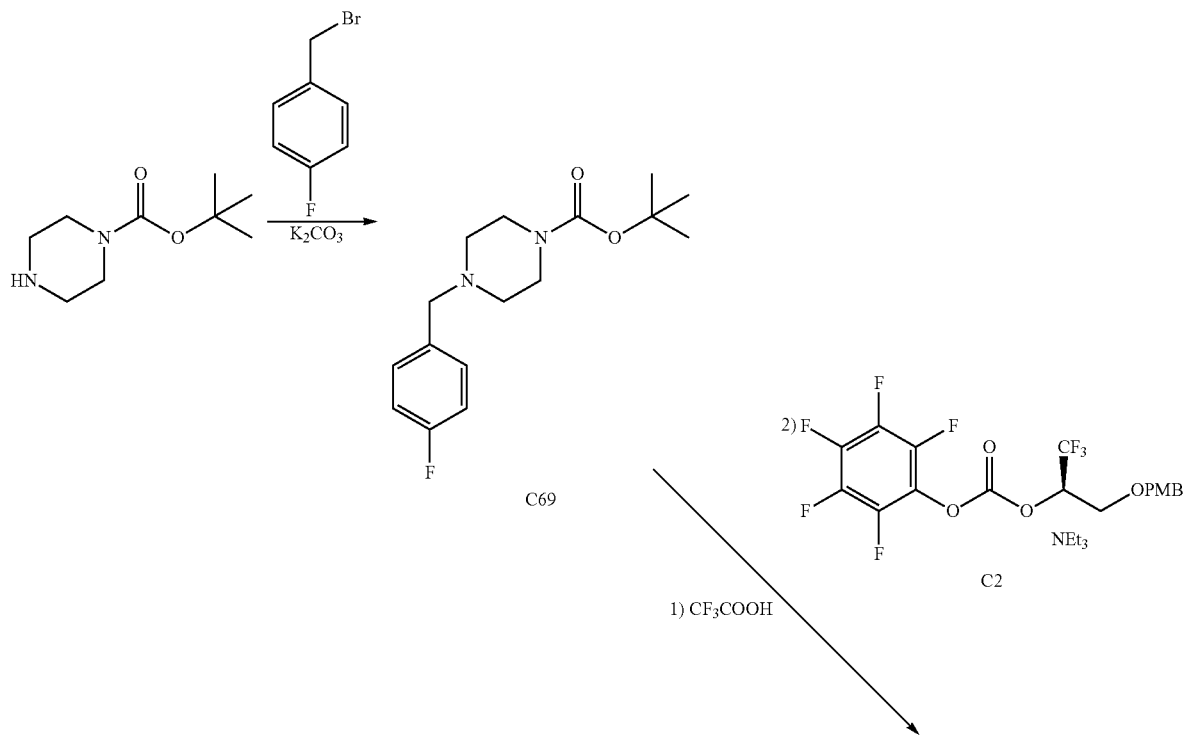

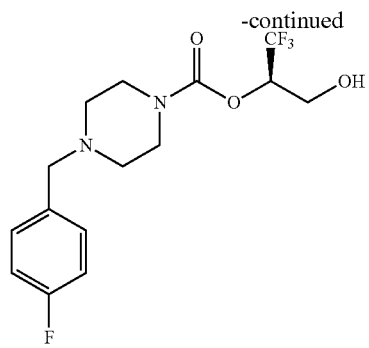

25

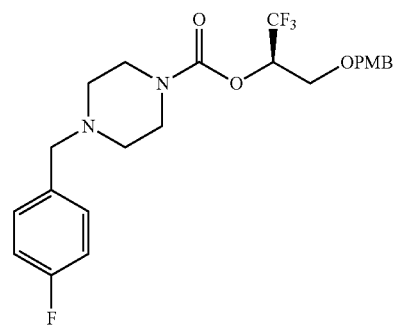

C70

Step 1. Synthesis of tert-butyl 4-(4-fluorobenzyl)piperazine-1-carboxylate (C69)

To a 30° C. solution of tert-butyl piperazine-1-carboxylate (200 mg, 1.07 mmol) and potassium carbonate (445 mg, 3.22 mmol) in acetonitrile (8 mL) was added a solution of 1-(bromomethyl)-4-fluorobenzene (203 mg, 1.07 mmol) in acetonitrile (2 mL), in a drop-wise manner. The reaction mixture was stirred for 16 hours at 30° C., whereupon it was concentrated in vacuo and purified via chromatography on silica gel (Gradient: 0% to 20% ethyl acetate in petroleum ether) to afford the product as a colorless gum. Yield: 250 mg, 0.849 mmol, 79%. $^1$H NMR (400 MHz, CDCl$_3$) δ 7.28 (br dd, J=8.2, 5.5 Hz, 2H), 7.01 (br dd, J=8.8, 8.7 Hz, 2H), 3.47 (s, 2H), 3.43 (br dd, J=5, 5 Hz, 4H), 2.37 (br dd, J=5, 5 Hz, 4H), 1.46 (s, 9H).

Step 2. Synthesis of (2R)-1,1,1-trifluoro-3-[(4-methoxybenzyl)oxy]propan-2-yl 4-(4-fluorobenzyl)piperazine-1-carboxylate (C70)

Conversion of C69 to C70 was carried out using the method described for synthesis of C34 from C33 in Examples 8 and 9. In this case, purification was carried out using preparative thin layer chromatography (Eluent: 3:1 petroleum ether/ethyl acetate) to afford the product as a colorless gum. Yield: 71 mg, 0.15 mmol, 74% over 2 steps. LCMS m/z 471.2 [M+H]$^+$. $^1$H NMR (400 MHz, CDCl$_3$) δ 7.31-7.22 (m, 4H), 7.01 (br dd, J=8.8, 8.7 Hz, 2H), 6.88 (br d, J=8.8 Hz, 2H), 5.53-5.43 (m, 1H), 4.51 (AB quartet, $J_{AB}$=11.7 Hz, $\Delta\nu_{AB}$=27.9 Hz, 2H), 3.81 (s, 3H), 3.76 (dd, half of ABX pattern, J=11.1, 4.0 Hz, 1H), 3.69 (dd, half of ABX pattern, J=11.2, 7.0 Hz, 1H), 3.60-3.45 (m, 4H), 3.50 (s, 2H), 2.51-2.36 (m, 4H).

Step 3. Synthesis of (2R)-1,1,1-trifluoro-3-hydroxypropan-2-yl 4-(4-fluorobenzyl)piperazine-1-carboxylate (25)

Trifluoroacetic acid (1 mL) was added to a 0° C. solution of C70 (61 mg, 0.13 mmol) in dichloromethane (4 mL). The reaction mixture was stirred at 25° C. for 1 hour, whereupon it was basified to pH 7 via addition of saturated aqueous sodium bicarbonate solution, and extracted with dichloromethane (2×10 mL). The combined organic layers were dried over sodium sulfate, filtered, and concentrated in vacuo. Preparative thin layer chromatography (Eluent: 10:1 dichloromethane/methanol) provided the product as a colorless gum. Yield: 24.2 mg, 69.1 μmol, 53%. LCMS m/z 351.1 [M+H]$^+$. $^1$H NMR (400 MHz, CDCl$_3$) δ 7.28 (br dd, J=8.2, 5.6 Hz, 2H), 7.02 (br dd, J=8.7, 8.7 Hz, 2H), 5.30-5.20 (m, 1H), 4.00 (br dd, half of ABX pattern, J=12, 3 Hz, 1H), 3.86 (dd, half of ABX pattern, J=12.4, 6.8 Hz, 1H), 3.63-3.43 (m, 4H), 3.49 (s, 2H), 2.52-2.34 (m, 4H).

Example 26

(2R)-1,1,1-Trifluoro-3-hydroxypropan-2-yl 4-(isoquinolin-1-yloxy)piperidine-1-carboxylate, trifluoroacetic acid salt (26)

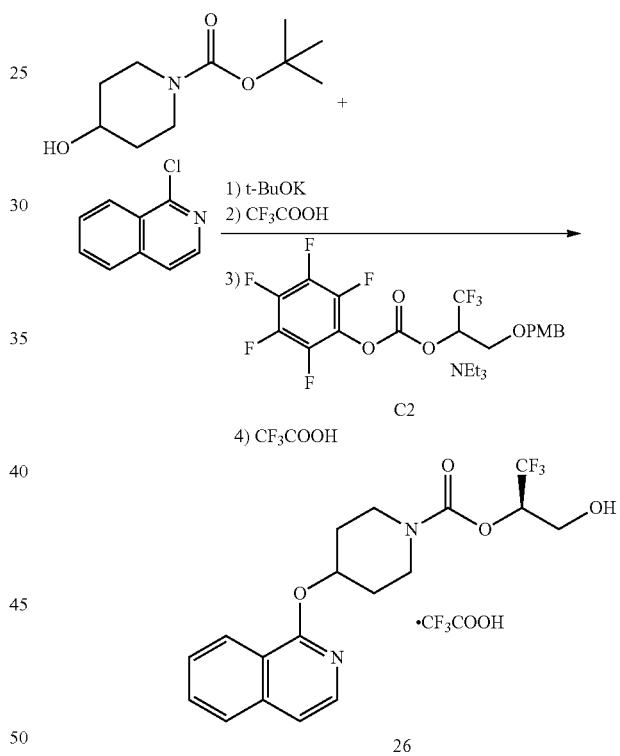

A solution of tert-butyl 4-hydroxypiperidine-1-carboxylate (30.2 mg, 0.15 mmol) in N,N-dimethylformamide (0.5 mL) was added to 1-chloroisoquinoline (24.5 mg, 0.15 mmol) in a reaction vial. Potassium tert-butoxide (1 M solution in tetrahydrofuran; 0.45 mL, 0.45 mmol) was added, and the reaction mixture was shaken at 60° C. for 18 hours, then at 100° C. for 1 hour. It was then partitioned between half-saturated aqueous sodium bicarbonate solution (1.5 mL) and ethyl acetate (2.4 mL) and subjected to vortexing, followed by centrifugation to break up an emulsion. The organic layer was eluted through a solid phase extraction cartridge (6 mL) charged with sodium sulfate (~1 g); this extraction procedure was repeated twice, and the combined eluents were concentrated in vacuo. A mixture of trifluoroacetic acid and 1,2-dichloroethane (1:1, 1 mL) was added, and the reaction mixture was shaken at room temperature for 2.5 hours, whereupon it was concentrated in vacuo and dissolved in 1,2-dichloroethane (2.4 mL) with vortexing. This material was loaded onto an SCX (strong cation exchanger) solid phase extraction cartridge (Silicycle, 6 mL, 1 g); the vial was rinsed with a mixture of methanol and 1,2-dichloroethane (1:1; 2×2.4 mL). The cartridge was eluted with methanol (5 mL), followed by a solution of triethylamine in methanol (1 M, 7.5 mL) to elute the deprotected intermediate. Fractions containing the desired material were concentrated in vacuo, and the residue was azeotroped with toluene (2×1 mL) to remove trace methanol. The residue was dissolved in dichloromethane (0.5 mL).

A crude solution of C2 was prepared separately, as follows: Bis(pentafluorophenyl) carbonate (1.89 g, 4.80 mmol) and triethylamine (13.4 ml, 96.1 mmol) were added to a stirring solution of C1 (1.23 g, 4.91 mmol) in tetrahydrofuran (15 mL). Sufficient tetrahydrofuran was added to bring the total volume to 32 mL, and the reaction mixture was stirred at room temperature for 1 hour. A portion of this crude C2 solution (1.0 mL, 0.15 mmol of C2 and 3 mmol of triethylamine) was added to the deprotected amine solution prepared above, and the reaction mixture was shaken at room temperature overnight. It was then partitioned between half-saturated aqueous sodium bicarbonate solution (1.5 mL) and ethyl acetate (2.4 mL) and subjected to vortexing. The organic layer was eluted through a solid phase extraction cartridge (6 mL) charged with sodium sulfate (~1 g); this extraction procedure was repeated twice, and the combined eluents were concentrated in vacuo. This material was treated with a mixture of trifluoroacetic acid and 1,2-dichloroethane (1:1, 1 mL) and shaken at room temperature for 1 hour, whereupon it was concentrated in vacuo and purified using reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 20% to 100% B) to afford the product. Yield: 2.5 mg, 6.5 μmol, 4%. LCMS m/z 385.1 [M+H]$^+$. Retention time 3.01 minutes [Analytical HPLC conditions—Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute].

Example 27

(2R)-1,1,1-Trifluoro-3-hydroxypropan-2-yl 3-(pyridin-2-ylamino)-1-oxa-8-azaspiro[4.5]decane-8-carboxylate (27)

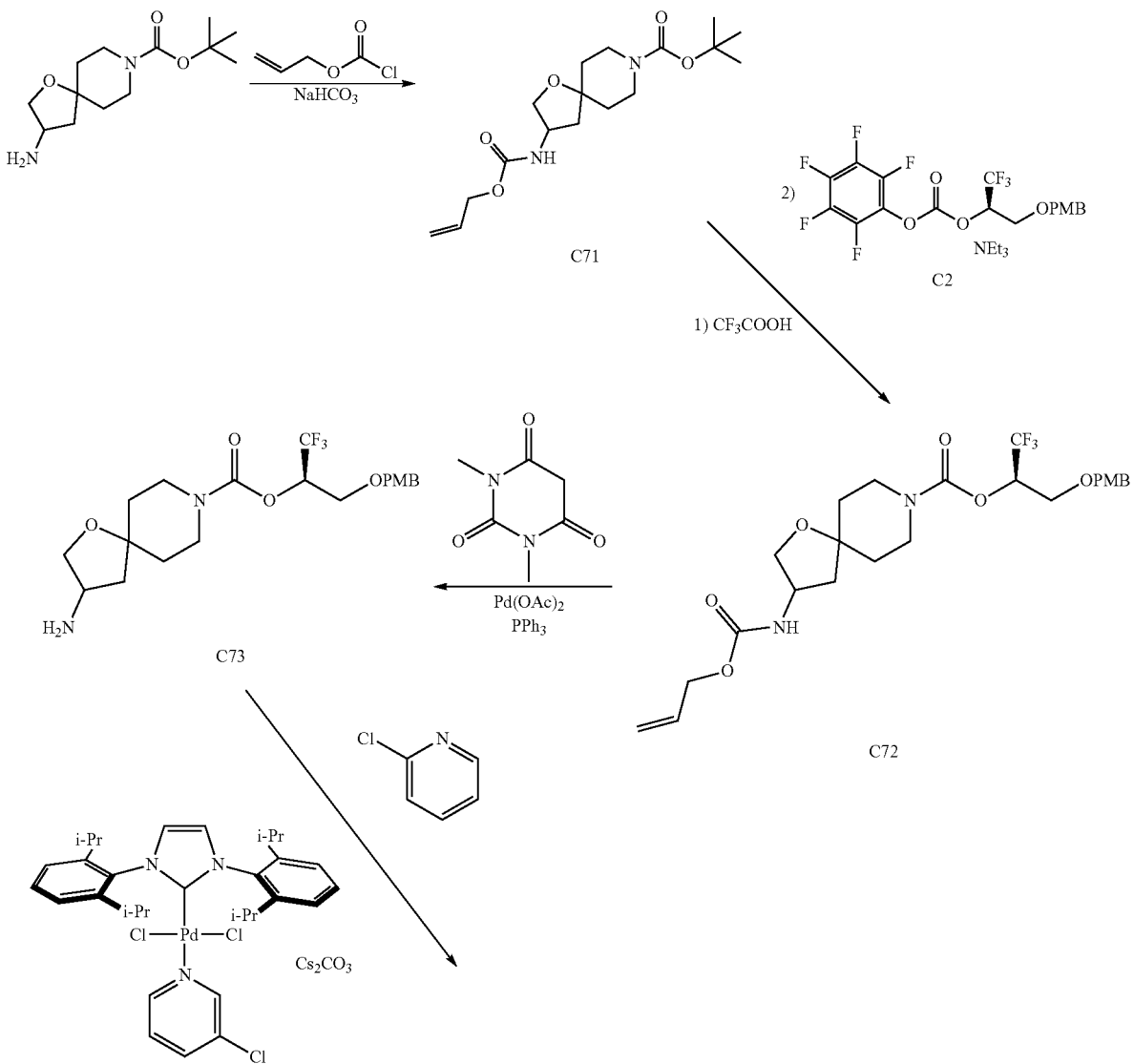

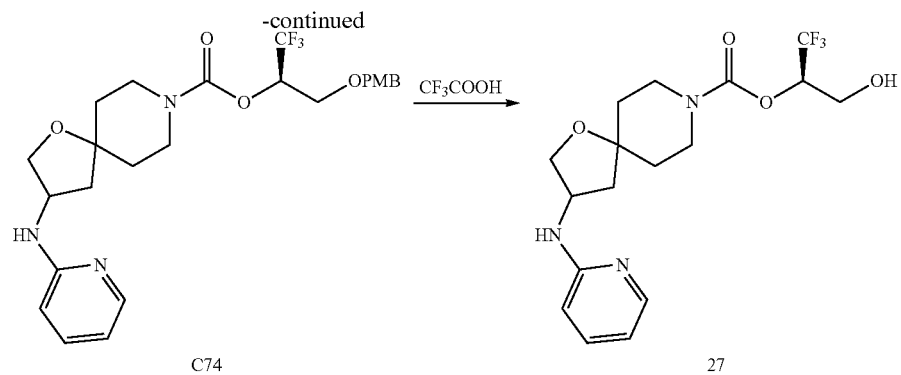

Step 1. Synthesis of tert-butyl 3-{[(prop-2-en-1-yloxy)carbonyl]amino}-1-oxa-8-azaspiro[4.5]decane-8-carboxylate (C71)

Prop-2-en-1-yl carbonochloridate (9.87 g, 81.9 mmol) was added to a 0° C. solution of tert-butyl 3-amino-1-oxa-8-azaspiro[4.5]decane-8-carboxylate (14.0 g, 54.6 mmol) in saturated aqueous sodium bicarbonate solution (400 mL) and tetrahydrofuran (100 mL). The reaction mixture was stirred at 22° C. for 16 hours, whereupon it was filtered and the filter cake was washed with ethyl acetate. The aqueous layer from the combined filtrates was extracted with ethyl acetate (2×200 mL), and the combined organic layers were washed with saturated ammonium chloride solution (3×100 mL), dried over sodium sulfate, filtered, and concentrated in vacuo to provide the product as a yellow oil, which solidified upon standing at room temperature. Yield: 18.3 g, 53.8 mmol, 98%. $^1$H NMR (400 MHz, CDCl$_3$) δ 5.98-5.85 (m, 1H), 5.34-5.27 (m, 1H), 5.26-5.20 (m, 1H), 4.95-4.86 (m, 1H), 4.56 (br d, J=4.6 Hz, 2H), 4.38-4.28 (m, 1H), 4.00 (dd, J=9.5, 5.6 Hz, 1H), 3.67 (br dd, J=9.7, 4.0 Hz, 1H), 3.66-3.52 (m, 2H), 3.37-3.24 (m, 2H), 2.13 (dd, J=13.3, 7.6 Hz, 1H), 1.72-1.49 (m, 5H, assumed; partially obscured by water peak), 1.46 (s, 9H).

Step 2. Synthesis of (2R)-1,1,1-trifluoro-3-[(4-methoxybenzyl)oxy]propan-2-yl 3-{[(prop-2-en-1-yloxy)carbonyl]amino}-1-oxa-8-azaspiro[4.5]decane-8-carboxylate (C72)

Conversion of C71 to C72 was effected using the method described for synthesis of C34 from C33 in Examples 8 and 9. The product was isolated as a light yellow oil. Yield: 12.6 g, 24.2 mmol, 89% over 2 steps. LCMS m/z 539.1 [M+Na$^+$]. $^1$H NMR (400 MHz, CDCl$_3$) δ 7.24 (br d, J=8.5 Hz, 2H), 6.88 (br d, J=8.7 Hz, 2H), 5.98-5.85 (m, 1H), 5.53-5.41 (m, 1H), 5.35-5.26 (m, 1H), 5.26-5.19 (m, 1H), 5.00-4.89 (m, 1H), 4.62-4.50 (m, 3H), 4.46 (d, half of AB quartet, J=11.7 Hz, 1H), 4.38-4.26 (m, 1H), 4.04-3.96 (m, 1H), 3.85-3.62 (m, 4H), 3.81 (s, 3H), 3.41-3.25 (m, 2H), 2.19-2.06 (m, 1H), 1.78-1.46 (m, 5H, assumed; partially obscured by water peak).

Step 3. Synthesis of (2R)-1,1,1-trifluoro-3-[(4-methoxybenzyl)oxy]propan-2-yl 3-amino-1-oxa-8-azaspiro[4.5]decane-8-carboxylate (C73)

Palladium(II) acetate (520 mg, 2.32 mmol) was added to a solution of C72 (12.6 g, 24.2 mmol), 1,3-dimethylpyrimidine-2,4,6(1H,3H,5H)-trione (7.62 g, 48.8 mmol), and triphenylphosphine (1.92 g, 7.32 mmol) in dichloromethane (100 mL). The reaction mixture was heated to 35° C. for 5 hours, whereupon it was concentrated in vacuo and purified via silica gel chromatography (Gradient: 0% to 100% ethyl acetate in petroleum, followed by a gradient of 0% to 10% methanol in dichloromethane) to afford the product as an orange solid. Yield: 9.40 g, 21.7 mmol, 90%. $^1$H NMR (400 MHz, CDCl$_3$) δ 7.24 (br d, J=8.5 Hz, 2H), 6.87 (br d, J=8.5 Hz, 2H), 5.53-5.41 (m, 1H), 4.50 (AB quartet, J$_{AB}$=11.7 Hz, Δν$_{AB}$=26.7 Hz, 2H), 4.02-3.94 (m, 1H), 3.87-3.62 (m, 4H), 3.80 (s, 3H), 3.42-3.17 (m, 4H), 2.18-2.05 (m, 1H), 1.86-1.59 (m, 4H), 1.55-1.46 (m, 1H).

Step 4. Synthesis of (2R)-1,1,1-trifluoro-3-[(4-methoxybenzyl)oxy]propan-2-yl 3-(pyridin-2-ylamino)-1-oxa-8-azaspiro[4.5]decane-8-carboxylate (C74)

A mixture of C73 (100 mg, 0.231 mmol), 2-chloropyridine (52.5 mg, 0.462 mmol), [1,3-bis(2,6-diisopropylphenyl)imidazol-2-ylidene](3-chloropyridyl)palladium(II) dichloride (15.8 mg, 23.2 μmol), and cesium carbonate (226 mg, 0.694 mmol) in toluene (9 mL) was heated at 130° C. for 18 hours. The reaction mixture was filtered, concentrated in vacuo, and subjected to preparative thin layer chromatography (Eluent: ethyl acetate), followed by a second preparative thin layer chromatographic purification [Eluent: (1:1 ethyl acetate/petroleum ether) containing 0.5% ammonium hydroxide] to provide the product as a light yellow gum. Yield: 36 mg, 71 μmol, 31%. LCMS m/z 532.2 [M+Na$^+$]. $^1$H NMR (400 MHz, CDCl$_3$) δ 8.10 (d, J=4 Hz, 1H), 7.43 (dd, J=8, 8 Hz, 1H), 7.24 (d, J=8.4 Hz, 2H), 6.88 (br d, J=8 Hz, 2H), 6.64-6.59 (m, 1H), 6.38 (d, J=8 Hz, 1H), 5.53-5.43 (m, 1H), 4.64-4.58 (m, 1H), 4.55 (d, half of AB quartet, J=12 Hz, 1H), 4.51-4.40 (m, 2H), 4.19-4.12 (m, 1H), 3.81 (s, 3H), 3.8-3.65 (m, 4H), 3.44-3.31 (m, 2H), 2.27-2.15 (m, 1H), 1.85-1.51 (m, 5H, assumed; partially obscured by water peak).

Step 5. Synthesis of (2R)-1,1,1-trifluoro-3-hydroxypropan-2-yl 3-(pyridin-2-ylamino)-1-oxa-8-azaspiro[4.5]decane-8-carboxylate (27)

Trifluoroacetic acid (1 mL) was added to a 0° C. solution of C74 (18 mg, 35 μmol) in dichloromethane (2 mL). The reaction mixture was stirred for 45 minutes, whereupon it was treated with aqueous sodium bicarbonate solution (10 mL) and extracted with dichloromethane (3×15 mL). The combined organic layers were dried over sodium sulfate, filtered, and concentrated in vacuo; purification via reversed phase HPLC (Column: Agela Durashell C18, 5 μm; Mobile phase A: 0.225% formic acid in water; Mobile phase B: acetonitrile; Gradient: 8% to 28% B) afforded the product as a white solid. Yield: 10.0 mg, 25.7 μmol, 73%. LCMS m/z 389.9 [M+H]$^+$. $^1$H NMR (400 MHz, CD$_3$OD), characteristic peaks: δ 7.93 (br d, J=5 Hz, 1H), 7.42 (br dd, J=8, 7 Hz, 1H), 6.59-6.52 (m, 2H), 5.33-5.24 (m, 1H), 4.49-4.40 (m, 1H), 4.14 (dd, J=9, 6 Hz, 1H), 3.91-3.83 (m, 1H), 3.81-3.67 (m, 4H), 2.26 (dd, J=13, 8 Hz, 1H).

Example 28

(2R)-1,1,1-Trifluoro-3-hydroxypropan-2-yl 4-(4-fluorobenzyl)-1-oxa-3-thia-4,9-diazaspiro[5.5]undecane-9-carboxylate 3,3-dioxide (28)

Step 1. Synthesis of tert-butyl 4-({[(chloromethyl)sulfonyl]amino}methyl)-4-hydroxypiperidine-1-carboxylate (C75)

Pyridine (3.0 mL, 37 mmol) was added to a solution of tert-butyl 4-(aminomethyl)-4-hydroxypiperidine-1-carboxylate (2 g, 8.7 mmol) in dichloromethane (40 mL), and the reaction mixture was cooled to 0° C. A solution of chloromethanesulfonyl chloride (0.930 mL, 10.2 mmol) in dichloromethane (40 mL) was then added drop-wise over 25 minutes, and the reaction mixture was allowed to stir at 0° C. for 5 minutes before being warmed to room temperature and stirred for 2 days. After solvents had been removed in vacuo, the residue was partitioned between dichloromethane and saturated aqueous ammonium chloride solution. The aqueous layer was extracted with dichloromethane, and the combined organic layers were dried over sodium sulfate,

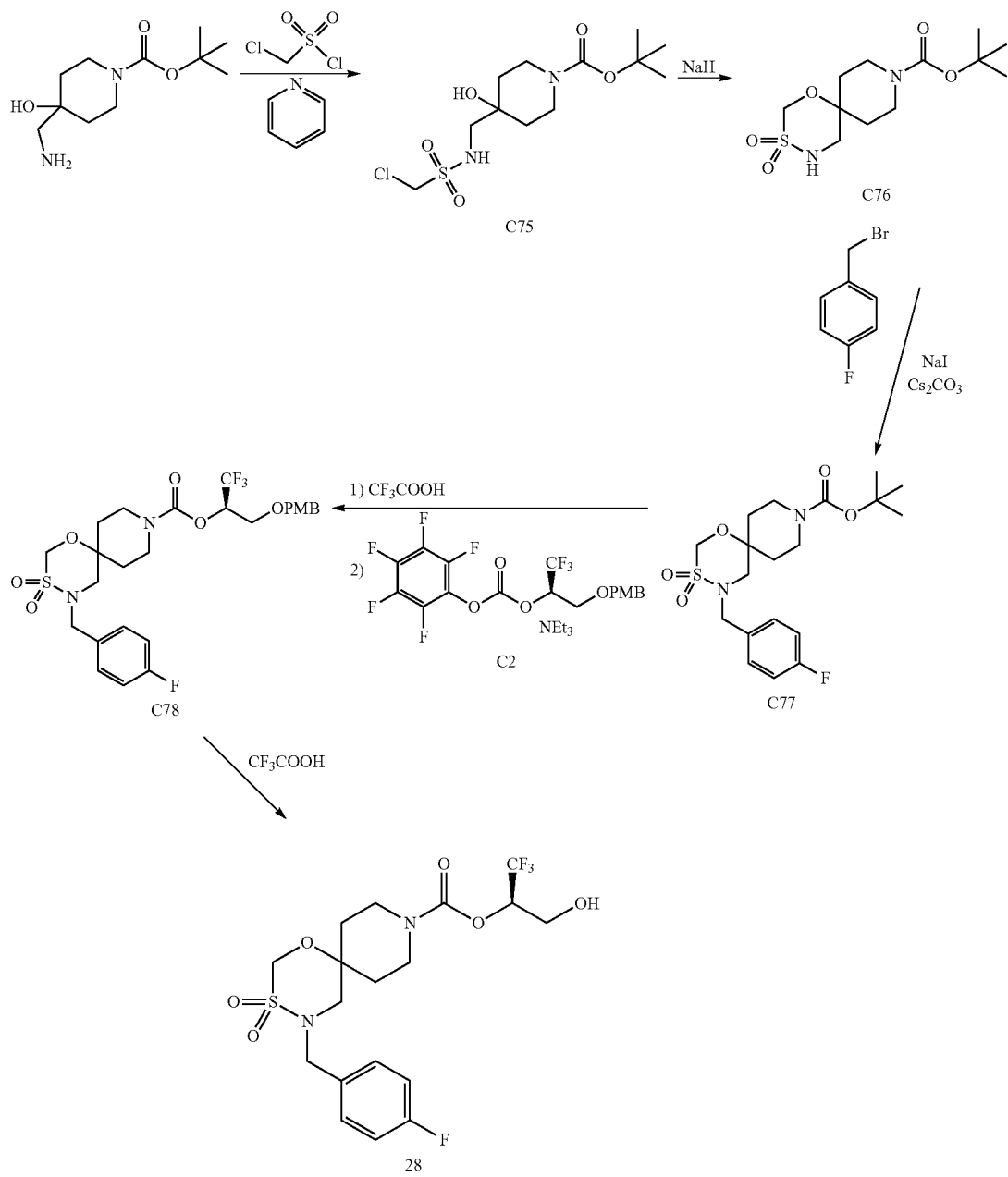

filtered, and concentrated under reduced pressure. Silica gel chromatography (Eluents: 50%, then 75%, then 90% ethyl acetate in heptane) provided the product as a tacky yellow solid. Yield: 851 mg, 2.48 mmol, 28%. LCMS m/z 341.5 [M−H+]. $^1$H NMR (400 MHz, CDCl$_3$) δ 5.28 (br t, J=6.2 Hz, 1H), 4.58 (s, 2H), 3.83 (br ddd, J=13.6, 4, 4 Hz, 2H), 3.24-3.15 (m, 4H), 1.69-1.61 (m, 2H), 1.56 (ddd, J=13.5, 11.1, 4.7 Hz, 2H), 1.46 (s, 9H).

Step 2. Synthesis of tert-butyl 1-oxa-3-thia-4,9-diazaspiro[5.5]undecane-9-carboxylate 3,3-dioxide (C76)

A solution of C75 (360 mg, 1.05 mmol) in tetrahydrofuran (7 mL) was cooled to 0° C. and treated with sodium hydride (60% suspension in mineral oil; 109 mg, 2.72 mmol). After the reaction mixture had been stirred for two days at room temperature, more sodium hydride (60% suspension in mineral oil; 109 mg, 2.72 mmol) was added, and stirring was continued for 2 days at room temperature. Saturated aqueous ammonium chloride solution was added, and the mixture was diluted with ethyl acetate; the aqueous layer was extracted with ethyl acetate, and the combined organic layers were washed with saturated aqueous sodium chloride solution, dried over sodium sulfate, filtered, and concentrated in vacuo. Chromatography on silica gel (Gradient: 25% to 50% ethyl acetate in heptane) afforded the product as a white solid. Yield: 430 mg, assumed quantitative. GCMS m/z 306.1 [M+]. $^1$H NMR (400 MHz, CDCl$_3$) δ 4.67 (s, 2H), 4.63 (br t, J=7 Hz, 1H), 3.99-3.81 (m, 2H), 3.45 (br d, J=7 Hz, 2H), 3.06 (br dd, J=12, 11 Hz, 2H), 2.08-1.92 (m, 2H), 1.49 (ddd, J=14.0, 11.8, 4.7 Hz, 2H), 1.47 (s, 9H).

Step 3. Synthesis of tert-butyl 4-(4-fluorobenzyl)-1-oxa-3-thia-4,9-diazaspiro[5.5]undecane-9-carboxylate 3,3-dioxide (C77)

A mixture of C76 (100 mg, 0.326 mmol), sodium iodide (74 mg, 0.49 mmol), cesium carbonate (319 mg, 0.979 mmol), and acetonitrile (3 mL) was treated with 1-(bromomethyl)-4-fluorobenzene (63 μL, 0.51 mmol) and stirred at room temperature overnight. The reaction mixture was then filtered through diatomaceous earth, and the filter pad was rinsed with acetonitrile. The combined filtrates were concentrated in vacuo, and the residue was purified twice via silica gel chromatography (#1—Gradient: 10% to 33% ethyl acetate in heptane; #2—dichloromethane as eluent, followed by a gradient of 5% to 33% ethyl acetate in heptane) to afford the product as a white solid. Yield: 128 mg, 0.309 mmol, 95%. $^1$H NMR (400 MHz, CDCl$_3$) δ 7.32-7.27 (m, 2H), 7.07 (br dd, J=8.6, 8.6 Hz, 2H), 4.68 (s, 2H), 4.27-4.17 (br s, 2H), 3.74-3.59 (m, 2H), 3.14-2.99 (m, 4H), 2.04-1.88 (m, 2H), 1.43 (s, 9H), 1.33 (ddd, J=14.1, 11.3, 4.6 Hz, 2H).

Step 4. Synthesis of (2R)-1,1,1-trifluoro-3-[(4-methoxybenzyl)oxy]propan-2-yl 4-(4-fluorobenzyl)-1-oxa-3-thia-4,9-diazaspiro[5.5]undecane-9-carboxylate 3,3-dioxide (C78)

Conversion of C77 to C78 was effected using the method described for synthesis of C34 from C33 in Examples 8 and 9. $^1$H NMR (400 MHz, CD$_3$OD) of intermediate 4-(4-fluorobenzyl)-1-oxa-3-thia-4,9-diazaspiro[5.5]undecane 3,3-dioxide, trifluoroacetic acid salt, δ 7.44-7.38 (m, 2H), 7.11 (br dd, J=8.8, 8.8 Hz, 2H), 4.82 (s, 2H), 4.26 (br s, 2H), 3.24-3.17 (m, 2H), 3.23 (s, 2H), 3.17-3.08 (m, 2H), 2.34-2.26 (m, 2H), 1.58 (ddd, J=15, 13, 5 Hz, 2H); LCMS m/z 315.3 [M+H]+. In this case, purification was effected via chromatography on silica gel (Eluents: 10%, then 25%, then 50% ethyl acetate in heptane), affording C78 as a tacky white solid. Yield: 156 mg, 0.264 mmol, 85%. LCMS m/z 613.1 [M+Na+] $^1$H NMR (400 MHz, CDCl$_3$) δ 7.29 (br dd, J=8.6, 5.3 Hz, 2H), 7.26-7.16 (br m, 2H), 7.07 (br dd, J=8.6, 8.6, 2H), 6.91-6.81 (br m, 2H), 5.49-5.38 (m, 1H), 4.73-4.63 (m, 2H), 4.55-4.39 (m, 2H), 4.33-4.14 (m, 2H), 3.88-3.7 (m, 2H), 3.81 (s, 3H), 3.73 (dd, half of ABX pattern, J=11.1, 3.8 Hz, 1H), 3.65 (dd, half of ABX pattern, J=11.1, 7.2 Hz, 1H), 3.22-2.99 (m, 4H), 2.12-1.91 (m, 2H), 1.40-1.23 (m, 2H).

Step 5. Synthesis of (2R)-1,1,1-trifluoro-3-hydroxypropan-2-yl 4-(4-fluorobenzyl)-1-oxa-3-thia-4,9-diazaspiro[5.5]undecane-9-carboxylate 3,3-dioxide (28)

Trifluoroacetic acid (1 mL) was added portion-wise to a 0° C. solution of C78 (151 mg, 0.256 mmol) in dichloromethane (4 mL). The reaction mixture was stirred for 1 hour at room temperature, whereupon it was concentrated in vacuo, and the residue was partitioned between saturated aqueous sodium bicarbonate solution and ethyl acetate. The organic layer was dried over sodium sulfate, filtered, concentrated under reduced pressure, and chromatographed on silica gel (Eluents: 10%, then 25%, then 50% ethyl acetate in heptane) to afford the product as a tacky white solid. Yield: 109 mg, 0.232 mmol, 91%. LCMS m/z 471.4 [M+H]+. $^1$H NMR (400 MHz, CDCl$_3$) δ 7.30 (br dd, J=8.5, 5.4 Hz, 2H), 7.08 (br dd, J=8.6, 8.5 Hz, 2H), 5.27-5.17 (m, 1H), 4.74-4.63 (m, 2H), 4.34-4.13 (m, 2H), 3.98 (dd, half of ABX pattern, J=12.5, 3.3 Hz, 1H), 3.92-3.73 (m, 3H), 3.27-3.01 (m, 4H), 2.15-1.96 (m, 2H), 1.43-1.3 (m, 2H).

Example 29

(2R)-1,1,1-Trifluoro-3-hydroxypropan-2-yl 4-[(4-fluorophenyl)sulfonyl]-3-hydroxy-1-oxa-4,9-diazaspiro[5.5]undecane-9-carboxylate (29)

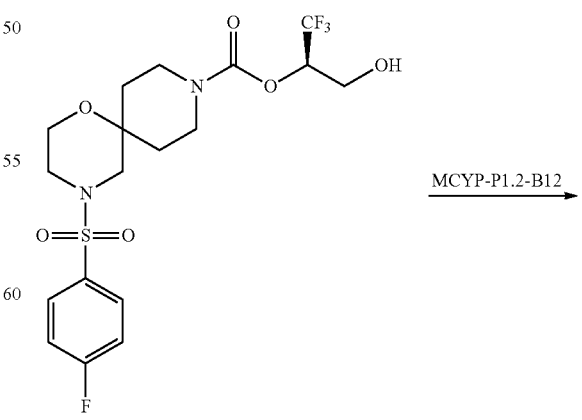

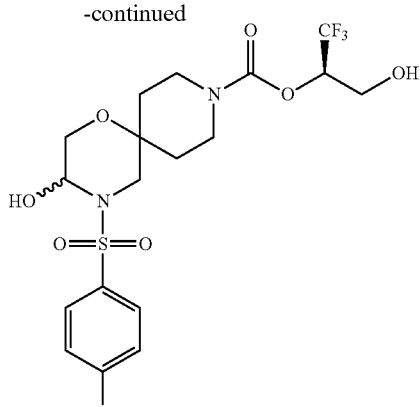

29

MicroCyp® Reaction Buffer mix (Codexis; 519.0 mg) was mixed with deionized water (28.1 mL) to provide a buffer solution containing NADP$^+$, glucose, glucose dehydrogenase, and potassium phosphate. Compound 6 (6.0 mg, 13 µmol) was dissolved in a mixture of dimethyl sulfoxide (0.72 mL) and the buffer solution (0.24 mL).

MCYP-P1.2-B12 (Codexis; 6.8 mg, 0.72 nmol/mg) was treated with the buffer solution prepared above (27.4 mL), followed by the solution of 6 prepared above. The reaction mixture was divided in half (14.2 mL each) and transferred into two 25 mL glass vials; the reaction mixtures were left open to the atmosphere and shaken on an orbital shaker (30° C., 225 rpm) for 24 hours. The combined reaction mixtures contained:

[MCYP-P1.2-B12]=0.24 mg/mL (0.17 µM, 6.8 mg, 4.89 nmol)

[6]=0.21 mg/mL (0.44 mM, 6.0 mg, 13 µmol)

2.5% dimethyl sulfoxide

[NADP$^+$]=0.75 mg/mL (0.99 mM, 21.5 mg, 28.1 µmol)

[Glucose]=3.55 mg/mL (19.7 mM, 100.8 mg, 559.7 µmol)

[Glucose dehydrogenase]=0.39 mg/mL (11.2 mg)

0.1 M potassium phosphate buffer, pH 8.0

After 24 hours, the crude reaction mixtures were combined and purified via reversed phase HPLC (Column: Phenomenex Luna (2) C18, 5 µm; Mobile phase A: 0.1% formic acid in water; Mobile phase B: 0.1% formic acid in acetonitrile; Gradient: 50% to 100% B) to afford the product as a solid (3.0 mg), presumed to be a mixture of diastereomers. 1-Dimensional and 2-dimensional NMR spectroscopic studies established the regiochemistry of oxidation as shown for 29. The $^1$H NMR indicated that some impurities were present; peaks belonging to the product were identified via 2D NMR. Yield, corrected by quantitative NMR: 1.6 mg, 3.3 µmol, 25%. LCMS m/z 469.2 [(M−H$_2$O)+H]$^+$ and 509.1 [M+Na]$^+$. $^1$H NMR (500 MHz, DMSO-d$_6$), characteristic peaks: δ 7.93-7.88 (m, 2H), 7.42 (br dd, J=8.9, 8.8 Hz, 2H), 5.25-5.17 (m, 1H), 5.17 (br s, 1H), 3.83-3.78 (m, 1H), 3.70-3.53 (m, 5H), 3.26-3.13 (m, 2H), 3.19 (d, J=12.0 Hz, 1H), 2.79 (d, J=12.0 Hz, 1H), 1.53-1.41 (m, 2H).

Example 30

(2R)-3,3,3-Trifluoro-2-[({(3R)-3-[methyl(phenylsulfonyl)amino]-1-oxa-8-azaspiro[4.5]dec-8-yl}carbonyl)oxy]propyl phosphate, disodium salt (30)

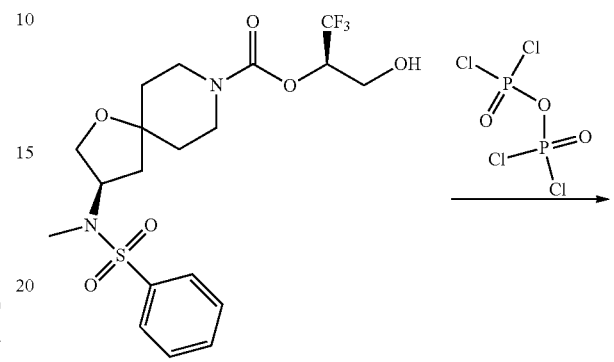

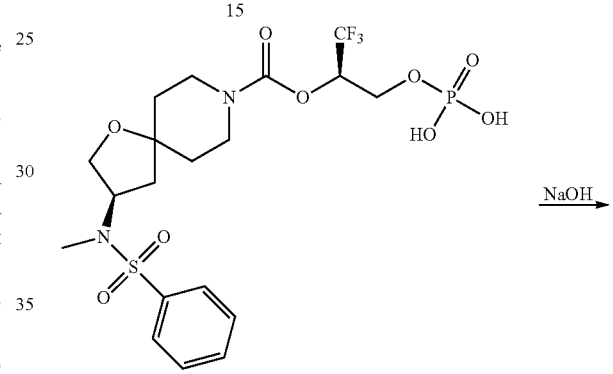

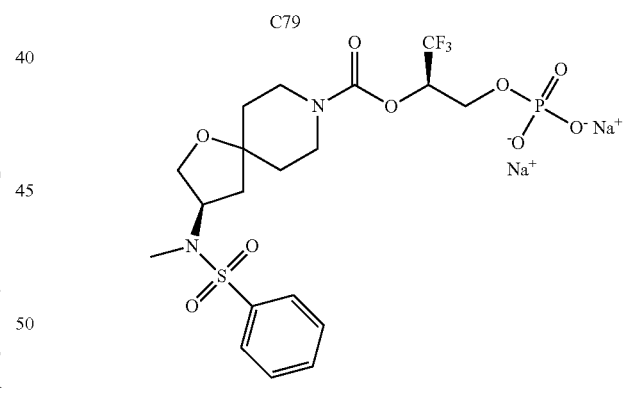

Step 1. Synthesis of (2R)-1,1,1-trifluoro-3-(phosphonooxy)propan-2-yl (3R)-3-[methyl(phenylsulfonyl)amino]-1-oxa-8-azaspiro[4.5]decane-8-carboxylate (C79)

Diphosphoryl tetrachloride (98%, 850 µL, 6.02 mmol) was added to a 0° C. solution of 15 (560 mg, 1.20 mmol) in acetonitrile (7.5 mL), and the reaction mixture was stirred at 0° C. for 3 hours, whereupon it was poured into ice. After it had been stirred at room temperature for 1.75 hours, the resulting mixture was concentrated in vacuo to remove acetonitrile. The aqueous residue was extracted 4 times with ethyl acetate, and the combined organic layers were dried over magnesium sulfate, filtered and concentrated under reduced pressure. The resulting clear oil was treated with diethyl ether and again concentrated in vacuo; this diethyl ether treatment was repeated, affording the product as a white solid. Yield: 510 mg, 0.933 mmol, 78%. LCMS m/z 547.2 [M+H]+. 1H NMR (400 MHz, CD3OD) δ 7.85-7.80 (m, 2H), 7.70-7.65 (m, 1H), 7.63-7.57 (m, 2H), 5.53-5.43 (m, 1H), 4.75-4.64 (m, 1H), 4.30-4.16 (m, 2H), 3.80 (dd, J=10.0, 7.4 Hz, 1H), 3.77-3.63 (m, 2H), 3.55 (dd, J=10.1, 5.0 Hz, 1H), 3.38-3.18 (m, 2H, assumed; partially obscured by solvent peak), 2.76 (s, 3H), 1.91 (br dd, J=13.3, 9.3 Hz, 1H), 1.78-1.57 (m, 3H), 1.51 (dd, J=13.5, 6.8 Hz, 1H), 1.48-1.37 (m, 1H).

Step 2. Synthesis of (2R)-3,3,3-trifluoro-2-[({(3R)-3-[methyl(phenylsulfonyl)amino]-1-oxa-8-azaspiro[4.5]dec-8-yl}carbonyl)oxy]propyl phosphate, disodium salt (30)

To a solution of C79 (820 mg, 1.50 mmol) in ethanol (9 mL) was added aqueous sodium hydroxide solution (1 M; 2.9 mL, 2.9 mmol) and the reaction mixture was stirred at room temperature for 3 hours. Ethanol (10 mL) was added, and the mixture was concentrated in vacuo; this ethanol treatment was repeated three times; the resulting solid was washed with ethanol and collected via filtration, affording the product as a white solid. Yield: 660 mg, 1.12 mmol, 75%. LCMS m/z 547.2 [M+H]+. 1H NMR (400 MHz, D2O) δ 7.85-7.80 (m, 2H), 7.75-7.69 (m, 1H), 7.65-7.60 (m, 2H), 5.46-5.36 (m, 1H), 4.78-4.65 (m, 1H, assumed; partially obscured by solvent peak), 4.15-4.08 (m, 1H), 4.07-3.99 (m, 1H), 3.85 (dd, J=10, 8 Hz, 1H), 3.63-3.25 (m, 5H), 2.76 (s, 3H), 1.94 (dd, J=13.6, 9.3 Hz, 1H), 1.79-1.57 (m, 3H), 1.57-1.40 (m, 1H), 1.49 (dd, J=13.7, 6.7 Hz, 1H).

Example 31

(2R)-3,3,3-Trifluoro-2-[({(3R)-3-[(phenylsulfonyl)amino]-1-oxa-8-azaspiro[4.5]dec-8-yl}carbonyl)oxy]propyl phosphate, disodium salt (31)

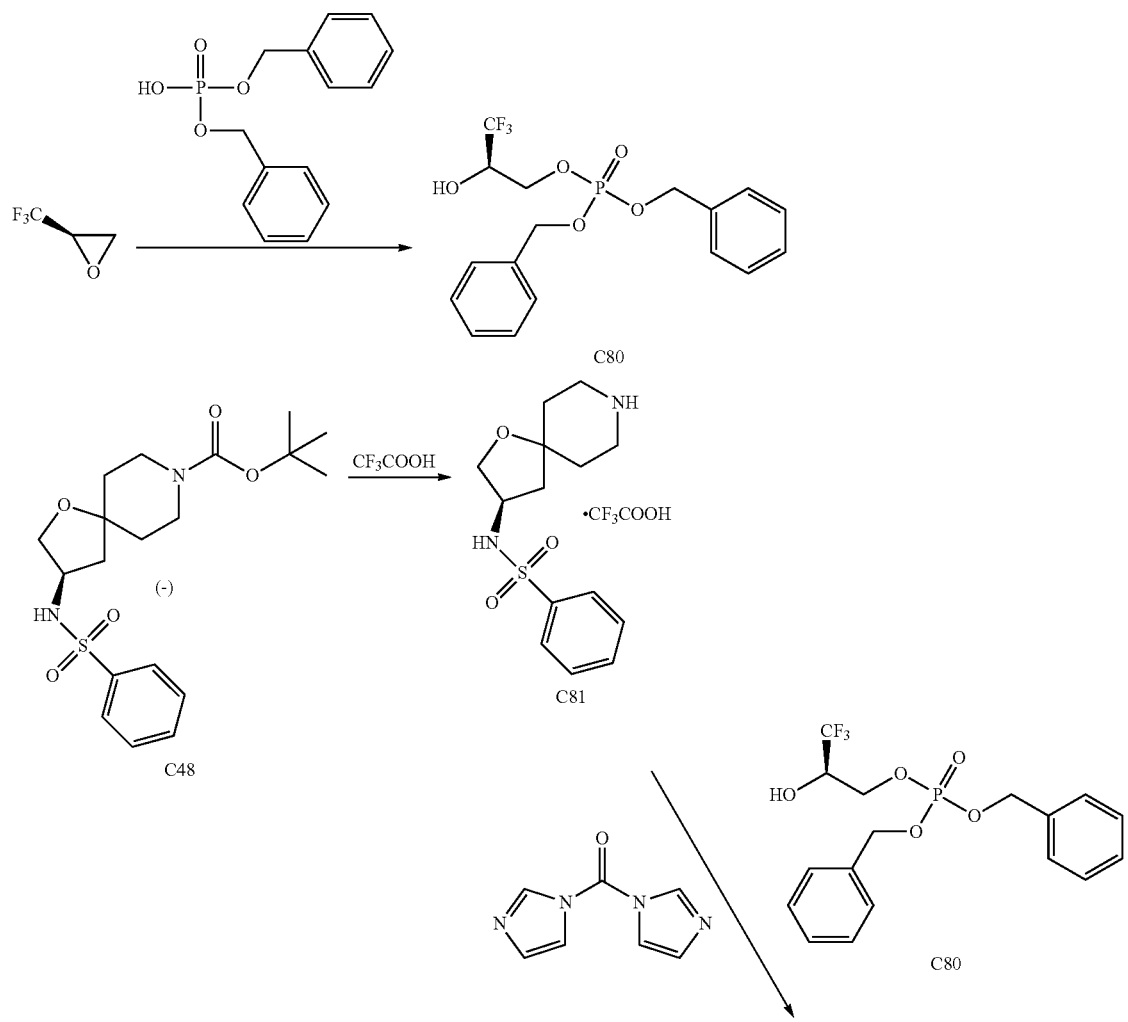

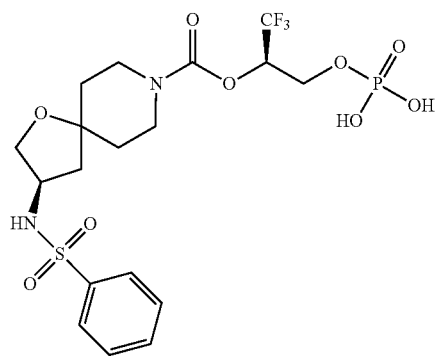

C83

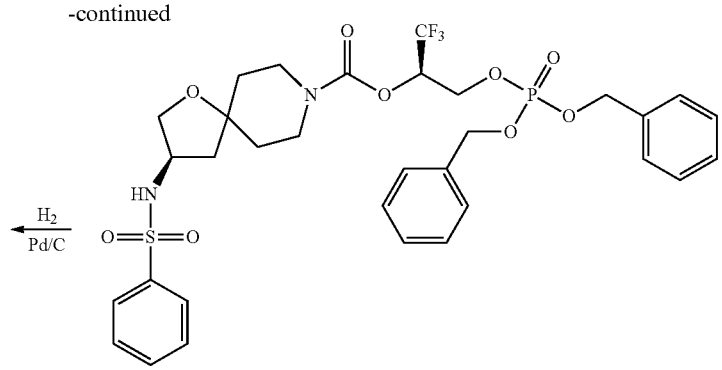

C82

H₂
Pd/C t-BuONa

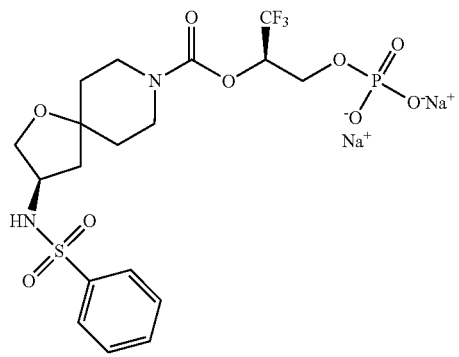

31

Step 1. Synthesis of dibenzyl (2R)-3,3,3-trifluoro-2-hydroxypropyl phosphate (C80)

(2R)-2-(Trifluoromethyl)oxirane (14.85 g, 132.5 mmol) was added to dibenzyl hydrogen phosphate (99%, 10.8 g, 38.4 mmol) in an amber bottle, and the thick slurry was heated in a 65° C. oil bath for 25 hours. Excess (2R)-2-(trifluoromethyl)oxirane was removed via concentration in vacuo. The resulting oil was diluted with dichloromethane (10 mL) and subjected to silica gel chromatography (Eluents: 5%, then 10%, then 15%, then 20% ethyl acetate in dichloromethane) to afford a pale yellow oil, which was treated with heptane (90 mL) and vigorously stirred. The resulting solids were allowed to granulate for 1.5 hours, whereupon they were collected via filtration and washed with heptane (38 mL), affording the product as a white solid. Yield: 9.11 g, 23.3 mmol, 61%. Melting point: ~45° C. by differential scanning calorimetry. ¹H NMR (400 MHz, CD₃CN) δ 7.42-7.34 (m, 10H), 5.06 (d, J=8.3 Hz, 4H), 4.27-4.14 (m, 2H), 4.14-4.05 (m, 1H).

Step 2. Synthesis of N-[(3R)-1-oxa-8-azaspiro[4.5]dec-3-yl]benzenesulfonamide, trifluoroacetic acid salt (C81)

Conversion of C48 (1.3 g, 3.3 mmol) to C81 was carried out using the method described for synthesis of C10 from C9 in Example 1. The product was obtained as a colorless oil, and taken on without additional purification. The ¹H NMR indicated that the product was impure. Yield: 2.17 g, assumed quantitative. LCMS m/z 297.2 [M+H]⁺. ¹H NMR (400 MHz, CDCl₃), product peaks only: δ 7.89-7.85 (m, 2H), 7.68-7.62 (m, 1H), 7.60-7.54 (m, 2H), 3.98-3.91 (m, 1H), 3.88 (dd, half of ABX pattern, J=9.7, 5.6 Hz, 1H), 3.62 (br dd, J=9.8, 4.4 Hz, 1H), 3.38-3.24 (m, 4H), 2.05 (dd, J=13.6, 7.3 Hz, 1H), 1.99-1.88 (m, 2H), 1.88-1.81 (m, 1H), 1.81-1.71 (m, 2H).

Step 3. Synthesis of (2R)-3-{[bis(benzyloxy)phosphoryl]oxy}-1,1,1-trifluoropropan-2-yl (3R)-3-[(phenylsulfonyl)amino]-1-oxa-8-azaspiro[4.5]decane-8-carboxylate (C82)

Compound C80 (1.90 g, 4.87 mmol) was added to a solution of 1,1'-carbonyldiimidazole (790 mg, 4.87 mmol) in acetonitrile (23 mL). The reaction mixture was allowed to stir for 1.5 hours at room temperature, whereupon a solution of C81 (from the previous step, 2.00 g) in acetonitrile (2 mL) was added in a drop-wise manner over 1 minute. After the reaction mixture had been stirred for an additional 5 hours at room temperature, it was partitioned between ethyl acetate (250 mL) and water (250 mL). The organic layer was dried over sodium sulfate, filtered, and concentrated in vacuo; silica gel chromatography (Gradient: 30% to 80% ethyl acetate in heptane) provided the product as a colorless oil. Yield: 2.02 g, 2.83 mmol, 66% over 2 steps. LCMS m/z 713.1 [M+H]⁺. ¹H NMR (400 MHz, CDCl₃) δ 7.88 (br d, J=8 Hz, 2H), 7.64-7.58 (m, 1H), 7.57-7.51 (m, 2H), 7.40-7.30 (m, 10H), 5.46-5.36 (m, 1H), 5.09-4.96 (m, 4H), 4.73-4.62 (m, 1H), 4.28-4.16 (m, 2H), 3.99-3.86 (m, 1H), 3.85-3.60 (m, 3H), 3.56-3.45 (m, 1H), 3.31-3.14 (m, 2H), 1.99-1.83 (m, 1H), 1.67-1.45 (m, 4H), 1.44-1.3 (m, 1H).

Step 4. Synthesis of (2R)-1,1,1-trifluoro-3-(phosphonooxy)propan-2-yl (3R)-3-[(phenylsulfonyl)amino]-1-oxa-8-azaspiro[4.5]decane-8-carboxylate (C83)

A solution of C82 (1.80 g, 2.53 mmol) in methanol (50 mL) was treated with 10% palladium on carbon (180 mg) and hydrogenated at 25 psi using a Parr reactor for 4 hours at room temperature. The reaction mixture was filtered through diatomaceous earth, and the filtrate was concentrated in vacuo to provide an oil, which was taken up in methanol (20 mL) and again concentrated under reduced pressure. The product was obtained as a brittle foam. Yield: 1.14 g, 2.14 mmol, 85%. LCMS m/z 533.0 [M+H]$^+$. $^1$H NMR (400 MHz, CDCl$_3$) δ 7.87 (br d, J=8 Hz, 2H), 7.63-7.57 (m, 1H), 7.56-7.49 (m, 2H), 5.53-5.41 (m, 1H), 4.39-4.15 (m, 2H), 3.98-3.18 (m, 7H), 2.06-1.92 (m, 1H), 1.88-1.43 (m, 5H).

Step 5. Synthesis of (2R)-3,3,3-trifluoro-2-[({(3R)-3-[(phenylsulfonyl)amino]-1-oxa-8-azaspiro[4.5]dec-8-yl}carbonyl)oxy]propyl phosphate, disodium salt (31)

Sodium tert-butoxide (2 M solution in tetrahydrofuran, 1.98 mL, 3.96 mmol) was added drop-wise over 5 minutes to a 0° C. solution of C83 (1.08 g, 2.03 mmol) in acetonitrile (20 mL), and the reaction mixture was allowed to warm to room temperature and stir for 2 hours. The resulting solid was collected on a Teflon filter, affording the product as a white solid. Yield: 1.02 g, 1.77 mmol, 87%. LCMS m/z 532.9 [M+H]$^+$. $^1$H NMR (400 MHz, D$_2$O) δ 7.90 (br d, J=8 Hz, 2H), 7.77-7.71 (m, 1H), 7.66 (br dd, J=8, 8 Hz, 2H), 5.47-5.37 (m, 1H), 4.14-4.05 (m, 1H), 4.02-3.86 (m, 3H), 3.68-3.31 (m, 5H), 2.08-1.97 (m, 1H), 1.80-1.49 (m, 5H).

Example 32

(2R)-3,3,3-Trifluoro-2-[({4-[(4-fluorophenyl)sulfonyl]-1-oxa-4,9-diazaspiro[5.5]undec-9-yl}carbonyl)oxy]propyl phosphate, disodium salt (32)

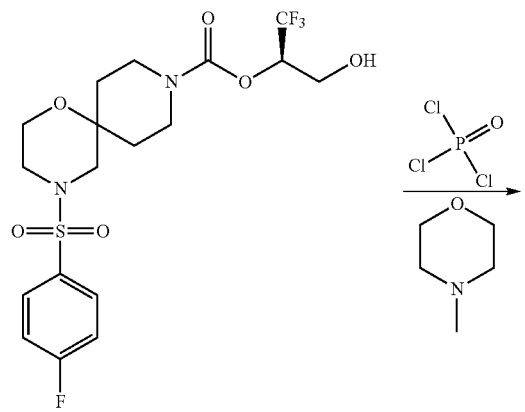

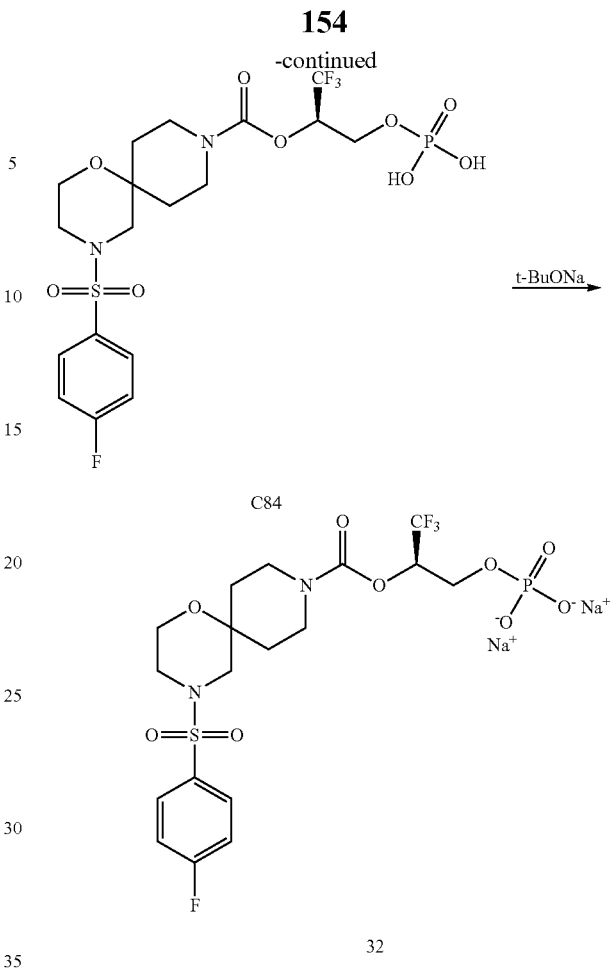

Step 1. Synthesis of (2R)-1,1,1-trifluoro-3-(phosphonooxy)propan-2-yl 4-[(4-fluorophenyl)sulfonyl]-1-oxa-4,9-diazaspiro[5.5]undecane-9-carboxylate (C84)

4-Methylmorpholine (14.5 mL, 132 mmol) was added to a solution of 6 (12.3 g, 26.1 mmol) in acetonitrile (750 mL) and the reaction mixture was cooled to −10° C. in an ice-salt bath. Phosphorus oxychloride (2.9 mL, 31 mmol) was added over 1 minute with vigorous stirring, and the reaction mixture was allowed to stir at −10° C. for one hour, whereupon it was poured into ice water (500 mL) and stirred for 1.5 hours to ensure complete quench of excess reagent. After concentration of the mixture to approximately one-half its original volume, the remaining liquid was extracted with ethyl acetate (1 L), and the organic layer was washed sequentially with aqueous hydrochloric acid (1 M; 3×300 mL) and with saturated aqueous sodium chloride solution, dried over sodium sulfate, filtered, and concentrated in vacuo to afford the product as a brittle foam (15.0 g) containing some ethyl acetate by $^1$H NMR analysis. Yield, corrected for ethyl acetate: 14.2 g, 25.8 mmol, 99%. LCMS m/z 550.9 [M+H]$^+$. $^1$H NMR (500 MHz, CDCl$_3$), characteristic peaks: δ 7.81-7.73 (m, 2H), 5.57-5.48 (m, 1H), 4.45-4.34 (m, 1H), 4.32-4.20 (m, 1H), 3.97-3.74 (m, 4H), 3.35-3.11 (m, 2H), 3.06-2.89 (m, 2H), 2.89-2.72 (m, 2H), 2.03-1.87 (m, 2H), 1.68-1.46 (m, 2H).

Step 2. Synthesis of (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, disodium salt (32)

A stirring solution of C84 (20.0 g, 36.3 mmol) in water (1.2 L) was treated with solid sodium bicarbonate until the pH of the mixture was approximately 7. The mixture was washed with ethyl acetate (500 mL), and the aqueous layer was acidified to pH 1.5-2 via portion-wise addition of concentrated hydrochloric acid. It was then extracted with ethyl acetate (1.5 L); the organic layer was washed with saturated aqueous sodium chloride solution (100 mL), dried over sodium sulfate, filtered, and concentrated in vacuo to provide a white solid (20 g). This material was dissolved in acetonitrile (600 mL), cooled to 0° C., and treated in a drop-wise manner over 5 minutes with a solution of sodium tert-butoxide in tetrahydrofuran (2 M; 35.4 mL, 70.9 mmol).

After the reaction had stirred for one hour at 0° C., it was concentrated under reduced pressure to afford a solid (21.4 g). This material was mixed with ethanol (30 mL) and stirred at room temperature for 30 minutes, whereupon the solid was collected via filtration to provide the product as a solid (21.3 g) that contained some solvents via $^1$H NMR analysis. Yield, corrected for solvents: 20.8 g, 35.0 mmol, 96%. LCMS m/z 551.3 [M+H]$^+$. $^1$H NMR (500 MHz, D$_2$O) δ 7.87-7.81 (m, 2H), 7.37 (dd, J=8.9, 8.7 Hz, 2H), 5.46-5.39 (m, 1H), 4.12-4.05 (m, 1H), 4.01-3.94 (m, 1H), 3.93-3.8 (m, 1H), 3.83 (dd, J=5.0, 4.8 Hz, 2H), 3.78-3.65 (m, 1H), 3.34-3.13 (m, 2H), 3.10-2.98 (m, 2H), 2.97-2.85 (m, 2H), 1.99-1.81 (m, 2H), 1.75-1.51 (m, 2H).

Alternate Synthesis of Example 32

(2R)-3,3,3-Trifluoro-2-[({4-[(4-fluorophenyl)sulfonyl]-1-oxa-4,9-diazaspiro[5.5]undec-9-yl}carbonyl)oxy]propyl phosphate, disodium salt (32)

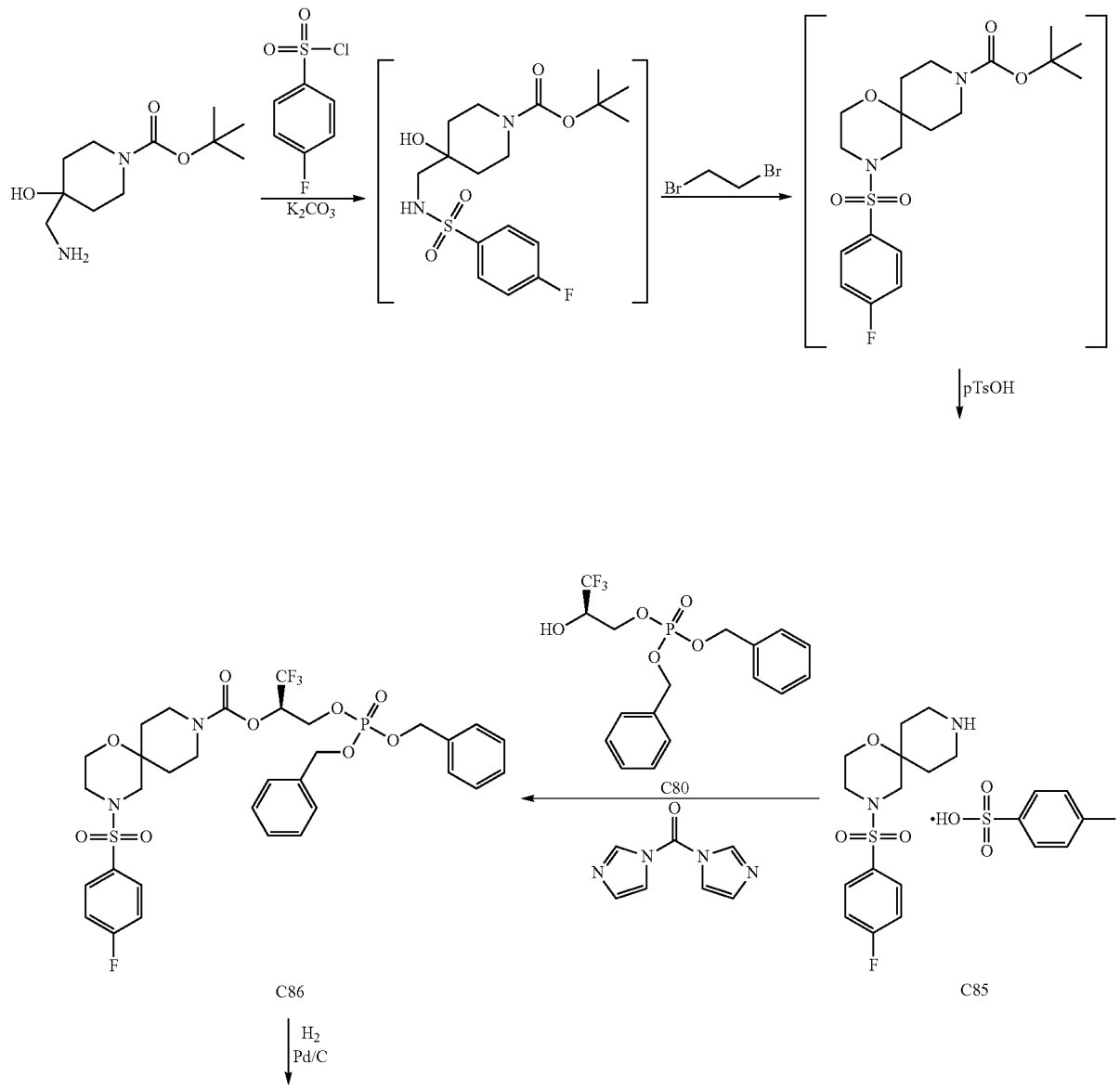

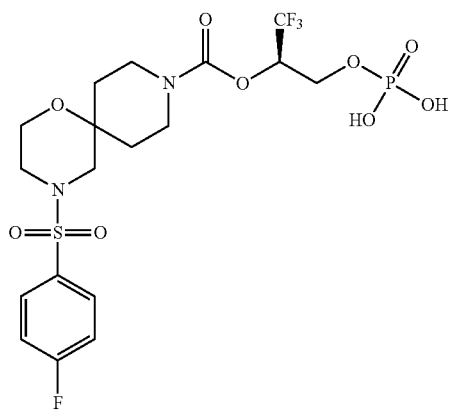

C84

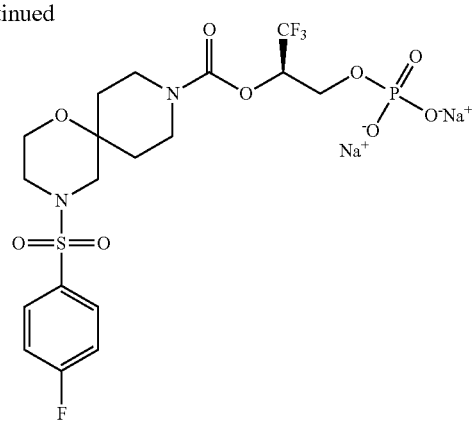

32

Step 1. Synthesis of 4-[(4-fluorophenyl)sulfonyl]-1-oxa-4,9-diazaspiro[5.5]undecane, para-toluenesulfonic acid salt (C85)

Potassium carbonate (24.0 g, 174 mmol) was added to a solution of tert-butyl 4-(aminomethyl)-4-hydroxypiperidine-1-carboxylate (5.00 g, 21.7 mmol) in acetonitrile (35 mL), and the reaction mixture was allowed to stir for 5 minutes. A solution of 4-fluorobenzenesulfonyl chloride (4.31 g, 22.1 mmol) in acetonitrile (15 mL) was slowly added over five minutes, and the resulting suspension was stirred at 25° C.; after 1 hour, 1,2-dibromoethane (7.50 mL, 87.0 mmol) was added, and the reaction mixture was heated at 80° C. for 27 hours, whereupon it was cooled to 25° C. and filtered. The reaction flask was rinsed with acetonitrile (2×18 mL), and the combined filtrates were concentrated under reduced pressure and diluted with ethyl acetate (72 mL). para-Toluenesulfonic acid monohydrate (8.38 g, 44.0 mmol) was added in one portion, and the reaction mixture was stirred at room temperature for 10 minutes, until a solution was obtained. It was then heated at 50° C. for 1.5 hours, at which point it was cooled to 25° C. and stirred for 2 hours to granulate the precipitate. This material was collected via filtration and rinsed with ethyl acetate, affording the product as a white solid. Yield: 7.26 g, 14.9 mmol, 69%. $^1$H NMR (600 MHz, CD$_3$OD) δ 7.84 (br dd, J=8, 5 Hz, 2H), 7.71 (br d, J=7.9 Hz, 2H), 7.38 (br dd, J=8.5, 8.5 Hz, 2H), 7.24 (br d, J=7.9 Hz, 2H), 3.81 (dd, J=5.0, 4.7 Hz, 2H), 3.26-3.20 (m, 2H), 3.19-3.12 (m, 2H), 3.03-2.98 (m, 2H), 2.86 (br s, 2H), 2.37 (s, 3H), 2.20 (br d, J=14.4 Hz, 2H), 1.74-1.67 (m, 2H).

Step 2. Synthesis of (2R)-3-{[bis(benzyloxy)phosphoryl]oxy}-1,1,1-trifluoropropan-2-yl 4-[(4-fluorophenyl) sulfonyl]-1-oxa-4,9-diazaspiro[5.5]undecane-9-carboxylate (C86)

A solution of C80 (28.0 g, 71.7 mmol) in acetonitrile (75 mL) was added over 15 minutes to a mixture of 1,1'-carbonyldiimidazole (97%, 12.6 g, 77.7 mmol) in acetonitrile (93 mL). The C80 solution was rinsed in with acetonitrile (5 mL) and the reaction mixture was allowed to stir at room temperature for 30 minutes. Compound C85 (37.0 g, 76.0 mmol) was added in one portion, and stirring was continued at room temperature for 6 hours, whereupon the reaction mixture was concentrated in vacuo. The residue was mixed with ethyl acetate (520 mL), and the mixture was washed twice with water (2×260 mL), then concentrated under reduced pressure. The residue was dissolved in a mixture of ethyl acetate and heptane (1:1, 206 mL) and eluted through a pad of silica gel (150 g) using a mixture of ethyl acetate and heptane (1:1, 1.3 L). Fractions containing the product were combined and concentrated under reduced pressure to provide the product. Yield: 42.1 g, 57.6 mmol, 80%. $^1$H NMR (600 MHz, CD$_3$CN) δ 7.80-7.74 (m, 2H), 7.44-7.34 (m, 10H), 7.34 (dd, J=8.8, 8.7 Hz, 2H), 5.52-5.46 (m, 1H), 5.09-4.99 (m, 4H), 4.35-4.21 (m, 2H), 3.77-3.67 (m, 4H), 3.16-3.02 (m, 2H), 2.96-2.86 (m, 2H), 2.79-2.63 (m, 2H), 1.86-1.72 (m, 2H), 1.51-1.26 (m, 2H).

Step 3. Synthesis of (2R)-1,1,1-trifluoro-3-(phosphonooxy)propan-2-yl 4-[(4-fluorophenyl)sulfonyl]-1-oxa-4,9-diazaspiro[5.5]undecane-9-carboxylate (C84)

A solution of C86 (2.0 grams, 2.7 mmol) in tetrahydrofuran (26 mL) was added to 5% palladium on carbon (Evonik Noblyst P1142; 40 mg) in a Biotage Atlantis reactor. Additional tetrahydrofuran (4.0 mL) was used to rinse the vessel containing starting material; this was added to the reaction mixture. The reactor was purged three times with nitrogen while the reaction mixture was stirred, and then three times with hydrogen without stirring. The hydrogen pressure was brought to 5 psig at 25° C., and then to 15 psig. The agitation was increased to 1200 rpm for 4 hours, whereupon the reactor was purged three times with nitrogen, and the reaction mixture was filtered. The filter cake was rinsed with tetrahydrofuran (20 mL), the combined filtrates were concentrated in vacuo, and the residue was dissolved in tert-butyl methyl ether (300 mL) and concentrated again. This dissolution/concentration was repeated, affording the product as a white foam. Yield: 1.35 g, 2.45 mmol, 91%.

Step 4. Synthesis of (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, disodium salt (32)

Aqueous sodium hydroxide solution (1 M, 12.0 mL, 12.0 mmol) was added drop-wise over 1 minute to a solution of C84 (97%, 3.50 g, 6.17 mmol) in ethanol (35.0 mL). The reaction mixture was stirred at room temperature for 1.5 hours; ethanol (120 mL) was added, and stirring was continued for 30 minutes, whereupon the reaction mixture was filtered. The filter cake was washed with ethanol (25 mL) to provide the product as a white solid. Yield: 2.88 g, 4.84 mmol, 78%. $^1$H NMR (600 MHz, D$_2$O) δ 7.85 (br dd, J=7, 5 Hz, 2H), 7.38 (br dd, J=9, 8 Hz, 2H), 5.47-5.39 (m, 1H), 4.12-4.06 (m, 1H), 4.01-3.95 (m, 1H), 3.94-3.66 (m, 2H), 3.84 (br dd, J=5, 4 Hz, 2H), 3.35-3.15 (m, 2H), 3.11-3.00 (m, 2H), 2.98-2.86 (m, 2H), 2.00-1.82 (m, 2H), 1.76-1.52 (m, 2H).

Example 33

(2R)-3,3,3-Trifluoro-2-[({4-[(4-fluorophenyl)sulfonyl]-1-oxa-4,9-diazaspiro[5.5]undec-9-yl}carbonyl)oxy]propyl phosphate, (bis)-L-lysine salt (33)

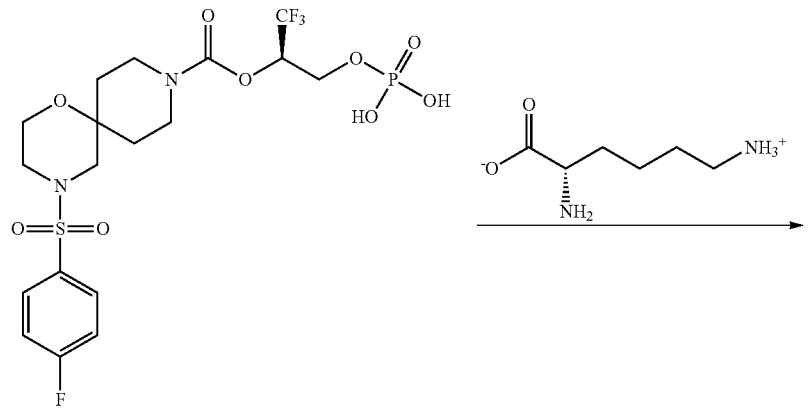

C84

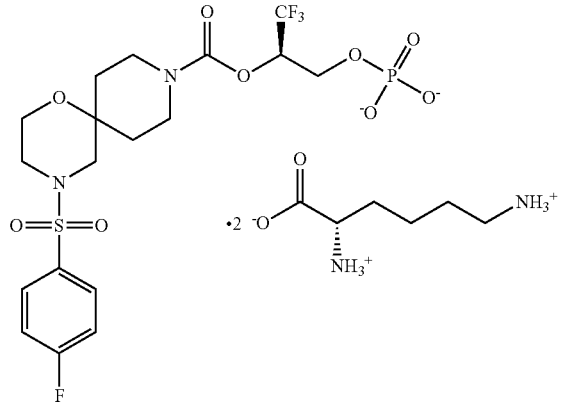

33

A solution of L-lysine (3.63 g, 24.8 mmol) in water (14 mL) was added to a solution of C84 (7.00 g, 12.7 mmol) in methanol (56 mL). The lysine solution was rinsed in with water (3 mL), and the reaction mixture was stirred at room temperature. Methanol (280 mL) was added to improve stirring of the slurry, and stirring was continued at room temperature for 1 hour. The reaction mixture was heated to 40° C. and stirred for 30 minutes, then cooled to 0° C. to 5° C. with stirring. After being held at 0° C. for 30 minutes, it was warmed to room temperature and stirred for 30 minutes, whereupon it was filtered through a Büchner funnel. The collected material was washed with methanol (140 mL) to afford a white solid (9.44 g). The bulk of this material (8.44 g) was slurried in methanol (140 mL) and stirred at room temperature for 4 hours, whereupon it was filtered through a Büchner funnel, providing the product as a white solid. Yield: 8.24 g, 9.77 mmol, 86% (corrected for material that was removed prior to reslurry). LCMS m/z 551.2 [M+H]$^+$. $^1$H NMR (400 MHz, D$_2$O) δ 7.88-7.81 (m, 2H), 7.38 (br dd, J=8.8, 8.8 Hz, 2H), 5.48-5.38 (m, 1H), 4.13-4.05 (m, 1H), 4.03-3.94 (m, 1H), 3.94-3.8 (m, 1H), 3.84 (br dd, J=5.0, 4.9 Hz, 2H), 3.79-3.64 (m, 1H), 3.71 (dd, J=6.2, 6.0 Hz, 2H), 3.36-3.13 (m, 2H), 3.10-3.02 (m, 2H), 2.99 (dd, J=7.7, 7.5 Hz, 4H), 2.95-2.86 (m, 2H), 2.01-1.81 (m, 6H), 1.76-1.54 (m, 6H), 1.54-1.34 (m, 4H).

Example 34

(2R)-3,3,3-Trifluoro-2-[({4-[(3-fluorophenyl)sulfonyl]-1-oxa-4,9-diazaspiro[5.5]undec-9-yl}carbonyl)oxy]propyl phosphate, disodium salt (34)

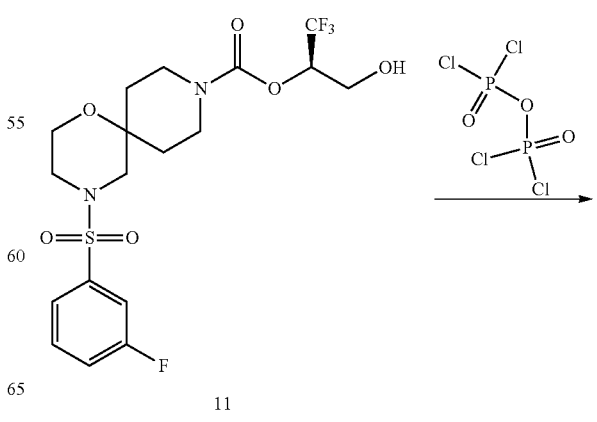

11

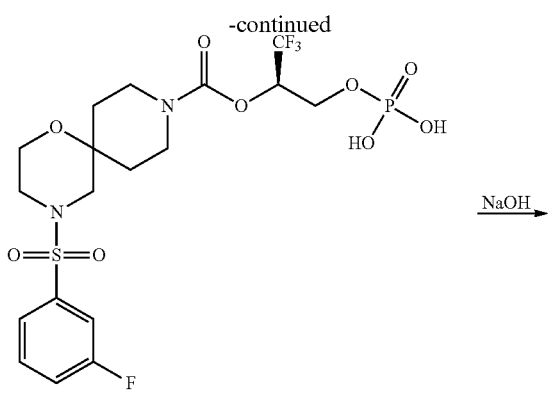

C87

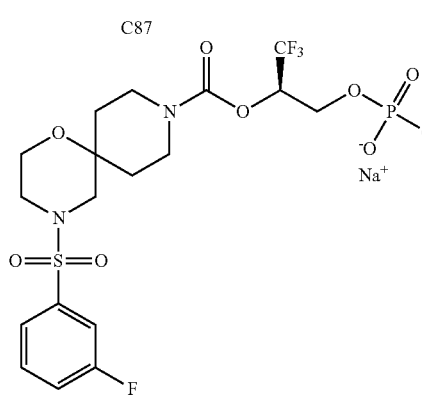

34

Step 1. Synthesis of (2R)-1,1,1-trifluoro-3-(phosphonooxy)propan-2-yl 4-[(3-fluorophenyl)sulfonyl]-1-oxa-4,9-diazaspiro[5.5]undecane-9-carboxylate (C87)

Diphosphoryl tetrachloride (2.63 mL, 19.0 mmol) was added drop-wise over 5 minutes to a 0° C. solution of 11 (1.74 g, 3.70 mmol) in acetonitrile (20 mL), and the reaction mixture was stirred at 0° C. for 3 hours, whereupon it was poured into ice (20 g) and stirred at room temperature for 1.75 hours. The reaction mixture was concentrated in vacuo, and the aqueous residue was partitioned between ethyl acetate (50 mL) and aqueous hydrochloric acid (1 M; 10 mL); the organic layer was washed sequentially with aqueous hydrochloric acid (1 M; 10 mL) and saturated aqueous sodium chloride solution (2×10 mL), then dried over sodium sulfate, filtered, and concentrated in vacuo. The resulting thick oil was taken up in water (75 mL), basified via addition of saturated aqueous sodium bicarbonate solution and solid sodium bicarbonate, and washed with ethyl acetate (50 mL). The pH of the aqueous layer was then adjusted to ~2 using concentrated hydrochloric acid, and the product was extracted with ethyl acetate (2×50 mL). The combined organic layers were dried over sodium sulfate, filtered, and concentrated in vacuo. The residue was mixed with ethyl acetate and filtered through a 0.45 μm membrane filter; the filtrate was concentrated under reduced pressure to provide the product as a white solid. Yield: 1.36 g, 2.47 mmol, 67%. LCMS m/z 551.1 [M+H]$^+$. $^1$H NMR (400 MHz, DMSO-d$_6$) δ 7.76-7.70 (m, 1H), 7.65-7.55 (m, 3H), 5.50-5.40 (m, 1H), 4.13-3.98 (m, 2H), 3.77-3.63 (m, 4H), 3.21-3.02 (m, 2H), 2.98-2.86 (m, 2H), 2.84-2.73 (m, 2H), 1.88-1.71 (m, 2H), 1.62-1.38 (m, 2H).

Step 2. Synthesis of (2R)-3,3,3-trifluoro-2-[({4-[(3-fluorophenyl)sulfonyl]-1-oxa-4,9-diazaspiro[5.5]undec-9-yl}carbonyl)oxy]propyl phosphate, disodium salt (34)

Aqueous sodium hydroxide solution (1 M, 4.78 mL, 4.78 mmol) was added drop-wise over 3 minutes to a solution of C87 (1.35 g, 2.45 mmol) in ethanol (15 mL), and the reaction mixture was allowed to stir at room temperature for 1 hour. Ethanol (50 mL) was then added to the suspension, which was allowed to stir for 5 minutes before being filtered. The filter cake was rinsed with ethanol (10 mL) to afford the product as a white solid. Yield: 1.01 g, 1.70 mmol, 69%. LCMS m/z 551.1 [M+H]$^+$. $^1$H NMR (400 MHz, D$_2$O) δ 7.67 (ddd, half of ABXY pattern, J=8.0, 7.8, 5.2 Hz, 1H), 7.62 (ddd, half of ABXY pattern, J=7.8, 1.4, 1.3 Hz, 1H), 7.60-7.56 (m, 1H), 7.49 (dddd, J=8.7, 8.0, 2.5, 1 Hz, 1H), 5.47-5.38 (m, 1H), 4.13-4.05 (m, 1H), 4.02-3.93 (m, 1H), 3.93-3.64 (m, 2H), 3.84 (dd, J=5.2, 4.8 Hz, 2H), 3.36-3.13 (m, 2H), 3.13-3.01 (m, 2H), 3.01-2.87 (m, 2H), 2.02-1.81 (m, 2H), 1.77-1.50 (m, 2H).

Method A

Method A describes a specific synthetic method for preparations of certain exemplar compounds of the invention.

Synthesis of (2R)-1,1,1-trifluoro-3-hydroxypropan-2-yl 4-(R$^{70}$-sulfonyl)-1-oxa-4,9-diazaspiro[5.5]undecane-9-carboxylate analogues (MA-2) via sulfonylation of C31 followed by deprotection

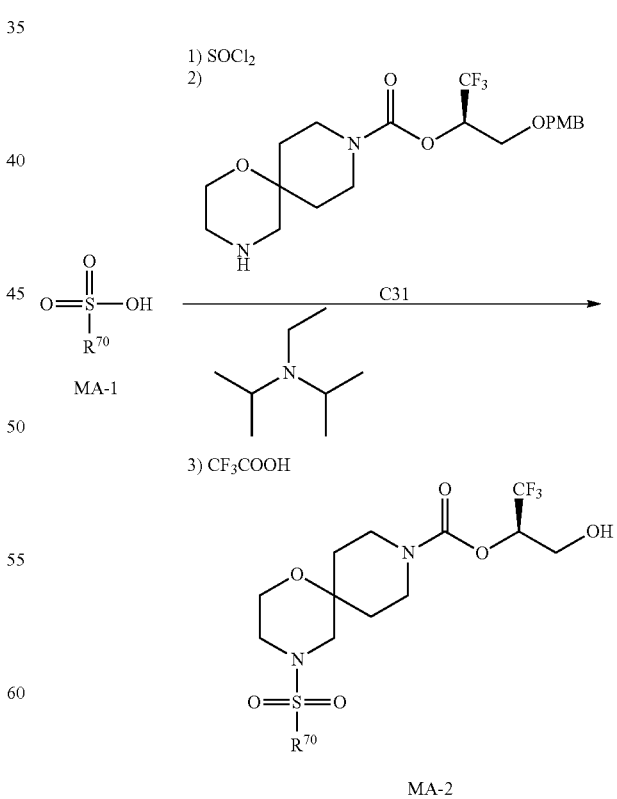

A solution of the sulfonic acid MA-1 (0.15 mmol) in N,N-dimethylformamide (0.15 mL) was treated with thionyl chloride (0.12 ml, 1.6 mmol), and the reaction mixture was heated with shaking at 50° C. for 16 hours. Volatiles were removed using a Genevac evaporator; 1,2-dichloroethane (2 mL) was added, and the mixture was concentrated again. A solution of C31 (25.9 mg, 60.0 mmol) in 1,2-dichloroethane (0.5 mL) was added to the crude sulfonyl chloride, followed by N,N-diisopropylethylamine (0.225 mL, 1.29 mmol), and the reaction mixture was shaken overnight at room temperature. It was then partitioned between half-saturated aqueous sodium bicarbonate solution (1.5 mL) and ethyl acetate (2.4 mL) and subjected to vortexing. The organic layer was eluted through a solid phase extraction cartridge (6 mL) charged with sodium sulfate (~1 g); this extraction procedure was repeated twice, and the combined eluents were concentrated in vacuo. A mixture of trifluoroacetic acid and 1,2-dichloroethane (1:1, 1 mL) was added, and the reaction mixture was shaken at room temperature for 2 hours, whereupon it was concentrated in vacuo and subjected to purification via reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 5% to 100% B).

TABLE 6

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 35 | Footnotes[1,2] | 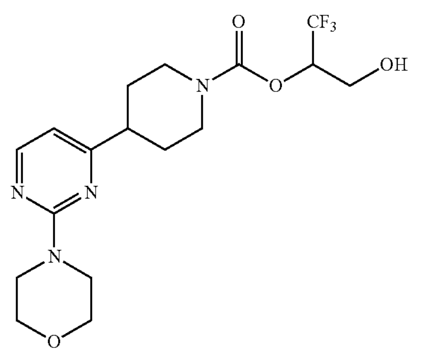 [SMILES: O=C(OC(CO)C(F)(F)F)N1CCC(c2ccnc(N3CCOCC3)n2)CC1] | 8.25 (d, J = 5.1 Hz, 1H), 6.41 (d, J = 5.0 Hz, 1H), 5.33-5.22 (m, 1H), 4.34-4.19 (m, 2H), 4.06-3.99 (m, 1H), 3.89 (br dd, half of ABX pattern, J = 12, 7 Hz, 1H), 3.83-3.74 (m, 8H), 3.08-2.88 (m, 2H), 2.68 (tt, J = 11.5, 3.6 Hz, 1H), 1.99-1.88 (m, 2H), 1.84-1.69 (m, 2H); 405.1 |
| 36 | C19[3,4] | 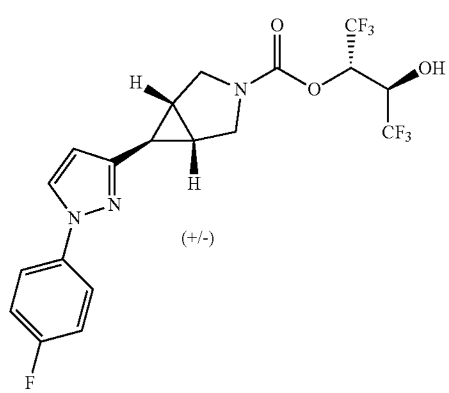 [SMILES: O=C(O[C@@H]([C@@H](O)C(F)(F)F)C(F)(F)F)N1C[C@@H]2[C@H](C1)[C@H]2c1ccn(-c2ccc(F)cc2)n1] | By $^1$H NMR analysis, this was judged to be a mixture of rotamers. $^1$H NMR (400 MHz, CD$_3$OD) δ 8.03 (d, J = 2.5 Hz, 1H), 7.72-7.66 (m, 2H), 7.20 (br dd, J = 8.9, 8.5 Hz, 2H), [6.27 (d, J = 2.5 Hz) and 6.26 (d, J = 2.5 Hz), total 1H], 5.50-5.40 (m, 1H), 4.43-4.33 (m, 1H), 3.83-3.76 (m, 2H), 3.63-3.55 (m, 2H), 2.08-2.01 (m, 2H), [1.77 (dd, J = 3.6, 3.5 Hz) and 1.72 (dd, J = 3.4, 3.4 Hz), total 1H]; 468.0 |
| 37 | Example 3[5]; C6, C17 | 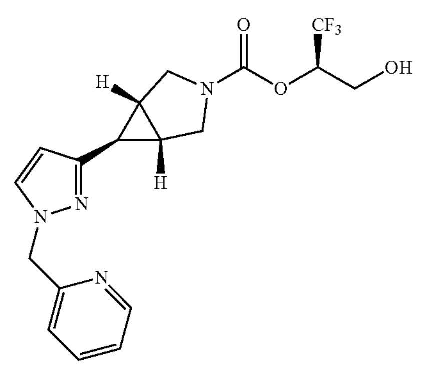 [SMILES: O=C(O[C@H](CO)C(F)(F)F)N1C[C@@H]2[C@H](C1)[C@H]2c1ccn(Cc2ccccn2)n1] | By $^1$H NMR analysis, this was judged to be a mixture of rotamers. $^1$H NMR (400 MHz, CD$_3$OD) δ 8.51 (br d, J = 5 Hz, 1H), 7.79 (ddd, J = 7.8, 7.8, 1.5 Hz, 1H), 7.64 (d, J = 2.3 Hz, 1H), 7.33 (ddd, J = 7.3, 5.0, 0.6 Hz, 1H), 7.03-6.98 (m, 1H), [6.11 (d, J = 2.3 Hz) and 6.10 (d, J = 2.4 Hz), total 1H], 5.37 (s, 2H), 5.32-5.22 (m, 1H), 3.90-3.71 (m, 4H), 3.65-3.52 (m, 2H), 1.98-1.91 (m, 2H), [1.76 (dd, J = 3.5, 3.4 Hz) and 1.70 (dd, J = 3.6, 3.4 Hz), total 1H]; 396.9 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 38 | Example 6$^{6,7}$; C13 | 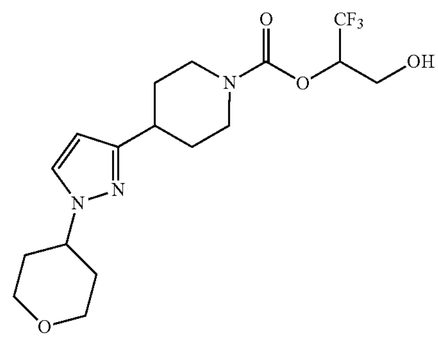 [SMILES: O=C(OC(CO)C(F)(F)F)N1CCC(c2ccn(C3CCOCC3)n2)CC1] | $^1$H NMR (400 MHz, CD$_3$OD) δ 7.58 (d, J = 2.4 Hz, 1H), 6.13 (d, J = 2.4 Hz, 1H), 5.35-5.26 (m, 1H), 4.38-4.28 (m, 1H), 4.27-4.14 (m, 2H), 4.09-4.01 (m, 2H), 3.88 (br dd, half of ABX pattern, J = 12, 4 Hz, 1H), 3.79 (dd, half of ABX pattern, J = 12.4, 6.9 Hz, 1H), 3.60-3.51 (m, 2H), 3.13-2.94 (m, 2H), 2.92-2.83 (m, 1H), 2.10-1.87 (m, 6H), 1.76-1.53 (m, 2H); 391.9 |
| 39 | Examples 19, 20 and 21; C19, C59 | 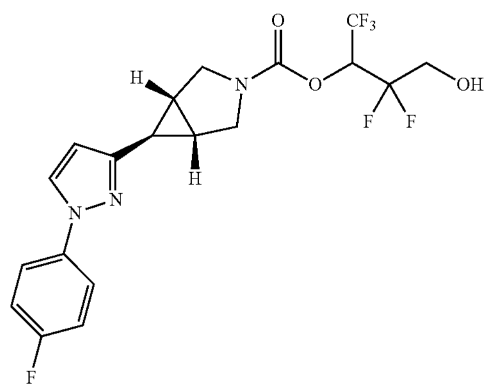 [SMILES: O=C(OC(C(F)(F)F)C(F)(F)CO)N1C[C@@H]2[C@H](C1)[C@H]2c1ccn(-c2ccc(F)cc2)n1] | By $^1$H NMR analysis, this was judged to be a mixture of rotamers. $^1$H NMR (600 MHz, DMSO-d$_6$) δ 8.33-8.30 (m, 1H), 7.81-7.76 (m, 2H), 7.30 (br dd, J = 8.9, 8.8 Hz, 2H), [6.33 (d, J = 2.4 Hz) and 6.31 (d, J = 2.4 Hz), total 1H], 5.88-5.83 (m, 1H), 5.82-5.73 (m, 1H), 3.83-3.56 (m, 6H), 2.06-1.98 (m, 2H), [1.82 (dd, J = 3.4, 3.4 Hz) and 1.76 (dd, J = 3.4, 3.3 Hz), total 1H]; 450.2 |
| 40 | Example 13; C17 | 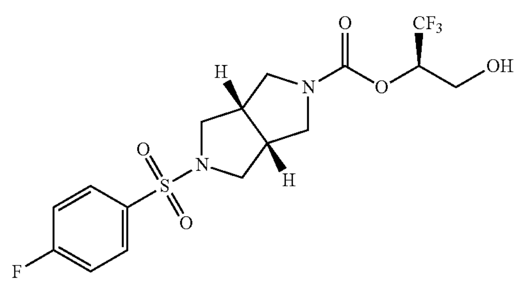 [SMILES: O=C(O[C@H](CO)C(F)(F)F)N1C[C@@H]2CN(S(=O)(=O)c3ccc(F)cc3)C[C@@H]2C1] | $^1$H NMR (400 MHz, CD$_3$OD) δ 7.94-7.87 (m, 2H), 7.40-7.32 (m, 2H), 5.29-5.18 (m, 1H), 3.90-3.81 (m, 1H), 3.79-3.69 (m, 1H), 3.68-3.51 (m, 2H), 3.49-3.25 (m, 3H, assumed; partially obscured by solvent peak), 3.21-3.00 (m, 3H), 2.96-2.82 (m, 2H); 426.9 |
| 41 | Example 6$^8$; C2 | 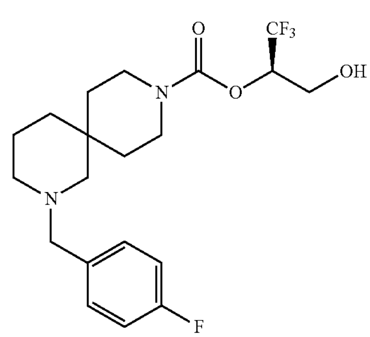 [SMILES: O=C(O[C@H](CO)C(F)(F)F)N1CCC2(CCCN(Cc3ccc(F)cc3)C2)CC1] | 7.32-7.21 (m, 2H, assumed; partially obscured by solvent peak), 7.05-6.95 (m, 2H), 5.27-5.16 (m, 1H), 4.03-3.93 (m, 1H), 3.90-3.80 (m, 1H), 3.55-3.35 (m, 2H), 3.40 (br s, 2H), 3.35-3.16 (m, 2H), 2.51-2.32 (m, 3H), 2.21-2.06 (m, 2H), 1.71-1.41 (m, 6H, assumed; partially obscured by water peak), 1.41-1.30 (m, 2H); 419.2 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 42 | Example 23; C23, C2 | 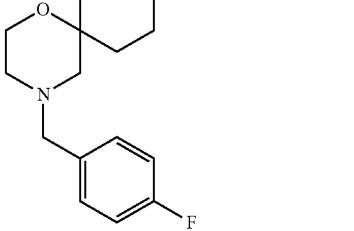 | 7.31-7.23 (m, 2H, assumed; partially obscured by solvent peak), 7.01 (br dd, J = 8.8, 8.5 Hz, 2H), 5.28-5.18 (m, 1H), 3.99 (br dd, half of ABX pattern, J = 12, 3 Hz, 1H), 3.91-3.77 (m, 3H), 3.77-3.70 (m, 2H), 3.46-3.36 (m, 2H), 3.33-3.15 (m, 2H), 2.48-2.38 (m, 2H), 2.25-2.15 (m, 2H), 2.13-1.97 (m, 2H), 1.48-1.36 (m, 2H); 421.1 |
| 43 | Example 13$^9$; C23, C2 | 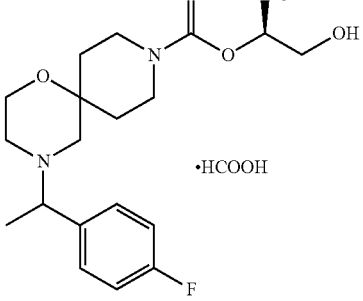 | 7.31-7.23 (m, 2H, assumed; partially obscured by solvent peak), 7.01 (br dd, J = 8.8, 8.5 Hz, 2H), 5.27-5.18 (m, 1H), 4.02-3.95 (m, 1H), 3.90-3.69 (m, 5H), 3.36-3.13 (m, 3H), 2.69-2.55 (m, 1H), 2.40-2.05 (m, 5H), 1.98-1.86 (m, 1H), 1.45-1.3 (m, 2H), 1.31 (d, J = 6.5 Hz, 3H); 435.2 |
| 44 | Example 13$^{10}$ | 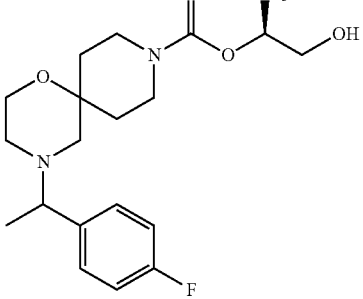 | 7.26 (br dd, J = 8.5, 5.6 Hz, 2H), 7.00 (br dd, J = 8.8, 8.7 Hz, 2H), 5.28-5.17 (m, 1H), 4.03-3.94 (m, 1H), 3.90-3.67 (m, 5H), 3.33-3.14 (m, 3H), 2.65-2.44 (m, 2H), 2.36-2.27 (m, 1H), 2.24-2.05 (m, 3H), 2.02-1.84 (m, 1H), 1.44-1.32 (m, 2H), 1.29 (d, J = 6.5 Hz, 3H); 435.2 |
| 45 | Example 13$^{10}$ | 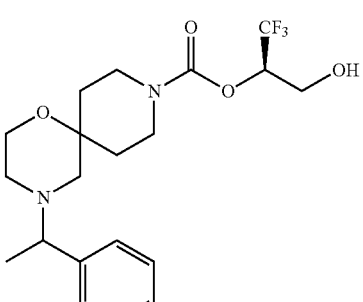 | 7.30-7.22 (m, 2H), 7.00 (br dd, J = 8.7, 8.7 Hz, 2H), 5.27-5.17 (m, 1H), 4.02-3.94 (m, 1H), 3.89-3.67 (m, 5H), 3.32-3.12 (m, 3H), 2.68-2.53 (m, 1H), 2.36-2.25 (m, 1H), 2.24-2.05 (m, 3H), 1.98-1.63 (m, 2H), 1.44-1.32 (m, 2H), 1.28 (d, J = 6.6 Hz, 3H); 435.2 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 46 | Example 24[11]; C2 | 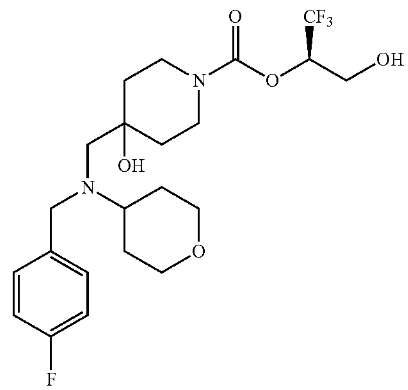 [SMILES: O=C(O[C@H](CO)C(F)(F)F)N1CCC(O)(CN(Cc2ccc(F)cc2)C2CCOCC2)CC1] | $^1$H NMR (400 MHz, CD$_3$OD) δ 7.42-7.33 (m, 2H), 7.02 (br dd, J = 8.5, 8.5 Hz, 2H), 5.33-5.22 (m, 1H), 4.01-3.91 (m, 2H), 3.91-3.72 (m, 6H), 3.3-3.12 (m, 4H, assumed; partially obscured by solvent peak), 2.83-2.71 (m, 1H), 2.55 (s, 2H), 1.78-1.69 (m, 2H), 1.67-1.43 (m, 6H); 479.1 |
| 47 | Example 13; C2 | 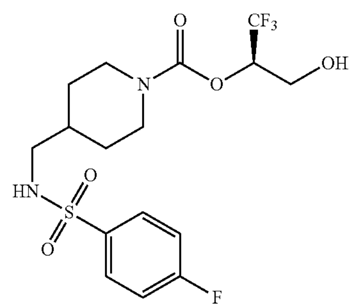 [SMILES: O=C(O[C@H](CO)C(F)(F)F)N1CCC(CNS(=O)(=O)c2ccc(F)cc2)CC1] | $^1$H NMR (400 MHz, CD$_3$OD) δ 7.95-7.88 (m, 2H), 7.32 (br dd, J = 8.8, 8.8 Hz, 2H), 5.33-5.24 (m, 1H), 4.21-4.08 (m, 2H), 3.88 (br dd, half of ABX pattern, J = 12, 4 Hz, 1H), 3.78 (dd, half of ABX pattern, J = 12.3, 6.7 Hz, 1H), 2.95-2.76 (m, 2H), 2.77 (d, J = 6.5 Hz, 2H), 1.79-1.61 (m, 3H), 1.24-1.01 (m, 2H); 429.0 |
| 48 | Example 14; C2 | 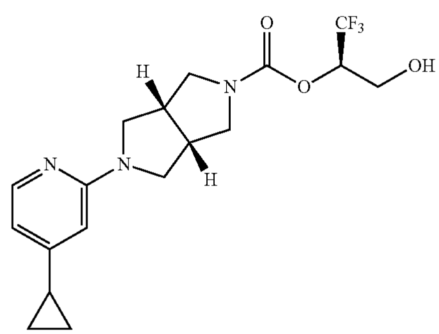 [SMILES: O=C(O[C@H](CO)C(F)(F)F)N1C[C@@H]2CN(c3cc(C4CC4)ccn3)C[C@@H]2C1] | By $^1$H NMR analysis, this was judged to be a mixture of rotamers. [8.01 (d, J = 6.0 Hz) and 7.96 (d, J = 6.0 Hz), total 1H], 6.35-6.23 (m, 2H), 5.32-5.21 (m, 1H), 4.03-3.64 (m, 7H), 3.61-3.38 (m, 3H), 3.18-3.07 (m, 2H), 1.93-1.82 (m, 1H), 1.22-1.11 (m, 2H), 0.92-0.83 (m, 2H); 386.0 |
| 49 | Example 13; C23, C2 | 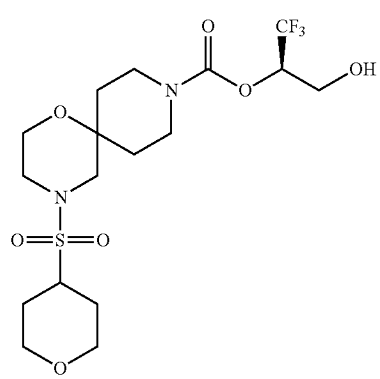 [SMILES: O=C(O[C@H](CO)C(F)(F)F)N1CCC2(CC1)CN(S(=O)(=O)C1CCOCC1)CCO2] | 5.32-5.20 (m, 1H), 4.14-4.04 (m, 2H), 4.04-3.95 (m, 1H), 3.95-3.80 (m, 3H), 3.76 (br dd, J = 4.9, 4.8 Hz, 2H), 3.45-3.32 (m, 4H), 3.32-3.10 (m, 5H), 2.53-2.34 (m, 1H), 2.05-1.80 (m, 6H), 1.60-1.43 (m, 2H); 461.1 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 50 | Example 23$^{12}$; C2 | 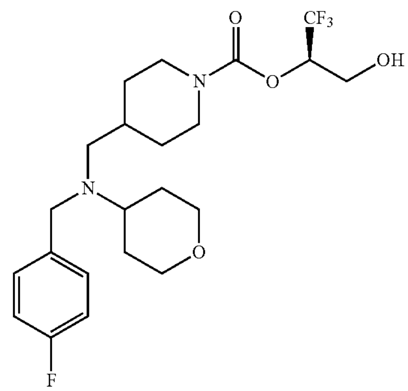 [SMILES: O=C(O[C@H](CO)C(F)(F)F)N1CCC(CN(Cc2ccc(F)cc2)C2CCOCC2)CC1] | 7.31-7.23 (m, 2H, assumed; partially obscured by solvent peak), 7.00 (br dd, J = 8.5, 8.5 Hz, 2H), 5.27-5.18 (m, 1H), 4.18-3.95 (m, 5H), 3.90-3.81 (m, 1H), 3.60 (s, 2H), 3.35-3.26 (m, 2H), 2.87-2.59 (m, 3H), 2.47-2.38 (m, 1H), 2.35 (d, J = 6.8 Hz, 2H), 1.84-1.73 (m, 2H), 1.70-1.46 (m, 4H, assumed; partially obscured by solvent peak), 1.09-0.92 (m, 2H); 463.2 |
| 51 | Example 13; C23, C2 | 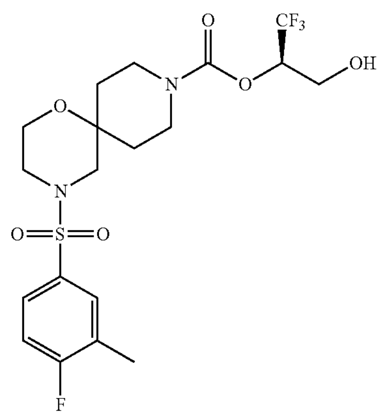 [SMILES: Cc1cc(S(=O)(=O)N2CCOC3(CCN(C(=O)O[C@H](CO)C(F)(F)F)CC3)C2)ccc1F] | 7.63-7.53 (m, 2H), 7.18 (dd, J = 9.0, 8.7 Hz, 1H), 5.31-5.21 (m, 1H), 4.06-3.96 (m, 1H), 3.95-3.82 (m, 3H), 3.80 (br dd, J = 5.0, 5.0 Hz, 2H), 3.32-3.13 (m, 2H), 3.09-2.91 (m, 2H), 2.89-2.71 (m, 2H), 2.43-2.24 (m, 1H), 2.37 (br s, 3H), 2.05-1.91 (m, 2H), 1.69-1.43 (m, 2H, assumed; partially obscured by water peak); 485.1 |
| 52 | Example 13; C23, C2 | 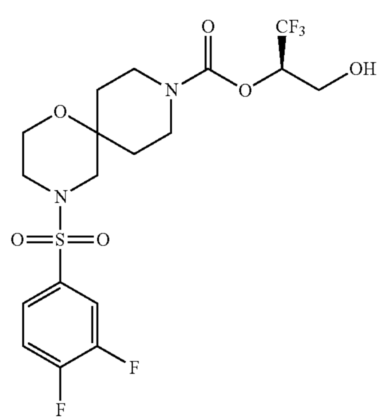 [SMILES: O=C(O[C@H](CO)C(F)(F)F)N1CCC2(CC1)CN(S(=O)(=O)c1ccc(F)c(F)c1)CCO2] | 7.59 (ddd, J = 9.2, 7.2, 2.1 Hz, 1H), 7.56-7.50 (m, 1H), 7.38 (ddd, J = 9.0, 8.8, 7.4 Hz, 1H), 5.32-5.21 (m, 1H), 4.05-3.97 (m, 1H), 3.96-3.83 (m, 3H), 3.81 (dd, J = 4.9, 4.9 Hz, 2H), 3.32-3.13 (m, 2H), 3.10-2.95 (m, 2H), 2.89-2.75 (m, 2H), 2.5-2.2 (br m, 1H), 2.05-1.92 (m, 2H), 1.6-1.43 (m, 2H); 489.1 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 53 | Example 13; C2 | 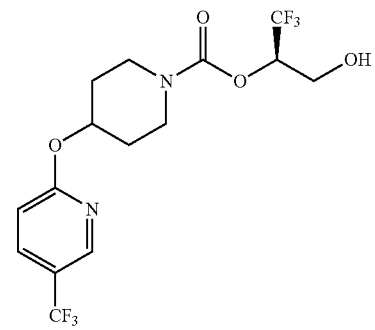 [SMILES: O=C(O[C@H](CO)C(F)(F)F)N1CCC(Oc2ccc(C(F)(F)F)cn2)CC1] | 8.42 (br s, 1H), 7.79 (br d, J = 8.8 Hz, 1H), 6.81 (d, J = 8.8 Hz, 1H), 5.41-5.32 (m, 1H), 5.32-5.23 (m, 1H), 4.06-3.98 (m, 1H), 3.93-3.72 (m, 3H), 3.59-3.40 (m, 2H), 2.55-2.32 (m, 1H), 2.12-1.95 (m, 2H), 1.92-1.75 (m, 2H); 403.0 |
| 54 | Method A | 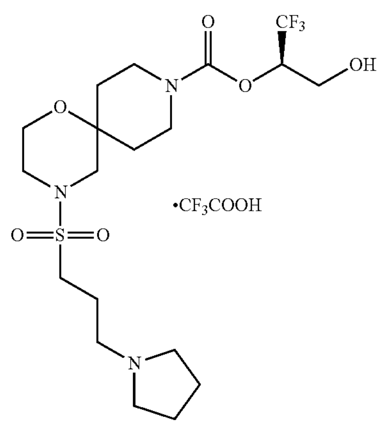 [SMILES: O=C(O[C@H](CO)C(F)(F)F)N1CCC2(CC1)CN(S(=O)(=O)CCCN1CCCC1)CCO2 ; "·CF3COOH"] | 1.65 minutes$^{13}$; 488.2 |
| 55 | Method A | 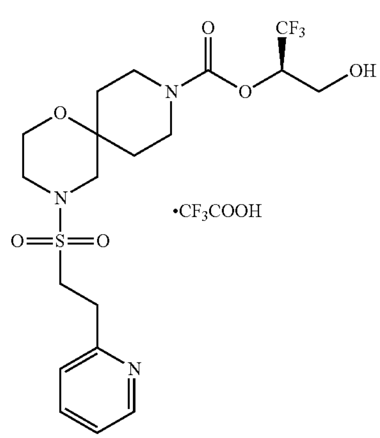 [SMILES: O=C(O[C@H](CO)C(F)(F)F)N1CCC2(CC1)CN(S(=O)(=O)CCc1ccccn1)CCO2 ; "·CF3COOH"] | 1.65 minutes$^{13}$; 482.1 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 56 | Method A | 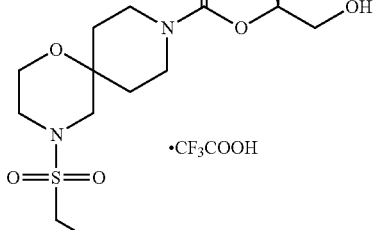 •CF$_3$COOH | 1.63 minutes$^{13}$; 485.1 |
| 57 | Example 10; C2 | 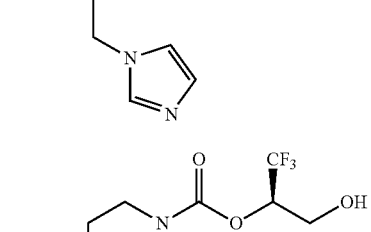 | 7.97-7.92 (m, 1H), 7.44-7.39 (m, 1H), 6.65 (d, J = 8.0 Hz, 1H), 5.32-5.20 (m, 2H), 4.02 (dd, half of ABX pattern, J = 12.4, 3.0 Hz, 1H), 3.89 (dd, half of ABX pattern, J = 12.5, 6.8 Hz, 1H), 3.88-3.72 (m, 2H), 3.57-3.41 (m, 2H), 2.25 (s, 3H), 2.07-1.96 (m, 2H), 1.94-1.73 (m, 2H, assumed; partially obscured by water peak); 348.9 |
| 58 | Example 10; C2 | 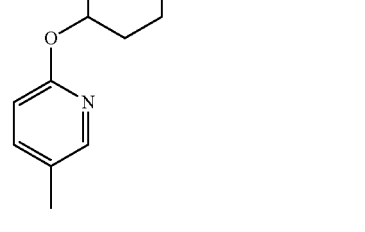 | 8.46 (s 1H) 7.57 (d, J = 2.0 Hz, 1H), 6.55 (d, J = 2.0 Hz, 1H), 5.32-5.22 (m, 2H), 4.07 (s, 3H), 4.05-3.98 (m, 1H), 3.93-3.73 (m, 3H), 3.63-3.45 (m, 2H), 2.32 (s, 3H), 2.10-1.87 (m, 4H); 430.1 |
| 59 | Example 13; C23, C2 | 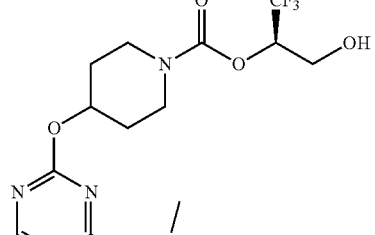 | 7.72 (d, J = 1.5 Hz, 1H), 7.52 (dd, half of ABX pattern, J = 8.0, 1.6 Hz, 1H), 7.43 (d, half of AB quartet, J = 8.3 Hz, 1H), 5.31-5.21 (m, 1H), 4.06-3.96 (m, 1H), 3.95-3.82 (m, 3H), 3.80 (dd, J = 5.0, 4.8 Hz, 2H), 3.32-3.13 (m, 2H), 3.10-2.94 (m, 2H), 2.89-2.73 (m, 2H), 2.48 (s, 3H), 2.39-2.26 (m, 1H), 2.05-1.92 (m, 2H), 1.6-1.44 (m, 2H, assumed; partially obscured by water peak); 523.1 [M + Na$^+$] |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 60 | Example 13; C23, C2 | 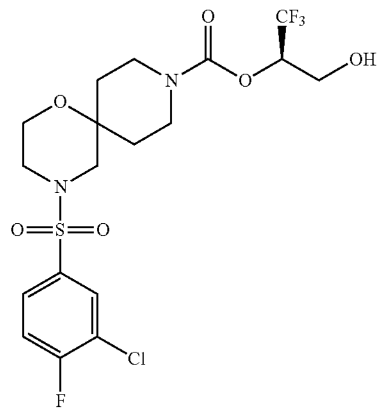 [SMILES: O=C(O[C@H](CO)C(F)(F)F)N1CCC2(CC1)CN(S(=O)(=O)c1ccc(F)c(Cl)c1)CCO2] | 7.82 (dd, J = 6.6, 2.3 Hz, 1H), 7.65 (ddd, J = 8.6, 4.3, 2.3 Hz, 1H), 7.34 (dd, J = 8.5, 8.4 Hz, 1H), 5.31-5.21 (m, 1H), 4.05-3.97 (m, 1H), 3.96-3.83 (m, 3H), 3.81 (dd, J = 5.0, 4.9 Hz, 2H), 3.31-3.13 (m, 2H), 3.11-2.96 (m, 2H), 2.90-2.75 (m, 2H), 2.35-2.23 (m, 1H), 2.04-1.93 (m, 2H), 1.6-1.45 (m, 2H, assumed; partially obscured by water peak); 527.1 [M + Na$^+$] |
| 61 | Example 10; C2 | 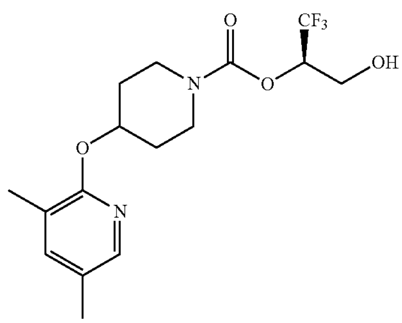 [SMILES: Cc1cnc(OC2CCN(C(=O)O[C@H](CO)C(F)(F)F)CC2)c(C)c1] | $^1$H NMR (400 MHz, CD$_3$OD) δ 7.73 (br s, 1H), 7.34 (br s, 1H), 5.36-5.27 (m, 1H), 5.27-5.19 (m, 1H), 3.89 (dd, half of ABX pattern, J = 12.4, 3.8 Hz, 1H), 3.84-3.69 (m, 2H), 3.79 (dd, half of ABX pattern, J = 12.4, 6.6 Hz, 1H), 3.60-3.44 (m, 2H), 2.20 (s, 3H), 2.16 (s, 3H), 2.08-1.92 (m, 2H), 1.86-1.68 (m, 2H), 363.0 |
| 62 | Example 13$^{14}$; C2 | 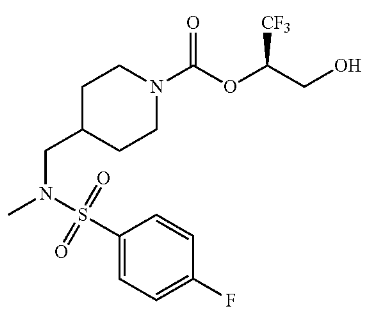 [SMILES: CN(CC1CCN(C(=O)O[C@H](CO)C(F)(F)F)CC1)S(=O)(=O)c1ccc(F)cc1] | 7.84-7.77 (m, 2H), 7.23 (dd, J = 8.7, 8.5 Hz, 2H), 5.31-5.20 (m, 1H), 4.28-4.12 (m, 2H), 4.05-3.97 (m, 1H), 3.88 (dd, half of ABX pattern, J = 12.5, 7 Hz, 1H), 2.96-2.78 (m, 4H), 2.76 (s, 3H), 1.88-1.75 (m, 3H), 1.30-1.15 (m, 2H); 443.1 |
| 63 | Example 10; C2 | 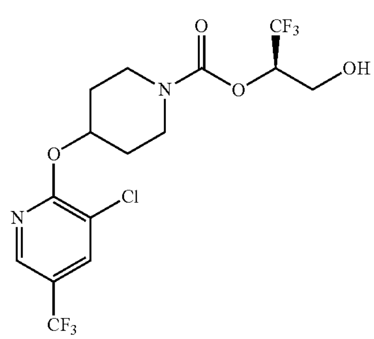 [SMILES: O=C(O[C@H](CO)C(F)(F)F)N1CCC(Oc2ncc(C(F)(F)F)cc2Cl)CC1] | 8.33-8.30 (m, 1H), 7.87 (d, J = 2.3 Hz, 1H), 5.50-5.41 (m, 1H), 5.33-5.24 (m, 1H), 4.07-3.98 (m, 1H), 3.94-3.85 (m, 1H), 3.83-3.54 (m, 4H), 2.38-2.27 (m, 1H), 2.09-1.87 (m, 3H); 437.0 |

TABLE 6-continued

Method of synthesis, structure, and physicochemical properties for Examples 35-91.

| Example Number | Method of Synthesis; Non-commercial starting materials | Structure | $^{1}$H NMR (400 MHz, CDCl$_3$) δ; Mass spectrum, observed ion m/z [M + H]$^{+}$ or HPLC retention time; Mass spectrum m/z [M + H]$^{+}$ (unless otherwise indicated) |
|---|---|---|---|
| 64 | Example 10[15]; C2 | 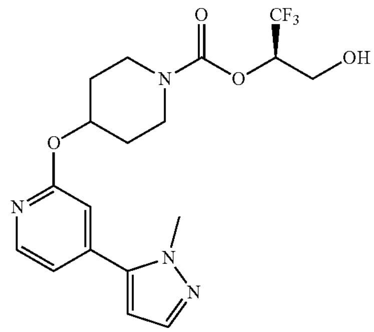 [SMILES: Cn1nccc1-c1ccnc(OC2CCN(C(=O)O[C@H](CO)C(F)(F)F)CC2)c1] | 8.21 (d, J = 5.4 Hz, 1H), 7.54 (d, J = 1.9 Hz, 1H), 6.95 (dd, J = 5.3, 1.5 Hz, 1H), 6.80-6.78 (m, 1H), 6.41 (d, J = 2.0 Hz, 1H), 5.39-5.31 (m, 1H), 5.31-5.24 (m, 1H), 4.03 (dd, half of ABX pattern, J = 12, 3 Hz, 1H), 3.97 (s, 3H), 3.92-3.76 (m, 2H), 3.90 (dd, J = 13, 7 Hz, 1H), 3.59-3.42 (m, 2H), 2.12-1.98 (m, 2H), 1.92-1.79 (m, 2H); 415.1 |
| 65 | Example 10[16]; C2 | 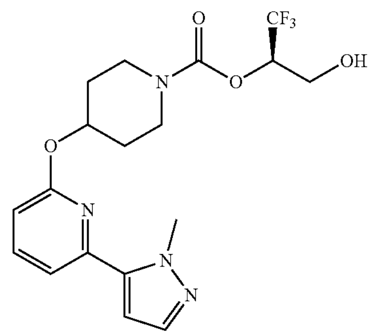 [SMILES: Cn1nccc1-c1cccc(OC2CCN(C(=O)O[C@H](CO)C(F)(F)F)CC2)n1] | 7.65 (dd, J = 7.9, 7.8 Hz, 1H), 7.49 (d, J = 1.6 Hz, 1H), 7.20 (d, J = 7.4 Hz, 1H), 6.70 (d, J = 8.3 Hz, 1H), 6.57 (d, J = 1.8 Hz, 1H), 5.37-5.24 (m, 2H), 4.21 (s, 3H), 4.06-3.97 (m, 1H), 3.93-3.69 (m, 3H), 3.62-3.45 (m, 2H), 2.72-2.64 (m, 1H), 2.09-1.96 (m, 2H), 1.95-1.83 (m, 2H); 415.1 |
| 66 | C31[17] | 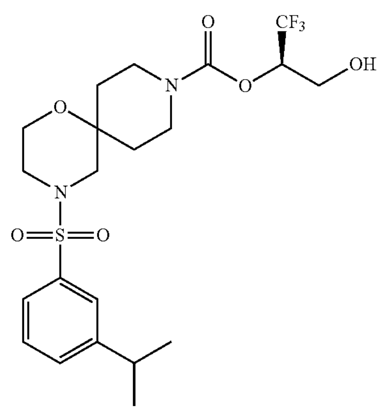 [SMILES: CC(C)c1cccc(S(=O)(=O)N2CCOC3(CCN(C(=O)O[C@H](CO)C(F)(F)F)CC3)C2)c1] | 3.22 minutes[18]; 495 |
| 67 | Example 7[19]; C31 | 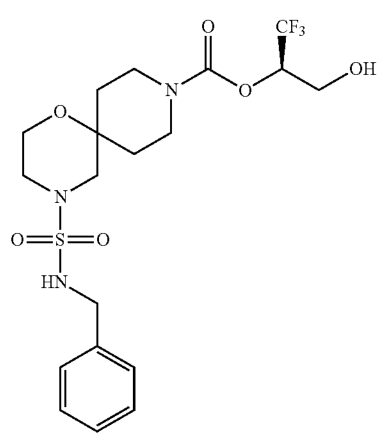 [SMILES: O=C(O[C@H](CO)C(F)(F)F)N1CCC2(CC1)CN(S(=O)(=O)NCc1ccccc1)CCO2] | 7.42-7.30 (m, 5H), 5.30-5.20 (m, 1H), 4.58-4.49 (m, 1H), 4.24 (d, J = 5.9 Hz, 2H), 4.04-3.95 (m, 1H), 3.92-3.77 (m, 3H), 3.71 (dd, J = 4.9, 4.8 Hz, 2H), 3.31-3.09 (m, 4H), 2.95 (br s, 2H), 2.44-2.30 (m, 1H), 1.98-1.87 (m, 2H), 1.53-1.36 (m, 2H); 481.9 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 68 | Example 7[20]; C31 | (structure) | $^1$H NMR (400 MHz, CD$_3$OD) δ 7.73 (br AB quartet, J$_{AB}$ = 8.5 Hz, Δv$_{AB}$ = 22.4 Hz, 4H), 5.33-5.24 (m, 1H), 3.92-3.73 (m, 7H), 3.3-3.14 (m, 2H), 3.05-2.93 (m, 2H), 2.89-2.76 (m, 2H), 2.02-1.88 (m, 2H), 1.64-1.45 (m, 2H); 477.5 |
| 69 | Example 3; C6, C17 | (structure) | By $^1$H NMR analysis, this was judged to be a mixture of rotamers. 8.39 (d, J = 2.7 Hz, 1H), 7.90-7.85 (m, 1H), 7.71 (d, J = 2.3 Hz, 1H), 6.83 (d, J = 8.9 Hz, 1H), [6.20 (d, J = 2.3 Hz) and 6.19 (d, J = 2.3 Hz), total 1H], 5.31-5.21 (m, 1H), 4.04-3.98 (m, 1H), 3.97 (s, 3H), 3.92-3.81 (m, 3H), 3.66-3.58 (m, 2H), 2.07-2.00 (m, 2H), 1.90-1.84 (m, 1H); 413.0 |
| 70 | Example 18[21,22]; C2 | (structure) DIAST-1 | By $^1$H NMR analysis, this was judged to be a mixture of rotamers. 7.84-7.76 (m, 2H), 7.20 (br dd, J = 8.5, 8.5 Hz, 2H), 5.31-5.21 (m, 1H), 4.04-3.63 (m, 7H), 3.54-3.45 (m, 1H), 3.31-2.96 (m, 3H), 2.59-2.47 (m, 1H), 1.62-1.23 (m, 4H), 1.04-0.91 (m, 3H); 485.0 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 71 | Example 18[21,22]; C2 | (structure shown) DIAST-2 | By $^1$H NMR analysis, this was judged to be a mixture of rotamers. 7.84-7.76 (m, 2H), 7.21 (br dd, J = 8.8, 8.3 Hz, 2H), 5.31-5.19 (m, 1H), 4.04-3.94 (m, 1H), 3.94-3.63 (m, 6H), 3.55-3.45 (m, 1H), 3.32-2.99 (m, 3H), 2.60-2.43 (m, 2H), 1.62-1.50 (m, 1H), 1.48-1.34 (m, 2H), 1.03-0.91 (m, 3H); 485.0 |
| 72 | Example 13[23,24]; C2 | (structure shown) | $^1$H NMR (600 MHz, DMSO-d$_6$) δ 7.32 (br dd, J = 8.4, 5.7 Hz, 2H), 7.19 (br dd, J = 9.0, 8.8 Hz, 2H), 5.26-5.17 (m, 2H), 4.35 (s, 2H), 3.77-3.71 (m, 1H), 3.71-3.61 (m, 3H), 3.38-3.24 (m, 2H, assumed; obscured by water peak), 3.24-3.20 (m, 2H), 1.86-1.63 (m, 4H); 421.2 |
| 73 | C31[25] | (structure shown) | 3.20 minutes[26]; 485 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 74 | Example 7[27]; C31 | 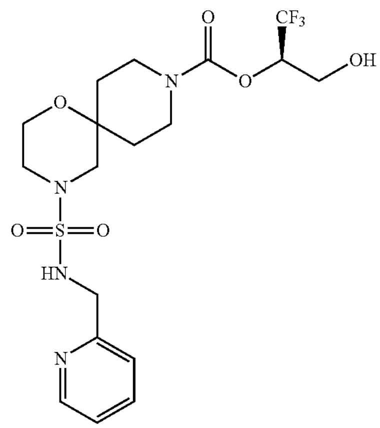 [SMILES: O=C(O[C@H](CO)C(F)(F)F)N1CCC2(CC1)CN(S(=O)(=O)NCc1ccccn1)CCO2] | 8.59-8.54 (m, 1H), 7.75-7.69 (m, 1H), 7.30-7.23 (m, 2H, assumed; partially obscured by solvent peak), 5.75 (br t, J = 5 Hz, 1H), 5.29-5.20 (m, 1H), 4.37 (d, J = 5.0 Hz, 2H), 4.04-3.96 (m, 1H), 3.91-3.77 (m, 3H), 3.74-3.69 (m, 2H), 3.30-3.11 (m, 4H), 3.04-2.98 (m, 2H), 1.98-1.89 (m, 2H), 1.52-1.33 (m, 2H); 483.0 |
| 75 | Example 26; C2 | 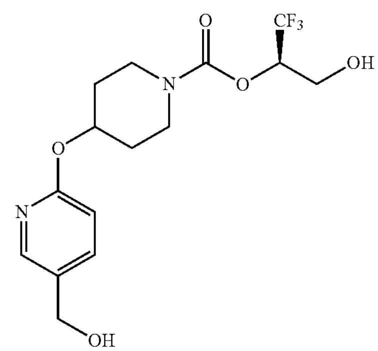 [SMILES: O=C(O[C@H](CO)C(F)(F)F)N1CCC(Oc2ccc(CO)cn2)CC1] | 1.72 minutes[13]; 365.1 |
| 76 | Example 27; C31 | 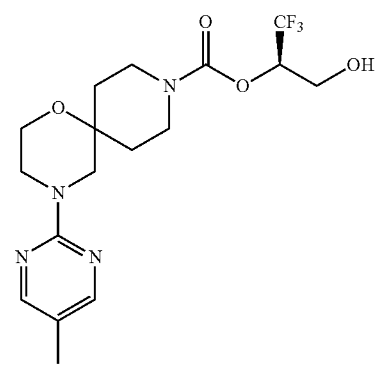 [SMILES: Cc1cnc(N2CCOC3(CCN(C(=O)O[C@H](CO)C(F)(F)F)CC3)C2)nc1] | 8.15 (s, 2H), 5.31-5.19 (m, 1H), 4.04-3.94 (m, 1H), 3.91-3.72 (m, 7H), 3.72-3.62 (m, 2H), 3.40-3.22 (m, 2H), 2.56-2.37 (br s, 1H), 2.13 (s, 3H), 1.96-1.83 (m, 2H), 1.63-1.48 (m, 2H); 405.0 |
| 77 | C31[17] | 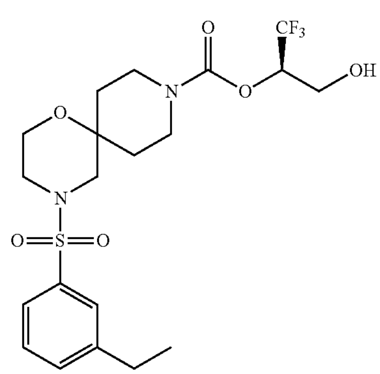 [SMILES: CCc1cccc(S(=O)(=O)N2CCOC3(CCN(C(=O)O[C@H](CO)C(F)(F)F)CC3)C2)c1] | 3.26 minutes[26]; 481 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 78 | C31[17] | 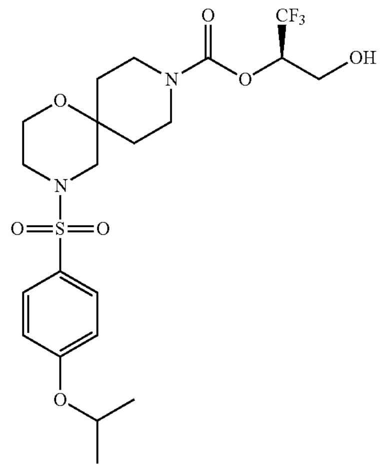 [SMILES: CC(C)Oc1ccc(S(=O)(=O)N2CCOC3(CCN(C(=O)O[C@H](CO)C(F)(F)F)CC3)C2)cc1] | 3.30 minutes[26]; 511 |
| 79 | Example 68; C31 | 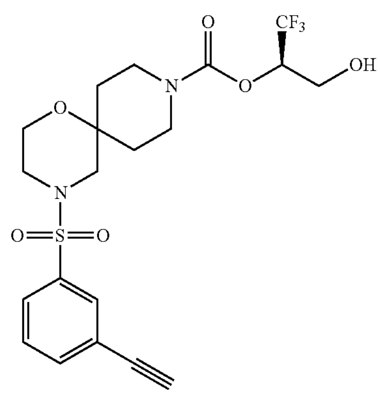 [SMILES: C#Cc1cccc(S(=O)(=O)N2CCOC3(CCN(C(=O)O[C@H](CO)C(F)(F)F)CC3)C2)c1] | $^1$H NMR (400 MHz, CD$_3$OD) δ 7.83 (br s, 1H), 7.80-7.75 (m, 2H), 7.62 (dd, J = 7.9, 7.7 Hz, 1H), 5.33-5.24 (m, 1H), 3.92-3.76 (m, 6H), 3.75 (s, 1H), 3.29-3.14 (m, 2H), 3.05-2.94 (m, 2H), 2.88-2.77 (m, 2H), 2.01-1.89 (m, 2H), 1.65-1.46 (m, 2H); 477.5 |
| 80 | Example 13[28]; C2 | 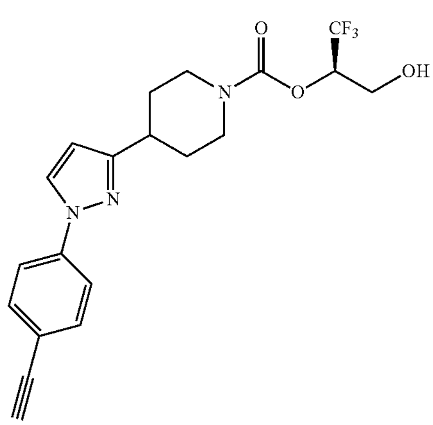 [SMILES: C#Cc1ccc(-n2ccc(C3CCN(C(=O)O[C@H](CO)C(F)(F)F)CC3)n2)cc1] | $^1$H NMR (400 MHz, CD$_3$OD) δ 8.14 (br s, 1H), 7.63 (AB quartet, J$_{AB}$ = 7.7 Hz, Δv$_{AB}$ = 66.8 Hz, 4H), 6.40 (br s, 1H), 5.36-5.27 (m, 1H), 4.28-4.15 (m, 2H), 3.89 (dd, half of ABX pattern, J = 12.4, 3.7 Hz, 1H), 3.79 (dd, half of ABX pattern, J = 12.3, 6.9 Hz, 1H), 3.53 (s, 1H), 3.18-2.93 (m, 3H), 2.08-1.96 (m, 2H), 1.85-1.61 (m, 2H); 408.2 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 81 | Example 3; C6, C17 | 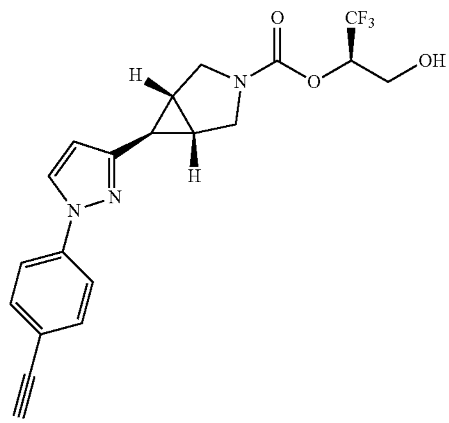 [SMILES: C#Cc1ccc(-n2ccc([C@H]3[C@@H]4CN(C(=O)O[C@H](CO)C(F)(F)F)C[C@@H]43)n2)cc1] | 7.84-7.80 (m, 1H), 7.58 (br AB quartet, J$_{AB}$ = 8.3 Hz, Δv$_{AB}$ = 21.3 Hz, 4H), 6.24-6.19 (m, 1H), 5.32-5.21 (m, 1H), 4.05-3.97 (m, 1H), 3.93-3.81 (m, 3H), 3.68-3.58 (m, 2H), 3.12 (s, 1H), 2.09-2.02 (m, 2H), 1.90-1.84 (m, 1H); 406.0 |
| 82 | Example 3$^{29}$; C6 | 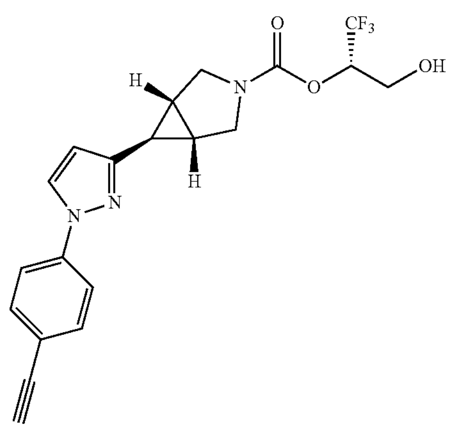 [SMILES: C#Cc1ccc(-n2ccc([C@H]3[C@@H]4CN(C(=O)O[C@@H](CO)C(F)(F)F)C[C@@H]43)n2)cc1] | 7.82 (d, J = 2.3 Hz, 1H), 7.58 (br AB quartet, J$_{AB}$ = 8.6 Hz, Δv$_{AB}$ = 21.2 Hz, 4H), 6.24-6.19 (m, 1H), 5.32-5.21 (m, 1H), 4.05-3.97 (m, 1H), 3.93-3.81 (m, 3H), 3.69-3.57 (m, 2H), 3.12 (s, 1H), 2.09-2.02 (m, 2H), 1.90-1.84 (m, 1H); 406.0 |
| 83 | Example 6; C23, C2 | 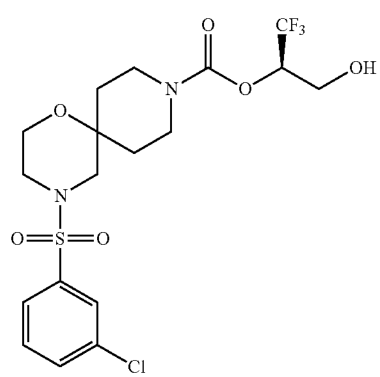 [SMILES: O=C(O[C@H](CO)C(F)(F)F)N1CCC2(CC1)CN(S(=O)(=O)c1cccc(Cl)c1)CCO2] | $^1$H NMR (400 MHz, CD$_3$OD) δ 7.81-7.77 (m, 1H), 7.74-7.69 (m, 2H), 7.63 (dd, component of ABC system, J = 7.8, 7.8 Hz, 1H), 5.33-5.25 (m, 1H), 3.92-3.74 (m, 6H), 3.3-3.12 (m, 2H, assumed; partially obscured by solvent peak), 3.04-2.97 (m, 2H), 2.88-2.81 (m, 2H), 2.00-1.90 (m, 2H), 1.64-1.46 (m, 2H); 486.9 |

TABLE 6-continued

Method of synthesis, structure, and physicochemical properties for Examples 35-91.

| Example Number | Method of Synthesis; Non-commercial starting materials | Structure | $^{1}$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 84 | C31[25] | 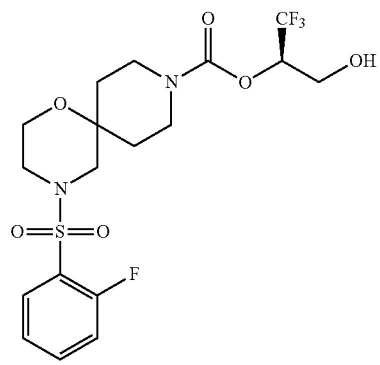 [SMILES: O=C(O[C@H](CO)C(F)(F)F)N1CCC2(CC1)CN(S(=O)(=O)c1ccccc1F)CCO2] | 3.00 minutes[26]; 471 |
| 85 | 6[30,31] | 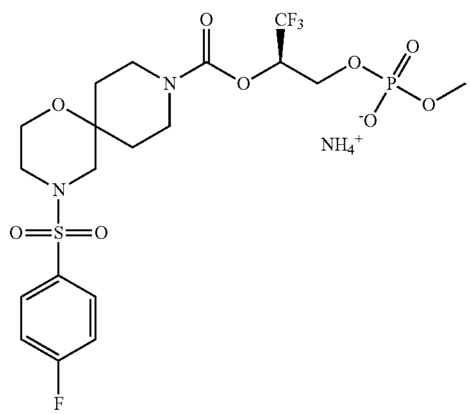 [SMILES: COP(=O)([O-])OC[C@@H](OC(=O)N1CCC2(CC1)CN(S(=O)(=O)c1ccc(F)cc1)CCO2)C(F)(F)F ; [NH4+]] | Presumed to be a mixture of diastereomers around the phosphorus atom; $^{1}$H NMR (400 MHz, CD$_3$OD) δ 7.88-7.81 (m, 2H), 7.37 (br d, J = 9.0, 8.6 Hz, 2H), 5.53-5.43 (m, 1H), 4.20-4.12 (m, 1H), 4.12-4.03 (m, 1H), 3.94-3.76 (m, 2H), 3.79 (dd, J = 5.1, 4.9 Hz, 2H), 3.62-3.52 (m, 3H), 3.29-3.12 (m, 2H), 3.06-2.90 (m, 2H), 2.90-2.73 (m, 2H), 2.02-1.83 (m, 2H), 1.67-1.44 (m, 2H); 565.3 |
| 86 | 6[30,31] | 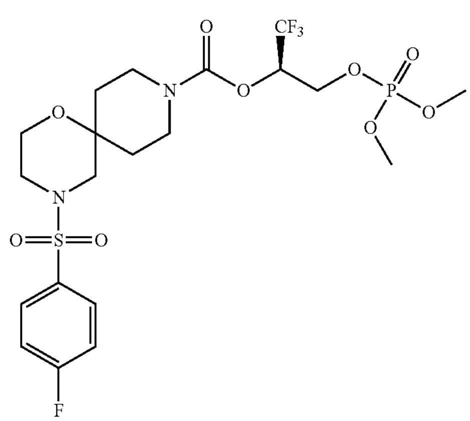 [SMILES: COP(=O)(OC)OC[C@@H](OC(=O)N1CCC2(CC1)CN(S(=O)(=O)c1ccc(F)cc1)CCO2)C(F)(F)F] | $^{1}$H NMR (400 MHz, CD$_3$OD), characteristic peaks: δ 7.87-7.81 (m, 2H), 7.37 (dd, J = 8.7, 8.7 Hz, 2H), 5.59-5.50 (m, 1H), 4.48-4.31 (m, 2H), 3.93-3.73 (m, 8H), 3.3-3.15 (m, 2H), 3.04-2.92 (m, 2H), 2.87-2.76 (m, 2H), 2.01-1.91 (m, 2H), 1.64-1.47 (m, 2H); 579.3 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 87 | 6[30,32] | 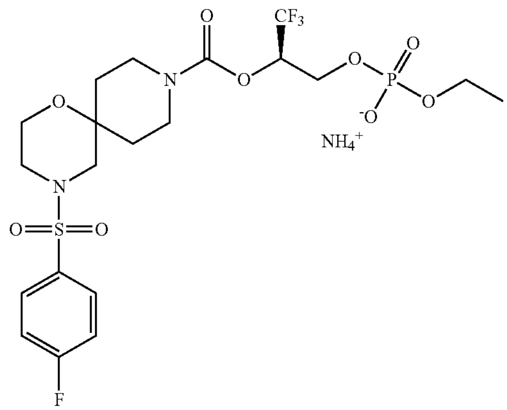 [SMILES: CCOP(=O)([O-])OC[C@@H](OC(=O)N1CCC2(CC1)CN(S(=O)(=O)c1ccc(F)cc1)CCO2)C(F)(F)F ; [NH4+]] | Presumed to be a mixture of diastereomers around the phosphorus atom; $^1$H NMR (400 MHz, CD$_3$OD) δ 7.87-7.81 (m, 2H), 7.37 (dd, J = 8.8, 8.7 Hz, 2H), 5.52-5.43 (m, 1H), 4.20-4.13 (m, 1H), 4.11-4.03 (m, 1H), 3.97-3.82 (m, 4H), 3.79 (dd, J = 5.1, 4.8 Hz, 2H), 3.3-3.12 (m, 2H), 3.06-2.89 (m, 2H), 2.89-2.74 (m, 2H), 2.02-1.84 (m, 2H), 1.66-1.44 (m, 2H), 1.31-1.20 (m, 3H); 579.2 |
| 88 | 6[30,32] | 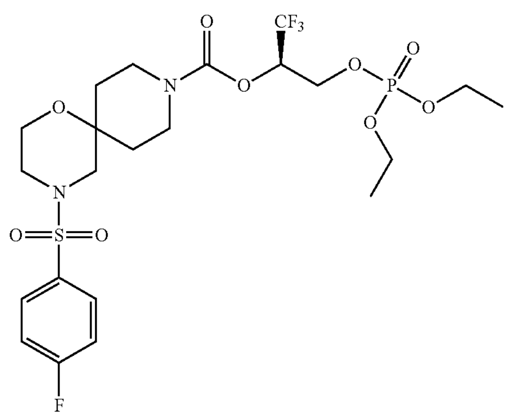 [SMILES: CCOP(=O)(OCC)OC[C@@H](OC(=O)N1CCC2(CC1)CN(S(=O)(=O)c1ccc(F)cc1)CCO2)C(F)(F)F] | $^1$H NMR (400 MHz, CD$_3$OD) δ 7.87-7.80 (m, 2H), 7.37 (dd, J = 8.7, 8.6 Hz, 2H), 5.58-5.49 (m, 1H), 4.44-4.28 (m, 2H), 4.21-4.07 (m, 4H), 3.93-3.8 (m, 2H), 3.80 (dd, J = 5.1, 4.8 Hz, 2H), 3.3-3.15 (m, 2H), 3.03-2.93 (m, 2H), 2.87-2.75 (m, 2H), 2.01-1.91 (m, 2H), 1.63-1.47 (m, 2H), 1.40-1.27 (m, 6H); 607.2 |
| 89 | Example 85[33]; 6 | 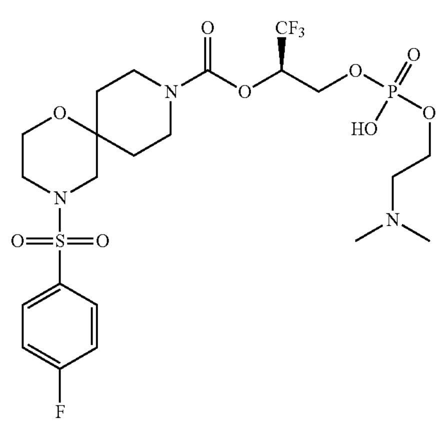 [SMILES: CN(C)CCOP(=O)(O)OC[C@@H](OC(=O)N1CCC2(CC1)CN(S(=O)(=O)c1ccc(F)cc1)CCO2)C(F)(F)F] | Presumed to be a mixture of diastereomers around the phosphorus atom; $^1$H NMR (400 MHz, CD$_3$OD) δ 7.87-7.81 (m, 2H), 7.37 (dd, J = 8.8, 8.7 Hz, 2H), 5.56-5.46 (m, 1H), 4.28-4.20 (m, 1H), 4.20-4.07 (m, 3H), 3.93-3.82 (m, 2H), 3.80 (dd, J = 5.0, 4.9 Hz, 2H), 3.43-3.34 (m, 2H), 3.3-3.14 (m, 2H), 3.00-2.90 (m, 8H), 2.85-2.79 (m, 2H), 2.01-1.89 (m, 2H), 1.68-1.44 (m, 2H); 622.5 |

TABLE 6-continued

Method of synthesis, structure, and physicochemical properties for Examples 35-91.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 90 | Example 85[34]; 6 | 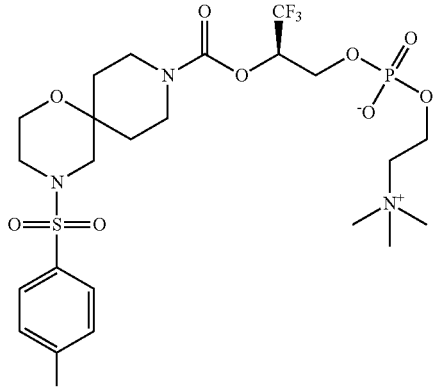 | Presumed to be a mixture of diastereomers around the phosphorus atom; $^1$H NMR (400 MHz, CD$_3$OD) δ 7.87-7.81 (m, 2H), 7.37 (dd, J = 8.7, 8.7 Hz, 2H), 5.55-5.46 (m, 1H), 4.33-4.20 (m, 3H), 4.15-4.07 (m, 1H), 3.93-3.82 (m, 2H), 3.80 (dd, J = 5.2, 4.7 Hz, 2H), 3.69-3.60 (m, 2H), 3.28-3.17 (m, 11H), 3.01-2.95 (m, 2H), 2.86-2.78 (m, 2H), 2.01-1.90 (m, 2H), 1.67-1.44 (m, 2H); 636.2 |
| 91 | Example 30; 7 | 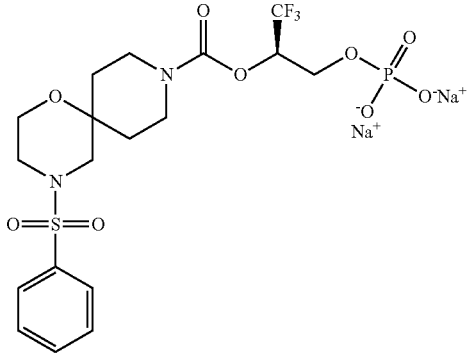 | $^1$H NMR (400 MHz, D$_2$O) δ 7.82-7.77 (m, 2H), 7.77-7.72 (m, 1H), 7.68-7.62 (m, 2H), 5.47-5.37 (m, 1H), 4.12-4.04 (m, 1H), 4.01-3.93 (m, 1H), 3.93-3.63 (m, 2H), 3.83 (dd, J = 5.1, 4.9 Hz, 2H), 3.36-3.12 (m, 2H), 3.11-2.98 (m, 2H), 2.97-2.84 (m, 2H), 2.00-1.80 (m, 2H), 1.76-1.49 (m, 2H); 533.1 |

1. 3,3,3-Trifluoropropane-1,2-diol was converted to 3-{[tert-butyl(dimethyl)silyl]oxy}-1,1,1-trifluoropropan-2-ol using the method described for synthesis of C59 from C58 in Examples 19, 20 and 21.

2. Reaction of 4-[4-(piperidin-4-yl)pyrimidin-2-yl]morpholine, hydrochloride salt with bis(trichloromethyl) carbonate and 3-{[tert-butyl(dimethyl)silyl]oxy}-1,1,1-trifluoropropan-2-ol (see footnote 1) in the presence of N,N-diisopropylethylamine afforded 3-{[tert-butyl(dimethyl)silyl]oxy}-1,1,1-trifluoropropan-2-yl 4-[2-(morpholin-4-yl)pyrimidin-4-yl]piperidine-1-carboxylate. This material was desilylated via treatment with acetic acid in a mixture of water and tetrahydrofuran to afford Example 35.

3. Examination of coupling constants in the NMR spectra of rel-(2S,3R)-1,1,1,4,4,4-hexafluorobutane-2,3-diol and rel-(2R,3R)-1,1,1,4,4,4-hexafluorobutane-2,3-diol allowed tentative assignment of the starting material used for Example 36 as the rel-(2S,3R) isomer.

4. Reaction of C19 with bis(trichloromethyl) carbonate and rel-(2S,3R)-1,1,1,4,4,4-hexafluorobutane-2,3-diol in the presence of N,N-diisopropylethylamine afforded Example 36.

5. Alkylation of C6 with 2-(chloromethyl)pyridine in the presence of potassium hydroxide in acetone provided the requisite tert-butyl (1α,5α,6α)-6-[1-(pyridin-2-ylmethyl)-1H-pyrazol-3-yl]-3-azabicyclo[3.1.0]hexane-3-carboxylate.

6. Reaction of C13 with tetrahydro-2H-pyran-4-yl methanesulfonate in the presence of cesium carbonate and potassium iodide, at elevated temperature in N,N-dimethylformamide, provided the requisite tert-butyl 4-[1-(tetrahydro-2H-pyran-4-yl)-1H-pyrazol-3-yl]piperidine-1-carboxylate.

7. The carbonate reagent employed in this case was 1-({[(3-{[tert-butyl(dimethyl)silyl]oxy}-1,1,1-trifluoropropan-2-yl)oxy]carbonyl}oxy)pyrrolidine-2,5-dione, prepared from 3-{[tert-butyl(dimethyl)silyl]oxy}-1,1,1-trifluoropropan-2-ol (see footnote 1) using the general method described for synthesis of C17 in Example 3.

8. tert-Butyl 2,9-diazaspiro[5.5]undecane-2-carboxylate was converted to 2-tert-butyl 9-{(2R)-1,1,1-trifluoro-3-[(4-methoxybenzyl)oxy]propan-2-yl} 2,9-diazaspiro[5.5]undecane-2,9-dicarboxylate using the method described for synthesis of C29 in Example 6. Treatment with trifluoroacetic acid removed both protecting groups, affording (2R)-1,1,1-trifluoro-3-hydroxypropan-2-yl 2,9-diazaspiro[5.5]undecane-9-carboxylate, which was then subjected to reductive amination with 4-fluorobenzaldehyde and sodium triacetoxyborohydride to afford Example 41.

9. Reaction of C23 with 4-fluorobenzaldehyde in the presence of 1H-benzotriazole and acetic acid provided the corresponding imine; in situ treatment with methylmagnesium bromide then afforded the requisite tert-butyl 4-[1-(4-fluorophenyl)ethyl]-1-oxa-4,9-diazaspiro[5.5]undecane-9-carboxylate. Example 43 is a diastereomeric mixture, with both stereochemistries present at the methyl group.

10. Separation of Example 43 into its component diastereomers was effected via supercritical fluid chromatography

[Column: Chiral Technologies Chiralpak AD, 5 μm; Mobile phase: 4:1 carbon dioxide: (0.1% ammonium hydroxide in ethanol)]. The first-eluting diastereomer was Example 44, and the second-eluting diastereomer was Example 45.

11. In this case, tert-butyl 1-oxa-6-azaspiro[2.5]octane-6-carboxylate was reacted with tetrahydro-2H-pyran-4-amine, and the resulting tert-butyl 4-hydroxy-4-[(tetrahydro-2H-pyran-4-ylamino)methyl]piperidine-1-carboxylate was N-alkylated with 1-(bromomethyl)-4-fluorobenzene in the presence of potassium carbonate; this afforded the requisite tert-butyl 4-{[(4-fluorobenzyl)(tetrahydro-2H-pyran-4-yl)amino]methyl}-4-hydroxypiperidine-1-carboxylate.

12. tert-Butyl 4-[(tetrahydro-2H-pyran-4-ylamino)methyl]piperidine-1-carboxylate was synthesized via reductive amination of tetrahydro-4H-pyran-4-one with tert-butyl 4-(aminomethyl)piperidine-1-carboxylate, using magnesium sulfate and silica gel followed by sodium triacetoxyborohydride.

13. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

14. Intermediate tert-butyl 4-({[(4-fluorophenyl)sulfonyl]amino}methyl)piperidine-1-carboxylate was reacted with iodomethane and potassium carbonate to provide tert-butyl 4-({[(4-fluorophenyl)sulfonyl](methyl)amino}methyl)piperidine-1-carboxylate.

15. The requisite 2-chloro-4-(1-methyl-1H-pyrazol-5-yl)pyridine was prepared via a Suzuki reaction between 2-chloro-4-iodopyridine and 1-methyl-5-(4,4,5,5-tetramethyl-1,3,2-dioxaborolan-2-yl)-1H-pyrazole, mediated via [1,1'-bis(diphenylphosphino)ferrocene]dichloropalladium (I).

16. Suzuki reaction of 2-bromo-6-chloropyridine and 1-methyl-5-(4,4,5,5-tetramethyl-1,3,2-dioxaborolan-2-yl)-1H-pyrazole, mediated via [1,1'-bis(diphenylphosphino)ferrocene]dichloropalladium(I), afforded 2-chloro-6-(1-methyl-1H-pyrazol-5-yl)pyridine.

17. The requisite sulfonic acid was prepared from the corresponding bromo compound via reaction with a mixture of potassium disulfite, palladium(II) acetate, triphenylphosphine, tetraethylammonium bromide, sodium formate and 1,10-phenanthroline in N,N-dimethylformamide at elevated temperature. The sulfonic acid was cooled to 0° C., treated with C31 and N-chlorosuccinimide, and stirred at 30° C. for 1 hour. The resulting sulfonamide was deprotected via treatment with trifluoroacetic acid in dichloromethane to provide the product of the Example.

18. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.

19. N-Benzyl-2-oxo-1,3-oxazolidine-3-sulfonamide was used as the sulfonylating reagent in this case, in a mixture of triethylamine and acetonitrile.

20. Reaction of C31 and 4-bromobenzenesulfonyl chloride provided (2R)-1,1,1-trifluoro-3-[(4-methoxybenzyl)oxy]propan-2-yl 4-[(4-bromophenyl)sulfonyl]-1-oxa-4,9-diazaspiro[5.5]undecane-9-carboxylate, which was then converted to (2R)-1,1,1-trifluoro-3-[(4-methoxybenzyl)oxy]propan-2-yl 4-({4-[(trimethylsilyl)ethynyl]phenyl}sulfonyl)-1-oxa-4,9-diazaspiro[5.5]undecane-9-carboxylate by reaction with ethynyl(trimethyl)silane, copper(I) iodide, and [1,1'-bis(diphenylphosphino)ferrocene]dichloropalladium(II). Desilylation was effected via treatment with potassium carbonate and methanol to afford (2R)-1,1,1-trifluoro-3-[(4-methoxybenzyl)oxy]propan-2-yl 4-[(4-ethynylphenyl)sulfonyl]-1-oxa-4,9-diazaspiro[5.5]undecane-9-carboxylate; final deprotection using trifluoroacetic acid provided Example 68.

21. Reaction of tert-butyl 4-oxopiperidine-1-carboxylate with nitroethane and triethylamine provided tert-butyl 4-hydroxy-4-(1-nitroethyl)piperidine-1-carboxylate, which was hydrogenated to afford tert-butyl 4-(1-aminoethyl)-4-hydroxypiperidine-1-carboxylate. This material was treated with 4-fluorobenzenesulfonyl chloride and potassium carbonate, followed by 1,2-dibromoethane, to provide the requisite intermediate tert-butyl 4-[(4-fluorophenyl)sulfonyl]-5-methyl-1-oxa-4,9-diazaspiro[5.5]undecane-9-carboxylate.

22. Separation to provide the diastereomers of Examples 70 and 71 was effected via supercritical fluid chromatography [Column: Chiral Technologies Chiralpak AD, 5 μm; Mobile phase A: carbon dioxide; Mobile phase B: 2-propanol; Gradient: 25% to 100% B). The first-eluting diastereomer was Example 70, and the second-eluting diastereomer was Example 71.

23. tert-Butyl 2-oxo-1-oxa-3,8-diazaspiro[4.5]decane-8-carboxylate was treated with sodium hydride and 1-(chloromethyl)-4-fluorobenzene to afford tert-butyl 3-(4-fluorobenzyl)-2-oxo-1-oxa-3,8-diazaspiro[4.5]decane-8-carboxylate; deprotection with hydrogen chloride in 1,4-dioxane provided the requisite 3-(4-fluorobenzyl)-1-oxa-3,8-diazaspiro[4.5]decan-2-one.

24. In this case, the final deprotection was effected with hydrogen chloride in 1,4-dioxane, rather than trifluoroacetic acid.

25. Compound C31 was allowed to react with the appropriate sulfonyl chloride and triethylamine; the resulting sulfonamide was deprotected with trifluoroacetic acid in dichloromethane to afford the product of the Example.

26. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

27. 2-Bromoethanol was slowly added to a solution of chlorosulfonyl isocyanate in dichloromethane at 0° C. After an hour, a mixture of 1-(pyridin-2-yl)methanamine and triethylamine was slowly added to the 0° C. reaction mixture. Removal of solvent provided 2-oxo-N-(pyridin-2-ylmethyl)-1,3-oxazolidine-3-sulfonamide, which was used as the sulfonylating reagent in this case, in a mixture of triethylamine and acetonitrile.

28. The requisite tert-butyl 4-[1-(4-ethynylphenyl)-1H-pyrazol-3-yl]piperidine-1-carboxylate was prepared as follows: tert-butyl 4-acetylpiperidine-1-carboxylate was converted to tert-butyl 4-[1-(4-bromophenyl)-1H-pyrazol-3-yl]piperidine-1-carboxylate using the methods described for synthesis of C18 from C4 that are found in Examples 1 and 3. Reaction with ethynyl(trimethyl)silane, copper(I) iodide and tetrakis(triphenylphosphine)palladium(0), followed by removal of the silyl group via treatment with potassium carbonate in methanol, provided tert-butyl 4-[1-(4-ethynylphenyl)-1H-pyrazol-3-yl]piperidine-1-carboxylate.

29. In this case, the enantiomer of C1 was employed; this may be prepared similarly, via the use of (2S)-2-(trifluoromethyl)oxirane rather than (2R)-2-(trifluoromethyl)oxirane.

30. A 0° C. solution of 6 in acetonitrile was treated with 5 equivalents of diphosphoryl tetrachloride; after one to two hours at 0° C., the appropriate alcohol (40 equivalents) was added, generating a mixture of the mono- and di-alkyl phosphate esters.

31. Reversed phase HPLC was used to separate the monomethyl and dimethyl phosphate esters. Column: Phenomenex Gemini NX C18, 5 μm; Mobile phase A: 0.1% ammonium hydroxide in water; Mobile phase B: 0.1% ammonium hydroxide in acetonitrile; Gradient: 50% to 100% B. The first-eluting product was Example 85, and the second-eluting product was Example 86.

32. Reversed phase HPLC was used to separate the monoethyl and diethyl phosphate esters. Column: Phenomenex Gemini NX C18, 5 μm; Mobile phase A: 0.1% ammonium hydroxide in water; Mobile phase B: 0.1% ammonium hydroxide in acetonitrile; Gradient: 50% to 100% B. The first-eluting product was Example 87, and the second-eluting product was Example 88.

33. In this case, 2-(dimethylamino)ethanol was used in place of methanol. The product was purified using reversed phase HPLC (Column: Phenomenex Luna C18, 5 μm; Mobile phase A: 0.1% formic acid in water; Mobile phase B: 0.1% formic acid in acetonitrile; Gradient: 50% to 100% B).

34. In this case, 2-hydroxy-N,N,N-trimethylethanaminium chloride was used in place of methanol.

Example 92

(2R)-1,1,1-Trifluoro-3-hydroxypropan-2-yl (3R)-3-[ethyl(phenylsulfonyl)amino]-1-oxa-8-azaspiro[4.5]decane-8-carboxylate (92)

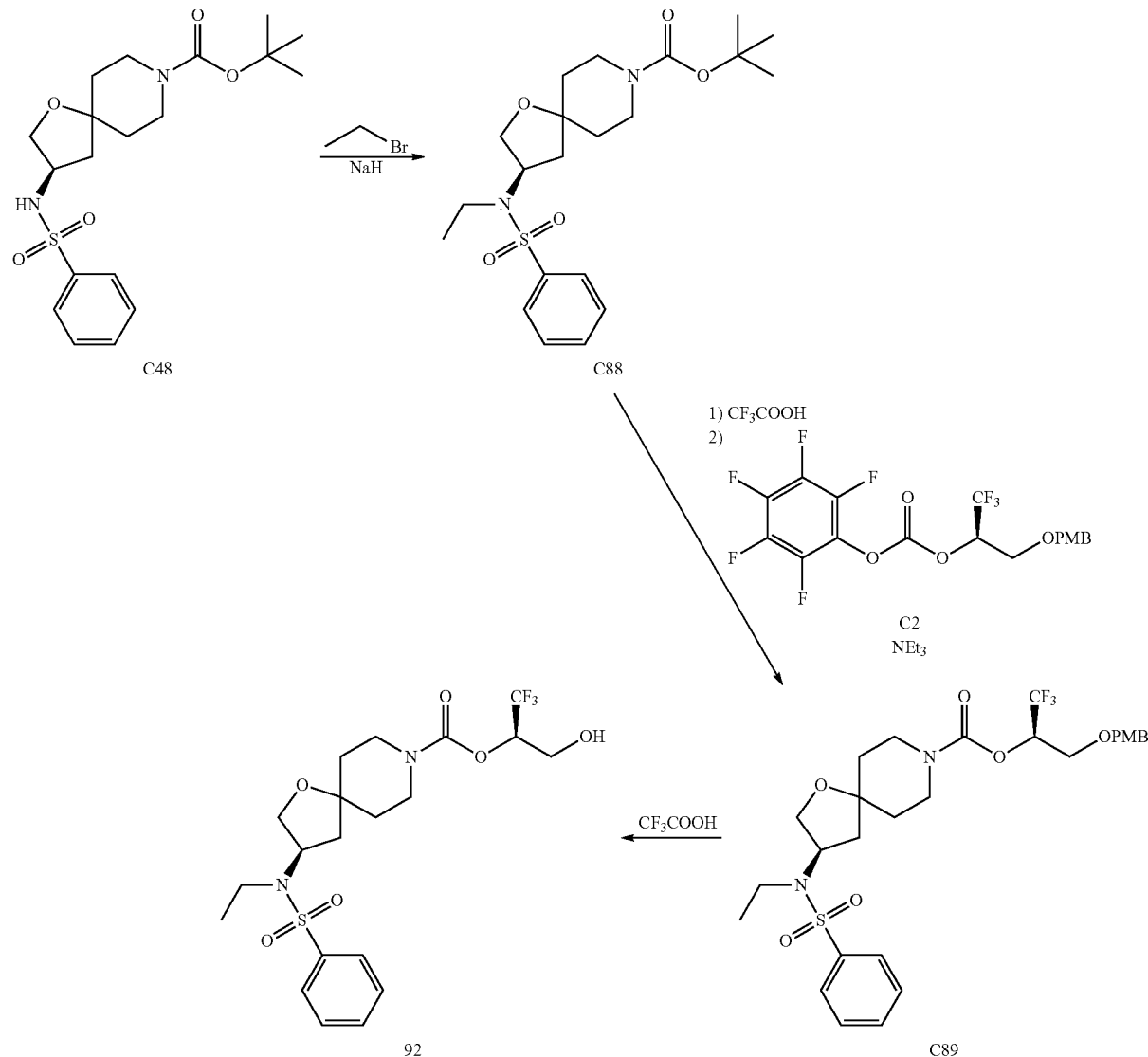

Step 1. Synthesis of tert-butyl (3R)-3-[ethyl(phenylsulfonyl)amino]-1-oxa-8-azaspiro[4.5]decane-8-carboxylate (C88)

Sodium hydride (60% dispersion in mineral oil; 15 mg, 0.38 mmol) was added to a 0° C. solution of C48 (50.0 mg, 0.126 mmol) in N,N-dimethylformamide (1 mL). After the reaction mixture had been stirred at 0° C. for 30 minutes, a solution of bromoethane (27.5 mg, 0.252 mmol) in N,N-dimethylformamide (0.1 mL) was added, and the reaction mixture was allowed to stir at 25° C. for 16 hours. It was subsequently cooled to 0° C., and additional sodium hydride (60% dispersion in mineral oil; 15 mg, 0.38 mmol) was added; stirring was continued at 0° C. for 30 minutes, whereupon a solution of bromoethane (20 mg, 0.18 mmol) in N,N-dimethylformamide (0.1 mL) was added. The reaction mixture was then stirred at 25° C. for 16 hours. Water (30 mL) was added, and the resulting mixture was extracted with dichloromethane (3×30 mL). The combined organic layers were dried over sodium sulfate, filtered, concentrated in vacuo, and subjected to preparative thin layer chromatography on silica gel (Eluent: 2:1 petroleum ether/ethyl acetate), providing the product as a light yellow gum. Yield: 40 mg, 94 µmol, 75%. LCMS m/z 447.2 [M+Na$^+$]. $^1$H NMR (400 MHz, CDCl$_3$) δ 7.81 (br d, J=7 Hz, 2H), 7.58 (br dd, J=7.4, 7.3 Hz, 1H), 7.51 (br dd, J=7.9, 7.2 Hz, 2H), 4.64-4.54 (m, 1H), 3.80 (dd, J=9.8, 7.6 Hz, 1H), 3.66-3.5 (m, 2H), 3.50 (dd, J=9.9, 6.2 Hz, 1H), 3.28-3.10 (m, 4H), 1.94 (dd, J=13.2, 8.8 Hz, 1H), 1.63-1.53 (m, 3H), 1.47 (dd, J=13.3, 8.0 Hz, 1H), 1.43 (s, 9H), 1.42-1.33 (m, 1H), 1.30 (t, J=7.0 Hz, 3H).

Step 2. Synthesis of (2R)-1,1,1-trifluoro-3-[(4-methoxybenzyl)oxy]propan-2-yl (3R)-3-[ethyl(phenylsulfonyl)amino]-1-oxa-8-azaspiro[4.5]decane-8-carboxylate (C89)

Trifluoroacetic acid (1 mL) was added in a drop-wise manner to a 0° C. solution of C88 (39.0 mg, 91.9 µmol) in dichloromethane (1 mL), and the reaction mixture was stirred at 15° C. for 1 hour. Removal of volatiles under reduced pressure provided N-ethyl-N-[(3R)-1-oxa-8-azaspiro[4.5]dec-3-yl]benzenesulfonamide, trifluoroacetate salt, as a yellow gum, LCMS m/z 325.1 [M+H]$^+$. This material was dissolved in acetonitrile (1 mL), cooled to 0° C., and treated with C2 (reaction solution in acetonitrile containing 0.11 mmol) and triethylamine (73.3 mg, 0.724 mmol). After the reaction mixture had been stirred at 20° C. for 16 hours, it was concentrated in vacuo and purified via chromatography on silica gel (Gradient: 0% to 50% ethyl acetate in petroleum ether) to afford the product as a colorless gum. Yield: 35 mg, 58 µmol, 63%. LCMS m/z 623.1 [M+Na$^+$]. $^1$H NMR (400 MHz, CDCl$_3$) δ 7.84-7.80 (m, 2H), 7.62-7.57 (m, 1H), 7.56-7.49 (m, 2H), 7.23 (br d, J=8.7 Hz, 2H), 6.87 (br d, J=8.7 Hz, 2H), 5.52-5.40 (m, 1H), 4.66-4.53 (m, 1H), 4.49 (AB quartet, upfield doublet is broadened, J$_{AB}$=11.7 Hz, Δv$_{AB}$=28.4 Hz, 2H), 3.88-3.62 (m, 5H), 3.81 (s, 3H), 3.58-3.47 (m, 1H), 3.36-3.10 (m, 4H), 1.93 (dd, J=13.2, 8.8 Hz, 1H), 1.7-1.55 (m, 3H, assumed; partially obscured by water peak), 1.50 (dd, J=13.2, 8.1 Hz, 1H), 1.39 (ddd, J=13.5, 11.2, 4.3 Hz, 1H), 1.31 (t, J=7.1 Hz, 3H).

Step 3. Synthesis of (2R)-1,1,1-trifluoro-3-hydroxypropan-2-yl (3R)-3-[ethyl(phenylsulfonyl)amino]-1-oxa-8-azaspiro[4.5]decane-8-carboxylate (92)

To a 0° C. suspension of C89 (35 mg, 58 µmol) in dichloromethane (1 mL) was added trifluoroacetic acid (1 mL). The reaction mixture was stirred at 18° C. for 1 hour, whereupon it was cooled to 0° C. and slowly treated with aqueous sodium bicarbonate solution (30 mL), while the purple mixture became colorless. It was then extracted with dichloromethane (3×30 mL), and the combined organic layers were dried over sodium sulfate, filtered, and concentrated in vacuo. The residue was purified using reversed phase HPLC (Column: Agela Durashell, 5 µm; Mobile phase A: water containing 0.225% formic acid; Mobile phase B: acetonitrile; Gradient: 44% to 84% B), to afford the product as a colorless oil. Yield: 7.5 mg, 16 µmol, 28%. LCMS m/z 481.0 [M+H]$^+$. $^1$H NMR (400 MHz, CDCl$_3$) δ 7.82 (br d, J=8 Hz, 2H), 7.60 (br dd, J=7.5, 7.5 Hz, 1H), 7.52 (br dd, J=7.5, 7.5 Hz, 2H), 5.30-5.17 (m, 1H), 4.66-4.55 (m, 1H), 4.04-3.93 (m, 1H), 3.91-3.69 (m, 4H), 3.58-3.48 (m, 1H), 3.39-3.09 (m, 4H), 2.50-2.36 (m, 1H), 2.01-1.88 (m, 1H), 1.7-1.6 (m, 2H, assumed; largely obscured by water peak), 1.57-1.35 (m, 2H), 1.31 (t, J=7.0 Hz, 3H).

Examples 93 and 94

(2R)-1,1,1-Trifluoro-3-hydroxypropan-2-yl (3R)-3-[(cyclopropylsulfonyl)(methyl)amino]-1-oxa-8-azaspiro[4.5]decane-8-carboxylate (93) and (2R)-1,1,1-Trifluoro-3-hydroxypropan-2-yl (3S)-3-[(cyclopropylsulfonyl)(methyl)amino]-1-oxa-8-azaspiro[4.5]decane-8-carboxylate (94)

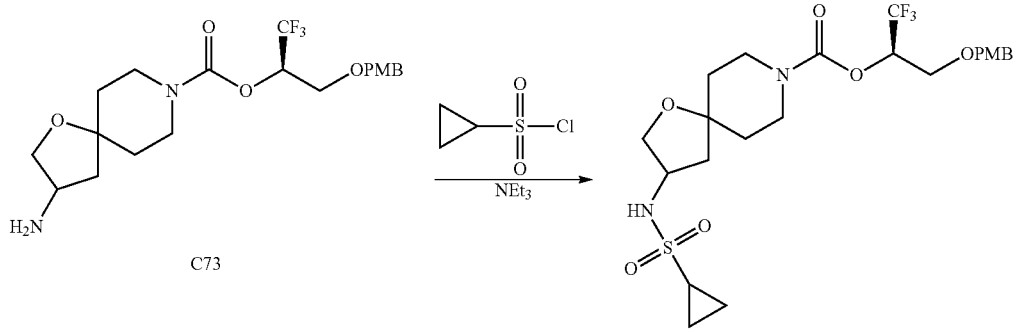

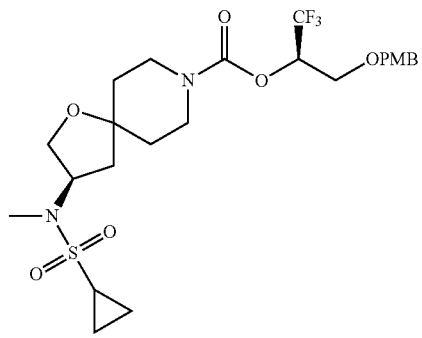

DIAST-1
C91

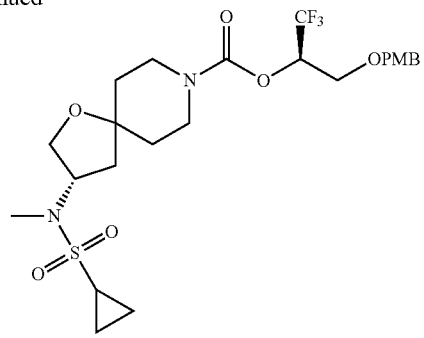

DIAST-2
C92

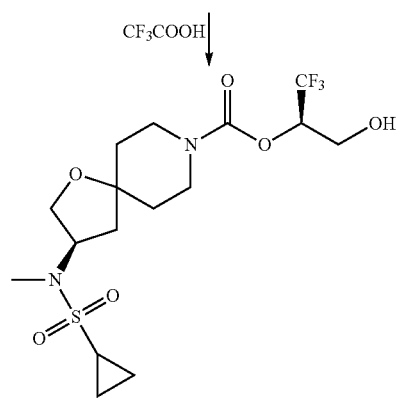

93

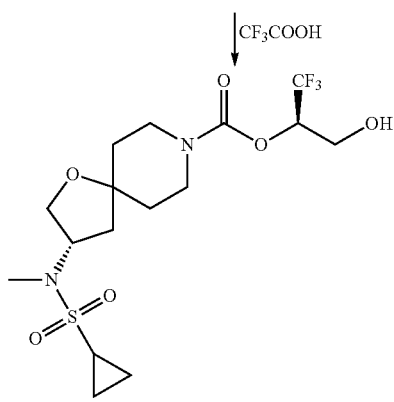

94

Step 1. Synthesis of (2R)-1,1,1-trifluoro-3-[(4-methoxybenzyl)oxy]propan-2-yl 3-[(cyclopropylsulfonyl)amino]-1-oxa-8-azaspiro[4.5]decane-8-carboxylate (C90)

Cyclopropanesulfonyl chloride (650 mg, 4.62 mmol) and triethylamine (1.17 g, 11.6 mmol) were added to an 18° C. suspension of C73 (1.00 g, 2.31 mmol) in dichloromethane (8 mL), and the reaction mixture was stirred at 10° C. for 12 hours. After the reaction mixture had been concentrated in vacuo, the residue was diluted with water (30 mL) and extracted with ethyl acetate (3×30 mL). The combined organic layers were dried over sodium sulfate, filtered, concentrated under reduced pressure, and purified using silica gel chromatography (Gradient: 0% to 15% methanol in dichloromethane), affording the product as a colorless gum. Yield: 641 mg, 1.19 mmol, 52%. LCMS m/z 559.1 [M+Na$^+$].

Step 2. Synthesis of (2R)-1,1,1-trifluoro-3-[(4-methoxybenzyl)oxy]propan-2-yl (3R)-3-[(cyclopropylsulfonyl)(methyl)amino]-1-oxa-8-azaspiro[4.5]decane-8-carboxylate (DIAST-1) (C91) and (2R)-1,1,1-trifluoro-3-[(4-methoxybenzyl)oxy]propan-2-yl (3S)-3-[(cyclopropylsulfonyl)(methyl)amino]-1-oxa-8-azaspiro[4.5]decane-8-carboxylate (DIAST-2) (C92)

To a 0° C. solution of C90 (641 mg, 1.19 mmol) in N,N-dimethylformamide (8 mL) was added sodium hydride (60% dispersion in mineral oil; 95.6 mg, 2.39 mmol), and the reaction mixture was stirred at 0° C. for 30 minutes. Iodomethane (254 mg, 1.79 mmol) was added at 0° C., and the reaction mixture was allowed to stir at 15° C. for 3 hours, whereupon it was diluted with water (50 mL) and extracted with ethyl acetate (3×30 mL). The combined organic layers were concentrated in vacuo, and the residue was purified by silica gel chromatography (Gradient: 0% to 50% ethyl acetate in petroleum ether) to afford a mixture of C91 and C92 as a colorless gum. Yield: 310 mg, 0.563 mmol, 47%. The component diastereomers were separated via supercritical fluid chromatography [Column: Chiral Technologies Chiralpak IC, 10 μm; Mobile phase: 40% (0.1% ammonium hydroxide in 2-propanol) in carbon dioxide], affording C91 as the first-eluting diastereomer, and C92 as the second-eluting diastereomer, both as colorless gums. The indicated stereochemistries at the sulfonamide positions were assigned on the basis of a chiral synthesis of 93 (see Alternate Synthesis of Example 93 below).

C91—Yield: 147 mg, 0.267 mmol, 22%. LCMS m/z 573.0 [M+Na$^+$]. $^1$H NMR (400 MHz, CDCl$_3$) δ 7.25 (br d, J=8.5 Hz, 2H), 6.88 (br d, J=8.5 Hz, 2H), 5.55-5.42 (m, 1H), 4.73-4.62 (m, 1H), 4.51 (AB quartet, $J_{AB}$=11.7 Hz, $\Delta\nu_{AB}$=29.3 Hz, 2H), 3.96 (dd, half of ABX pattern, J=10.0, 7.5 Hz, 1H), 3.85 (dd, half of ABX pattern, J=10.1, 5.2 Hz, 1H), 3.82 (s, 3H), 3.8-3.64 (m, 4H), 3.41-3.22 (m, 2H), 2.88 (s, 3H), 2.26 (tt, J=8.0, 4.9 Hz, 1H), 2.11-1.97 (m, 1H), 1.85-1.64 (m, 4H), 1.45 (ddd, J=13.7, 11.2, 4.4 Hz, 1H), 1.21-1.15 (m, 2H), 1.03-0.97 (m, 2H).

C92—Yield: 155 mg, 0.282 mmol, 24%. LCMS m/z 573.0 [M+Na$^+$]. $^1$H NMR (400 MHz, CDCl$_3$), characteristic peaks: δ 7.25 (br d, J=8.7 Hz, 2H), 6.88 (br d, J=8.5 Hz, 2H), 5.54-5.43 (m, 1H), 4.73-4.63 (m, 1H), 4.51 (AB quartet, upfield d is broadened, $J_{AB}$=11.9 Hz, $\Delta v_{AB}$=290.0 Hz, 2H), 4.01-3.91 (m, 1H), 3.89-3.78 (m, 2H), 3.82 (s, 3H), 3.79-3.64 (m, 3H), 3.40-3.20 (m, 2H), 2.88 (s, 3H), 2.26 (tt, J=8, 5 Hz, 1H), 2.14-1.95 (m, 1H), 1.84-1.7 (m, 4H, assumed; partially obscured by water peak), 1.21-1.15 (m, 2H), 1.03-0.97 (m, 2H).

Step 3. Synthesis of (2R)-1,1,1-trifluoro-3-hydroxy-propan-2-yl (3R)-3-[(cyclopropylsulfonyl)(methyl)amino]-1-oxa-8-azaspiro[4.5]decane-8-carboxylate (93)

Trifluoroacetic acid (2 mL) was added to a 0° C. solution of C91 (147 mg, 0.267 mmol) in dichloromethane (8 mL). The reaction mixture was stirred at 16° C. for 1 hour, whereupon it was cooled to 0° C., and slowly treated with aqueous sodium bicarbonate solution (20 mL), while the purple mixture became colorless. The resulting mixture was extracted sequentially with dichloromethane (20 mL) and ethyl acetate (2×20 mL); the combined organic layers were dried over sodium sulfate, filtered, and concentrated in vacuo. Chromatography on silica gel (Gradient: 0% to 70% ethyl acetate in petroleum ether) afforded the product as a yellow oil. Yield: 49.7 mg, 0.115 mmol, 43%. LCMS m/z 431.2 [M+H]$^+$. $^1$H NMR (400 MHz, CDCl$_3$) δ 5.32-5.20 (m, 1H), 4.73-4.64 (m, 1H), 4.05-3.93 (m, 2H), 3.94-3.75 (m, 4H), 3.46-3.24 (m, 2H), 2.89 (s, 3H), 2.39-2.21 (m, 1H), 2.26 (tt, J=8.0, 4.9 Hz, 1H), 2.13-2.04 (m, 1H), 1.86-1.69 (m, 4H), 1.56-1.41 (m, 1H), 1.22-1.15 (m, 2H), 1.04-0.96 (m, 2H).

Step 4. Synthesis of (2R)-1,1,1-trifluoro-3-hydroxy-propan-2-yl (3S)-3-[(cyclopropylsulfonyl)(methyl)amino]-1-oxa-8-azaspiro[4.5]decane-8-carboxylate (94)

Conversion of C92 to the product was carried out using the method described for synthesis of 93 from C91. The product was isolated as a yellow oil. Yield: 63 mg, 0.15 mmol, 53%. LCMS m/z 431.2 [M+H]$^+$. $^1$H NMR (400 MHz, CDCl$_3$) δ 5.31-5.20 (m, 1H), 4.74-4.64 (m, 1H), 4.05-3.93 (m, 2H), 3.92-3.71 (m, 4H), 3.42-3.20 (m, 2H), 2.89 (s, 3H), 2.37-2.22 (m, 2H), 2.08 (dd, J=13.3, 9.0 Hz, 1H), 1.86-1.67 (m, 3H), 1.81 (dd, J=13.6, 7.0 Hz, 1H), 1.55-1.45 (m, 1H, assumed; partially obscured by water peak), 1.22-1.15 (m, 2H), 1.04-0.96 (m, 2H).

Alternate Synthesis of Example 93

(2R)-1,1,1-Trifluoro-3-hydroxypropan-2-yl (3R)-3-[(cyclopropylsulfonyl)(methyl)amino]-1-oxa-8-azaspiro[4.5]decane-8-carboxylate (93)

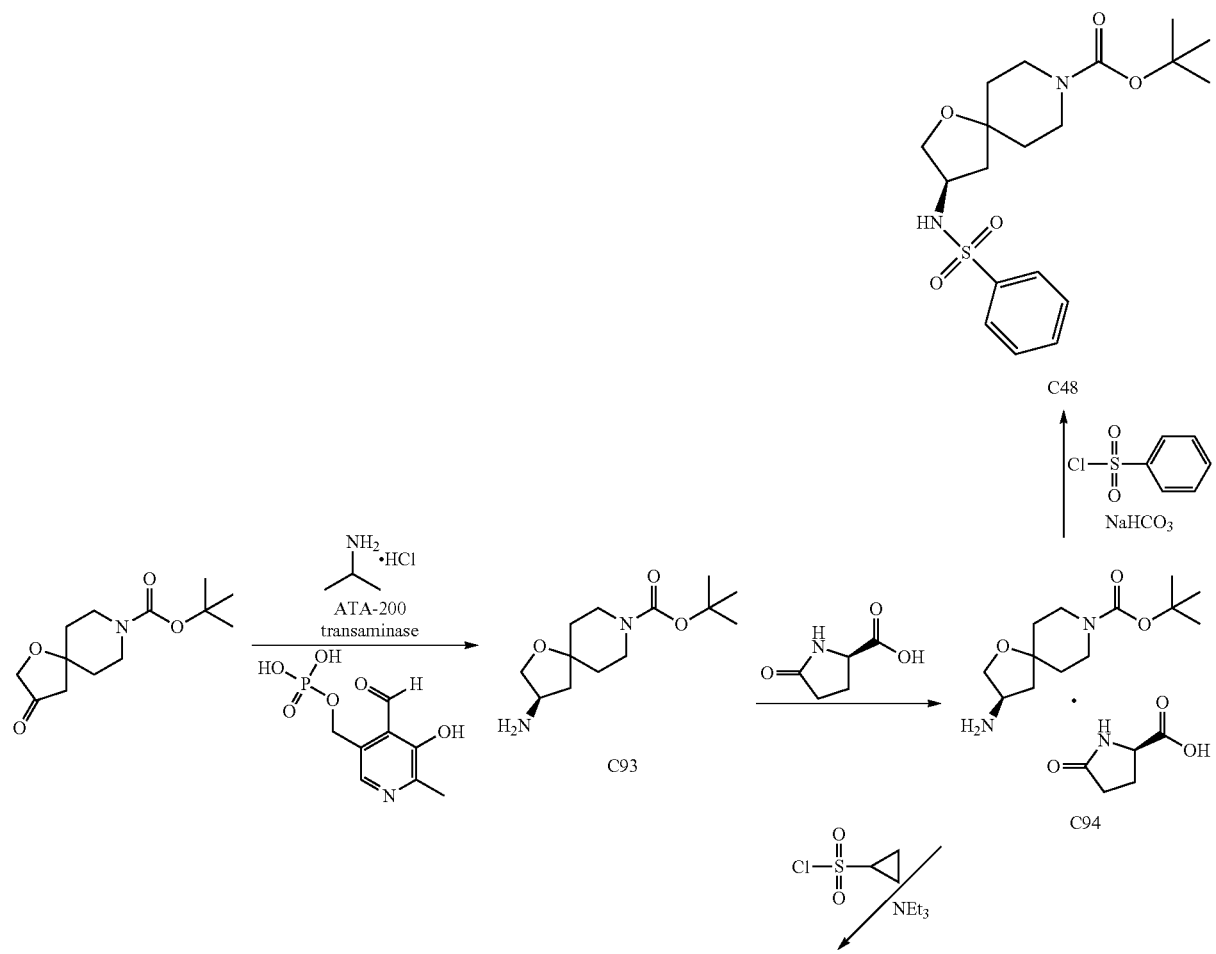

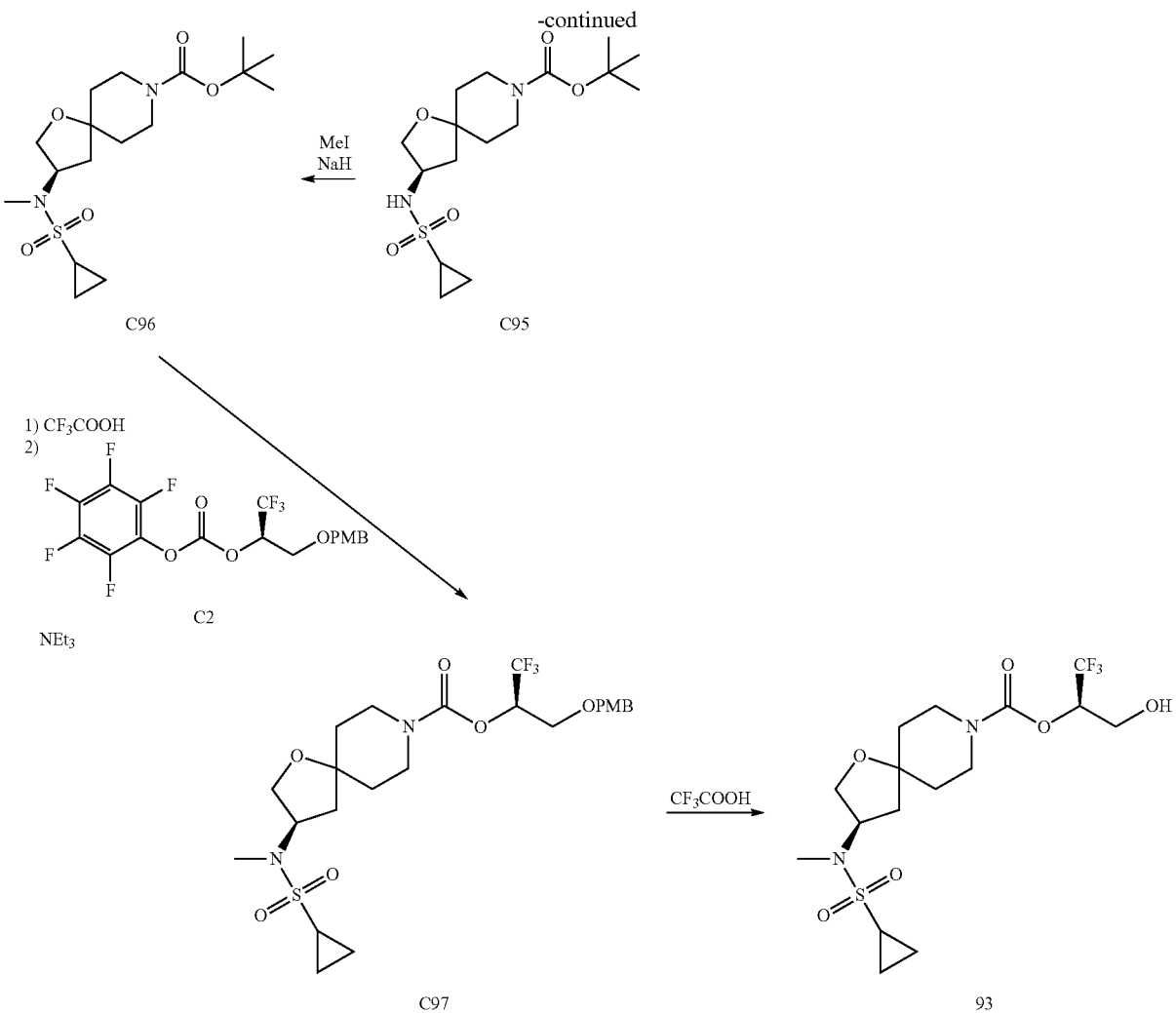

Step 1. Synthesis of tert-butyl (3R)-3-amino-1-oxa-8-azaspiro[4.5]decane-8-carboxylate (C93)

A pH 8.0 buffer solution was prepared, containing 0.1 M aqueous potassium phosphate and 2 mM magnesium chloride. A stock solution of substrate was prepared as follows: tert-butyl 3-oxo-1-oxa-8-azaspiro[4.5]decane-8-carboxylate (18.0 g, 70.5 mmol) was dissolved in water containing 4% dimethyl sulfoxide (14.4 mL). Warming and stirring were required for dissolution, and the resulting solution was maintained at 40° C. Propan-2-amine, hydrochloride salt (16.8 g, 176 mmol) was added to a mixture of pyridoxal 5'-phosphate monohydrate (1.87 g, 7.05 mmol) and the pH 8.0 buffer (300 mL). The resulting pH was approximately 6.5; the pH was adjusted to 8 via addition of aqueous potassium hydroxide solution (6 M; approximately 4 mL). The stock solution of substrate was added via syringe, in 5 mL portions, resulting in a suspension, still at 15 pH 8. Codex® ATA-200 transaminase (batch #11099; 1.4 g) was almost completely dissolved in pH 8 buffer (20 mL), and poured into the reaction mixture. Additional pH 8 buffer (25.6 mL) was used to ensure complete transfer of the enzyme. The reaction mixture was stirred at 35° C. with a nitrogen sweep (32 mL/minute) through a needle placed approximately 0.5 cm above the reaction surface. Due to difficulties in stirring, vacuum (220 Torr, 300 mbar) was applied after 3 hours, to remove the acetone generated by the transamination reaction. The suspended solids were broken up manually, which improved the stirring of the reaction mixture. After 26 hours, the reaction mixture was allowed to cool to room temperature, and aqueous hydrochloric acid (6 M, 5 mL) was added, to bring the pH from 8 to 6.5. After addition of ethyl acetate (200 mL), the mixture was vigorously stirred for 5 minutes and then filtered through diatomaceous earth (43 g; this filter aid had been slurried in water prior to being introduced into the filter funnel. The water was then removed, providing a tightly packed bed). The filter pad was washed sequentially with water (120 mL) and ethyl acetate (100 mL), and the aqueous layer of the combined filtrates was adjusted to pH 9-9.5 with aqueous potassium hydroxide solution (6 M; approximately 10 mL). The aqueous layer was then treated with dichloromethane (200 mL), and the resulting mixture was vigorously stirred for 5 minutes before being filtered through a pad of diatomaceous earth. The filter pad was washed with dichloromethane (100 mL), and the aqueous layer of the combined filtrates was extracted twice with dichloromethane, in the same manner as that described above, with adjustment of the pH to 9-10 (this required approximately 2 mL of the 6 M aqueous potassium hydroxide solution in both cases). All of the dichloromethane extracts were combined and dried over sodium sulfate with vigorous stirring. Filtration and concentration in vacuo afforded the product as an oily yellow solid (14.76 g). A fourth extraction was carried out in the same manner, but in this case the aqueous layer was adjusted to a pH of >10. The product obtained from this extraction was a white solid (1.9 g). Combined yield: 16.61 g, 64.79 mmol, 92%. $^1$H NMR (500 MHz, CDCl$_3$) δ 3.95 (dd, J=9.0, 5.6 Hz, 1H), 3.69-3.63 (m, 1H), 3.62-3.52 (m, 3H), 3.38-3.27 (m, 2H), 2.6-2.2 (v br s, 2H), 2.07 (dd, J=13.0, 7.6 Hz, 1H), 1.78-1.71 (m, 1H), 1.69-1.56 (m, 2H), 1.55-1.47 (m, 2H), 1.45 (s, 9H).

Step 2. Synthesis of tert-butyl (3R)-3-amino-1-oxa-8-azaspiro[4.5]decane-8-carboxylate, (2R)-5-oxopyrrolidine-2-carboxylate salt (C94)

A solution of C93 (16.61 g, 64.79 mmol) in ethanol (400 mL) was heated to 63° C. and treated portion-wise with (2R)-5-oxopyrrolidine-2-carboxylic acid (7.78 g, 60.3 mmol). The reaction mixture was then removed from the heating bath, and allowed to cool overnight. The mixture was cooled to 12° C. in an ice bath, and filtered. The collected solids were washed with cold ethanol (2×50 mL) and then with diethyl ether (100 mL), affording the product as a pale yellow solid (19.2 g). The combined filtrates were concentrated in vacuo, with removal of approximately 400 mL of solvents. A thin line of solid formed around the inner surface of the flask. This was swirled back into the remaining solvents; diethyl ether (100 mL) was added, and the mixture was cooled in an ice bath with stirring. After approximately 15 minutes, the mixture was filtered and the collected solids were washed with diethyl ether (100 mL), affording additional product as a yellow solid (1.5 g). Combined yield: 20.7 g, 53.7 mmol, 89%. $^1$H NMR (500 MHz, D$_2$O) δ 4.16 (dd, J=8.9, 5.9 Hz, 1H), 4.11 (dd, half of ABX pattern, J=10.4, 5.8 Hz, 1H), 4.09-4.03 (m, 1H), 3.93 (dd, J=10.3, 3.1 Hz, 1H), 3.61-3.46 (m, 2H), 3.46-3.30 (m, 2H), 2.53-2.36 (m, 4H), 2.06-1.97 (m, 1H), 1.85 (dd, J=14.1, 4.6 Hz, 1H), 1.82-1.72 (m, 2H), 1.72-1.65 (m, 1H), 1.59 (ddd, half of ABXY pattern, J=18, 9, 4.5 Hz, 1H), 1.43 (s, 9H).

Conversion of C94 to C48, for Assessment of Absolute Stereochemistry

A small sample of C94 was derivatized via reaction with benzenesulfonyl chloride and saturated aqueous sodium bicarbonate solution for 1 hour at 40° C. The reaction mixture was extracted with ethyl acetate, and the solvent was removed from the extract under a stream of nitrogen. Supercritical fluid chromatographic analysis (Column: Chiral Technologies Chiralcel OJ-H, 5 μm; Mobile phase A: carbon dioxide; Mobile phase B: methanol; Gradient: 5% to 60% B) revealed the product to have an enantiomeric excess of >99%. Injection under the same conditions of samples of C48 and C49 established the derivatization product as identical to C48, the absolute configuration of which was determined via X-ray crystallographic analysis (see above).

Step 3. Synthesis of tert-butyl (3R)-3-[(cyclopropylsulfonyl)amino]-1-oxa-8-azaspiro[4.5]decane-8-carboxylate (C95)

Cyclopropanesulfonyl chloride (56.8 mg, 0.404 mmol) and triethylamine (136 mg, 1.34 mmol) were added to a suspension of C94 (100 mg, 0.26 mmol) in dichloromethane (1 mL) at 16° C. The reaction mixture was stirred at 10° C. for 14 hours, whereupon it was concentrated in vacuo and combined with material from a similar reaction carried out using C94 (30 mg, 78 μmol). The resulting mixture was purified via silica gel chromatography (Gradient: 0% to 15% methanol in dichloromethane) to provide the product as a yellow gum. Yield: 90 mg, 0.25 mmol, 74%. LCMS m/z 383.3 [M+Na$^+$].

Step 4. Synthesis of tert-butyl (3R)-3-[(cyclopropylsulfonyl)(methyl)amino]-1-oxa-8-azaspiro[4.5] decane-8-carboxylate (C96)

To a 0° C. suspension of C95 (90 mg, 0.25 mmol) in N,N-dimethylformamide (1 mL) was added sodium hydride (60% dispersion in mineral oil; 20 mg, 0.50 mmol), and the reaction mixture was stirred at 0° C. for 30 minutes. Iodomethane (53.2 mg, 0.375 mmol) was added at 0° C., and the reaction mixture was stirred at 15° C. for 2 hours. It was then treated with saturated aqueous sodium chloride solution (40 mL) and extracted with ethyl acetate (3×30 mL). The combined organic layers were dried over sodium sulfate, filtered, and concentrated in vacuo. Silica gel chromatography (Gradient: 0% to 50% ethyl acetate in petroleum ether) provided the product as a colorless gum. Yield: 78 mg, 0.21 mmol, 84%. LCMS m/z 397.3 [M+Na$^+$].

Step 5. Synthesis of (2R)-1,1,1-trifluoro-3-[(4-methoxybenzyl)oxy]propan-2-yl (3R)-3-[(cyclopropylsulfonyl)(methyl)amino]-1-oxa-8-azaspiro[4.5] decane-8-carboxylate (C97)

Conversion of C96 to the product was carried out using the method described for synthesis of C89 from C88 in Example 92. The product was obtained as a colorless gum. Yield: 67 mg, 0.12 mmol, 57%. LCMS m/z 573.0 [M+Na$^+$].

Step 6. Synthesis of (2R)-1,1,1-trifluoro-3-hydroxypropan-2-yl (3R)-3-[(cyclopropylsulfonyl)(methyl) amino]-1-oxa-8-azaspiro[4.5]decane-8-carboxylate (93)

Conversion of C97 (67 mg, 0.12 mmol) to the product was carried out using the method described for synthesis of 93 from C91 in Example 93. In this case, purification was effected using reversed phase HPLC (Column: Agela Durashell C18, 5 μm; Mobile phase A: water containing 0.225% formic acid; Mobile phase B: acetonitrile; Gradient: 35% to 55% B), affording the product as a brown gum. Yield: 10.0 mg, 23.2 μmol, 19%. LCMS m/z 431.2 [M+H]$^+$. $^1$H NMR (400 MHz, CDCl$_3$) δ 5.32-5.20 (m, 1H), 4.73-4.63 (m, 1H), 4.04-3.93 (m, 2H), 3.93-3.74 (m, 4H), 3.46-3.24 (m, 2H), 2.88 (s, 3H), 2.55-2.25 (v br s, 1H), 2.30-2.21 (m, 1H), 2.14-2.02 (m, 1H), 1.86-1.68 (m, 4H), 1.56-1.41 (m, 1H), 1.22-1.14 (m, 2H), 1.04-0.96 (m, 2H).

Example 95
(2R)-1,1,1-Trifluoro-3-hydroxypropan-2-yl 3-phenyl-1-oxa-8-azaspiro[4.5]decane-8-carboxylate [From C101, ENT-2] (95)
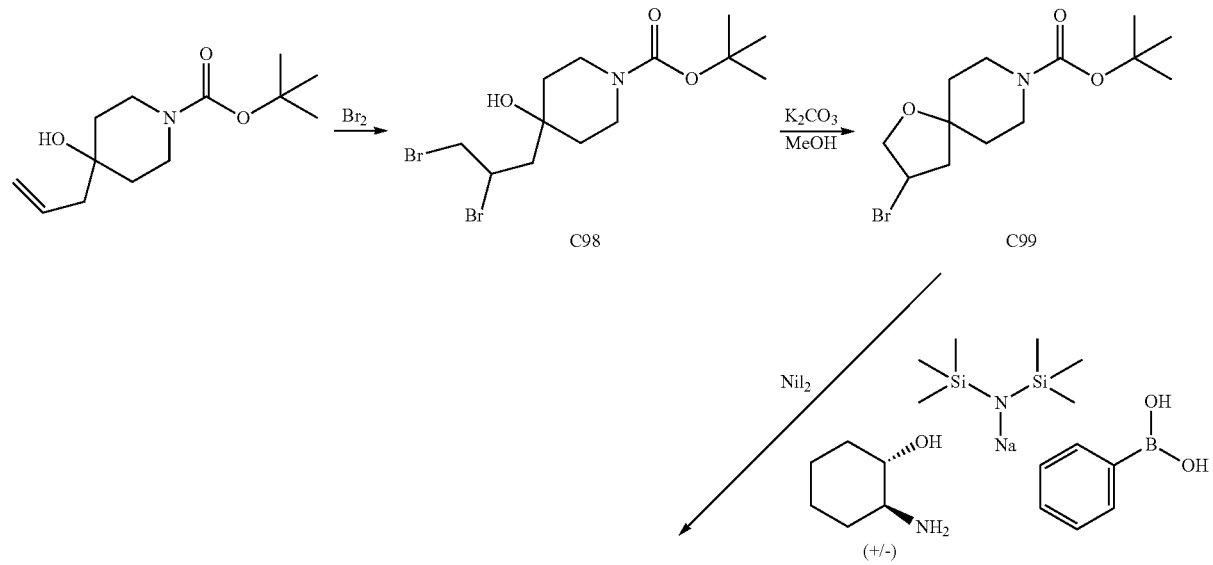
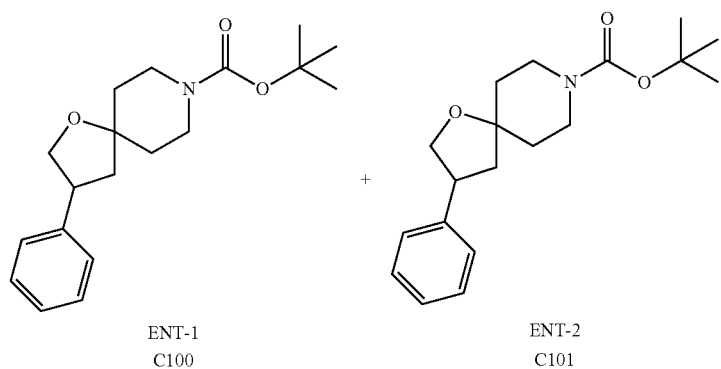
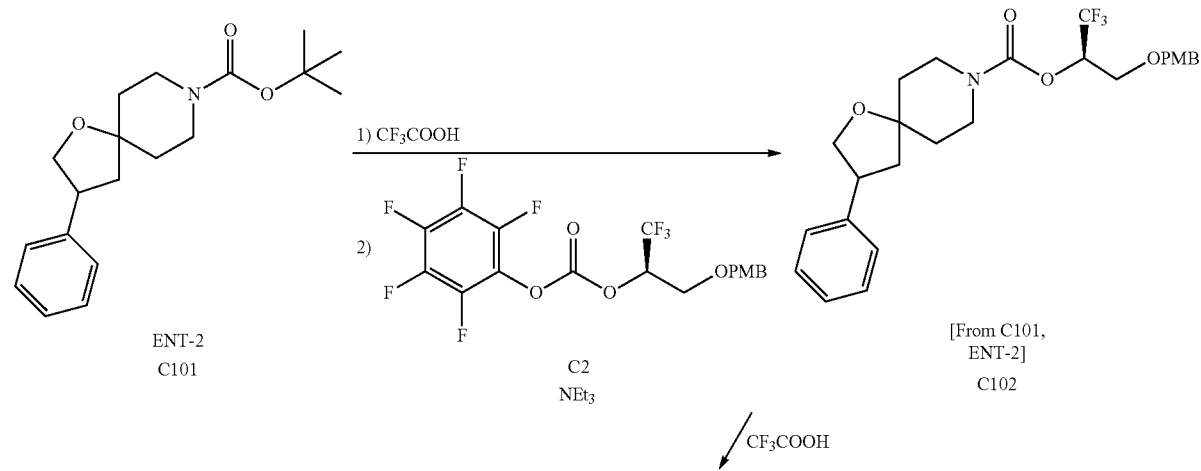

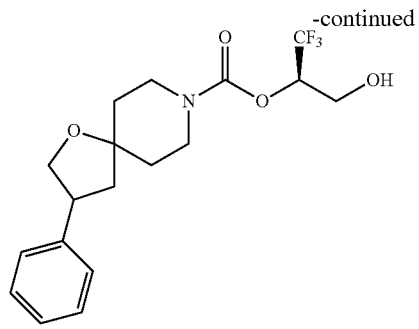

[From C101, ENT-2]
95

Step 1. Synthesis of tert-butyl 4-(2,3-dibromopropyl)-4-hydroxypiperidine-1-carboxylate (C98)

This reaction was carried out in two identical batches. A solution of tert-butyl 4-hydroxy-4-(prop-2-en-1-yl)piperidine-1-carboxylate (209 g, 0.866 mol) in dichloromethane (1.2 L) was cooled in a cold water bath. A solution of bromine (152 g, 0.951 mol) in dichloromethane (250 mL) was added at such a rate that the color of the reaction mixture did not become intense. At the conclusion of the addition, an aqueous solution containing sodium thiosulfate and sodium bicarbonate was added to the reaction mixture, and stirring was continued until the mixture had completely decolorized. At this point, the two batches were combined. The aqueous layer was extracted with dichloromethane (3×400 mL), and the combined organic layers were washed with saturated aqueous sodium chloride solution (2×200 mL), dried over sodium sulfate, and concentrated in vacuo to afford the product as a red gum. Yield: 600 g, 1.5 mol, 87%. $^1$H NMR (400 MHz, CDCl$_3$) δ 4.43-4.33 (m, 1H), 3.96-3.74 (m, 2H), 3.91 (dd, J=10.3, 4.0 Hz, 1H), 3.66 (dd, J=10.0, 9.8 Hz, 1H), 3.27-3.13 (m, 2H), 2.47 (dd, half of ABX pattern, J=15.8, 2.8 Hz, 1H), 2.13 (dd, half of ABX pattern, J=15.7, 8.9 Hz, 1H), 1.78-1.68 (m, 2H), 1.65-1.53 (m, 2H, assumed; partially obscured by water peak), 1.47 (s, 9H).

Step 2. Synthesis of tert-butyl 3-bromo-1-oxa-8-azaspiro[4.5]decane-8-carboxylate (C99)

Potassium carbonate (119 g, 861 mmol) was added to a cooled solution of C98 (230 g, 573 mmol) in methanol (1.5 L), and the reaction mixture was stirred at 10° C. to 15° C. for 16 hours. The crude reaction mixture was combined with the crude reaction mixtures from two similar reactions using C98 (350 g, 873 mmol; and 20 g, 50 mmol) and filtered. The filtrate was concentrated in vacuo, and the resulting red oil was recrystallized from petroleum ether (150 mL) at 0° C. to provide a light yellow solid (360 g). This was subjected to silica gel chromatography (Eluent: dichloromethane), and the purified material was recrystallized from petroleum ether (120 mL) and washed with petroleum ether (3×40 mL) to afford the product as a white solid (180 g). The mother liquors from recrystallization were concentrated under reduced pressure and purified by silica gel chromatography (Gradient: 0% to 20% ethyl acetate in petroleum ether). The resulting material was recrystallized from petroleum ether (100 mL) and washed with petroleum ether (3×40 mL), affording additional product as a white solid (95 g). Combined yield: 275 g, 0.859 mol, 57%. $^1$H NMR (400 MHz, DMSO-d$_6$) δ 4.71-4.63 (m, 1H), 4.12 (dd, J=10.4, 4.9 Hz, 1H), 3.90 (dd, J=10.5, 3.8 Hz, 1H), 3.52-3.40 (m, 2H), 3.3-3.15 (m, 2H), 2.41 (dd, J=14.3, 7.3 Hz, 1H), 2.10 (dd, J=14.0, 4.0 Hz, 1H), 1.79-1.71 (m, 1H), 1.65 (br ddd, half of ABXY pattern, J=13, 10, 4 Hz, 1H), 1.55-1.41 (m, 2H), 1.39 (s, 9H).

Step 3. Synthesis of tert-butyl 3-phenyl-1-oxa-8-azaspiro[4.5]decane-8-carboxylate, ENT-1 (C100) and tert-butyl 3-phenyl-1-oxa-8-azaspiro[4.5]decane-8-carboxylate, ENT-2 (C101)

A mixture of C99 (150 mg, 0.468 mmol), phenylboronic acid (114 mg, 0.935 mmol), trans-2-aminocyclohexanol (10.8 mg, 93.7 μmol) and nickel(II) iodide (29.3 mg, 93.7 μmol) in 2-propanol (3 mL, previously dried over molecular sieves) was treated with sodium bis(trimethylsilyl)amide (1 M solution in tetrahydrofuran; 0.937 mL, 0.937 mmol). The reaction vessel was then capped, warmed to 60° C., and stirred for 14 hours. The resulting suspension was combined with a similar reaction mixture carried out using C99 (50 mg, 0.16 mmol), filtered through a pad of diatomaceous earth, and concentrated in vacuo. The residue was purified via chromatography on silica gel (Gradient: 0% to 40% ethyl acetate in petroleum ether) to afford the racemic product as a white solid. Yield: 170 mg, 0.536 mmol, 85%. $^1$H NMR (400 MHz, CDCl$_3$) δ 7.36-7.30 (m, 2H), 7.3-7.21 (m, 3H, assumed; partially obscured by solvent peak), 4.23 (dd, J=8, 8 Hz, 1H), 3.80 (dd, J=9, 9 Hz, 1H), 3.70-3.47 (m, 3H), 3.44-3.33 (m, 2H), 2.27 (dd, J=12.5, 8 Hz, 1H), 1.84 (dd, J=12, 11 Hz, 1H), 1.79-1.67 (m, 3H), 1.64-1.55 (m, 1H, assumed; partially obscured by water peak), 1.47 (s, 9H).

The component enantiomers were separated using supercritical fluid chromatography [Column: Chiral Technologies Chiralpak AD, 10 μm; Mobile phase: 35% (0.1% ammonium hydroxide in methanol) in carbon dioxide]. The first-eluting enantiomer was assigned as C100. Yield: 65 mg, 38% for the separation. LCMS m/z 262.1 [(M−2-methylprop-1-ene)+H]$^+$. The second-eluting enantiomer was assigned as C101. Yield: 70 mg, 41% for the separation. LCMS m/z 262.1 [(M−2-methylprop-1-ene)+H]$^+$.

Step 4. Synthesis of (2R)-1,1,1-trifluoro-3-[(4-methoxybenzyl)oxy]propan-2-yl 3-phenyl-1-oxa-8-azaspiro[4.5]decane-8-carboxylate [From C101, ENT-2] (C102)

Trifluoroacetic acid (0.6 mL) was added drop-wise to a solution of C101 (70.0 mg, 0.220 mmol) in dichloromethane (2 mL), and the reaction mixture was stirred at 25° C. for 2 hours. Volatiles were removed under reduced pressure to provide 3-phenyl-1-oxa-8-azaspiro[4.5]decane, trifluoroacetate salt, as a yellow gum. This material was dissolved in acetonitrile (2 mL), cooled to 0° C., and slowly treated with triethylamine (89.5 mg, 0.884 mmol). After this solution had stirred for 30 minutes, C2 (reaction solution in acetonitrile containing 0.221 mmol) was added at 0° C. The reaction mixture was stirred at 25° C. for 18 hours, whereupon it was concentrated in vacuo and purified by preparative thin layer chromatography on silica gel (Eluent: 3:1 petroleum ether/ ethyl acetate), affording the product as a yellow gum (120 mg). This material was taken directly to the following step. LCMS m/z 516.1 [M+Na⁺].

Step 5. Synthesis of (2R)-1,1,1-trifluoro-3-hydroxypropan-2-yl 3-phenyl-1-oxa-8-azaspiro[4.5]decane-8-carboxylate [From C101, ENT-2] (95)

Trifluoroacetic acid (0.5 mL) was added to a 0° C. solution of C102 (from the previous step; 120 mg, ≤0.220 mmol) in dichloromethane (1.5 mL). The reaction mixture was stirred at 25° C. for 2 hours, whereupon it was concentrated in vacuo and subjected to preparative thin layer chromatography on silica gel (Eluent: 3:1 petroleum ether/ ethyl acetate). The material obtained (40 mg) was then purified using reversed phase HPLC (Column: Daiso C18, 5 μm; Mobile phase A: water containing 0.225% formic acid; Mobile phase B: acetonitrile; Gradient: 42% to 72% B) to afford the product as a colorless gum. Yield: 10.1 mg, 27.0 μmol, 12% over 2 steps. LCMS m/z 373.9 [M+H]⁺. ¹H NMR (400 MHz, CDCl₃) δ 7.36-7.30 (m, 2H), 7.27-7.22 (m, 3H), 5.32-5.21 (m, 1H), 4.24 (dd, J=8.0, 8.0 Hz, 1H), 4.01 (dd, half of ABX pattern, J=12.4, 2.9 Hz, 1H), 3.92-3.74 (m, 4H), 3.60-3.35 (m, 3H), 2.32-2.22 (m, 1H), 1.92-1.55 (m, 5H, assumed; partially obscured by water peak).

Example 96

(2R)-1,1,1-Trifluoro-3-hydroxypropan-2-yl 3-phenyl-1-oxa-8-azaspiro[4.5]decane-8-carboxylate [From C100, ENT-1] (96)

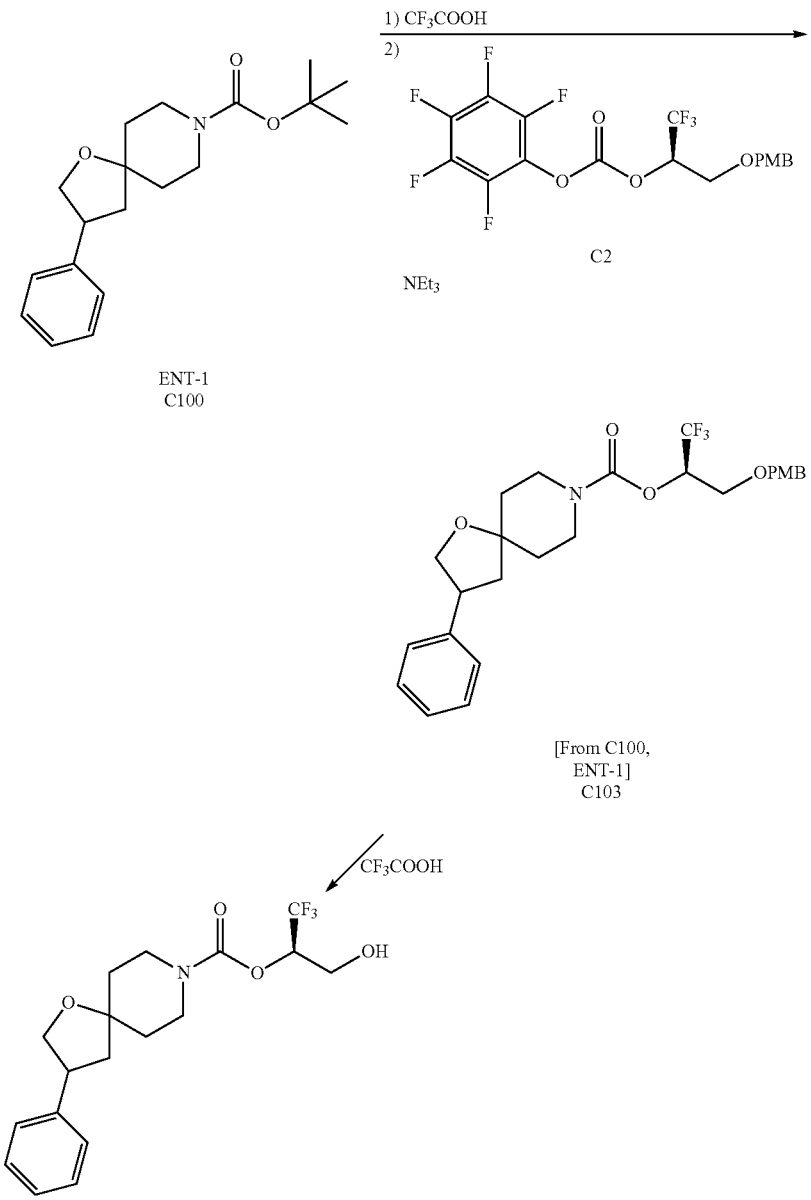

Step 1. Synthesis of (2R)-1,1,1-trifluoro-3-[(4-methoxybenzyl)oxy]propan-2-yl 3-phenyl-1-oxa-8-azaspiro[4.5]decane-8-carboxylate [From C100, ENT-1] (C103)

Trifluoroacetic acid (2 mL) was added to a 0° C. suspension of C100 (65 mg, 0.20 mmol) in dichloromethane (3 mL). The reaction mixture was stirred at 18° C. for 2 hours, whereupon it was concentrated in vacuo to provide the deprotected material as a yellow gum. The gum was dissolved in acetonitrile (1 mL), cooled to 0° C., and treated with C2 (reaction solution in acetonitrile containing 0.24 mmol) and triethylamine (166 mg, 1.64 mmol). This reaction mixture was stirred at 18° C. for 16 hours, and then treated with additional C2 (reaction solution in acetonitrile containing 0.24 mmol). Stirring was continued at 18° C. for an additional 16 hours. Volatiles were removed under reduced pressure, and the residue was subjected to chromatography on silica gel (Gradient: 0% to 100% ethyl acetate in petroleum ether) to afford the product as a yellow gum (101 mg). This material was used in the following step without additional purification. LCMS m/z 516.1 [M+Na$^+$]

Step 2. Synthesis of (2R)-1,1,1-trifluoro-3-hydroxypropan-2-yl 3-phenyl-1-oxa-8-azaspiro[4.5]decane-8-carboxylate [From C100, ENT-1] (96)

Trifluoroacetic acid (2 mL) was added to a 0° C. suspension of C103 (from the previous step; ≤0.20 mmol) in dichloromethane (2 mL), and the reaction mixture was stirred at 20° C. for 1 hour. After the reaction mixture had been cooled to 0° C., aqueous sodium bicarbonate solution (40 mL) was slowly added, and the purple mixture became colorless. It was extracted with dichloromethane (3×20 mL), and the combined organic layers were dried over sodium sulfate, filtered, and concentrated in vacuo. Silica gel chromatography (Gradient: 0% to 50% ethyl acetate in petroleum ether) was followed by reversed phase HPLC (Column: Agela Durashell, 5 μm; Mobile phase A: water containing 0.225% formic acid; Mobile phase B: acetonitrile; Gradient: 5% to 95% B), affording the product as a yellow oil. Yield: 15.2 mg, 40.7 μmol, 20% over 2 steps. LCMS m/z 373.9 [M+H]$^+$. $^1$H NMR (400 MHz, CDCl$_3$) δ 7.36-7.30 (m, 2H), 7.28-7.21 (m, 3H), 5.32-5.21 (m, 1H), 4.24 (dd, J=8.3, 7.8 Hz, 1H), 4.06-3.97 (m, 1H), 3.93-3.74 (m, 4H), 3.60-3.32 (m, 3H), 2.49-2.38 (m, 1H), 2.27 (dd, J=12.6, 8.3 Hz, 1H), 1.89-1.6 (m, 4H), 1.87 (dd, J=12.0, 10.8 Hz, 1H).

Example 97

(2R)-1,1,1-Trifluoro-3-hydroxypropan-2-yl 3-(5-fluoropyridin-2-yl)-1-oxa-8-azaspiro[4.5]decane-8-carboxylate, trifluoroacetate salt (97)

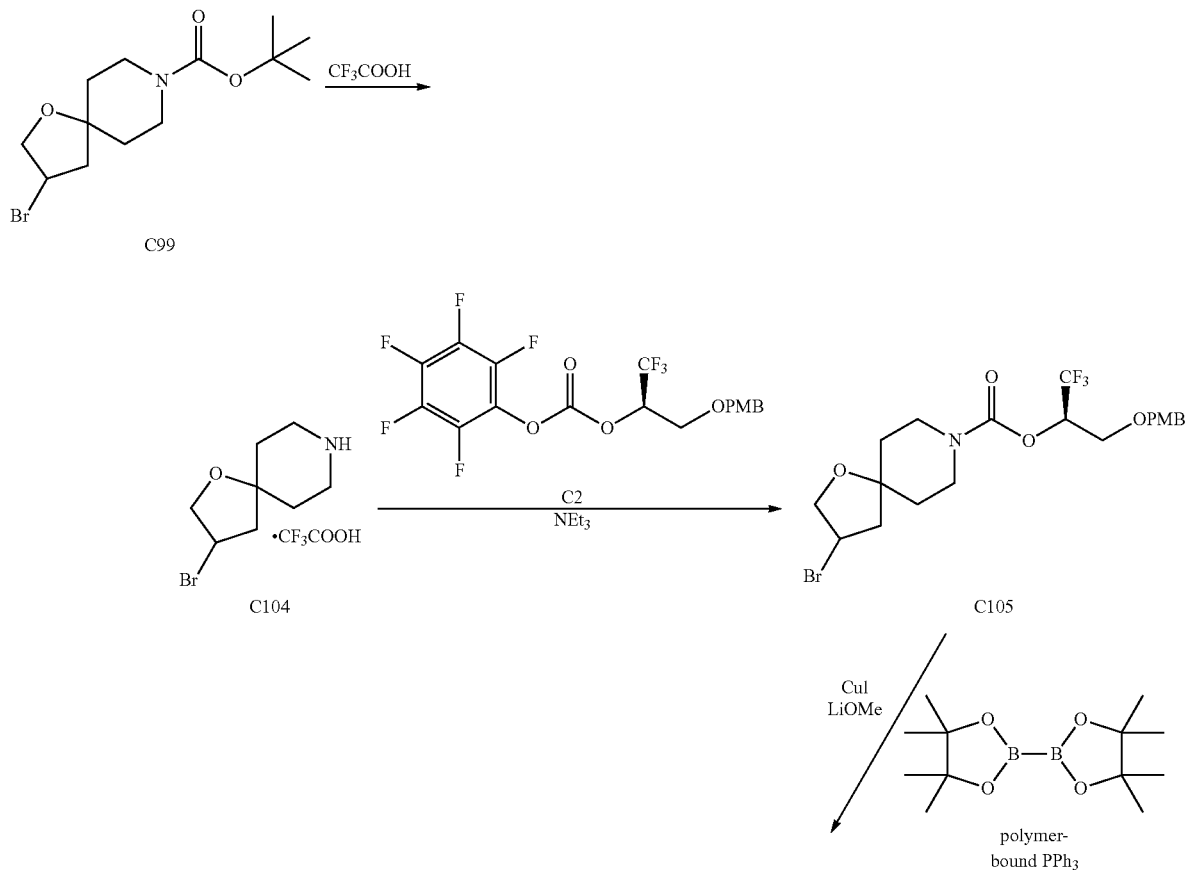

-continued
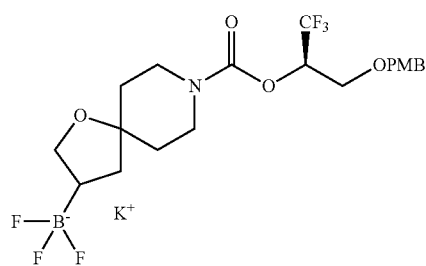
C107
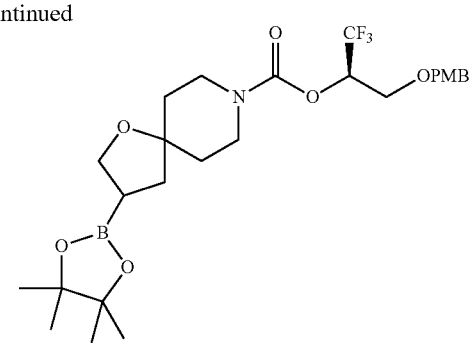
C106
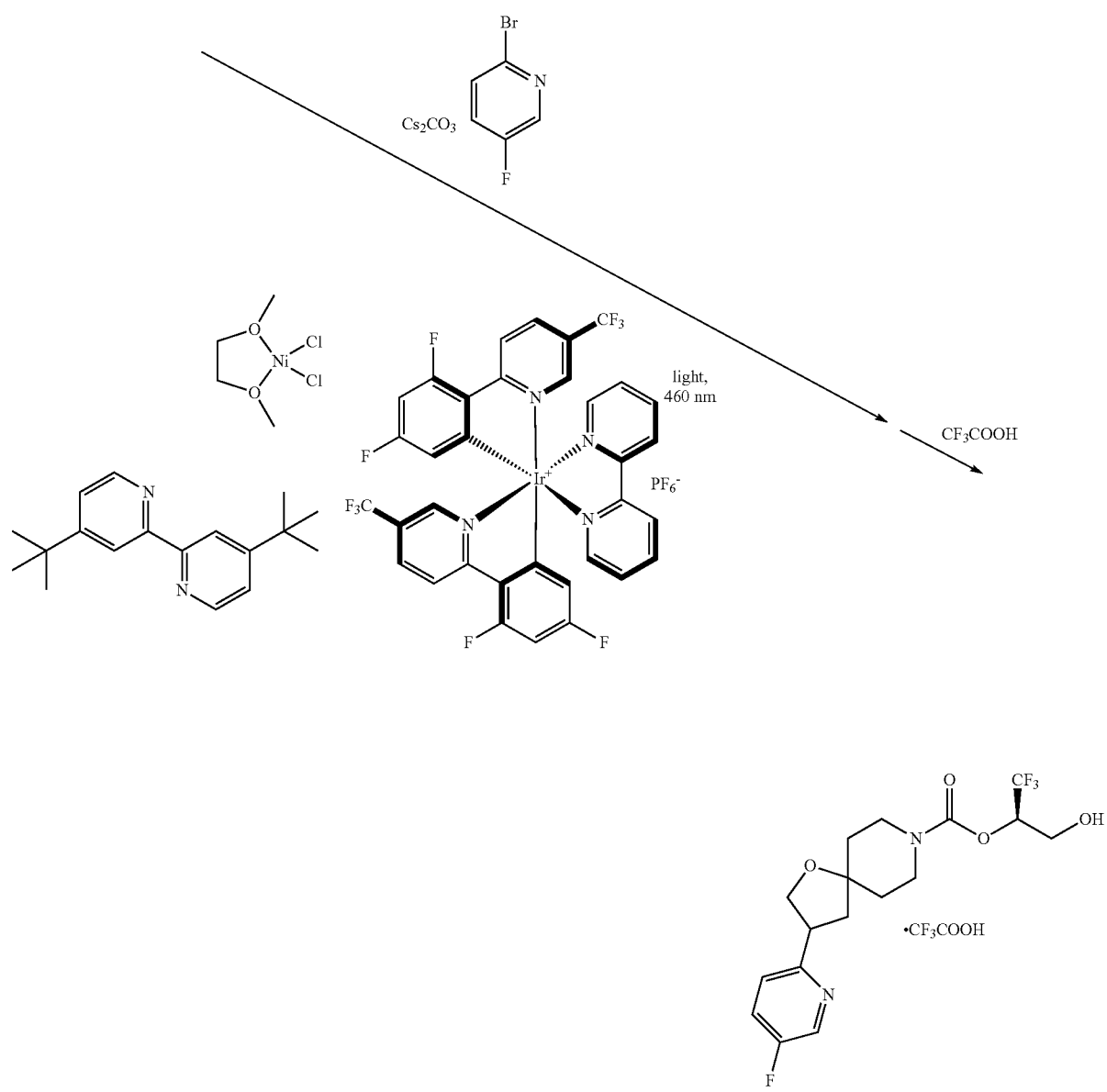
97

Step 1. Synthesis of 3-bromo-1-oxa-8-azaspiro[4.5]decane, trifluoroacetate salt (C104)

Trifluoroacetic acid (100 mL) was added drop-wise to a 0° C. solution of C99 (25.0 g, 78.1 mmol) in dichloromethane (400 mL). After the reaction mixture had been stirred at 13° C. for 15 hours, it was concentrated in vacuo to afford the product as a brown oil (30 g). This material was used in the next step without additional purification. $^1$H NMR (400 MHz, CD$_3$OD) δ 4.63-4.55 (m, 1H), 4.20 (dd, half of ABX pattern, J=10.5, 4.5 Hz, 1H), 4.04 (dd, half of ABX pattern, J=10.5, 3.5 Hz, 1H), 3.3-3.21 (m, 4H), 2.50 (dd, half of ABX pattern, J=14.6, 7.0 Hz, 1H), 2.30-2.18 (m, 2H), 1.97 (ddd, J=14, 10, 6.5 Hz, 1H), 1.91-1.77 (m, 2H).

Step 2. Synthesis of (2R)-1,1,1-trifluoro-3-[(4-methoxybenzyl)oxy]propan-2-yl 3-bromo-1-oxa-8-azaspiro[4.5]decane-8-carboxylate (C105)

Triethylamine (39.5 g, 390 mmol) was added to a 15° C. solution of C104 (from the previous step; 30 g, ≤78.1 mmol) in acetonitrile (400 mL). The resulting solution was stirred at 15° C. for 1 hour, whereupon it was cooled to 0° C. and treated with C2 [reaction solution in acetonitrile (400 mL) containing 85.9 mmol]. After the reaction mixture had been stirred at 13° C. for 15 hours, it was concentrated in vacuo and purified twice via chromatography on silica gel (Gradient: 5% to 9% ethyl acetate in petroleum ether). A final silica gel chromatographic purification (Gradient: 0% to 9% ethyl acetate in petroleum ether) afforded the product as a colorless gum. Yield: 20.3 g, 40.9 mmol, 52% over 2 steps. LCMS m/z 519.8 (bromine isotope pattern observed) [M+Na$^+$]. $^1$H NMR (400 MHz, CDCl$_3$) δ 7.25 (d, J=8.5 Hz, 2H), 6.89 (d, J=8.7 Hz, 2H), 5.54-5.43 (m, 1H), 4.51 (AB quartet, upfield doublet is broadened, J$_{AB}$=11.7 Hz, Δν$_{AB}$=290.1 Hz, 2H), 4.44-4.36 (m, 1H), 4.19 (dd, J=10.4, 5.3 Hz, 1H), 4.07-3.99 (m, 1H), 3.91-3.63 (m, 4H), 3.82 (s, 3H), 3.44-3.27 (m, 2H), 2.42-2.25 (m, 1H), 2.24-2.08 (m, 1H), 2.04-1.89 (m, 1H), 1.81-1.47 (m, 3H).

Step 3. Synthesis of (2R)-1,1,1-trifluoro-3-[(4-methoxybenzyl)oxy]propan-2-yl 3-(4,4,5,5-tetramethyl-1,3,2-dioxaborolan-2-yl)-1-oxa-8-azaspiro[4.5]decane-8-carboxylate (C106)

A mixture of C105 (6.50 g, 13.1 mmol), 4,4,4',4',5,5,5',5'-octamethyl-2,2'-bi-1,3,2-dioxaborolane (4.99 g, 19.6 mmol), polymer-bound triphenylphosphine (687 mg, 2.62 mmol), lithium methoxide (995 mg, 26.2 mmol), and copper (I) iodide (249 mg, 1.31 mmol) in N,N-dimethylformamide (50 mL) was stirred at 1° C. to 10° C. for 16 hours. The reaction mixture was then diluted with dichloromethane (150 mL) and filtered; the filter cake was washed with dichloromethane (150 mL), and the combined filtrates were concentrated in vacuo. The resulting oil was mixed with saturated aqueous ammonium chloride solution (150 mL) and extracted with diethyl ether (3×150 mL). The combined organic layers were washed sequentially with water (150 mL) and saturated aqueous sodium chloride solution (150 mL), dried over sodium sulfate, filtered, and concentrated under reduced pressure to provide the product as a pale yellow gum. Yield: 7.00 g, 12.9 mmol, 98%. $^1$H NMR (400 MHz, CDCl$_3$) δ 7.24 (br d, J=8.8 Hz, 2H), 6.88 (br d, J=8.8 Hz, 2H), 5.53-5.42 (m, 1H), 4.51 (AB quartet, J$_{AB}$=11.7 Hz, Δν$_{AB}$=27.2 Hz, 2H), 4.03 (dd, J=8.3, 8.2 Hz, 1H), 3.81 (s, 3H), 3.80-3.63 (m, 5H), 3.45-3.30 (m, 2H), 1.98-1.74 (m, 2H), 1.72-1.40 (m, 5H), 1.25 (s, 12H).

Step 4. Synthesis of potassium trifluoro{8-[({(2R)-1,1,1-trifluoro-3-[(4-methoxybenzyl)oxy]propan-2-yl}oxy)carbonyl]-1-oxa-8-azaspiro[4.5]dec-3-yl}borate(1-) (C107)

Aqueous potassium hydrogen fluoride solution (4.5 M, 11.5 mL, 51.8 mmol) was added to a 0° C. solution of C106 (7.00 g, 12.9 mmol) in tetrahydrofuran (50 mL) and the reaction mixture was stirred at 0° C. to 5° C. for 16 hours. Removal of volatiles in vacuo provided a thick oil, which was extracted with acetone (4×75 mL). The combined acetone layers were filtered, and the filtrate was concentrated to a volume of approximately 20 mL, cooled to 0° C., and diluted with diethyl ether (150 mL). A white tacky material appeared; the solvent was removed via decantation, and the remaining gum was triturated with diethyl ether (150 mL) to afford the product as a white solid. Yield: 3.8 g, 7.26 mmol, 56%. LCMS m/z 483.9 [M$^-$]. $^1$H NMR (400 MHz, acetone-d$_6$) δ 7.27 (br d, J=8.7 Hz, 2H), 6.91 (br d, J=8.7 Hz, 2H), 5.55-5.43 (m, 1H), 4.52 (AB quartet, J$_{AB}$=11.6 Hz, Δν$_{AB}$=19.0 Hz, 2H), 3.84-3.70 (m, 3H), 3.79 (s, 3H), 3.70-3.53 (m, 3H), 3.44-3.23 (m, 2H), 1.70-1.58 (m, 1H), 1.58-1.45 (m, 4H), 1.45-1.34 (m, 1H), 1.30-1.14 (m, 1H).

Step 5. Synthesis of (2R)-1,1,1-trifluoro-3-hydroxypropan-2-yl 3-(5-fluoropyridin-2-yl)-1-oxa-8-azaspiro[4.5]decane-8-carboxylate, trifluoroacetate salt (97)

A mixture of 2-bromo-5-fluoropyridine (17.6 mg, 0.100 mmol), C107 (78.3 mg, 0.150 mmol), [Ir{dFCF$_3$ppy}$_2$(bpy)$^+$] PF$_6^-$ (2.5 mg, 2.4 μmol), cesium carbonate (48.9 mg, 0.150 mmol), nickel(II) chloride, 1,2-dimethoxyethane adduct (1.1 mg, 5.0 μmol), and 4,4'-di-tert-butyl-2,2'-bipyridine (1.4 mg, 5.2 μmol) was degassed under vacuum and then purged with nitrogen; this evacuation-purge cycle was carried out a total of three times. 1,4-Dioxane (7 mL) was added, and the reaction mixture was sonicated and shaken to provide a suspension. The reaction mixture was then irradiated with blue visible light (wavelength: 460 nm) from a 60 watt blue LED strip for 18 hours. After removal of volatiles in vacuo, a mixture of dichloromethane (0.5 mL) and trifluoroacetic acid (0.5 mL) was added, and the resulting reaction mixture was stirred at room temperature for 30 minutes. The reaction mixture was concentrated in vacuo, and the residue was purified via reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 10% to 100% B). The product was assumed to be a mixture of two diastereomers. Yield: 1.4 mg, 2.7 μmol, 3%. LCMS m/z 393.3 [M+H]$^+$. Retention time: 2.96 minutes [Analytical HPLC conditions—Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes Flow rate: 2 mL/minute].

Example 98

(2R)-1,1,1-Trifluoro-3-hydroxypropan-2-yl 2-(2-fluorobenzoyl)-2,8-diazaspiro[4.5]decane-8-carboxylate (98)

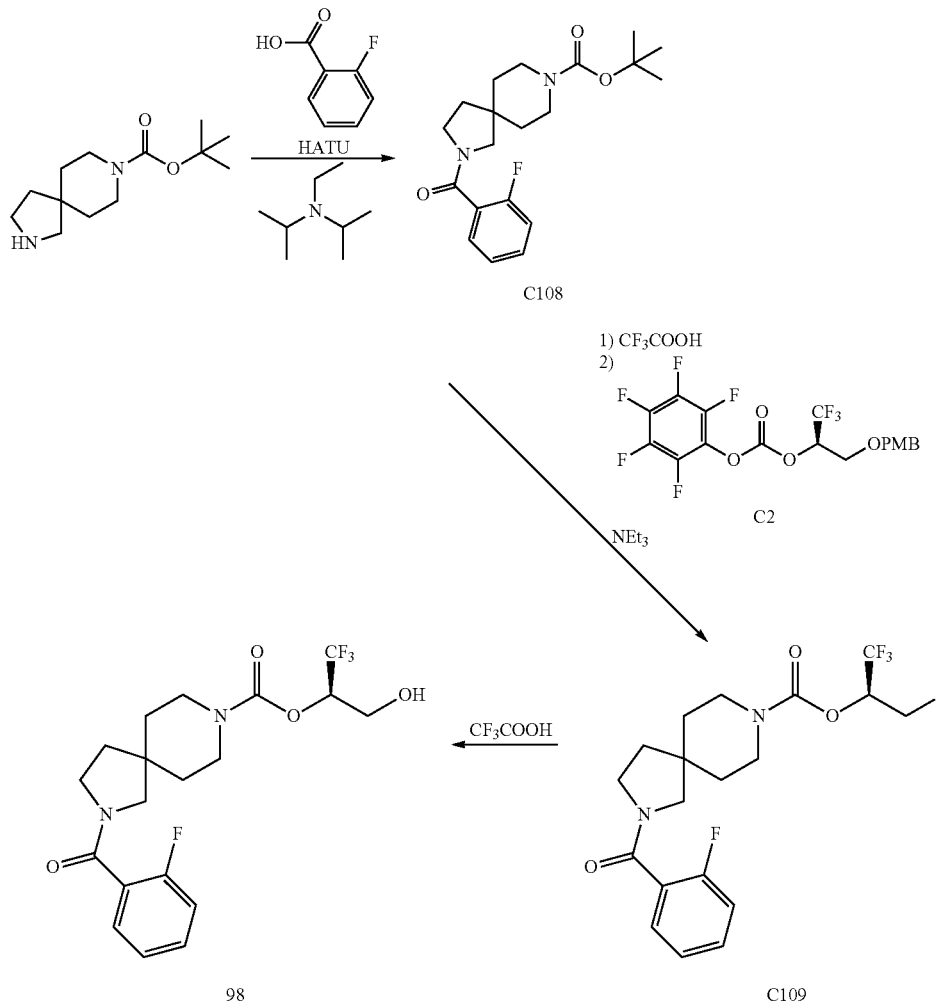

Step 1. Synthesis of tert-butyl 2-(2-fluorobenzoyl)-2,8-diazaspiro[4.5]decane-8-carboxylate (C108)

To a suspension of tert-butyl 2,8-diazaspiro[4.5]decane-8-carboxylate (200 mg, 0.832 mmol) in acetonitrile (2 mL) were added 2-fluorobenzoic acid (175 mg, 1.25 mmol), O-(7-azabenzotriazol-1-yl)-N,N,N',N'-tetramethyluronium hexafluorophosphate (HATU; 506 mg, 1.33 mmol), and N,N-diisopropylethylamine (323 mg, 2.50 mmol). The reaction mixture was stirred at 25° C. for 16 hours, whereupon it was concentrated in vacuo. The residue was dissolved in methanol (8 mL), treated with ion exchange resin Amberlyst® A26, hydroxide form [3.6 g, pre-washed with methanol (7 mL)], stirred at 25° C. for 1 hour, and filtered. The filtrate was concentrated under reduced pressure and subjected to silica gel chromatography (Gradient: 0% to 50% ethyl acetate in petroleum ether), affording the product as a colorless gum. By $^1$H NMR analysis, this was judged to be a mixture of rotamers. Yield: 231 mg, 0.637 mmol, 77%. $^1$H NMR (400 MHz, CD$_3$OD) δ 7.55-7.46 (m, 1H), 7.45-7.38 (m, 1H), 7.32-7.26 (m, 1H), 7.26-7.18 (m, 1H), 3.72-3.66 (m, 1H), 3.56-3.47 (m, 1H), 3.51 (s, 1H), 3.46-3.3 (m, 4H), 3.21 (br s, 1H), [1.94 (dd, J=7.5, 7.3 Hz) and 1.87 (dd, J=7.3, 7.0 Hz), total 2H], 1.66-1.48 (m, 4H), [1.47 (s) and 1.43 (s), total 9H].

Step 2. Synthesis of (2R)-1,1,1-trifluoro-3-[(4-methoxybenzyl)oxy]propan-2-yl 2-(2-fluorobenzoyl)-2,8-diazaspiro[4.5]decane-8-carboxylate (C109)

Conversion of C108 to the product was carried out using the method described for synthesis of C89 from C88 in Example 92. The product was obtained as a colorless gum. Yield: 500 mg, 0.93 mmol, quantitative. LCMS m/z 539.1 [M+H]$^+$.

Step 3. Synthesis of (2R)-1,1,1-trifluoro-3-hydroxypropan-2-yl 2-(2-fluorobenzoyl)-2,8-diazaspiro[4.5]decane-8-carboxylate (98)

Conversion of C109 to the product was carried out using the method described for synthesis of 92 from C89 in Example 92. In this case, the gradient used for HPLC purification was 36% to 56% B, and the product was isolated as a colorless gum. By $^1$H NMR analysis, this was judged to be a mixture of rotamers. Yield: 89 mg, 0.21 mmol, 23%. LCMS m/z 419.0 [M+H]$^+$. $^1$H NMR (400 MHz, CDCl$_3$) δ 7.46-7.37 (m, 2H), 7.25-7.19 (m, 1H), 7.15-7.08 (m, 1H), 5.32-5.19 (m, 1H), 4.04-3.94 (m, 1H), 3.92-3.79 (m, 1H), 3.79-3.62 (m, 2H), 3.58 (s, 1H), 3.56-3.30 (m, 4H), 3.20 (s, 1H), 2.6-2.3 (br m, 1H), [1.90 (dd, J=7.5, 7.3 Hz) and 1.82 (dd, J=7.0, 7.0 Hz), total 2H], 1.74-1.47 (m, 4H, assumed; partially obscured by water peak).

Examples 99 and 100

(2R)-1,1,1-Trifluoro-3-hydroxypropan-2-yl 3-[benzoyl(methyl)amino]-1-oxa-8-azaspiro[4.5]decane-8-carboxylate [From C112, DIAST-2] (99) and (2R)-1,1,1-Trifluoro-3-hydroxypropan-2-yl 3-[benzoyl(methyl)amino]-1-oxa-8-azaspiro[4.5]decane-8-carboxylate [From C111, DIAST-1] (100)

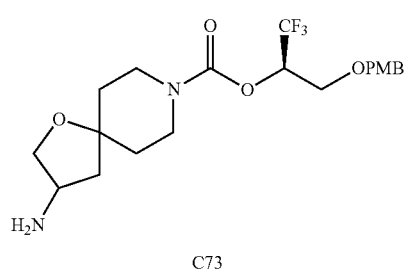

C73

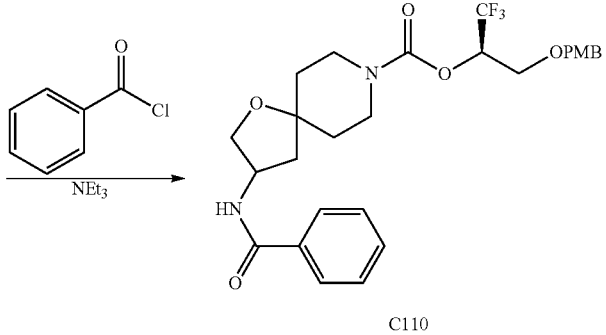

C110

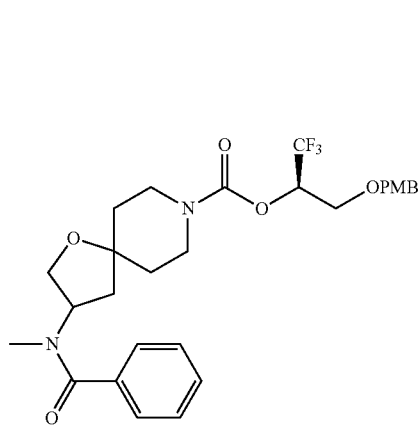

DIAST-1
C111

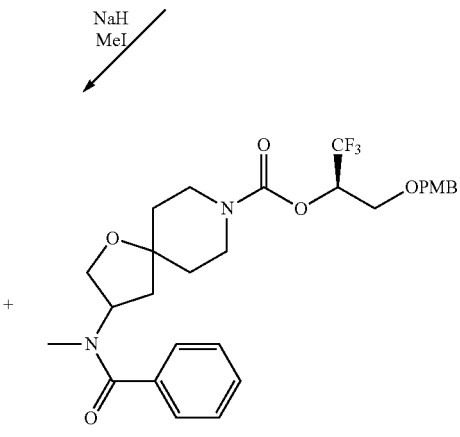

DIAST-2
112

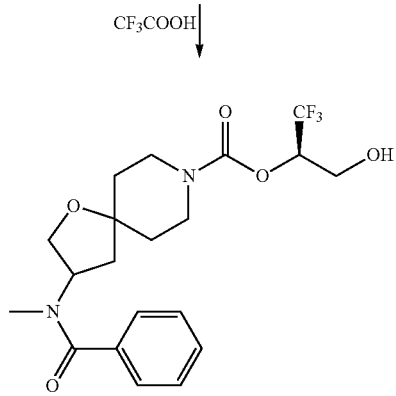

[From C111, DIAST-1]
100

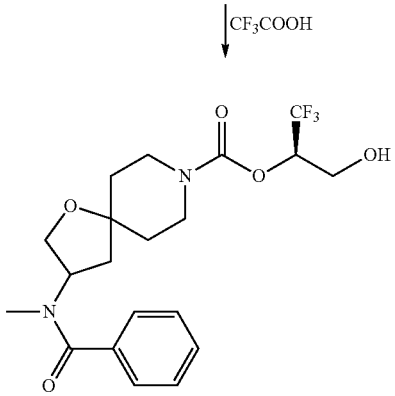

[From C112, DIAST-2]
99

Step 1. Synthesis of (2R)-1,1,1-trifluoro-3-[(4-methoxybenzyl)oxy]propan-2-yl 3-(benzoylamino)-1-oxa-8-azaspiro[4.5]decane-8-carboxylate (C110)

A solution of benzoyl chloride (58.5 mg, 0.416 mmol) in dichloromethane (0.5 mL) was added to a 0° C. solution of C73 (150 mg, 0.347 mmol) and triethylamine (105 mg, 1.04 mmol) in dichloromethane (2 mL). The reaction mixture was stirred at 25° C. for 3 hours, whereupon saturated aqueous ammonium chloride solution (2 mL) was added, and the resulting mixture was extracted with dichloromethane (2×3 mL). The combined organic layers were washed with saturated aqueous sodium chloride solution (2×3 mL), filtered, and concentrated in vacuo. Silica gel chromatography (Gradient: 5% to 20% ethyl acetate in petroleum ether) provided the product as a colorless gum. Yield: 135 mg, 0.252 mmol, 73%. LCMS m/z 559.1 [M+Na$^+$].

Step 2. Synthesis of (2R)-1,1,1-trifluoro-3-[(4-methoxybenzyl)oxy]propan-2-yl 3-[benzoyl(methyl)amino]-1-oxa-8-azaspiro[4.5]decane-8-carboxylate, DIAST-1 (C111) and (2R)-1,1,1-trifluoro-3-[(4-methoxybenzyl)oxy]propan-2-yl 3-[benzoyl(methyl)amino]-1-oxa-8-azaspiro[4.5]decane-8-carboxylate, DIAST-2 (C112)

Sodium hydride (60% dispersion in mineral oil; 17.1 mg, 0.428 mmol) was added to a 0° C. solution of C110 (115 mg, 0.214 mmol) in dry tetrahydrofuran (2 mL), and the reaction mixture was stirred at 0° C. for 30 minutes. Iodomethane (45.6 mg, 0.321 mmol) was added, and stirring was continued at 25° C. for 2 hours. The reaction mixture was then combined with a similar reaction mixture using C110 (20 mg, 37 μmol) and cooled to 0° C. Saturated aqueous ammonium chloride solution (5 mL) was added, and the resulting mixture was extracted with ethyl acetate (2×5 mL). The combined organic layers were washed with saturated aqueous sodium chloride solution (2×5 mL), filtered, and concentrated in vacuo to afford the product, a diastereomeric mixture of C111 and C112, as a colorless gum. Yield of diastereomeric product mixture: 130 mg, 0.236 mmol, 94%. LCMS m/z 573.2 [M+Na$^+$]. $^1$H NMR (400 MHz, CDCl$_3$), characteristic peaks: δ 7.46-7.40 (m, 3H), 7.40-7.34 (m, 2H), 7.24 (br d, J=8.5 Hz, 2H), 6.88 (br d, J=8.7 Hz, 2H), 5.53-5.42 (m, 1H), 4.51 (AB quartet, $J_{AB}$=11.7 Hz, $\Delta v_{AB}$=28.4 Hz, 2H), 3.91-3.85 (m, 1H), 3.85-3.63 (m, 3H), 3.82 (s, 3H), 3.42-3.19 (m, 2H), 3.07-2.89 (m, 3H), 1.85-1.67 (m, 3H).

The component diastereomers were separated via supercritical fluid chromatography (Column: Chiral Technologies Chiralpak IC, 10 μm; Mobile phase: 40% (0.1% ammonium hydroxide in 2-propanol) in carbon dioxide]. The first-eluting diastereomer was C111 (50 mg) and the second-eluting diastereomer was C112 (55 mg).

Step 3. Synthesis of (2R)-1,1,1-trifluoro-3-hydroxypropan-2-yl 3-[benzoyl(methyl)amino]-1-oxa-8-azaspiro[4.5]decane-8-carboxylate [From C112, DIAST-2] (99)

Trifluoroacetic acid (0.5 mL) was added to a solution of C112 (55 mg, 0.10 mmol) in dichloromethane (1 mL), and the reaction mixture was stirred at 18° C. for 2 hours. Saturated aqueous sodium bicarbonate solution was added until the pH reached 8~9, and the resulting mixture was extracted with dichloromethane (2×2 mL). The combined organic layers were washed with saturated aqueous sodium chloride solution, filtered, dried over sodium sulfate, and concentrated in vacuo. Reversed phase HPLC (Column: Agela Durashell, 5 μm; Mobile phase A: water containing 0.225% formic acid; Mobile phase B: acetonitrile; Gradient: 8% to 58% B) afforded the product as a white solid. Yield: 15.6 mg, 36.2 μmol, 36%. LCMS m/z 431.0 [M+H]$^+$. $^1$H NMR (400 MHz, CDCl$_3$), characteristic peaks: δ 7.46-7.34 (m, 5H), 5.30-5.20 (m, 1H), 4.04-3.96 (m, 1H), 3.92-3.68 (m, 4H), 3.44-3.15 (m, 2H), 3.07-2.89 (m, 3H), 2.46-1.96 (m, 2H), 1.87-1.72 (m, 3H).

Step 4. Synthesis of (2R)-1,1,1-trifluoro-3-hydroxypropan-2-yl 3-[benzoyl(methyl)amino]-1-oxa-8-azaspiro[4.5]decane-8-carboxylate [From C111, DIAST-1] (100)

Conversion of C111 to the product was effected using the method employed for synthesis of 99 from C112. Yield: 17.4 mg, 40.4 μmol, 44%. LCMS m/z 431.0 [M+H]$^+$. $^1$H NMR (400 MHz, CDCl$_3$), characteristic peaks: δ 7.46-7.40 (m, 3H), 7.40-7.34 (m, 2H), 5.30-5.20 (m, 1H), 4.06-3.95 (m, 1H), 3.94-3.70 (m, 4H), 3.48-3.21 (m, 2H), 3.08-2.88 (m, 3H), 2.43-2.27 (m, 1H), 1.88-1.72 (m, 3H).

Example 101

(2R)-1,1,1-Trifluoro-3-hydroxypropan-2-yl 3-(1,1-dioxido-1,2-benzothiazol-2(3H)-yl)-1-oxa-8-azaspiro[4.5]decane-8-carboxylate (101)

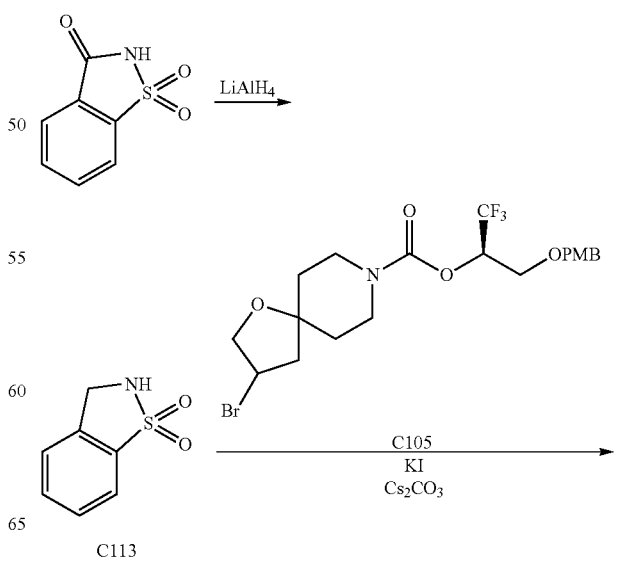

-continued

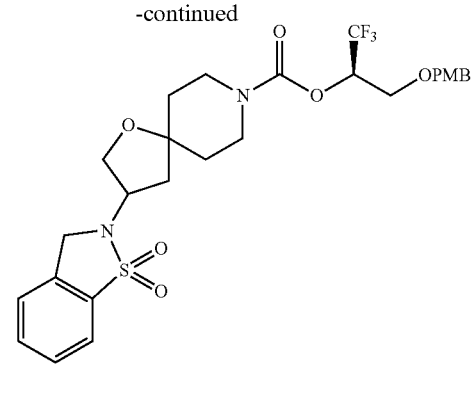

C114

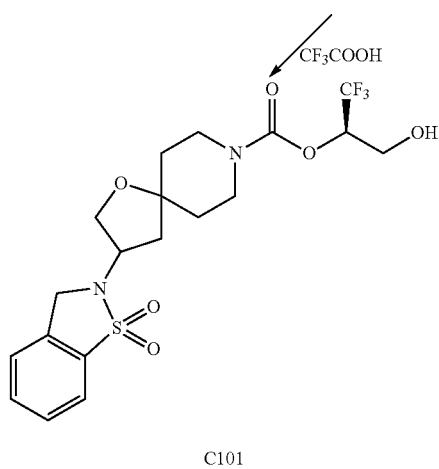

C101

Step 1. Synthesis of 2,3-dihydro-1,2-benzothiazole 1,1-dioxide (C113)

A solution of 1,2-benzothiazol-3(2H)-one 1,1-dioxide (200 mg, 1.09 mmol) in tetrahydrofuran (2 mL) was added drop-wise to a 0° C. suspension of lithium aluminum hydride (45.6 mg, 1.20 mmol) in tetrahydrofuran (3 mL). After the reaction mixture had stirred for 30 minutes at 0° C., it was gradually warmed to 15° C. and stirred at 15° C. for 16 hours. The white suspension was treated with saturated aqueous ammonium chloride solution, and then extracted with ethyl acetate (20 mL). The organic layer was dried over sodium sulfate, filtered, and concentrated in vacuo to provide the product as a grey solid. Yield: 160 mg, 0.946 mmol, 87%. $^1$H NMR (400 MHz, CDCl$_3$) δ 7.81 (d, J=7.8 Hz, 1H), 7.63 (dd, half of ABX pattern, J=7.5, 7.3 Hz, 1H), 7.54 (dd, half of ABX pattern, J=7.5, 7.5 Hz, 1H), 7.41 (d, J=7.8 Hz, 1H), 4.95-4.80 (br s, 1H), 4.55 (s, 2H).

Step 2. Synthesis of (2R)-1,1,1-trifluoro-3-[(4-methoxybenzyl)oxy]propan-2-yl 3-(1, 1-dioxido-1, 2-benzothiazol-2(3H)-yl)-1-oxa-8-azaspiro[4.5]decane-8-carboxylate (C114)

A mixture of C105 (80 mg, 0.16 mmol), C113 (39.3 mg, 0.232 mmol), cesium carbonate (114 mg, 0.350 mmol), and potassium iodide (28.9 mg, 0.174 mmol) in N,N-dimethylformamide (2 mL) was stirred at 80° C. for 16 hours. The reaction mixture was then diluted with ethyl acetate (30 mL), washed with saturated aqueous sodium chloride solution (3×30 mL), dried over sodium sulfate, filtered, and concentrated in vacuo. Preparative thin layer chromatography on silica gel (Eluent: 1:3 ethyl acetate/petroleum ether) provided the product as a light yellow oil. Yield: 55 mg, 94 µmol, 59%. LCMS m/z 607.0 [M+Na$^+$].

Step 3. Synthesis of (2R)-1,1,1-trifluoro-3-hydroxypropan-2-yl 3-(1, 1-dioxido-1,2-benzothiazol-2(3H)-yl)-1-oxa-8-azaspiro[4.5]decane-8-carboxylate (101)

Trifluoroacetic acid (2 mL) was added in a drop-wise manner to a 0° C. solution of C114 (55 mg, 94 µmol) in dichloromethane (6 mL). The reaction mixture was stirred at 0° C. for 1 hour, whereupon it was diluted with saturated aqueous sodium bicarbonate (30 mL) and extracted with ethyl acetate (30 mL). The organic layer was dried over sodium sulfate, filtered, concentrated in vacuo, and purified via reversed phase HPLC (Column: Agela Durashell C18, 5 µm; Mobile phase A: water containing 0.225% formic acid; Mobile phase B: acetonitrile; Gradient: 30% to 50% B). The product was obtained as a white solid, presumed to be a mixture of diastereomers. Yield: 6.0 mg, 13 µmol, 14%. LCMS m/z 487.0 [M+Na$^+$]. $^1$H NMR (400 MHz, CDCl$_3$) δ 7.81 (br d, J=7.5 Hz, 1H), 7.64 (ddd, J=7.5, 7.5, 1.2 Hz, 1H), 7.56 (br dd, J=7, 7 Hz, 1H), 7.42 (br d, J=7.8 Hz, 1H), 5.31-5.21 (m, 1H), 4.41 (br AB quartet, J$_{AB}$=14 Hz, Δv$_{AB}$=12 Hz, 2H), 4.4-4.30 (m, 1H), 4.16 (dd, half of ABX pattern, J=9.7, 6.4 Hz, 1H), 4.05 (dd, half of ABX pattern, J=9.8, 5.5 Hz, 1H), 4.05-3.96 (m, 1H), 3.93-3.73 (m, 3H), 3.50-3.28 (m, 2H), 2.42-2.25 (m, 2H), 2.21-2.08 (m, 1H), 1.89-1.70 (m, 3H).

Example 102

(2R)-1,1,1-Trifluoro-3-hydroxypropan-2-yl 3-[(5-methylpyridin-2-yl)methyl]-1-oxa-8-azaspiro[4.5]decane-8-carboxylate (102)

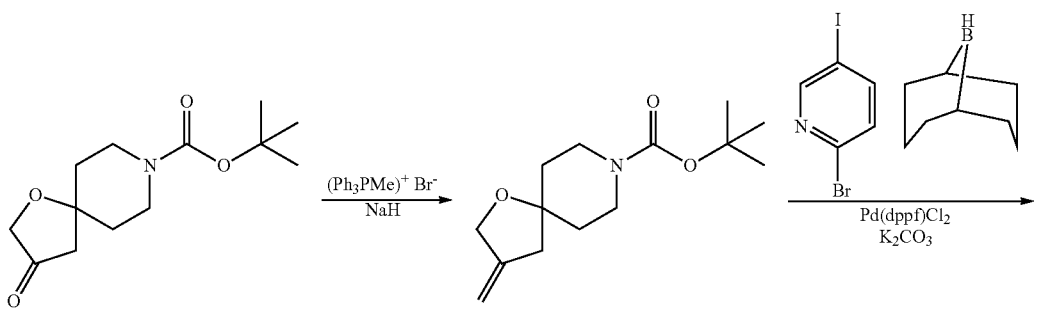

C115

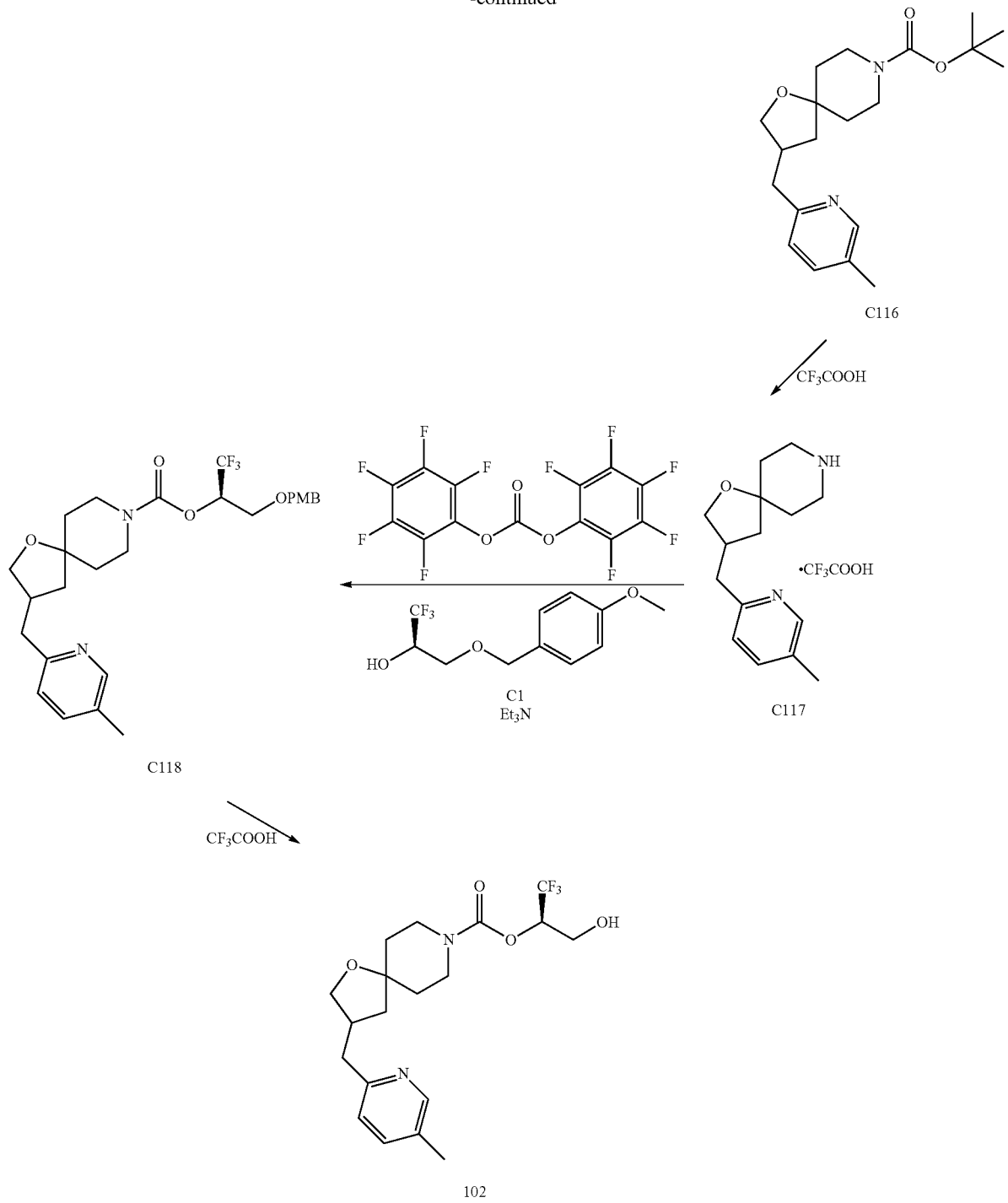

Step 1. Synthesis of tert-butyl 3-methylidene-1-oxa-8-azaspiro[4.5]decane-8-carboxylate (C115)

Methyltriphenylphosphonium bromide (8.4 g, 24 mmol) was added portion-wise to a mixture of sodium hydride (60% dispersion in mineral oil; 940 mg, 23.5 mmol) in dimethyl sulfoxide (40 mL), and the reaction mixture was stirred for 30 minutes at room temperature. A solution of tert-butyl 3-oxo-1-oxa-8-azaspiro[4.5]decane-8-carboxylate (2.0 g, 7.8 mmol) in dimethyl sulfoxide (18 mL) was then added drop-wise, and the reaction mixture was allowed to continue stirring at room temperature for 72 hours. The reaction was then carefully quenched with water (250 mL), and extracted with diethyl ether (5×50 mL). The combined organic layers were washed with water (2×25 mL), dried over magnesium sulfate, filtered, and concentrated in vacuo. The residue was triturated three times with heptane to afford an off-white solid, which proved to be largely triphenylphosphine oxide on analysis. The combined heptane portions from the triturations were concentrated in vacuo and subjected to silica gel chromatography (Eluents: 0%, followed by 10% and 20% ethyl acetate in heptane), which afforded the product as a colorless oil. Yield: 1.77 g, 6.99 mmol, 90%. GCMS m/z 253.1 [M$^+$]. $^1$H NMR (400 MHz, CDCl$_3$) δ 5.02-4.98 (m, 1H), 4.95-4.91 (m, 1H), 4.37-4.33 (m, 2H), 3.60 (ddd, J=13, 5, 5 Hz, 2H), 3.34 (ddd, J=13.3, 9.9, 3.3 Hz, 2H), 2.42-2.38 (m, 2H), 1.70-1.63 (m, 2H), 1.55 (ddd, J=13.3, 10.0, 4.5 Hz, 2H), 1.46 (s, 9H).

Step 2. Synthesis of tert-butyl 3-[(5-methylpyridin-2-yl)methyl]-1-oxa-8-azaspiro[4.5]decane-8-carboxylate (C116)

Compound C115 (200 mg, 0.789 mmol) was dissolved in a 9-borabicyclo[3.3.1]nonane solution (0.5 M in tetrahydrofuran; 1.58 mL, 0.79 mmol). After the reaction vessel had been capped, the reaction mixture was stirred at 70° C. for 1 hour, whereupon it was cooled to room temperature and added to a mixture of 2-bromo-5-methylpyridine (123 mg, 0.715 mmol), [1,1'-bis(diphenylphosphino)ferrocene]dichloropalladium(II), dichloromethane complex (32 mg, 39 μmol), and potassium carbonate (109 mg, 0.789 mmol) in a mixture of N,N-dimethylformamide (1.7 mL) and water (170 μL). The reaction vessel was capped and stirred at 60° C. overnight. After the reaction mixture had cooled to room temperature, it was poured into water and extracted three times with ethyl acetate. The combined organic layers were washed with saturated aqueous sodium chloride solution, dried over sodium sulfate, filtered, and concentrated in vacuo. The residue was purified via silica gel chromatography (Eluents: 10%, followed by 25%, 50%, and 75% ethyl acetate in heptane) to afford the product as a colorless oil. Yield: 91 mg, 0.26 mmol, 36%. LCMS m/z 347.3 [M+H]$^+$. $^1$H NMR (400 MHz, CDCl$_3$) δ 8.39-8.35 (m, 1H), 7.44 (br d, J=7 Hz, 1H), 7.04 (d, J=7.7 Hz, 1H), 3.95 (dd, J=8.6, 6.6 Hz, 1H), 3.61-3.47 (m, 2H), 3.55 (dd, J=8.5, 7.8 Hz, 1H), 3.40-3.26 (m, 2H), 2.92-2.75 (m, 3H), 2.32 (s, 3H), 1.92 (dd, J=12.5, 7.3 Hz, 1H), 1.7-1.5 (m, 4H), 1.51-1.41 (m, 1H), 1.45 (s, 9H).

Step 3. Synthesis of 3-[(5-methylpyridin-2-yl)methyl]-1-oxa-8-azaspiro[4.5]decane, trifluoroacetate salt (C117)

A solution of C116 (91 mg, 0.26 mmol) in dichloromethane (3 mL) was cooled to 0° C. Trifluoroacetic acid (1.5 mL) was added, and the reaction mixture was stirred at room temperature for 1 hour. Solvents were removed under reduced pressure to provide the product as a pale yellow oil (185 mg), which was used directly in the following step. GCMS m/z 246.1 [M$^+$]. $^1$H NMR (400 MHz, CDCl$_3$) δ 8.65-8.62 (br s, 1H), 8.17 (br d, J=8 Hz, 1H), 7.60 (d, J=8.1 Hz, 1H), 3.99 (dd, J=8.8, 7.0 Hz, 1H), 3.58 (dd, J=8.6, 8.2 Hz, 1H), 3.40-3.26 (m, 4H), 3.25 (dd, half of ABX pattern, J=14.4, 7.0 Hz, 1H), 3.13 (dd, half of ABX pattern, J=14.3, 8.3 Hz, 1H), 2.90-2.77 (m, 1H), 2.58 (s, 3H), 2.11-1.80 (m, 5H), 1.63-1.54 (m, 1H, assumed; partially obscured by water peak).

Step 4. Synthesis of (2R)-1,1,1-trifluoro-3-[(4-methoxybenzyl)oxy]propan-2-yl 3-[(5-methylpyridin-2-yl)methyl]-1-oxa-8-azaspiro[4.5]decane-8-carboxylate (C118)

Bis(pentafluorophenyl) carbonate (132 mg, 0.335 mmol) was added to a 0° C. solution of C1 (84 mg, 0.34 mmol) in acetonitrile (5 mL). Triethylamine (180 μL, 1.29 mmol) was then added, and the reaction mixture was stirred at room temperature for 1 hour. In a separate flask, a solution of C117 (from the previous step; 185 mg, ≤0.26 mmol) in acetonitrile (3 mL) was cooled to 0° C. and treated with triethylamine (360 μL, 2.6 mmol); after this mixture had stirred in the ice bath for a few minutes, the carbonate solution prepared from C1 was added drop-wise to the solution containing C117. The reaction mixture was stirred at 0° C. for a few minutes, and then allowed to stir at room temperature overnight. It was then concentrated in vacuo, and the resulting oil was taken up in ethyl acetate and washed sequentially with aqueous 1 M hydrochloric acid, saturated aqueous sodium bicarbonate solution, and saturated aqueous sodium chloride solution. The organic layer was dried over sodium sulfate, filtered, and concentrated under reduced pressure. Silica gel chromatography (Eluents: 10%, followed by 25%, 50%, and 75% ethyl acetate in heptane) afforded the product as a colorless oil. Yield: 93 mg, 0.18 mmol, 69% over two steps. LCMS m/z 523.4 [M+H]$^+$. $^1$H NMR (400 MHz, CDCl$_3$) δ 8.38-8.35 (m, 1H), 7.42 (br dd, J=7.8, 1.8 Hz, 1H), 7.24 (br d, J=8.6 Hz, 2H), 7.02 (d, J=7.9 Hz, 1H), 6.88 (br d, J=8.5 Hz, 2H), 5.53-5.41 (m, 1H), 4.50 (AB quartet, upfield doublet is broadened, $J_{AB}$=11.7 Hz, $\Delta v_{AB}$=26.8 Hz, 2H), 4.00-3.92 (m, 1H), 3.81 (s, 3H), 3.79-3.62 (m, 4H), 3.59-3.51 (m, 1H), 3.44-3.27 (m, 2H), 2.90-2.75 (m, 3H), 2.32 (s, 3H), 1.96-1.83 (m, 1H), 1.74-1.38 (m, 5H).

Step 5. Synthesis of (2R)-1,1,1-trifluoro-3-hydroxypropan-2-yl 3-[(5-methylpyridin-2-yl)methyl]-1-oxa-8-azaspiro[4.5]decane-8-carboxylate (102)

Trifluoroacetic acid (2.5 mL) was added portion-wise to a 0° C. solution of C118 (93 mg, 0.18 mmol) in dichloromethane (5 mL). The reaction mixture was allowed to stir at room temperature for 75 minutes, whereupon it was concentrated in vacuo and partitioned between dichloromethane and saturated aqueous sodium bicarbonate solution. The organic layer was extracted twice with dichloromethane, and the combined organic layers were washed with saturated aqueous sodium chloride solution, dried over sodium sulfate, filtered, and concentrated under reduced pressure. Chromatography on silica gel (Eluents: 50%, followed by 100% ethyl acetate in heptane) provided the product as a colorless oil, presumed to be a mixture of diastereomers. Yield: 54 mg, 0.13 mmol, 72%. LCMS m/z 403.2 [M+H]$^+$. $^1$H NMR (400 MHz, CDCl$_3$) δ 8.38-8.34 (m, 1H), 7.43 (br dd, J=7.8, 2.0 Hz, 1H), 7.03 (d, J=7.8 Hz, 1H), 5.30-5.18 (m, 1H), 4.03-3.91 (m, 2H), 3.85 (dd, half of ABX pattern, J=12.3, 6.8 Hz, 1H), 3.82-3.62 (m, 2H), 3.59-3.51 (m, 1H), 3.48-3.25 (m, 2H), 2.90-2.72 (m, 3H), 2.31 (s, 3H), 1.95-1.86 (m, 1H), 1.75-1.59 (m, 3H), 1.56-1.41 (m, 2H).

Examples 103 and 104
(2R)-1,1,1-Trifluoro-3-hydroxypropan-2-yl 3-(1H-pyrazol-1-yl)-1-oxa-8-azaspiro[4.5]decane-8-carboxylate [From C120, DIAST-2] (103) and (2R)-1,1,1-Trifluoro-3-hydroxypropan-2-yl 3-(1H-pyrazol-1-yl)-1-oxa-8-azaspiro[4.5]decane-8-carboxylate [From C119, DIAST-1] (104)
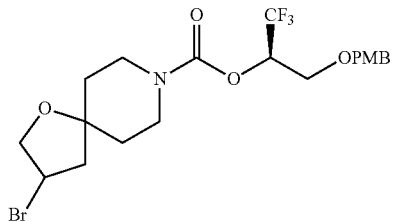
C105
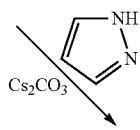
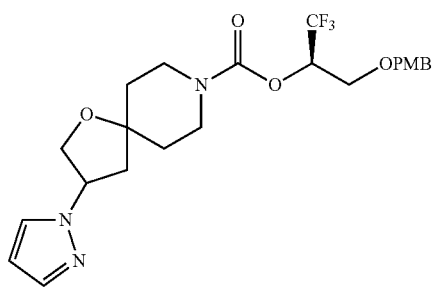
DIAST-1
C119
+
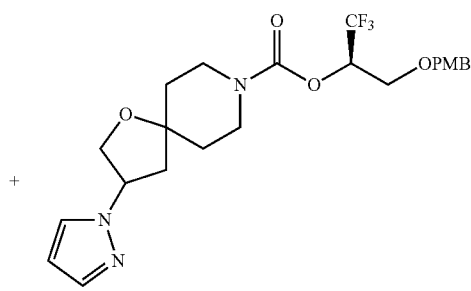
DIAST-2
C120
 CF₃COOH
 CF₃COOH
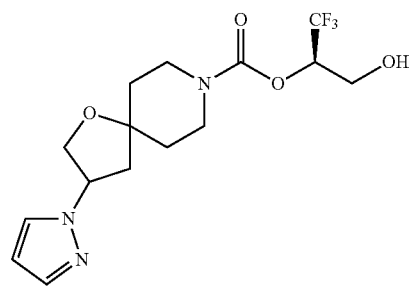
[from C119, DIAST-1]
104
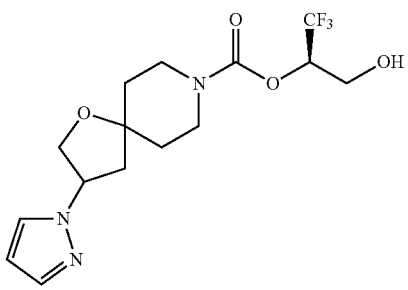
[from C120, DIAST-2]
103

Step 1. Synthesis of (2R)-1,1,1-trifluoro-3-[(4-methoxybenzyl)oxy]propan-2-yl 3-(1H-pyrazol-1-yl)-1-oxa-8-azaspiro[4.5]decane-8-carboxylate, DIAST-1 (C119) and (2R)-1,1,1-trifluoro-3-[(4-methoxybenzyl)oxy]propan-2-yl 3-(1H-pyrazol-1-yl)-1-oxa-8-azaspiro[4.5]decane-8-carboxylate, DIAST-2 (C120)

A mixture of C105 (200 mg, 0.403 mmol), 1H-pyrazole (54.9 mg, 0.806 mmol), and cesium carbonate (394 mg, 1.21 mmol) in N,N-dimethylformamide (6 mL) was stirred at 20° C. for 16 hours. The reaction mixture was diluted with water (20 mL) and extracted with ethyl acetate (3×20 mL); the combined organic layers were washed with water (3×10 mL) and with saturated aqueous sodium chloride solution (3×10 mL), dried over sodium sulfate, filtered, and concentrated in vacuo. Silica gel chromatography (Eluents: 0%, then 10%, then 25% ethyl acetate in petroleum ether) provided a mixture of diastereomeric products C119 and C120 as a colorless oil. Yield: 60 mg, 0.124 mmol, 31%. This material was combined with the diastereomeric product mixture (30 mg) from a similar reaction carried out on C105, and subjected to separation via supercritical fluid chromatography (Column: Chiral Technologies Chiralpak AD, 10 μm; Mobile phase: 2:3 (0.1% ammonium hydroxide in methanol)/carbon dioxide). The first-eluting diastereomer was assigned as C119, and the second-eluting diastereomer as C120. Both were obtained as colorless oils. C119: Yield: 43 mg, 48% for the separation. LCMS m/z 506.1 [M+Na$^+$]. C120: Yield: 38 mg, 42% for the separation. LCMS m/z 506.1 [M+Na$^+$].

Step 2. Synthesis of (2R)-1,1,1-trifluoro-3-hydroxypropan-2-yl 3-(1H-pyrazol-1-yl)-1-oxa-8-azaspiro[4.5]decane-8-carboxylate [From C120, DIAST-2] (103)

To a 0° C. solution of C120 (38 mg, 78 μmol) in dichloromethane (4 mL) was added trifluoroacetic acid (1 mL), and the reaction mixture was stirred for 1 hour. After solvents had been removed in vacuo, the residue was partitioned between dichloromethane (10 mL) and saturated aqueous sodium bicarbonate solution (20 mL). The aqueous layer was extracted with ethyl acetate (2×10 mL), and the combined organic layers were dried over sodium sulfate, filtered, and concentrated under reduced pressure. Reversed phase HPLC (Column: Phenomenex Synergi C18, 4 μm; Mobile phase A: water containing 0.225% formic acid; Mobile phase B: acetonitrile; Gradient: 19% to 49% B) provided the product as a brown gum. Yield: 17.0 mg, 46.7 μmol, 60%. LCMS m/z 363.8 [M+H]$^+$. $^1$H NMR (400 MHz, CDCl$_3$) δ 7.54 (d, J=1.5 Hz, 1H), 7.50 (d, J=2.1 Hz, 1H), 6.28 (dd, J=2, 2 Hz, 1H), 5.30-5.21 (m, 1H), 5.05-4.97 (m, 1H), 4.26-4.17 (m, 2H), 4.01 (br dd, J=12.5, 3 Hz, 1H), 3.92-3.73 (m, 3H), 3.50-3.31 (m, 2H), 2.38-2.25 (m, 2H), 1.94-1.56 (m, 4H, assumed; partially obscured by water peak).

Step 3. Synthesis of (2R)-1,1,1-trifluoro-3-hydroxypropan-2-yl 3-(1H-pyrazol-1-yl)-1-oxa-8-azaspiro[4.5]decane-8-carboxylate [From C119, DIAST-1] (104)

Conversion of C119 to the product was effected using the method described for synthesis of 103 from C120. In this case, the reversed phase HPLC was carried out using a gradient of 37% to 57% B, to provide the product as a brown gum. Yield: 18.2 mg, 50.0 μmol, 56%. LCMS m/z 363.8 [M+H]$^+$. $^1$H NMR (400 MHz, CDCl$_3$), characteristic peaks: δ 7.55 (d, J=1.5 Hz, 1H), 7.50 (br s, 1H), 6.28 (br s, 1H), 5.31-5.20 (m, 1H), 5.05-4.96 (m, 1H), 4.26-4.16 (m, 2H), 4.05-3.97 (m, 1H), 3.93-3.74 (m, 3H), 3.49-3.30 (m, 2H), 2.39-2.25 (m, 2H).

Example 105

(2R)-1,1,1-Trifluoro-3-hydroxypropan-2-yl 2-(phenylsulfonyl)-2,8-diazaspiro[4.5]decane-8-carboxylate (105)

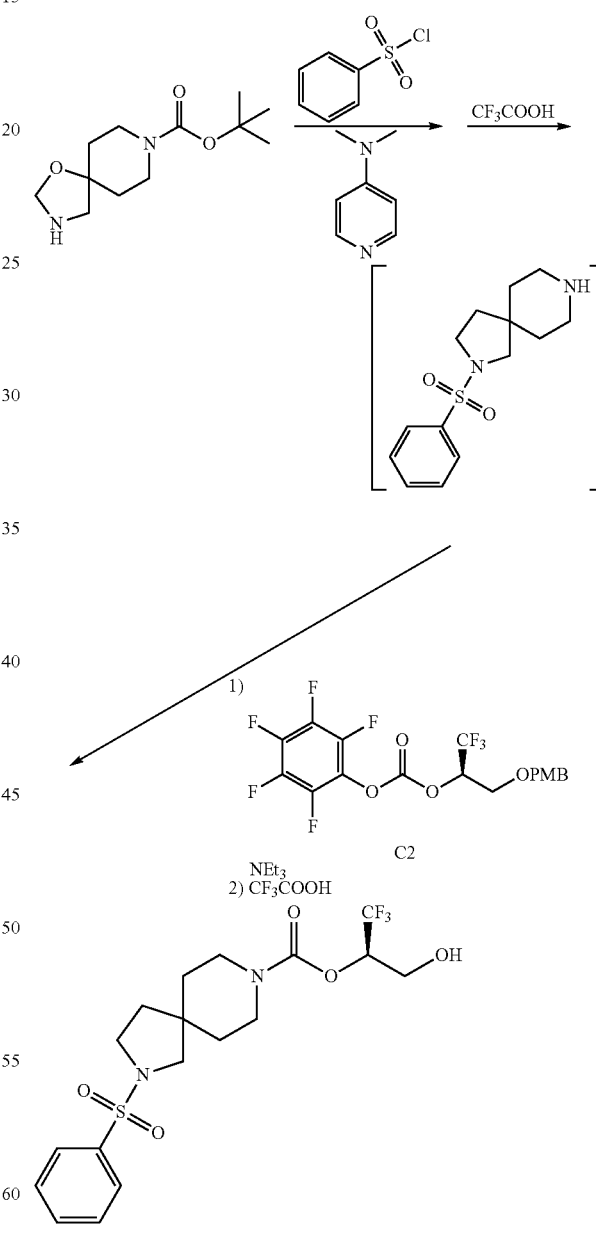

A solution of tert-butyl 2,8-diazaspiro[4.5]decane-8-carboxylate (36 mg, 0.15 mmol) in pyridine (0.4 mL) was added to a solution of benzenesulfonyl chloride (39.7 mg, 0.225 mmol) and N,N-dimethylpyridin-4-amine (0.25 mg, 2.0 μmol) in pyridine (0.4 mL), and the reaction mixture was shaken at room temperature for 2 days. The pyridine was removed in vacuo, and the residue was partitioned between half-saturated aqueous sodium bicarbonate solution (1.5 mL) and ethyl acetate (2.4 mL). After the mixture had been vortexed, the organic layer was eluted through a solid phase extraction cartridge (6 mL) charged with sodium sulfate (~1 g); this extraction procedure was repeated twice, and the combined eluents were concentrated in vacuo. The residue was treated with a mixture of 1,2-dichloroethane and trifluoroacetic acid (1:1; 1 mL), shaken at room temperature for 2.5 hours, and concentrated under reduced pressure. The remaining material was dissolved in 1,2-dichloroethane (2.4 mL), vortexed, and loaded onto an SCX (strong cation exchanger) solid phase extraction cartridge (Silicycle, 6 mL, 1 g); the vial was rinsed with a mixture of methanol and 1,2-dichloroethane (1:1; 2×2.4 mL). The cartridge was eluted with methanol (5 mL), followed by a solution of triethylamine in methanol (1 M, 7.5 mL) to elute the deprotected intermediate. Fractions containing the desired material were concentrated in vacuo, and the residue was azeotroped with toluene (2×1 mL) to remove trace methanol. The resulting material was dissolved in dichloromethane (0.5 mL).

A crude solution of C2 was prepared separately, as follows: Bis(pentafluorophenyl) carbonate (5.8 g, 15 mmol) and triethylamine (41 mL, 290 mmol) were added to a stirring solution of C1 (3.75 g, 15.0 mmol) in tetrahydrofuran (30 mL). Sufficient tetrahydrofuran was added to bring the total volume to 98 mL, and the reaction mixture was stirred at room temperature for 1 hour. A portion of this crude C2 solution (1.0 mL, 0.15 mmol of C2 and 3 mmol of triethylamine) was added to the deprotected amine solution prepared above, and the reaction mixture was shaken at room temperature for 5 days. It was then partitioned between half-saturated aqueous sodium bicarbonate solution (1.5 mL) and ethyl acetate (2.4 mL) and subjected to vortexing. The organic layer was eluted through a solid phase extraction cartridge (6 mL) charged with sodium sulfate (~1 g); this extraction procedure was repeated twice, and the combined eluents were concentrated in vacuo. This material was treated with a mixture of trifluoroacetic acid and 1,2-dichloroethane (1:1, 1 mL) and shaken at room temperature for 1 hour, whereupon it was concentrated in vacuo and purified using reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 25% to 95% B). Yield: 4.8 mg, 11 μmol, 7%. Analytical retention time: 2.64 minutes (Analytical HPLC conditions—Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute). LCMS m/z 437.1 [M+H]$^+$.

Example 106

(2R)-1,1,1-Trifluoro-3-hydroxypropan-2-yl (3R)-3-{[(cyclopropylmethyl)sulfonyl](methyl)amino}-1-oxa-8-azaspiro[4.5]decane-8-carboxylate (106)

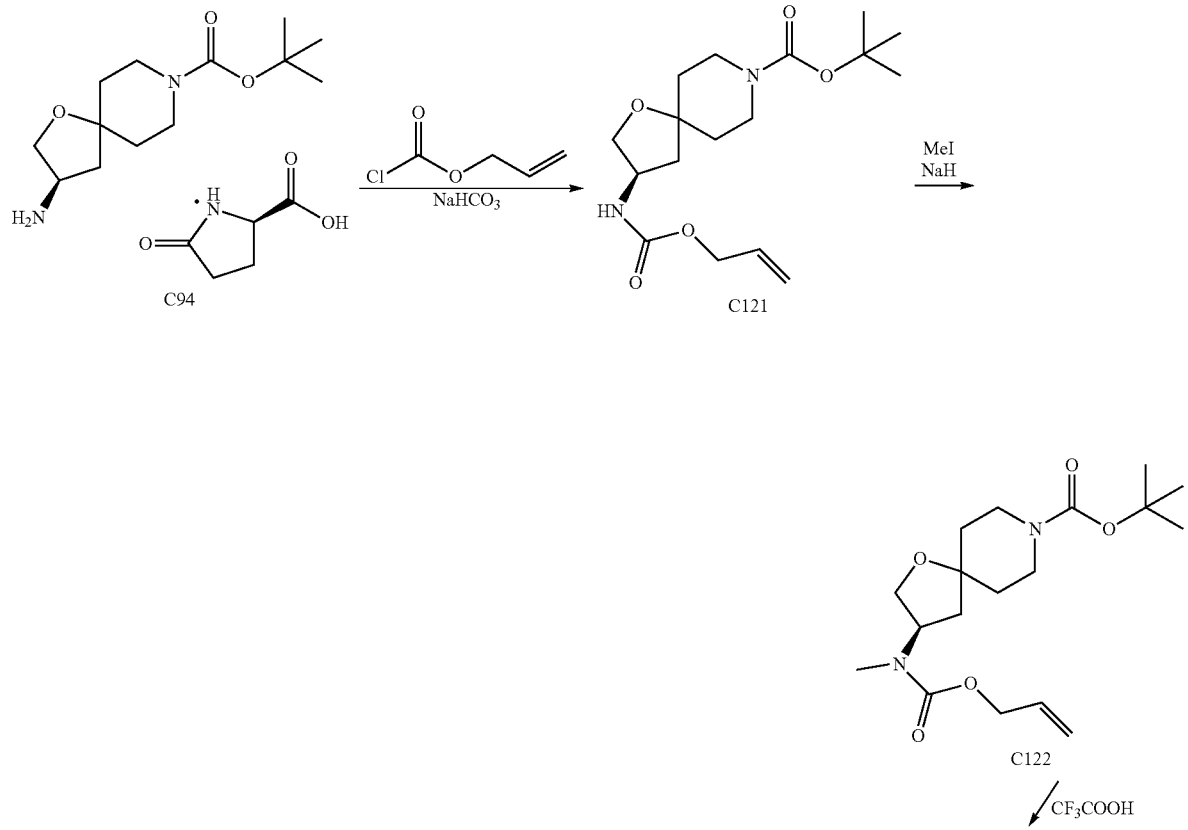

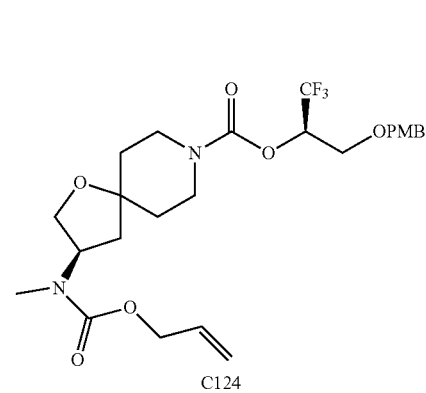
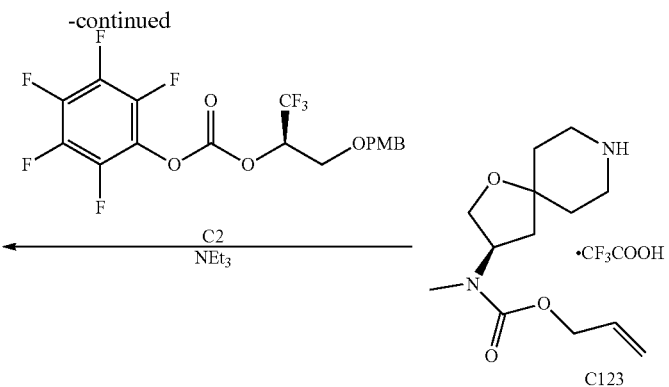
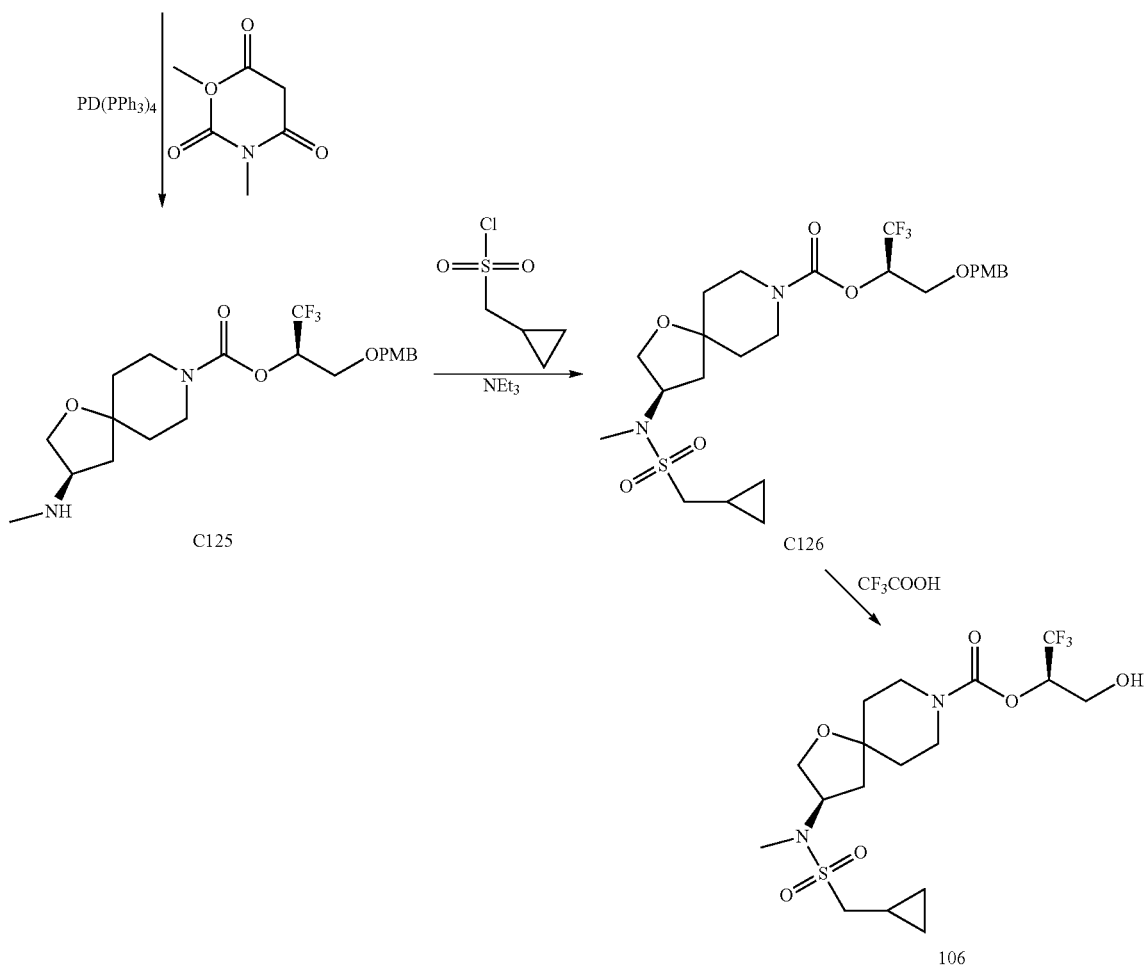

Step 1. Synthesis of tert-butyl (3R)-3-{[(prop-2-en-1-yloxy)carbonyl]amino}-1-oxa-8-azaspiro[4.5]decane-8-carboxylate (C121)

Prop-2-en-1-yl carbonochloridate (7.13 g, 59.2 mmol) was added drop-wise to a 0° C. solution of C94 (15.2 g, 39.4 mmol) in saturated aqueous sodium bicarbonate solution (160 mL) and tetrahydrofuran (40 mL). The reaction mixture was stirred at 10° C. for 14 hours, whereupon it was extracted with ethyl acetate (3×100 mL). The combined organic layers were dried over sodium sulfate, filtered, and concentrated in vacuo to afford the product as a pale yellow gum (13.6 g). This material was used directly in the following step. $^1$H NMR (400 MHz, CDCl$_3$) δ 5.98-5.85 (m, 1H), 5.31 (apparent br dd, J=17.2, 1.4 Hz, 1H), 5.23 (br d, J=10.3 Hz, 1H), 4.95-4.84 (m, 1H), 4.62-4.51 (m, 2H), 4.39-4.27 (m, 1H), 4.00 (dd, J=9.4, 5.6 Hz, 1H), 3.73-3.52 (m, 3H), 3.38-3.24 (m, 2H), 2.13 (dd, J=13.3, 7.8 Hz, 1H), 1.74-1.57 (m, 4H, assumed; partially obscured by water peak), 1.56-1.46 (m, 1H), 1.46 (s, 9H).

Step 2. Synthesis of tert-butyl (3R)-3-{methyl [(prop-2-en-1-yloxy)carbonyl]amino}-1-oxa-8-azaspiro[4.5]decane-8-carboxylate (C122)

Sodium hydride (60% dispersion in mineral oil; 2.36 g, 59.0 mmol) was added to a 0° C. solution of C121 (from the previous step; 13.4 g, ≤38.8 mmol) in tetrahydrofuran (200 mL), and the reaction mixture was stirred at 0° C. for 30 minutes. Iodomethane (16.8 g, 118 mmol) was added dropwise, and stirring was continued for 16 hours at 0° C. to 5° C. Sodium hydride (60% dispersion in mineral oil; 2.36 g, 59.0 mmol) was again added, and the reaction mixture was stirred at 25° C. for 16 hours, whereupon it was poured into saturated aqueous ammonium chloride solution (200 mL) and extracted with ethyl acetate (3×300 mL). The combined organic layers were washed with saturated aqueous sodium chloride solution (600 mL), dried over sodium sulfate, filtered, and concentrated under reduced pressure to afford the product as a brown gum (16 g). This was used in the following step without additional purification. $^1$H NMR (400 MHz, CDCl$_3$) δ 5.99-5.89 (m, 1H), 5.34-5.27 (m, 1H), 5.24-5.19 (m, 1H), 5.09-4.85 (br m, 1H), 4.59 (ddd, J=5.5, 1.5, 1.4 Hz, 2H), 3.94 (dd, half of ABX pattern, J=9.7, 7.6 Hz, 1H), 3.76 (dd, half of ABX pattern, J=9.9, 5.4 Hz, 1H), 3.69-3.52 (m, 2H), 3.38-3.23 (m, 2H), 2.87 (s, 3H), 2.09 (dd, J=13.1, 9.0 Hz, 1H), 1.75-1.60 (m, 4H, assumed; partially obscured by water peak), 1.51-1.41 (m, 1H), 1.46 (s, 9H).

Step 3. Synthesis of prop-2-en-1-yl methyl[(3R)-1-oxa-8-azaspiro[4.5]dec-3-yl]carbamate, trifluoroacetate salt (C123)

Trifluoroacetic acid (20 mL) was added to a solution of C122 (from the previous step; 16 g, ≤38.8 mmol) in dichloromethane (100 mL), and the reaction mixture was stirred at 15° C. for 2 hours. Removal of volatiles in vacuo afforded the product as a brown gum (20 g). This material was used directly in the following step. LCMS m/z 255.2 [M+H]$^+$.

Step 4. Synthesis of (2R)-1,1,1-trifluoro-3-[(4-methoxybenzyl)oxy]propan-2-yl (3R)-3-{methyl[(prop-2-en-1-yloxy)carbonyl]amino}-1-oxa-8-azaspiro[4.5]decane-8-carboxylate (C124)

Triethylamine (19.9 g, 197 mmol) was slowly added to a 0° C. solution of C123 (from the previous step; 20 g, ≤38.8 mmol) in acetonitrile (250 mL). The reaction mixture was stirred at 0° C. for 30 minutes, whereupon C2 [reaction solution in acetonitrile (80 mL) containing 40 mmol], was added, and stirring was continued at 13° C. for 18 hours. The reaction mixture was concentrated in vacuo, and the residue was purified via silica gel chromatography (Gradient: 9% to 50% ethyl acetate in petroleum ether) to provide the product as a pale yellow gum. Yield: 16.67 g, 31.4 mmol, 81% over 4 steps. LCMS m/z 553.1 [M+Na]$^+$. $^1$H NMR (400 MHz, CDCl$_3$) δ 7.24 (br d, J=8.8 Hz, 2H), 6.88 (br d, J=8.8 Hz, 2H), 6.01-5.89 (m, 1H), 5.53-5.43 (m, 1H), 5.35-5.27 (m, 1H), 5.26-5.20 (m, 1H), 5.08-4.86 (br m, 1H), 4.60 (ddd, J=5.5, 1.5, 1.2 Hz, 2H), 4.51 (AB quartet, J$_{AB}$=11.5 Hz, Δν$_{AB}$=28.3 Hz, 2H), 3.94 (dd, J=9.8, 7.5 Hz, 1H), 3.81 (s, 3H), 3.80-3.64 (m, 5H), 3.43-3.25 (m, 2H), 2.88 (s, 3H), 2.13-2.00 (m, 1H), 1.80-1.60 (m, 4H), 1.47 (ddd, J=13.6, 10.8, 4.3 Hz, 1H).

Step 5. Synthesis of (2R)-1,1,1-trifluoro-3-[(4-methoxybenzyl)oxy]propan-2-yl (3R)-3-(methylamino)-1-oxa-8-azaspiro[4.5]decane-8-carboxylate (C125)

Tetrakis(triphenylphosphine)palladium(0) (2.12 g, 1.83 mmol) was added to a 10° C. solution of C124 (6.50 g, 12.2 mmol) and 1,3-dimethylpyrimidine-2,4,6(1H,3H,5H)-trione (2.87 g, 18.4 mmol) in tetrahydrofuran (100 mL). After the reaction mixture had been stirred at 25° C. for 2 hours, solid sodium carbonate (65 mg, 0.61 mmol) was added, and stirring was continued at 10° C. for 20 minutes. The reaction mixture was filtered, and the filtrate was concentrated in vacuo. The residue was purified twice by silica gel chromatography (Gradient: 0% to 10% methanol in dichloromethane) to afford the product as a yellow gum. Yield: 3.8 g, 8.5 mmol, 70%. LCMS m/z 447.3 [M+H]$^+$. $^1$H NMR (400 MHz, CDCl$_3$) δ 7.24 (br d, J=8.7 Hz, 2H), 6.88 (br d, J=8.7 Hz, 2H), 5.53-5.42 (m, 1H), 4.51 (AB quartet, J$_{AB}$=11.6 Hz, Δν$_{AB}$=280.0 Hz, 2H), 3.96 (dd, J=9.2, 6.0 Hz, 1H), 3.81 (s, 3H), 3.8-3.64 (m, 5H), 3.43-3.28 (m, 3H), 2.43 (s, 3H), 2.08-1.97 (m, 1H), 1.85-1.46 (m, 5H, assumed; partially obscured by water peak).

Step 6. Synthesis of (2R)-1,1,1-trifluoro-3-[(4-methoxybenzyl)oxy]propan-2-yl (3R)-3-{[(cyclopropylmethyl)sulfonyl](methyl)amino}-1-oxa-8-azaspiro[4.5]decane-8-carboxylate (C126)

To a 15° C. solution of C125 (400 mg, 0.896 mmol) in dichloromethane (5 mL) were added cyclopropylmethanesulfonyl chloride (208 mg, 1.35 mmol) and triethylamine (453 mg, 4.48 mmol). The reaction mixture was stirred at 15° C. for 16 hours, whereupon it was concentrated in vacuo and purified via chromatography on silica gel (Gradient: 0% to 50% ethyl acetate in petroleum ether). The product was obtained as a colorless gum. Yield: 430 mg, 0.762 mmol, 85%. LCMS m/z 587.1 [M+Na]$^+$.

Step 7. Synthesis of (2R)-1,1,1-trifluoro-3-hydroxypropan-2-yl (3R)-3-{[(cyclopropylmethyl)sulfonyl](methyl)amino}-1-oxa-8-azaspiro[4.5]decane-8-carboxylate (106)

Trifluoroacetic acid (3 mL) was added to a 0° C. solution of C126 (430 mg, 0.762 mmol) in dichloromethane (12 mL). The reaction mixture was stirred at 15° C. for 2 hours, whereupon the pH was adjusted to 6-7 via addition of sodium bicarbonate. The resulting mixture was extracted with dichloromethane (15 mL) and with ethyl acetate (2×15 mL). The combined organic layers were dried over sodium sulfate, filtered, and concentrated in vacuo. Silica gel chromatography (Gradient: 0% to 50% ethyl acetate in petroleum ether) was followed by reversed phase HPLC (Column: Agela Durashell C18, 5 μm; Mobile phase A: water containing 0.225% formic acid; Mobile phase B: acetonitrile; Gradient: 30% to 50% B), affording the product as a colorless gum. Yield: 211 mg, 0.475 mmol, 62%. LCMS m/z 445.2 [M+H]$^+$. $^1$H NMR (400 MHz, CDCl$_3$) δ 5.30-5.19 (m, 1H), 4.72-4.62 (m, 1H), 4.01-3.90 (m, 2H), 3.89-3.69 (m, 4H), 3.44-3.23 (m, 2H), 2.88-2.83 (m, 2H), 2.86 (s, 3H), 2.82-2.64 (br m, 1H), 2.13-2.01 (m, 1H), 1.81-1.65 (m, 4H), 1.55-1.39 (m, 1H), 1.13-1.01 (m, 1H), 0.76-0.62 (m, 2H), 0.42-0.29 (m, 2H).

TABLE 6A

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 107 | Example 92[35]; C48, C2 | 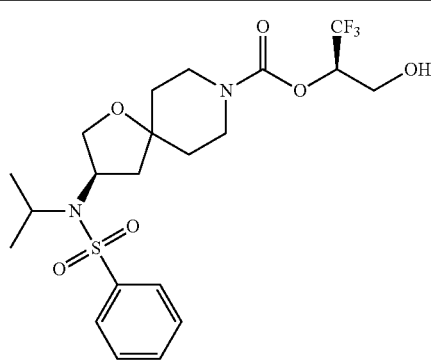 | 7.83 (d, J = 7.5 Hz, 2H), 7.57 (br dd, half of ABX pattern, J = 7.5, 7.0 Hz, 1H), 7.51 (br dd, half of ABX pattern, J = 7.5, 7.0 Hz, 2H), 5.31-5.19 (m, 1H), 4.16-3.95 (m, 3H), 3.92-3.68 (m, 5H), 3.50-3.30 (m, 2H), 2.52-2.35 (m, 1H), 2.29-2.15 (m, 1H), 1.99-1.82 (m, 2H), 1.79-1.47 (m, 3H, assumed; partially obscured by water peak), 1.26-1.18 (m, 6H); 495.1 |
| 108 | Example 11[36,37]; C73 | 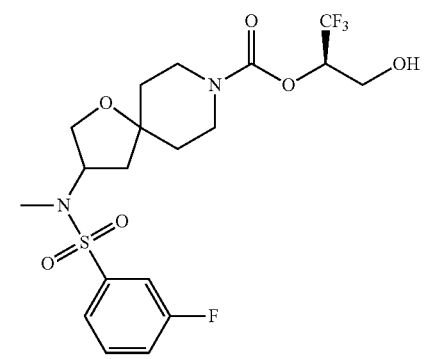

DIAST-1 | $^1$H NMR (400 MHz, DMSO-d$_6$) δ 7.72-7.63 (m, 3H), 7.61-7.55 (m, 1H), 5.24-5.14 (m, 1H), 4.68-4.59 (m, 1H), 3.77-3.59 (m, 4H), 3.57-3.44 (m, 3H), 3.3-3.12 (m, 2H), 2.70 (s, 3H), 1.96-1.85 (m, 1H), 1.65-1.49 (m, 3H), 1.49-1.35 (m, 2H); 485.3 |
| 109 | Example 11[36,37]; C73 | 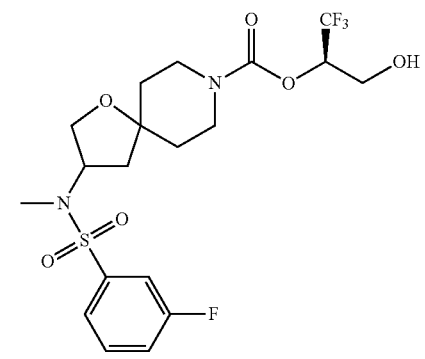

DIAST-2 | $^1$H NMR (400 MHz, DMSO-d$_6$) δ 7.73-7.62 (m, 3H), 7.62-7.54 (m, 1H), 5.23-5.14 (m, 1H), 4.69-4.58 (m, 1H), 3.78-3.58 (m, 4H), 3.58-3.44 (m, 3H), 3.3-3.11 (m, 2H), 2.70 (s, 3H), 1.91 (dd, J = 13.4, 9.1 Hz, 1H), 1.67-1.49 (m, 3H), 1.48-1.31 (m, 2H); 485.3 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 110 | Example 109[38]; C73 | 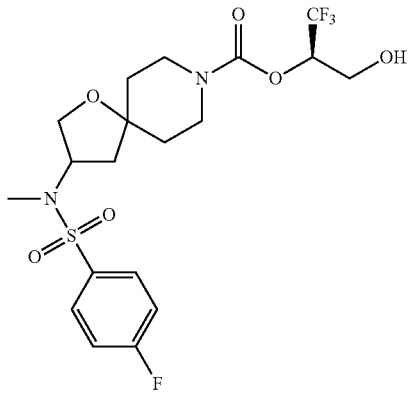DIAST-1 | $^1$H NMR (400 MHz, DMSO-d$_6$) δ 7.91-7.84 (m, 2H), 7.46 (br dd, J = 8.8, 8.8 Hz, 2H), 5.24-5.14 (m, 1H), 4.64-4.55 (m, 1H), 3.78-3.68 (m, 3H), 3.68-3.58 (m, 1H), 3.57-3.43 (m, 3H), 3.3-3.12 (m, 2H), 2.67 (s, 3H), 1.89 (br dd, J = 13, 9.5 Hz, 1H), 1.65-1.49 (m, 3H), 1.49-1.34 (m, 2H); 485.3 |
| 111 | Example 109[38]; C73 | 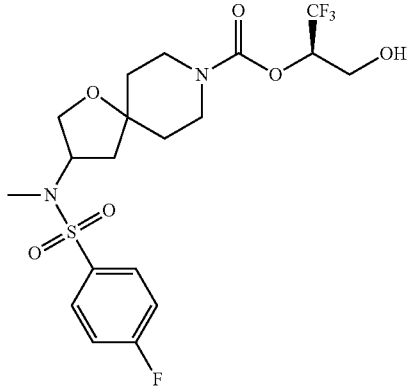DIAST-2 | $^1$H NMR (400 MHz, DMSO-d$_6$) δ 7.91-7.85 (m, 2H), 7.46 (br dd, J = 8.8, 8.8 Hz, 2H), 5.24-5.14 (m, 1H), 4.64-4.55 (m, 1H), 3.78-3.68 (m, 3H), 3.68-3.59 (m, 1H), 3.57-3.44 (m, 3H), 3.3-3.13 (m, 2H), 2.67 (s, 3H), 1.89 (br dd, J = 13, 9.5 Hz, 1H), 1.65-1.48 (m, 3H), 1.48-1.34 (m, 2H); 485.3 |
| 112 | Examples 93 and 94[39]; C73 | 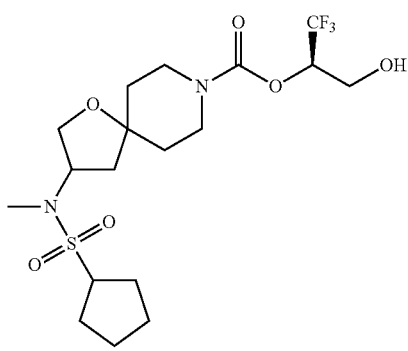 [SMILES: CN(C1COC2(CCN(C(=O)O[C@H](CO)C(F)(F)F)CC2)C1)S(=O)(=O)C1CCCC1] | Mixture of 2 diastereomers; characteristic peaks: 5.30-5.20 (m, 1H), 4.76-4.66 (m, 1H), 4.05-3.92 (m, 2H), 3.92-3.70 (m, 4H), 3.48-3.23 (m, 3H), 2.87 (s, 3H), 2.35-2.22 (m, 1H), 2.13-2.02 (m, 1H), 2.02-1.91 (m, 3H), 1.88-1.59 (m, 7H); 459.3 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 113 | Examples 93 and 94[39]; C73 | 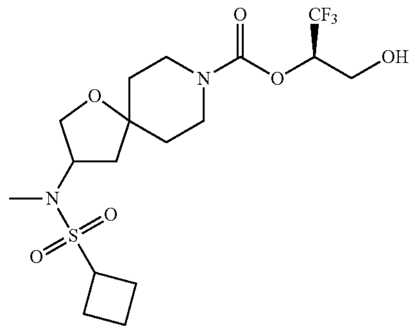 [SMILES: CN(C1COC2(CCN(C(=O)O[C@H](CO)C(F)(F)F)CC2)C1)S(=O)(=O)C1CCC1] | Mixture of 2 diastereomers; 5.32-5.19 (m, 1H), 4.72-4.61 (m, 1H), 4.05-3.96 (m, 1H), 3.96-3.68 (m, 6H), 3.44-3.19 (m, 2H), 2.83 (s, 3H), 2.60-2.46 (m, 2H), 2.46-2.19 (m, 3H), 2.10-1.96 (m, 3H), 1.81-1.67 (m, 4H), 1.55-1.43 (m, 1H); 445.2 |
| 114 | Example 11[40,39]; C73 | 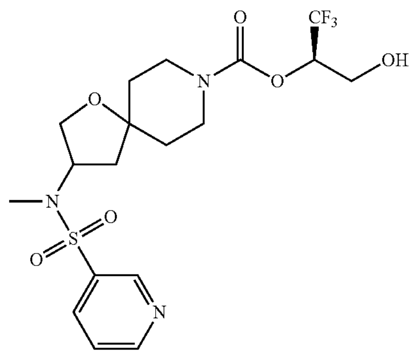 [SMILES: CN(C1COC2(CCN(C(=O)O[C@H](CO)C(F)(F)F)CC2)C1)S(=O)(=O)c1cccnc1] | Mixture of 2 diastereomers; 9.02 (d, J = 2.0 Hz, 1H), 8.85 (dd, J = 4.8, 1.5 Hz, 1H), 8.09 (ddd, J = 8.0, 2.1, 1.8 Hz, 1H), 7.51 (dd, J = 8.0, 5.0 Hz, 1H), 5.29-5.18 (m, 1H), 4.80-4.69 (m, 1H), 4.04-3.94 (m, 1H), 3.91-3.69 (m, 4H), 3.65 (dd, J = 10. 4.5 Hz, 1H), 3.38-3.13 (m, 2H), 2.81 (s, 3H), 2.37-2.22 (m, 1H), 1.98-1.86 (m, 1H), 1.74-1.6 (m, 3H), 1.54-1.39 (m, 2H); 468.0 |
| 115 | Example 114[41]; C73 | 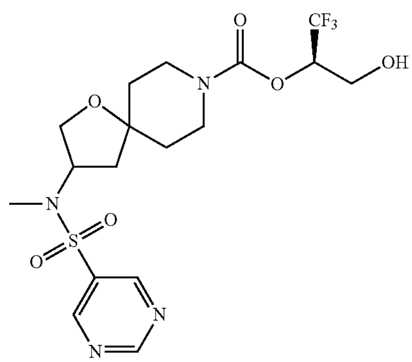 [SMILES: CN(C1COC2(CCN(C(=O)O[C@H](CO)C(F)(F)F)CC2)C1)S(=O)(=O)c1cncnc1] | Mixture of 2 diastereomers; 9.42 (s, 1H), 9.10 (s, 2H), 5.29-5.19 (m, 1H), 4.81-4.71 (m, 1H), 4.04-3.95 (m, 1H), 3.95-3.74 (m, 4H), 3.70 (dd, J = 10.4, 4.6 Hz, 1H), 3.38-3.14 (m, 2H), 2.85 (s, 3H), 2.45-2.22 (br m, 1H), 2.05-1.91 (m, 1H), 1.76-1.6 (m, 3H, assumed; partially obscured by water peak), 1.52 (dd, J = 13.6, 6.5 Hz, 1H), 1.5-1.40 (m, 1H); 469.0 |
| 116 | Example 92[42,43]; C99, C2 | 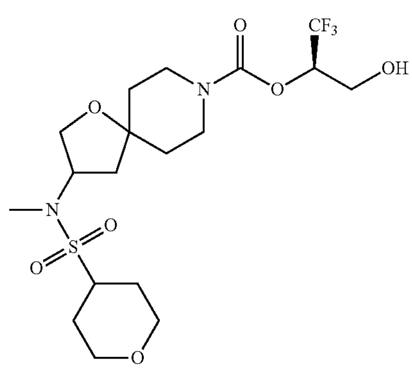 | 5.31-5.20 (m, 1H), 4.70-4.61 (m, 1H), 4.14-4.05 (m, 2H), 4.05-3.92 (m, 2H), 3.92-3.70 (m, 4H), 3.43-3.20 (m, 4H), 3.16-3.05 (m, 1H), 2.89 (s, 3H), 2.44-2.23 (m, 1H), 2.10 (dd, J = 13.3, 9.0 Hz, 1H), 1.98-1.67 (m, 8H), 1.6-1.46 (m, 1H); 475.1 |

[from DIAST-2; see footnote[43]]

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 117 | Example 92[42,43]; C99, C2 | [structure] [from DIAST-1; see footnote[43]] | 5.32-5.20 (m, 1H), 4.70-4.60 (m, 1H), 4.14-4.06 (m, 2H), 4.05-3.92 (m, 2H), 3.92-3.73 (m, 4H), 3.46-3.26 (m, 4H), 3.16-3.06 (m, 1H), 2.89 (s, 3H), 2.41-2.24 (m, 1H), 2.15-2.04 (m, 1H), 1.98-1.68 (m, 8H), 1.6-1.42 (m, 1H); 475.1 |
| 118 | Example 102[44]; C99, C1 | [structure] | Mixture of 2 diastereomers; 3.35 minutes[13]; 458.2 |
| 119 | Example 102[45]; C1 | [structure] | Mixture of 2 diastereomers; 3.25 minutes[13]; 408.2 |
| 120 | Example 97; C107 | [structure] | Mixture of 2 diastereomers; 2.45 minutes[13]; 393.3 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 121 | Example 97; C107 | 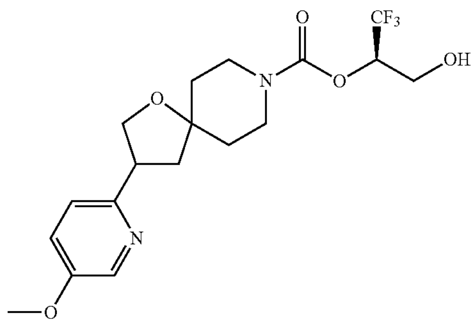 [SMILES: COc1ccc(C2COC3(CCN(C(=O)O[C@H](CO)C(F)(F)F)CC3)C2)nc1] | Mixture of 2 diastereomers; 2.18 minutes[13]; 405.3 |
| 122 | Example 97; C107 | ·CF$_3$COOH | Mixture of 2 diastereomers; 1.40 minutes[13]; 375.1 |
| 123 | Example 97; C107 | ·CF$_3$COOH | Mixture of 2 diastereomers; 2.36 minutes[13]; 389.3 |
| 124 | Example 98; C2 | 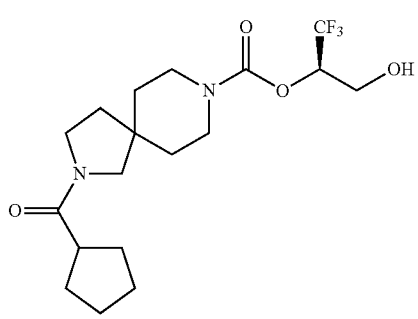 [SMILES: O=C(O[C@H](CO)C(F)(F)F)N1CCC2(CC1)CCN(C(=O)C1CCCC1)C2] | 5.33-5.20 (m, 1H), 4.02-3.91 (m, 1H), 3.89-3.77 (m, 1H), 3.76-3.07 (m, 9H), 2.81-2.66 (m, 1H), 1.90-1.66 (m, 8H), 1.64-1.46 (m, 6H); 392.9 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 125 | Example 105[46]; C2 | 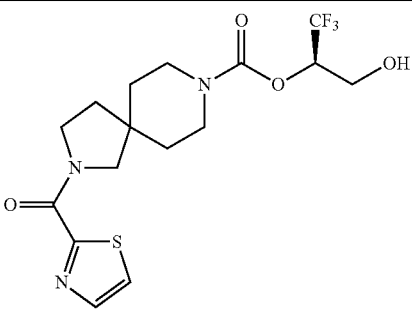 | 2.35 minutes[13]; 408.2 |
| 126 | Example 105[46]; C2 | 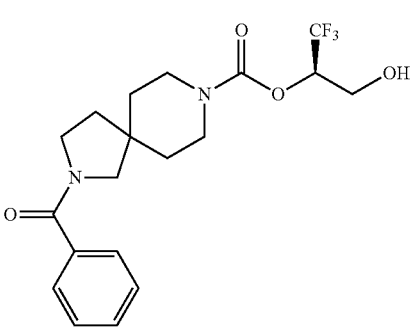 [SMILES: O=C(O[C@H](CO)C(F)(F)F)N1CCC2(CC1)CCN(C(=O)c1ccccc1)C2] | 2.38 minutes[13]; 401.3 |
| 127 | Example 98; C2 | 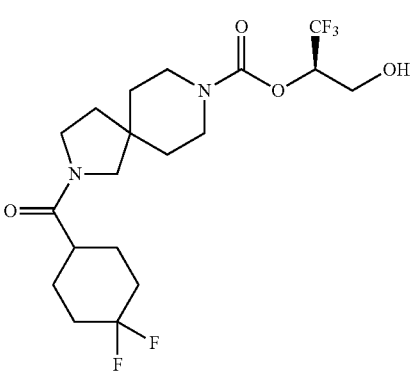 [SMILES: O=C(O[C@H](CO)C(F)(F)F)N1CCC2(CC1)CCN(C(=O)C1CCC(F)(F)CC1)C2] | Characteristic peaks: 5.33-5.20 (m, 1H), 4.05-3.96 (m, 1H), 3.92-3.82 (m, 1H), 3.78-3.24 (m, 8H), 2.47-2.33 (m, 1H), 2.29-2.15 (m, 2H), 1.99-1.65 (m, 9H); 443.0 |
| 128 | Example 105[46]; C2 | 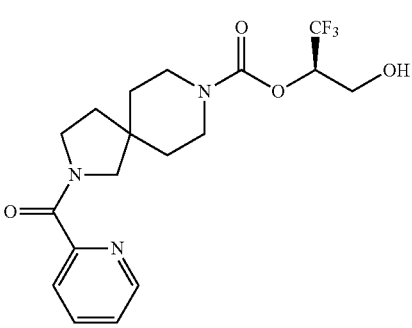 [SMILES: O=C(O[C@H](CO)C(F)(F)F)N1CCC2(CC1)CCN(C(=O)c1ccccn1)C2] | 1.97 minutes[13]; 402.3 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 129 | Example 92[47,48]; C2 | 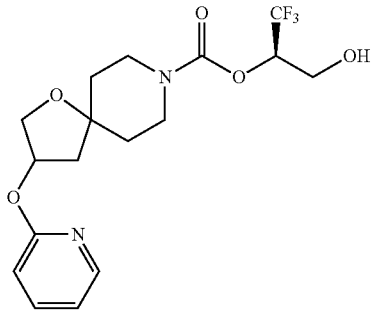<br>DIAST-1 | $^1$H NMR (400 MHz, CD$_3$OD) δ 8.11 (ddd, J = 5.0, 2.0, 0.8 Hz, 1H), 7.67 (ddd, J = 8.4, 7.1, 2.0 Hz, 1H), 6.94 (ddd, J = 7.2, 5.1, 0.9 Hz, 1H), 6.79 (ddd, J = 8.3, 0.9, 0.8 Hz, 1H), 5.55-5.50 (m, 1H), 5.33-5.24 (m, 1H), 4.18 (dd, J = 10.5, 4.6 Hz, 1H), 4.01-3.96 (m, 1H), 3.90-3.84 (m, 1H), 3.84-3.69 (m, 3H), 3.50-3.3 (m, 2H), 2.20 (dd, half of ABX pattern, J = 13.9, 6.8 Hz, 1H), 2.07 (ddd, half of ABXY pattern, J = 14.0, 2.0, 1.1 Hz, 1H), 1.98-1.88 (m, 1H), 1.78-1.62 (m, 3H); 390.9 |
| 130 | Example 92[47,48]; C2 | 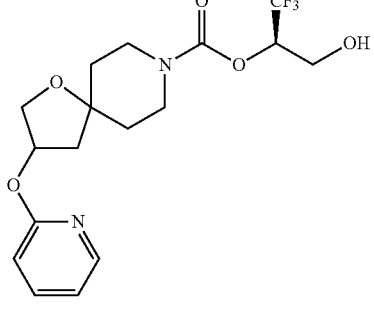<br>DIAST-2 | $^1$H NMR (400 MHz, CD$_3$OD) δ 8.11 (ddd, J = 5.0, 2.0, 0.8 Hz, 1H), 7.67 (ddd, J = 8.5, 7.0, 2.0 Hz, 1H), 6.94 (ddd, J = 7.0, 5.0, 1.0 Hz, 1H), 6.78 (br d, J = 8.5 Hz, 1H), 5.55-5.50 (m, 1H), 5.33-5.24 (m, 1H), 4.18 (dd, J = 10.4, 4.6 Hz, 1H), 3.99 (ddd, J = 10.4, 2.0, 1.1 Hz, 1H), 3.87 (br dd, half of ABX pattern, J = 12.3, 4.0 Hz, 1H), 3.84-3.70 (m, 3H), 3.50-3.33 (m, 2H), 2.20 (dd, half of ABX pattern, J = 13.9, 6.7 Hz, 1H), 2.07 (br d, J = 14.0 Hz, 1H), 1.98-1.85 (m, 1H), 1.81-1.58 (m, 3H); 390.9 |
| 131 | Example 101; C105 | 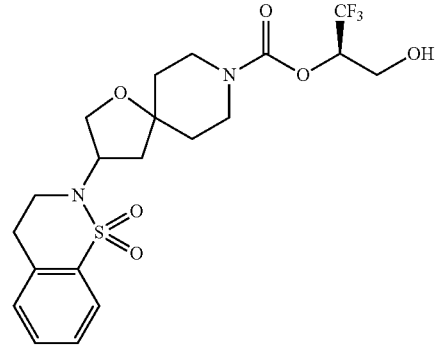 [SMILES: O=C(O[C@H](CO)C(F)(F)F)N1CCC2(CC1)CC(N1CCc3ccccc3S1(=O)=O)CO2] | Mixture of 2 diastereomers; 7.85 (br d, J = 7.8 Hz, 1H), 7.52-7.46 (m, 1H), 7.44-7.38 (m, 1H), 7.29-7.23 (m, 1H, assumed; partially obscured by solvent peak), 5.30-5.19 (m, 1H), 4.59-4.45 (m, 1H), 4.11-3.95 (m, 2H), 3.92-3.68 (m, 6H), 3.46-3.20 (m, 2H), 3.12-3.03 (m, 2H), 2.41-2.24 (m, 1H), 2.21-2.11 (m, 1H), 1.88-1.79 (m, 1H), 1.79-1.64 (m, 3H), 1.6-1.43 (m, 1H, assumed; partially obscured by water peak); 479.2 |
| 132 | Example 102[49]; C1 | 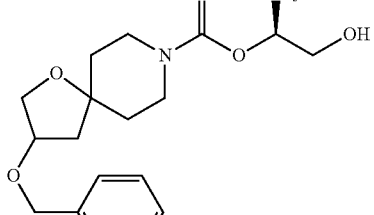 | Mixture of 2 diastereomers; 2.92 minutes[13]; 404.2 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 133 | C2[50,51] | 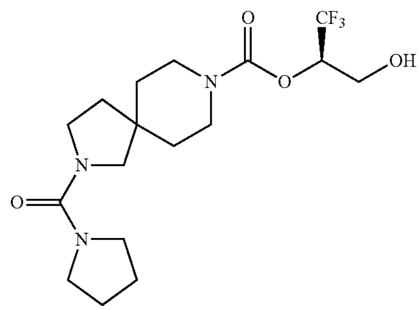 [SMILES: O=C(O[C@H](CO)C(F)(F)F)N1CCC2(CC1)CCN(C(=O)N1CCCC1)C2] | 5.31-5.21 (m, 1H), 3.96 (dd, half of ABX pattern, J = 12.4, 3.4 Hz, 1H), 3.83 (dd, half of ABX pattern, J = 12.3, 6.8 Hz, 1H), 3.66-3.29 (m, 10H), 3.29-3.22 (br s, 2H), 1.87-1.77 (m, 4H), 1.74 (dd, J = 7.3, 7.0 Hz, 2H), 1.62-1.47 (m, 4H); 394.1 |
| 134 | Example 6[50] | 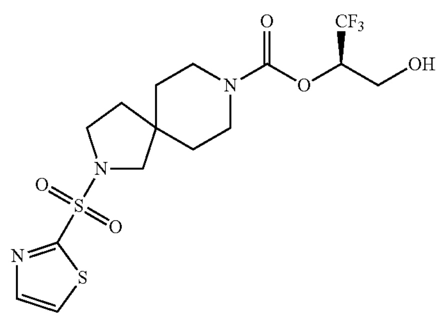 [SMILES: O=C(O[C@H](CO)C(F)(F)F)N1CCC2(CC1)CCN(S(=O)(=O)c1nccs1)C2] | 8.00 (d, J = 3.0 Hz, 1H), 7.66 (d, J = 3.0 Hz, 1H), 5.29-5.19 (m, 1H), 4.03-3.94 (m, 1H), 3.90-3.80 (m, 1H), 3.67-3.47 (m, 4H), 3.45-3.18 (m, 4H), 2.58-2.43 (br s, 1H), 1.79 (dd, J = 7.0, 7.0 Hz, 2H), 1.51-1.37 (m, 4H); 443.8 |
| 135 | Example 6[50] | 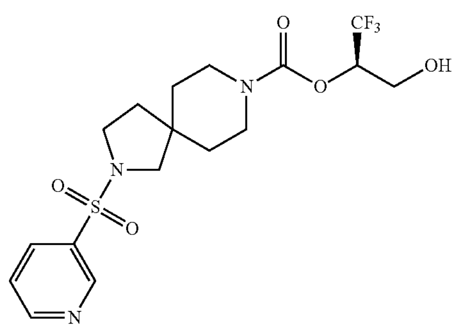 [SMILES: O=C(O[C@H](CO)C(F)(F)F)N1CCC2(CC1)CCN(S(=O)(=O)c1cccnc1)C2] | 9.09-9.05 (br s, 1H), 8.85 (d, J = 4.5 Hz, 1H), 8.13 (br d, J = 8.0 Hz, 1H), 7.52 (dd, J = 7.9, 4.9 Hz, 1H), 5.29-5.20 (m, 1H), 3.99 (br dd, half of ABX pattern, J = 12.5, 3 Hz, 1H), 3.85 (br dd, half of ABX pattern, J = 12, 7 Hz, 1H), 3.59-3.25 (m, 6H), 3.21-3.11 (m, 2H), 2.47-2.30 (br s, 1H), 1.74 (dd, J = 7.0, 7.0 Hz, 2H), 1.47-1.39 (m, 4H); 437.9 |
| 136 | Example 106; C125 | 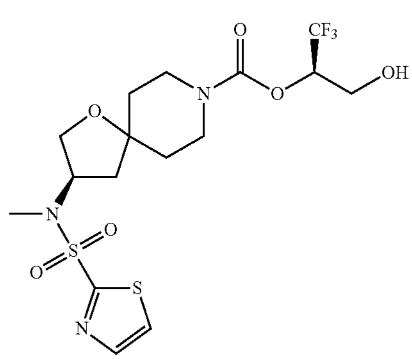 [SMILES: CN([C@H]1COC2(CCN(C(=O)O[C@H](CO)C(F)(F)F)CC2)C1)S(=O)(=O)c1nccs1] | 7.98 (d, J = 3.0 Hz, 1H), 7.65 (d, J = 3.0 Hz, 1H), 5.30-5.19 (m, 1H), 4.94-4.84 (m, 1H), 4.04-3.95 (m, 1H), 3.92 (dd, half of ABX pattern, J = 10.4, 7.4 Hz, 1H), 3.91-3.71 (m, 4H), 3.42-3.21 (m, 2H), 2.95 (s, 3H), 2.10-1.97 (m, 1H), 1.7-1.37 (m, 5H, assumed; partially obscured by water peak); 474.0 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 137 | Example 106; C125 | 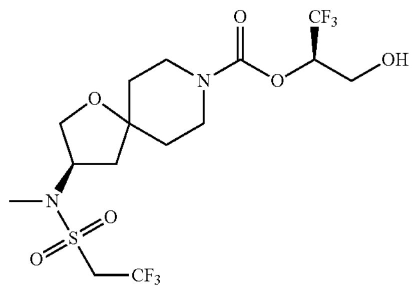 [SMILES: CN([C@H]1COC2(CCN(C(=O)O[C@H](CO)C(F)(F)F)CC2)C1)S(=O)(=O)CC(F)(F)F] | 5.32-5.20 (m, 1H), 4.75-4.65 (m, 1H), 4.05-3.93 (m, 2H), 3.93-3.7 (m, 4H), 3.74 (q, J$_{HF}$ = 9.3 Hz, 2H), 3.45-3.23 (m, 2H), 2.93 (s, 3H), 2.19-2.07 (m, 1H), 1.84-1.67 (m, 4H), 1.57-1.41 (m, 1H); 473.2 |
| 138 | Example 106; C125 | 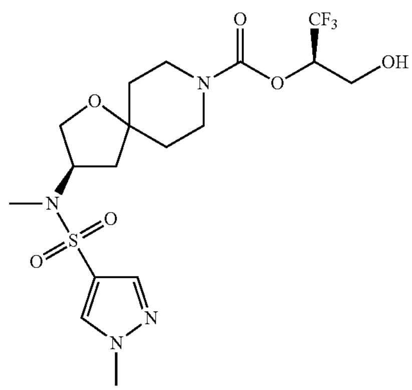 [SMILES: CN([C@H]1COC2(CCN(C(=O)O[C@H](CO)C(F)(F)F)CC2)C1)S(=O)(=O)c1cnn(C)c1] | 7.76 (s, 1H), 7.70 (s, 1H), 5.30-5.18 (m, 1H), 4.66-4.54 (m, 1H), 4.03-3.93 (m, 1H), 3.96 (s, 3H), 3.88-3.71 (m, 3H), 3.87 (dd, half of ABX pattern, J = 10.2, 7.4 Hz, 1H), 3.67 (br dd, half of ABX pattern, J = 10.2, 5.1 Hz, 1H), 3.40-3.19 (m, 2H), 2.74 (s, 3H), 2.69-2.52 (m, 1H), 2.01-1.88 (m, 1H), 1.82-1.63 (m, 3H, assumed; partially obscured by water peak), 1.58 (dd, J = 13.3, 7.0 Hz, 1H), 1.51-1.36 (m, 1H); 471.2 |
| 139 | Example 106; C125 | 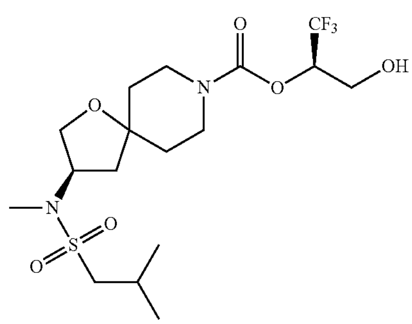 [SMILES: CC(C)CS(=O)(=O)N(C)[C@H]1COC2(CCN(C(=O)O[C@H](CO)C(F)(F)F)CC2)C1] | 5.31-5.19 (m, 1H), 4.70-4.59 (m, 1H), 4.03-3.90 (m, 2H), 3.90-3.70 (m, 4H), 3.45-3.23 (m, 2H), 2.82 (s, 3H), 2.75 (br d, J = 6.5 Hz, 2H), 2.73-2.64 (m, 1H), 2.30-2.16 (m, 1H), 2.12-2.00 (m, 1H), 1.80-1.66 (m, 4H), 1.55-1.40 (m, 1H), 1.09 (br d, J = 6.8 Hz, 6H); 447.3 |
| 140 | Example 106; C125 | 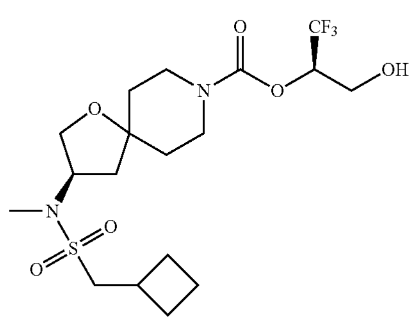 [SMILES: CN([C@H]1COC2(CCN(C(=O)O[C@H](CO)C(F)(F)F)CC2)C1)S(=O)(=O)CC1CCC1] | 5.31-5.19 (m, 1H), 4.67-4.56 (m, 1H), 4.03-3.90 (m, 2H), 3.90-3.70 (m, 4H), 3.45-3.24 (m, 2H), 2.99 (br d, J = 7.5 Hz, 2H), 2.84-2.70 (m, 1H), 2.81 (s, 3H), 2.69-2.58 (m, 1H), 2.25-2.14 (m, 2H), 2.12-2.01 (m, 1H), 2.01-1.91 (m, 1H), 1.91-1.79 (m, 3H), 1.79-1.66 (m, 4H), 1.55-1.40 (m, 1H); 459.2 |

TABLE 6A-continued
Method of synthesis, structure, and physicochemical properties for Examples 107-150.
| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 141 | C125[52] | 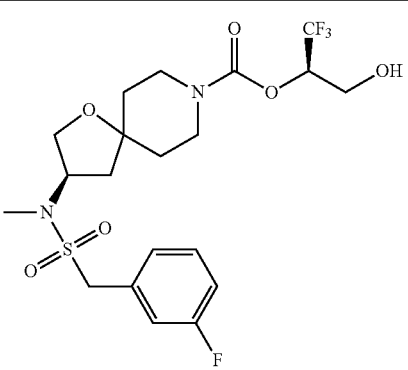 | 2.82 minutes[26]; 449 |
| 142 | C125[52] | 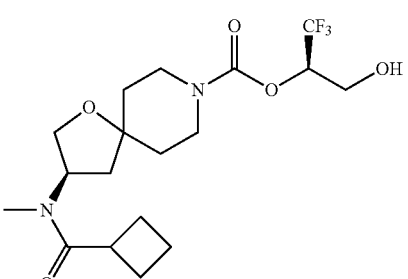 | 2.47 minutes[53]; 409 |
| 143 | C125[52] | 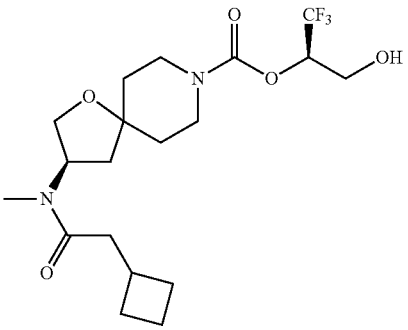 [SMILES: CN(C(=O)CC1CCC1)[C@H]1COC2(CCN(C(=O)O[C@H](CO)C(F)(F)F)CC2)C1] | 2.86 minutes[26]; 423 |
| 144 | C125[52] | 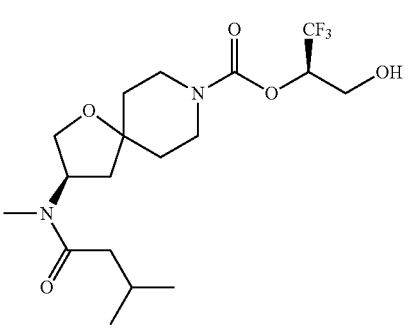 [SMILES: CC(C)CC(=O)N(C)[C@H]1COC2(CCN(C(=O)O[C@H](CO)C(F)(F)F)CC2)C1] | 2.80 minutes[26]; 411 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 145 | C125[52] | 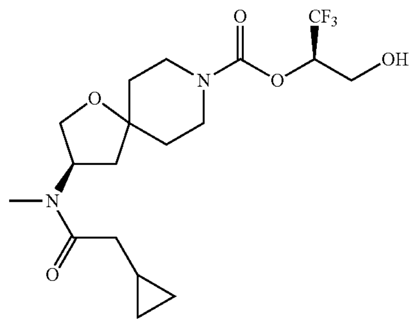 [SMILES: CN(C(=O)CC1CC1)[C@H]1COC2(CCN(C(=O)O[C@H](CO)C(F)(F)F)CC2)C1] | 2.44 minutes[53]; 409 |
| 146 | C125[52] | 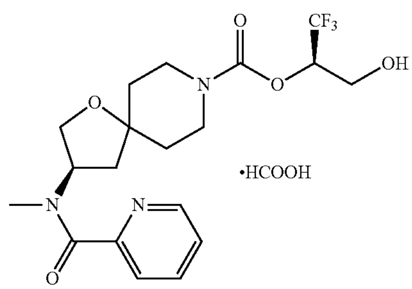 [SMILES: CN(C(=O)c1ccccn1)[C@H]1COC2(CCN(C(=O)O[C@H](CO)C(F)(F)F)CC2)C1 ; "·HCOOH"] | 2.26 minutes[53]; 432 |
| 147 | Example 97; C107 | 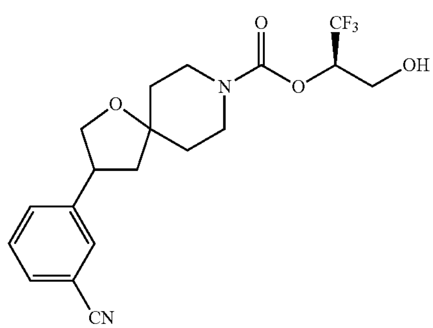 | Mixture of 2 diastereomers; 2.77 minutes[13]; 399.3 |
| 148 | Example 33[54,55]; C79 | 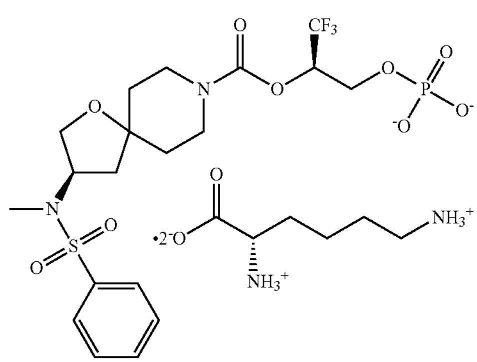 | $^1$H NMR (400 MHz, D$_2$O), characteristic peaks: δ 7.84 (br d, J = 7.6 Hz, 2H), 7.76-7.69 (m, 1H), 7.63 (br dd, half of ABX pattern, J = 7.8, 7.6 Hz, 2H), 5.44-5.34 (m, 1H), 4.10-4.01 (m, 1H), 4.00-3.90 (m, 1H), 3.90-3.81 (m, 1H), 3.70 (t, J = 6.0 Hz, 2H), 3.65-3.22 (m, 5H), 2.98 (dd, J = 7.6, 7.4 Hz, 4H), 2.76 (s, 3H), 1.95 (dd, J = 13.7, 9.2 Hz, 1H), 1.91-1.81 (m, 4H), 1.74-1.62 (m, 7H), 1.54-1.33 (m, 6H); 547.3 |

TABLE 6A-continued

Method of synthesis, structure, and physicochemical properties for Examples 107-150.

| Example Number | Method of Synthesis; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 149 | Example 33[56,57]; Example 91 | 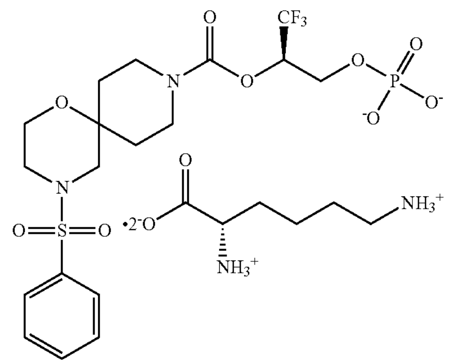 | $^1$H NMR (400 MHz, D$_2$O) δ 7.83-7.78 (m, 2H), 7.77-7.72 (m, 1H), 7.65 (br dd, J = 7.8, 7.4 Hz, 2H), 5.47-5.37 (m, 1H), 4.13-4.05 (m, 1H), 4.02-3.93 (m, 1H), 3.93-3.79 (m, 1H), 3.83 (br dd, J = 5.1, 4.9 Hz, 2H), 3.78-3.63 (m, 1H), 3.71 (t, J = 6.1 Hz, 2H), 3.36-3.13 (m, 2H), 3.11-3.0 (m, 2H), 2.99 (dd, J = 7.6, 7.4 Hz, 4H), 2.95-2.86 (m, 2H), 2.00-1.82 (m, 6H), 1.74-1.64 (m, 6H), 1.53-1.34 (m, 4H); 533.1 |
| 150 | Example 33[58,59]; C125 | 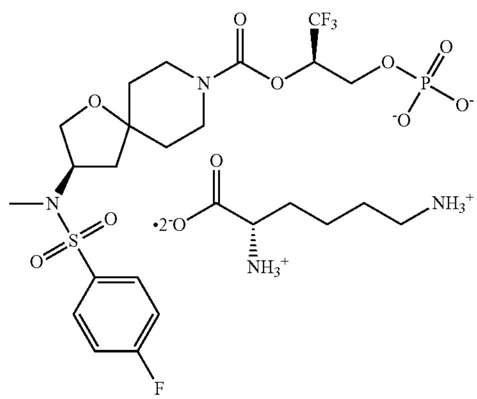 | $^1$H NMR (400 MHz, D$_2$O), characteristic peaks: δ 7.92-7.85 (m, 2H), 7.35 (br dd, J = 8.9, 8.8 Hz, 2H), 5.44-5.35 (m, 1H), 4.78-4.66 (m, 1H, assumed; partially obscured by solvent peak), 4.10-4.02 (m, 1H), 3.99-3.91 (m, 1H), 3.87 (dd, J = 10.0, 7.9 Hz, 1H), 3.68 (t, J = 6.1 Hz, 2H), 3.67-3.60 (m, 2H), 2.98 (dd, J = 7.7, 7.5 Hz, 4H), 2.77 (s, 3H), 1.97 (dd, J = 13.5, 9.3 Hz, 1H), 1.91-1.79 (m, 5H), 1.73-1.63 (m, 5H), 1.55-1.33 (m, 7H); 565.3 |

35. Intermediate tert-butyl (3R)-3-[(phenylsulfonyl)(propan-2-yl)amino]-1-oxa-8-azaspiro[4.5]decane-8-carboxylate was synthesized via a Mitsunobu reaction between C48 and 2-propanol.

36. Prior to the final deprotection, intermediate (2R)-1,1,1-trifluoro-3-[(4-methoxybenzyl)oxy]propan-2-yl 3-{[(3-fluorophenyl)sulfonyl]amino}-1-oxa-8-azaspiro[4.5]decane-8-carboxylate was deprotonated with potassium tert-butoxide and methylated with dimethyl sulfate to afford (2R)-1,1,1-trifluoro-3-[(4-methoxybenzyl)oxy]propan-2-yl 3-{[(3-fluorophenyl)sulfonyl](methyl)amino}-1-oxa-8-azaspiro[4.5]decane-8-carboxylate.

37. Examples 108 and 109 were synthesized as a mixture and separated into the component diastereomers using supercritical fluid chromatography (Column: Phenomenex Lux Amylose-2, 5 μm; Mobile phase: 87.5:12.5 carbon dioxide/2-propanol). Example 108 was the first-eluting diastereomer, and Example 109 was the second-eluting diastereomer.

38. Examples 110 and 111 were synthesized as a mixture and separated into the component diastereomers using supercritical fluid chromatography (Column: Phenomenex Lux Amylose-2, 5 μm; Mobile phase: 85:15 carbon dioxide/2-propanol). Example 110 was the first-eluting diastereomer, and Example 111 was the second-eluting diastereomer.

39. In this case, the 2 diastereomers of the product were not separated.

40. Prior to the final deprotection, intermediate (2R)-1,1,1-trifluoro-3-[(4-methoxybenzyl)oxy]propan-2-yl 3-[(pyridin-3-ylsulfonyl)amino]-1-oxa-8-azaspiro[4.5]decane-8-carboxylate was deprotonated with sodium bis(trimethylsilyl)amide and methylated with iodomethane, affording (2R)-1,1,1-trifluoro-3-[(4-methoxybenzyl)oxy]propan-2-yl 3-[methyl(pyridin-3-ylsulfonyl)amino]-1-oxa-8-azaspiro[4.5]decane-8-carboxylate.

41. In this case, the sulfonylation of C73 was effected using pyridine in tetrahydrofuran, rather than aqueous sodium bicarbonate in dichloromethane.

42. The requisite tert-butyl 3-[methyl(tetrahydro-2H-pyran-4-ylsulfonyl)amino]-1-oxa-8-azaspiro[4.5]decane-8-carboxylate was synthesized via potassium carbonate-mediated reaction of C99 with tetrahydro-2H-pyran-4-sulfonamide. The resulting tert-butyl 3-[(tetrahydro-2H-pyran-4-ylsulfonyl)amino]-1-oxa-8-azaspiro[4.5]decane-8-carboxylate was then methylated using sodium hydride and iodomethane.

43. Prior to the final deprotection, intermediate (2R)-1,1,1-trifluoro-3-[(4-methoxybenzyl)oxy]propan-2-yl 3-[methyl(tetrahydro-2H-pyran-4-ylsulfonyl)amino]-1-oxa-8-azaspiro[4.5]decane-8-carboxylate was separated into its component diastereomers via supercritical fluid chromatography (Column: Chiral Technologies Chiralcel OD, 5 μm; Mobile phase A: carbon dioxide; Mobile phase B: 0.1% ammonium hydroxide in 2-propanol; Gradient: 30% to 35% B). The first-eluting diastereomer was assigned as DIAST-1, and the second-eluting diastereomer as DIAST-2.

44. Reaction of C99 with [3-(trifluoromethoxy)phenyl]boronic acid was carried out using the method described for synthesis of the mixture of C100 and C101 from C99 in Example 95. The product was deprotected with hydrogen chloride in 1,4-dioxane and dichloromethane to afford the requisite 3-[3-(trifluoromethoxy)phenyl]-1-oxa-8-azaspiro [4.5]decane, hydrochloride salt.

45. Reaction of tert-butyl 3-oxo-1-oxa-8-azaspiro[4.5]decane-8-carboxylate with 3-chlorophenylmagnesium bromide provided tert-butyl 3-(3-chlorophenyl)-3-hydroxy-1-oxa-8-azaspiro[4.5]decane-8-carboxylate. This was subjected to triethylsilane, boron trifluoride diethyl etherate and trifluoroacetic acid, providing partial deoxygenation, followed by hydrogenation in methanol and acetic acid, to afford 3-(3-chlorophenyl)-1-oxa-8-azaspiro[4.5]decane.

46. In this case, the first step was an amide formation, rather than a sulfonamide formation. tert-Butyl 2,8-diazaspiro[4.5]decane-8-carboxylate was reacted with the appropriate carboxylic acid using 2-[2-oxo-1(2H)-pyridyl]-1,1,3,3-tetramethyluronium tetrafluoroborate (TPTU) and N,N-diisopropylethylamine in N,N-dimethylformamide.

47. tert-Butyl 3-hydroxy-1-oxa-8-azaspiro[4.5]decane-8-carboxylate was deprotonated with potassium tert-butoxide and reacted with 2-chloropyridine to afford the requisite tert-butyl 3-(pyridin-2-yloxy)-1-oxa-8-azaspiro[4.5]decane-8-carboxylate.

48. The mixture of Examples 129 and 130 was separated into its component diastereomers using reversed phase HPLC (Column: Phenomenex Luna C18, 5 μm; Mobile phase A: water containing 0.225% formic acid; Mobile phase B: acetonitrile; Gradient: 25% to 45% B). The first-eluting diastereomer was Example 129, and the second-eluting diastereomer was Example 130.

49. Reaction of tert-butyl 3-hydroxy-1-oxa-8-azaspiro[4.5]decane-8-carboxylate with sodium hydride and benzyl bromide afforded tert-butyl 3-(benzyloxy)-1-oxa-8-azaspiro[4.5]decane-8-carboxylate, which was deprotected with hydrochloric acid to provide the requisite 3-(benzyloxy)-1-oxa-8-azaspiro[4.5]decane.

50. tert-Butyl 2,8-diazaspiro[4.5]decane-8-carboxylate was converted to (2R)-1,1,1-trifluoro-3-[(4-methoxybenzyl)oxy] propan-2-yl 2,8-diazaspiro[4.5]decane-8-carboxylate using the method described for synthesis of C73 from tert-butyl 3-amino-1-oxa-8-azaspiro[4.5]decane-8-carboxylate in Example 27. In this case, the palladium catalyst employed for the final step was tetrakis(triphenylphosphine)palladium (0).

51. Reaction of (2R)-1,1,1-trifluoro-3-[(4-methoxybenzyl) oxy]propan-2-yl 2,8-diazaspiro[4.5]decane-8-carboxylate (see footnote 50) with 4-nitrophenyl pyrrolidine-1-carboxylate (see E. Bridgeman and N. C. O. Tomkinson, Synlett 2006, 243-246) in the presence of N,N-diisopropylethylamine provided (2R)-1,1,1-trifluoro-3-[(4-methoxybenzyl)oxy] propan-2-yl 2-(pyrrolidin-1-ylcarbonyl)-2,8-diazaspiro[4.5] decane-8-carboxylate, which was deprotected with trifluoroacetic acid to afford Example 133.

52. Compound C125 was reacted with the appropriate carboxylic acid using 2,4,6-tripropyl-1,3,5,2,4,6-trioxatriphosphinane 2,4,6-trioxide and N,N-diisopropylethylamine in 1,4-dioxane. The resulting product was deprotected with trifluoroacetic acid to afford the Example.

53. Conditions for analytical HPLC. Column: Waters XBridge C18, 2.1×50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute.

54. In this case, C79 was synthesized from C50, via deprotection with p-toluenesulfonic acid and conversion of the resulting amine to C79 using the method described for synthesis of C84 from C85 in Alternate Synthesis of Example 32.

55. In this case, the final product did not precipitate out of the reaction mixture. The reaction mixture was therefore concentrated in vacuo; the residue was dissolved in hot methanol, filtered, concentrated under reduced pressure, and crystallized from methanol/tert-butyl methyl ether to afford Example 148.

56. An aqueous solution of Example 91 was acidified with concentrated hydrochloric acid at 0° C. After 30 minutes at room temperature, the reaction mixture was extracted three times with ethyl acetate, and the combined organic layers were washed with saturated aqueous sodium chloride solution, dried over sodium sulfate, filtered, and concentrated in vacuo to afford the requisite (neutral) phosphate of Example 91.

57. In this case, the final product did not precipitate out of the reaction mixture. The reaction mixture was therefore concentrated in vacuo; the residue was dissolved in hot methanol, cooled to 0° C. and treated with tert-butyl methyl ether. Filtration afforded Example 149.

58. Using the method described in Example 11, C125 was converted to (2R)-1,1,1-trifluoro-3-hydroxypropan-2-yl (3R)-3-{[(4-fluorophenyl)sulfonyl](methyl)amino}-1-oxa-8-azaspiro[4.5]decane-8-carboxylate. Phosphate formation, using the chemistry employed for conversion of 15 to C79 in Example 30, then provided the requisite (2R)-1,1,1-trifluoro-3-(phosphonooxy)propan-2-yl (3R)-3-{[(4-fluorophenyl)sulfonyl](methyl)amino}-1-oxa-8-azaspiro[4.5]decane-8-carboxylate.

59. In this case, after the reaction mixture had been heated at 40° C., it was slowly treated with tert-butyl methyl ether (3 mL). After the suspension had cooled to room temperature and then to 0° C., it was filtered to afford Example 150.

Example AA: MAGL and FAAH Enzymatic Assays

Assessment of MAGL inhibition utilizes human recombinant Monoacylglycerol Lipase and the fluorogenic substrate 7-hydroxycoumarinyl arachidonate (7-HCA, Biomol ST-502). 400 nL of a test compound at decreasing concentration (ranging from 150 μM down to 1.5 nM) was spotted into a 384-well back plate (PerkinElmer, 6007279) using a Labcyte Echo, followed by addition of 10 μL of MAGL enzyme in assay buffer (50 mM HEPES, pH 7.4, 100 mM NaCl, 5 mM $MgCl_2$, 0.1% Triton X-100 and 25% glycerin). An equal volume of 7-HCA in assay buffer with 10% DMSO was added either immediately (T=0 min) or after a 30 minute incubation (T=min) to initiate the reaction. The final concentration of MAGL enzyme was 88 μM and 7-HCA substrate was 5 μM. After these dilutions, the final concentration of the test compound ranged from 3 μM to 0.03 nM. The reaction was allowed to progress for 60 minutes, after which the plate was read at an Ex/Em of 340/465. Percent inhibitions were calculated based on control wells containing no compound (0% inhibition) and a control compound (e.g., a MAGL inhibitor whose activity is known or was previously reported in the literature, such as one with about 100% inhibition). $IC_{50}$ values were generated based on a four parameter fit model using ABASE software from IDBS. See e.g., Wang, Y. et al., "A Fluorescence-Based Assay for Monoacylglycerol Lipase Compatible with Inhibitor Screening," *Assay and Drug Development Technologies*, 2008, Vol. 6 (3) pp 387-393 (reporting an assay for measuring MAGL activity).

To measure MAGL inactivation, the same protocol for the (T=0 min) MAGL inhibition $IC_{50}$ assay was performed with data collected every minute to acquire enzyme progress curves at decreasing concentrations of compound. $K_{obs}$ values were calculated from this data and $k_{inact}/K_I$ ratios were determined from a plot of $K_{obs}$ values vs. compound concentrations.

Assessment of FAAH inhibition utilizes human recombinant FAAH and the fluorescent substrate, Arachidonoyl-AMC. 400 nL of a test compound at decreasing concentrations was spotted into a 384-well back plate (PerkinElmer, 6007279) using a Labcyte Echo, followed by addition of 10 µl of FAAH enzyme (Cayman 10010183) in assay buffer (50 mM Tris, pH 9.0, 1 mM EDTA). After a 30 minute incubation at room temperature, 10 µL of Arachidonyl-AMCA was added in assay buffer with 16% DMSO. Final concentration of FAAH enzyme was 0.0125 Units and AAMCA substrate was used at the $K_m$ of 5 µM. After these dilutions, the final concentration of the test compound ranged from 3 µM to 0.03 nM. The reaction was allowed to progress for 60 minutes, after which the plate was read on a Molecular Devices FlexStation reader at an Ex/Em of 355/460. Percent inhibitions were calculated based on controls wells containing either no compound (0% inhibition) or a control compound (e.g., an FAAH inhibitor whose activity is known or was previously reported in the literature, such as one with about 100% inhibition). $IC_{50}$ values were generated based on a four parameter fit model using ABASE software from IDBS.

TABLE AA-1

Biological Data (MAGL $IC_{50}$, FAAH $IC_{50}$, and MAGL $k_{inact}/K_I$) for Examples 1-150.

| Example Number | Compound Name | MAGL (T = 0 min) $IC_{50}$ (µM)$^a$ | MAGL (T = 30 min) $IC_{50}$ (µM)$^a$ | FAAH (T = 30 min) $IC_{50}$ (µM)$^a$ | MAGL $k_{inact}/K_I$ (1/s per M)$^a$ |
|---|---|---|---|---|---|
| 1 | (2R)-1,1,1-trifluoro-3-hydroxypropan-2-yl (1α,5α,6α)-6-[1-(5-methoxypyridin-2-yl)-1H-pyrazol-3-yl]-3-azabicyclo[3.1.0]hexane-3-carboxylate | 0.085 | 0.014 | N.D.$^b$ | 7806 |
| 2 | (2R)-1,1,1-trifluoro-3-hydroxypropan-2-yl 4-[1-(4-fluorophenyl)-1H-pyrazol-3-yl]piperidine-1-carboxylate | 0.056 | 0.008 | 1.14$^d$ | 6109 |
| 3 | (2R)-1,1,1-trifluoro-3-hydroxypropan-2-yl (1α,5α,6α)-6-[1-(4-fluorophenyl)-1H-pyrazol-3-yl]-3-azabicyclo[3.1.0]hexane-3-carboxylate | 0.035 | 0.003 | 2.48 | 20005 |
| 4 | (2R)-1,1,1-trifluoro-3-hydroxypropan-2-yl 4-(tetrahydro-2H-pyran-3-ylmethyl)-1-oxa-4,9-diazaspiro[5.5]undecane-9-carboxylate [from C25, DIAST-1] | 0.166$^d$ | 0.019$^d$ | N.D. | 5489 |
| 5 | (2R)-1,1,1-trifluoro-3-hydroxypropan-2-yl 4-(tetrahydro-2H-pyran-3-ylmethyl)-1-oxa-4,9-diazaspiro[5.5]undecane-9-carboxylate [from C26, DIAST-2] | 1.70$^d$ | 0.161$^d$ | N.D. | N.D. |
| 6 | (2R)-1,1,1-trifluoro-3-hydroxypropan-2-yl 4-[(4-fluorophenyl)sulfonyl]-1-oxa-4,9-diazaspiro[5.5]undecane-9-carboxylate | 0.083$^c$ | 0.007$^c$ | >30.0$^d$ | 13406 |
| 7 | (2R)-1,1,1-trifluoro-3-hydroxypropan-2-yl 4-(phenylsulfonyl)-1-oxa-4,9-diazaspiro[5.5]undecane-9-carboxylate | 0.029$^c$ | 0.003$^c$ | >24.1 | 29124 |
| 8 | (2R)-1,1,1-trifluoro-3-hydroxypropan-2-yl (3S)-3-[(phenylsulfonyl)amino]-1-oxa-8-azaspiro[4.5]decane-8-carboxylate | 0.057 | 0.005 | >30.0$^d$ | 6754 |
| 9 | (2R)-1,1,1-trifluoro-3-hydroxypropan-2-yl (3R)-3-[(phenylsulfonyl)amino]-1-oxa-8-azaspiro[4.5]decane-8-carboxylate | 0.040 | 0.004 | >30.0$^d$ | 8588 |
| 10 | (2R)-1,1,1-trifluoro-3-hydroxypropan-2-yl 4-[(5-cyclopropylpyridin-2-yl)oxy]piperidine-1-carboxylate | 0.077$^c$ | 0.007$^c$ | >30.0$^d$ | 5205 |
| 11 | (2R)-1,1,1-trifluoro-3-hydroxypropan-2-yl 4-[(3-fluorophenyl)sulfonyl]-1-oxa-4,9-diazaspiro[5.5]undecane-9-carboxylate | 0.014 | 0.001 | >30.0$^d$ | 147964 |
| 12 | (2R)-1,1,1-trifluoro-3-hydroxypropan-2-yl 2-[(4-fluorophenyl)sulfonyl]-2,9-diazaspiro[5.5]undecane-9-carboxylate | 0.188 | 0.017 | >30.0$^d$ | 1801 |
| 13 | (2R)-1,1,1-trifluoro-3-hydroxypropan-2-yl (3aR,6aS)-5-[(3,4-difluorophenyl)sulfonyl]hexahydropyrrolo[3,4-c]pyrrole-2(1H)-carboxylate | 0.368 | 0.035 | N.D. | N.D. |
| 14 | (2R)-1,1,1-trifluoro-3-hydroxypropan-2-yl 4-(5-fluoropyridin-2-yl)-1-oxa-4,9-diazaspiro[5.5]undecane-9-carboxylate | 0.485 | 0.045 | N.D. | N.D. |
| 15 | (2R)-1,1,1-trifluoro-3-hydroxypropan-2-yl (3R)-3-[methyl(phenylsulfonyl)amino]-1-oxa-8-azaspiro[4.5]decane-8-carboxylate | 0.017 | 0.002 | N.D. | 44421 |

TABLE AA-1-continued

Biological Data (MAGL $IC_{50}$, FAAH $IC_{50}$, and MAGL $k_{inact}/K_I$) for Examples 1-150.

| Example Number | Compound Name | MAGL (T = 0 min) $IC_{50}$ (µM)$^a$ | MAGL (T = 30 min) $IC_{50}$ (µM)$^a$ | FAAH (T = 30 min) $IC_{50}$ (µM)$^a$ | MAGL $k_{inact}/K_I$ (1/s per M)$^a$ |
|---|---|---|---|---|---|
| 16 | (2R)-1,1,1-trifluoro-3-hydroxypropan-2-yl 4-hydroxy-4-{[(phenylsulfonyl)amino]methyl}piperidine-1-carboxylate | 1.84 | 0.161 | N.D. | N.D. |
| 17 | (2R)-1,1,1-trifluoro-3-hydroxypropan-2-yl 4-(4-fluorobenzyl)-3-oxo-1-oxa-4,9-diazaspiro[5.5]undecane-9-carboxylate | 0.951 | 0.110 | N.D. | N.D. |
| 18 | (2R)-1,1,1-trifluoro-3-hydroxypropan-2-yl 2-ethyl-4-[(4-fluorophenyl)sulfonyl]-1-oxa-4,9-diazaspiro[5.5]undecane-9-carboxylate | 0.524 | 0.049 | N.D. | N.D. |
| 19 | 1,1,1,3,3-pentafluoro-4-hydroxybutan-2-yl 4-[(4-fluorophenyl)sulfonyl]-1-oxa-4,9-diazaspiro[5.5]undecane-9-carboxylate | 0.095 | 0.008 | >30.0$^d$ | 2397 |
| 20 | 1,1,1,3,3-pentafluoro-4-hydroxybutan-2-yl 4-[(4-fluorophenyl)sulfonyl]-1-oxa-4,9-diazaspiro[5.5]undecane-9-carboxylate, ENT-1 | 0.061 | 0.006 | >30.0$^d$ | 4611 |
| 21 | 1,1,1,3,3-pentafluoro-4-hydroxybutan-2-yl 4-[(4-fluorophenyl)sulfonyl]-1-oxa-4,9-diazaspiro[5.5]undecane-9-carboxylate, ENT-2 | 0.599 | 0.053 | N.D. | N.D. |
| 22 | (2R)-1,1,1-trifluoro-3-hydroxypropan-2-yl 4-(morpholin-4-ylsulfonyl)-1-oxa-4,9-diazaspiro[5.5]undecane-9-carboxylate | 2.638 | 0.192 | N.D. | N.D. |
| 23 | (2R)-1,1,1-trifluoro-3-hydroxypropan-2-yl 3-(4-fluorobenzyl)-3,8-diazabicyclo[3.2.1]octane-8-carboxylate | >1.52 | 0.078 | N.D. | N.D. |
| 24 | (2R)-1,1,1-trifluoro-3-hydroxypropan-2-yl 4-hydroxy-4-{[methyl(phenylsulfonyl)amino]methyl}piperidine-1-carboxylate | 1.90$^d$ | 0.195$^d$ | N.D. | N.D. |
| 25 | (2R)-1,1,1-trifluoro-3-hydroxypropan-2-yl 4-(4-fluorobenzyl)piperazine-1-carboxylate | 0.794$^d$ | 0.071$^d$ | N.D. | N.D. |
| 26 | (2R)-1,1,1-trifluoro-3-hydroxypropan-2-yl 4-(isoquinolin-1-yloxy)piperidine-1-carboxylate, trifluoroacetic acid salt | 0.031 | 0.002 | 7.73$^d$ | 16949 |
| 27 | (2R)-1,1,1-trifluoro-3-hydroxypropan-2-yl 3-(pyridin-2-ylamino)-1-oxa-8-azaspiro[4.5]decane-8-carboxylate | 0.484 | 0.043 | N.D. | N.D. |
| 28 | (2R)-1,1,1-trifluoro-3-hydroxypropan-2-yl 4-(4-fluorobenzyl)-1-oxa-3-thia-4,9-diazaspiro[5.5]undecane-9-carboxylate 3,3-dioxide | 0.696 | 0.085 | N.D. | N.D. |
| 29 | (2R)-1,1,1-trifluoro-3-hydroxypropan-2-yl 4-[(4-fluorophenyl)sulfonyl]-3-hydroxy-1-oxa-4,9-diazaspiro[5.5]undecane-9-carboxylate | 0.109$^c$ | 0.024$^c$ | N.D. | 85270 |
| 30 | (2R)-3,3,3-trifluoro-2-[({(3R)-3-[methyl(phenylsulfonyl)amino]-1-oxa-8-azaspiro[4.5]dec-8-yl}carbonyl)oxy]propyl phosphate, disodium salt | >3.00$^{d,e}$ | 0.549$^e$ | N.D. | N.D. |
| 31 | (2R)-3,3,3-trifluoro-2-[({(3R)-3-[(phenylsulfonyl)amino]-1-oxa-8-azaspiro[4.5]dec-8-yl}carbonyl)oxy]propyl phosphate disodium salt | >3.00$^d$ | >3.00$^d$ | N.D. | N.D. |
| 32 | (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, disodium salt | >3.00$^{d,e}$ | >3.00$^{d,e}$ | N.D. | N.D. |
| 33 | (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, (bis)-L-lysine salt | >3.00$^{d,e}$ | >3.00$^{d,e}$ | N.D. | N.D. |

TABLE AA-1-continued

Biological Data (MAGL IC$_{50}$, FAAH IC$_{50}$, and MAGL k$_{inact}$/K$_I$) for Examples 1-150.

| Example Number | Compound Name | MAGL (T = 0 min) IC$_{50}$ (μM)$^a$ | MAGL (T = 30 min) IC$_{50}$ (μM)$^a$ | FAAH (T = 30 min) IC$_{50}$ (μM)$^a$ | MAGL k$_{inact}$/K$_I$ (1/s per M)$^a$ |
|---|---|---|---|---|---|
| 34 | (2R)-3,3,3-trifluoro-2-[({4-[(3-fluorophenyl)sulfonyl]-1-oxa-4,9-diazaspiro[5.5]undec-9-yl}carbonyl)oxy]propyl phosphate, disodium salt | N.D. | N.D. | N.D. | N.D. |
| 35 | 1,1,1-trifluoro-3-hydroxypropan-2-yl 4-[2-(morpholin-4-yl)pyrimidin-4-yl]piperidine-1-carboxylate | 0.339 | 0.032$^d$ | N.D. | N.D. |
| 36 | rel-(2S,3R)-1,1,1,4,4,4-hexafluoro-3-hydroxybutan-2-yl (1α,5α,6α)-6-[1-(4-fluorophenyl)-1H-pyrazol-3-yl]-3-azabicyclo[3.1.0]hexane-3-carboxylate | 0.132 | 0.012 | 13.2 | 3736 |
| 37 | (2R)-1,1,1-trifluoro-3-hydroxypropan-2-yl (1α,5α,6α)-6-[1-(pyridin-2-ylmethyl)-1H-pyrazol-3-yl]-3-azabicyclo[3.1.0]hexane-3-carboxylate | 0.357$^c$ | 0.027 | N.D. | 1616 |
| 38 | 1,1,1-trifluoro-3-hydroxypropan-2-yl 4-[1-(tetrahydro-2H-pyran-4-yl)-1H-pyrazol-3-yl]piperidine-1-carboxylate | 1.47 | 0.077 | N.D. | N.D. |
| 39 | 1,1,1,3,3-pentafluoro-4-hydroxybutan-2-yl (1α,5α,6α)-6-[1-(4-fluorophenyl)-1H-pyrazol-3-yl]-3-azabicyclo[3.1.0]hexane-3-carboxylate | 0.034 | 0.002 | 6.012 | 9893 |
| 40 | (2R)-1,1,1-trifluoro-3-hydroxypropan-2-yl (3aR,6aS)-5-[(4-fluorophenyl)sulfonyl]hexahydropyrrolo[3,4-c]pyrrole-2(1H)-carboxylate | 0.494 | 0.050 | N.D. | N.D. |
| 41 | (2R)-1,1,1-trifluoro-3-hydroxypropan-2-yl 2-(4-fluorobenzyl)-2,9-diazaspiro[5.5]undecane-9-carboxylate | 1.58 | 0.166 | N.D. | N.D. |
| 42 | (2R)-1,1,1-trifluoro-3-hydroxypropan-2-yl 4-(4-fluorobenzyl)-1-oxa-4,9-diazaspiro[5.5]undecane-9-carboxylate | 0.304$^c$ | 0.032 | N.D. | 2591 |
| 43 | (2R)-1,1,1-trifluoro-3-hydroxypropan-2-yl 4-[1-(4-fluorophenyl)ethyl]-1-oxa-4,9-diazaspiro[5.5]undecane-9-carboxylate, formate salt | 0.145 | 0.013 | >30.0$^d$ | 3478 |
| 44 | (2R)-1,1,1-trifluoro-3-hydroxypropan-2-yl 4-[1-(4-fluorophenyl)ethyl]-1-oxa-4,9-diazaspiro[5.5]undecane-9-carboxylate, DIAST-1 | 0.179 | 0.017 | >30.0$^d$ | 3701 |
| 45 | (2R)-1,1,1-trifluoro-3-hydroxypropan-2-yl 4-[1-(4-fluorophenyl)ethyl]-1-oxa-4,9-diazaspiro[5.5]undecane-9-carboxylate, DIAST-2 | 0.191 | 0.018 | >30.0$^d$ | 3134 |
| 46 | (2R)-1,1,1-trifluoro-3-hydroxypropan-2-yl 4-{[(4-fluorobenzyl)(tetrahydro-2H-pyran-4-yl)amino]methyl}-4-hydroxypiperidine-1-carboxylate | 0.560 | 0.046 | N.D. | N.D. |
| 47 | (2R)-1,1,1-trifluoro-3-hydroxypropan-2-yl 4-({[(4-fluorophenyl)sulfonyl]amino}methyl)piperidine-1-carboxylate | 0.174 | 0.017 | >30.0 | 5046 |
| 48 | (2R)-1,1,1-trifluoro-3-hydroxypropan-2-yl (3aR,6aS)-5-(4-cyclopropylpyridin-2-yl)hexahydropyrrolo[3,4-c]pyrrole-2(1H)-carboxylate | >3.00$^d$ | 0.926 | N.D. | N.D. |
| 49 | (2R)-1,1,1-trifluoro-3-hydroxypropan-2-yl 4-(tetrahydro-2H-pyran-4-ylsulfonyl)-1-oxa-4,9-diazaspiro[5.5]undecane-9-carboxylate | >3.00$^d$ | 0.654 | N.D. | N.D. |
| 50 | (2R)-1,1,1-trifluoro-3-hydroxypropan-2-yl 4-{[(4-fluorobenzyl)(tetrahydro-2H-pyran-4-yl)amino]methyl}piperidine-1-carboxylate | 0.857 | 0.071 | N.D. | N.D. |
| 51 | (2R)-1,1,1-trifluoro-3-hydroxypropan-2-yl 4-[(4-fluoro-3-methylphenyl)sulfonyl]-1-oxa-4,9-diazaspiro[5.5]undecane-9-carboxylate | 0.043 | 0.004 | >30.0$^d$ | 10340 |
| 52 | (2R)-1,1,1-trifluoro-3-hydroxypropan-2-yl 4-[(3,4-difluorophenyl)sulfonyl]-1-oxa-4,9-diazaspiro[5.5]undecane-9-carboxylate | 0.056 | 0.005 | >30.0$^d$ | 7262 |

TABLE AA-1-continued

Biological Data (MAGL IC$_{50}$, FAAH IC$_{50}$, and MAGL k$_{inact}$/K$_I$) for Examples 1-150.

| Example Number | Compound Name | MAGL (T = 0 min) IC$_{50}$ (µM)$^a$ | MAGL (T = 30 min) IC$_{50}$ (µM)$^a$ | FAAH (T = 30 min) IC$_{50}$ (µM)$^a$ | MAGL k$_{inact}$/K$_I$ (1/s per M)$^a$ |
|---|---|---|---|---|---|
| 53 | (2R)-1,1,1-trifluoro-3-hydroxypropan-2-yl 4-{[5-(trifluoromethyl)pyridin-2-yl]oxy}piperidine-1-carboxylate | 0.053 | 0.006 | >30.0 | 6900 |
| 54 | (2R)-1,1,1-trifluoro-3-hydroxypropan-2-yl 4-{[3-(pyrrolidin-1-yl)propyl]sulfonyl}-1-oxa-4,9-diazaspiro[5.5]undecane-9-carboxylate, trifluoroacetic acid salt | >3.00$^d$ | >1.68 | N.D. | N.D. |
| 55 | (2R)-1,1,1-trifluoro-3-hydroxypropan-2-yl 4-{[2-(pyridin-2-yl)ethyl]sulfonyl}-1-oxa-4,9-diazaspiro[5.5]undecane-9-carboxylate, trifluoroacetic acid salt | 0.447 | 0.043 | N.D. | N.D. |
| 56 | (2R)-1,1,1-trifluoro-3-hydroxypropan-2-yl 4-{[3-(1H-imidazol-1-yl)propyl]sulfonyl}-1-oxa-4,9-diazaspiro[5.5]undecane-9-carboxylate, trifluoroacetic acid salt | 2.34 | 0.167 | N.D. | N.D. |
| 57 | (2R)-1,1,1-trifluoro-3-hydroxypropan-2-yl 4-[(5-methylpyridin-2-yl)oxy]piperidine-1-carboxylate | 0.126 | 0.010 | N.D. | 5998 |
| 58 | (2R)-1,1,1-trifluoro-3-hydroxypropan-2-yl 4-{[5-methyl-4-(1-methyl-1H-pyrazol-5-yl)pyrimidin-2-yl]oxy}piperidine-1-carboxylate | 0.249 | 0.033 | N.D. | N.D. |
| 59 | (2R)-1,1,1-trifluoro-3-hydroxypropan-2-yl 4-[(3-chloro-4-methylphenyl)sulfonyl]-1-oxa-4,9-diazaspiro[5.5]undecane-9-carboxylate | 0.015 | 0.001 | N.D. | 59048 |
| 60 | (2R)-1,1,1-trifluoro-3-hydroxypropan-2-yl 4-[(3-chloro-4-fluorophenyl)sulfonyl]-1-oxa-4,9-diazaspiro[5.5]undecane-9-carboxylate | 0.037 | 0.002 | N.D. | 19870 |
| 61 | (2R)-1,1,1-trifluoro-3-hydroxypropan-2-yl 4-[(3,5-dimethylpyridin-2-yl)oxy]piperidine-1-carboxylate | 0.053 | 0.005 | N.D. | 7304 |
| 62 | (2R)-1,1,1-trifluoro-3-hydroxypropan-2-yl 4-({[(4-fluorophenyl)sulfonyl](methyl)amino}methyl)piperidine-1-carboxylate | 0.067$^d$ | 0.007$^d$ | >30.0$^d$ | 216 |
| 63 | (2R)-1,1,1-trifluoro-3-hydroxypropan-2-yl 4-{[3-chloro-5-(trifluoromethyl)pyridin-2-yl]oxy}piperidine-1-carboxylate | 0.007 | 0.001 | 3.01 | 7347 |
| 64 | (2R)-1,1,1-trifluoro-3-hydroxypropan-2-yl 4-{[4-(1-methyl-1H-pyrazol-5-yl)pyridin-2-yl]oxy}piperidine-1-carboxylate | 0.550 | 0.042 | N.D. | N.D. |
| 65 | (2R)-1,1,1-trifluoro-3-hydroxypropan-2-yl 4-{[6-(1-methyl-1H-pyrazol-5-yl)pyridin-2-yl]oxy}piperidine-1-carboxylate | 0.359 | 0.030 | N.D. | N.D. |
| 66 | (2R)-1,1,1-trifluoro-3-hydroxypropan-2-yl 4-{[3-(propan-2-yl)phenyl]sulfonyl}-1-oxa-4,9-diazaspiro[5.5]undecane-9-carboxylate | 0.003 | 0.0002 | 7.87$^d$ | 430364 |
| 67 | (2R)-1,1,1-trifluoro-3-hydroxypropan-2-yl 4-(benzylsulfamoyl)-1-oxa-4,9-diazaspiro[5.5]undecane-9-carboxylate | 0.029 | 0.004 | N.D. | 30591 |
| 68 | (2R)-1,1,1-trifluoro-3-hydroxypropan-2-yl 4-[(4-ethynylphenyl)sulfonyl]-1-oxa-4,9-diazaspiro[5.5]undecane-9-carboxylate | 0.056 | 0.006 | >30.0$^d$ | 16586 |
| 69 | (2R)-1,1,1-trifluoro-3-hydroxypropan-2-yl (1α,5α,6α)-6-[1-(6-methoxypyridin-3-yl)-1H-pyrazol-3-yl]-3-azabicyclo[3.1.0]hexane-3-carboxylate | 0.104 | 0.011 | N.D. | 4621 |
| 70 | (2R)-1,1,1-trifluoro-3-hydroxypropan-2-yl 4-[(4-fluorophenyl)sulfonyl]-5-methyl-1-oxa-4,9-diazaspiro[5.5]undecane-9-carboxylate, DIAST-1 | 0.655 | 0.069 | N.D. | N.D. |
| 71 | (2R)-1,1,1-trifluoro-3-hydroxypropan-2-yl 4-[(4-fluorophenyl)sulfonyl]-5-methyl-1-oxa-4,9-diazaspiro[5.5]undecane-9-carboxylate, DIAST-2 | 0.099 | 0.017 | N.D. | 9358 |

TABLE AA-1-continued

Biological Data (MAGL IC$_{50}$, FAAH IC$_{50}$, and MAGL k$_{inact}$/K$_I$) for Examples 1-150.

| Example Number | Compound Name | MAGL (T = 0 min) IC$_{50}$ (μM)$^a$ | MAGL (T = 30 min) IC$_{50}$ (μM)$^a$ | FAAH (T = 30 min) IC$_{50}$ (μM)$^a$ | MAGL k$_{inact}$/K$_I$ (1/s per M)$^a$ |
|---|---|---|---|---|---|
| 72 | (2R)-1,1,1-trifluoro-3-hydroxypropan-2-yl 3-(4-fluorobenzyl)-2-oxo-1-oxa-3,8-diazaspiro[4.5]decane-8-carboxylate | 0.220 | 0.028 | N.D. | N.D. |
| 73 | (2R)-1,1,1-trifluoro-3-hydroxypropan-2-yl 4-[(3-fluoro-4-methylphenyl)sulfonyl]-1-oxa-4,9-diazaspiro[5.5]undecane-9-carboxylate | 0.005 | 0.001 | >30.0$^d$ | 96515 |
| 74 | (2R)-1,1,1-trifluoro-3-hydroxypropan-2-yl 4-[(pyridin-2-ylmethyl)sulfamoyl]-1-oxa-4,9-diazaspiro[5.5]undecane-9-carboxylate | 0.392 | 0.052 | N.D. | N.D. |
| 75 | (2R)-1,1,1-trifluoro-3-hydroxypropan-2-yl 4-{[5-(hydroxymethyl)pyridin-2-yl]oxy}piperidine-1-carboxylate | 0.688 | 0.079 | N.D. | N.D. |
| 76 | (2R)-1,1,1-trifluoro-3-hydroxypropan-2-yl 4-(5-methylpyrimidin-2-yl)-1-oxa-4,9-diazaspiro[5.5]undecane-9-carboxylate | 0.658 | 0.083 | N.D. | N.D. |
| 77 | (2R)-1,1,1-trifluoro-3-hydroxypropan-2-yl 4-[(3-ethylphenyl)sulfonyl]-1-oxa-4,9-diazaspiro[5.5]undecane-9-carboxylate | 0.005 | 0.001 | 5.95$^d$ | 403739 |
| 78 | (2R)-1,1,1-trifluoro-3-hydroxypropan-2-yl 4-{[4-(propan-2-yloxy)phenyl]sulfonyl}-1-oxa-4,9-diazaspiro[5.5]undecane-9-carboxylate | 0.006 | 0.001 | 2.58$^d$ | 16865 |
| 79 | (2R)-1,1,1-trifluoro-3-hydroxypropan-2-yl 4-[(3-ethynylphenyl)sulfonyl]-1-oxa-4,9-diazaspiro[5.5]undecane-9-carboxylate | 0.007 | 0.001 | 10.0 | 26513 |
| 80 | (2R)-1,1,1-trifluoro-3-hydroxypropan-2-yl 4-[1-(4-ethynylphenyl)-1H-pyrazol-3-yl]piperidine-1-carboxylate | 0.007 | 0.001 | 7.92$^d$ | 126124 |
| 81 | (2R)-1,1,1-trifluoro-3-hydroxypropan-2-yl (1α,5α,6α)-6-[1-(4-ethynylphenyl)-1H-pyrazol-3-yl]-3-azabicyclo[3.1.0]hexane-3-carboxylate | 0.008 | 0.001 | 7.54$^d$ | 45138 |
| 82 | (2S)-1,1,1-trifluoro-3-hydroxypropan-2-yl (1α,5α,6α)-6-[1-(4-ethynylphenyl)-1H-pyrazol-3-yl]-3-azabicyclo[3.1.0]hexane-3-carboxylate | >2.75 | 0.598 | N.D. | N.D. |
| 83 | (2R)-1,1,1-trifluoro-3-hydroxypropan-2-yl 4-[(3-chlorophenyl)sulfonyl]-1-oxa-4,9-diazaspiro[5.5]undecane-9-carboxylate | 0.019$^c$ | 0.002$^c$ | >30.0$^d$ | 21997$^d$ |
| 84 | (2R)-1,1,1-trifluoro-3-hydroxypropan-2-yl 4-[(2-fluorophenyl)sulfonyl]-1-oxa-4,9-diazaspiro[5.5]undecane-9-carboxylate | 0.026 | 0.002 | 19.2$^d$ | 49166 |
| 85 | methyl (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, ammonium salt | >3.00$^d$ | 0.818 | N.D. | N.D. |
| 86 | (2R)-3-[(dimethoxyphosphoryl)oxy]-1,1,1-trifluoropropan-2-yl 4-[(4-fluorophenyl)sulfonyl]-1-oxa-4,9-diazaspiro[5.5]undecane-9-carboxylate | 0.097 | 0.008 | N.D. | 132 |
| 87 | ethyl (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, ammonium salt | 0.198 | 0.015 | N.D. | N.D. |
| 88 | (2R)-3-[(diethoxyphosphoryl)oxy]-1,1,1-trifluoropropan-2-yl 4-[(4-fluorophenyl)sulfonyl]-1-oxa-4,9-diazaspiro[5.5]undecane-9-carboxylate | >3.00$^d$ | >3.00$^d$ | N.D. | N.D. |
| 89 | (9R)-10,10,10-trifluoro-6-hydroxy-2-methyl-6-oxido-5,7-dioxa-2-aza-6λ$^5$-phosphadecan-9-yl 4-[(4-fluorophenyl)sulfonyl]-1-oxa-4,9-diazaspiro[5.5]undecane-9-carboxylate | >3.00$^d$ | >3.00$^d$ | N.D. | N.D. |

TABLE AA-1-continued

Biological Data (MAGL IC$_{50}$, FAAH IC$_{50}$, and MAGL k$_{inact}$/K$_I$) for Examples 1-150.

| Example Number | Compound Name | MAGL (T = 0 min) IC$_{50}$ (μM)$^a$ | MAGL (T = 30 min) IC$_{50}$ (μM)$^a$ | FAAH (T = 30 min) IC$_{50}$ (μM)$^a$ | MAGL k$_{inact}$/K$_I$ (1/s per M)$^a$ |
|---|---|---|---|---|---|
| 90 | (2R)-3,3,3-trifluoro-2-[({4-[(4-fluorophenyl)sulfonyl]-1-oxa-4,9-diazaspiro[5.5]undec-9-yl}carbonyl)oxy]propyl 2-(trimethylammonio)ethyl phosphate | >3.00$^d$ | >3.00$^d$ | N.D. | N.D. |
| 91 | (2R)-3,3,3-trifluoro-2-({[4-(phenylsulfonyl)-1-oxa-4,9-diazaspiro[5.5]undec-9-yl]carbonyl}oxy)propyl phosphate, disodium salt | N.D. | N.D. | N.D. | N.D. |
| 92 | (2R)-1,1,1-trifluoro-3-hydroxypropan-2-yl (3R)-3-[ethyl(phenylsulfonyl)amino]-1-oxa-8-azaspiro[4.5]decane-8-carboxylate | 0.006 | 0.001 | >30$^d$ | 215500 |
| 93 | (2R)-1,1,1-trifluoro-3-hydroxypropan-2-yl (3R)-3-[(cyclopropylsulfonyl)(methyl)amino]-1-oxa-8-azaspiro[4.5]decane-8-carboxylate | 0.318$^c$ | 0.029$^c$ | >30$^d$ | 3282 |
| 94 | (2R)-1,1,1-trifluoro-3-hydroxypropan-2-yl (3S)-3-[(cyclopropylsulfonyl)(methyl)amino]-1-oxa-8-azaspiro[4.5]decane-8-carboxylate | 0.316$^c$ | 0.027$^c$ | >30$^d$ | 3764 |
| 95 | (2R)-1,1,1-trifluoro-3-hydroxypropan-2-yl 3-phenyl-1-oxa-8-azaspiro[4.5]decane-8-carboxylate [From C101, ENT-2] | 0.016 | 0.001 | 8.72 | 131495 |
| 96 | (2R)-1,1,1-trifluoro-3-hydroxypropan-2-yl 3-phenyl-1-oxa-8-azaspiro[4.5]decane-8-carboxylate [From C100, ENT-1] | 0.062 | 0.005 | 9.52 | 18560 |
| 97 | (2R)-1,1,1-trifluoro-3-hydroxypropan-2-yl 3-(5-fluoropyridin-2-yl)-1-oxa-8-azaspiro[4.5]decane-8-carboxylate | 0.192 | 0.020 | >30$^d$ | 1897 |
| 98 | (2R)-1,1,1-trifluoro-3-hydroxypropan-2-yl 2-(2-fluorobenzoyl)-2,8-diazaspiro[4.5]decane-8-carboxylate | 0.071$^c$ | 0.007$^c$ | >30$^d$ | 4933 |
| 99 | (2R)-1,1,1-trifluoro-3-hydroxypropan-2-yl 3-[benzoyl(methyl)amino]-1-oxa-8-azaspiro[4.5]decane-8-carboxylate [From C112, DIAST-2] | 0.107 | 0.011 | >30$^d$ | 16883 |
| 100 | (2R)-1,1,1-trifluoro-3-hydroxypropan-2-yl 3-[benzoyl(methyl)amino]-1-oxa-8-azaspiro[4.5]decane-8-carboxylate [From C111, DIAST-1] | 0.086 | 0.010 | >28.7 | 5664 |
| 101 | (2R)-1,1,1-trifluoro-3-hydroxypropan-2-yl 3-(1,1-dioxido-1,2-benzothiazol-2(3H)-yl)-1-oxa-8-azaspiro[4.5]decane-8-carboxylate | 0.180 | 0.021 | 6.54 | 2454 |
| 102 | (2R)-1,1,1-trifluoro-3-hydroxypropan-2-yl 3-[(5-methylpyridin-2-yl)methyl]-1-oxa-8-azaspiro[4.5]decane-8-carboxylate | 0.215 | 0.026 | 18.3 | 1336 |
| 103 | (2R)-1,1,1-trifluoro-3-hydroxypropan-2-yl 3-(1H-pyrazol-1-yl)-1-oxa-8-azaspiro[4.5]decane-8-carboxylate [From C120, DIAST-2] | 0.334 | 0.030 | >30$^d$ | N.D. |
| 104 | (2R)-1,1,1-trifluoro-3-hydroxypropan-2-yl 3-(1H-pyrazol-1-yl)-1-oxa-8-azaspiro[4.5]decane-8-carboxylate [From C119, DIAST-1] | 1.86 | 0.157 | N.D. | N.D. |
| 105 | (2R)-1,1,1-trifluoro-3-hydroxypropan-2-yl 2-(phenylsulfonyl)-2,8-diazaspiro[4.5]decane-8-carboxylate | 0.022 | 0.002 | 9.76 | 59993 |
| 106 | (2R)-1,1,1-trifluoro-3-hydroxypropan-2-yl (3R)-3-{[(cyclopropylmethyl)sulfonyl](methyl)amino}-1-oxa-8-azaspiro[4.5]decane-8-carboxylate | 0.238 | 0.020 | >30$^d$ | 2856 |

TABLE AA-1-continued

Biological Data (MAGL IC$_{50}$, FAAH IC$_{50}$, and MAGL k$_{inact}$/K$_I$) for Examples 1-150.

| Example Number | Compound Name | MAGL (T = 0 min) IC$_{50}$ (μM)$^a$ | MAGL (T = 30 min) IC$_{50}$ (μM)$^a$ | FAAH (T = 30 min) IC$_{50}$ (μM)$^a$ | MAGL k$_{inact}$/K$_I$ (1/s per M)$^a$ |
|---|---|---|---|---|---|
| 107 | (2R)-1,1,1-trifluoro-3-hydroxypropan-2-yl (3R)-3-[(phenylsulfonyl)(propan-2-yl)amino]-1-oxa-8-azaspiro[4.5]decane-8-carboxylate | 0.010 | 0.001 | >30$^d$ | 127771 |
| 108 | (2R)-1,1,1-trifluoro-3-hydroxypropan-2-yl 3-{[(3-fluorophenyl)sulfonyl](methyl)amino}-1-oxa-8-azaspiro[4.5]decane-8-carboxylate, DIAST-1 | 0.051 | 0.003 | 10.7 | 15960 |
| 109 | (2R)-1,1,1-trifluoro-3-hydroxypropan-2-yl 3-{[(3-fluorophenyl)sulfonyl](methyl)amino}-1-oxa-8-azaspiro[4.5]decane-8-carboxylate, DIAST-2 | 0.021 | 0.002 | >30$^d$ | 34918 |
| 110 | (2R)-1,1,1-trifluoro-3-hydroxypropan-2-yl 3-{[(4-fluorophenyl)sulfonyl](methyl)amino}-1-oxa-8-azaspiro[4.5]decane-8-carboxylate, DIAST-1 | 0.070 | 0.006 | 7.09 | 8796 |
| 111 | (2R)-1,1,1-trifluoro-3-hydroxypropan-2-yl 3-{[(4-fluorophenyl)sulfonyl](methyl)amino}-1-oxa-8-azaspiro[4.5]decane-8-carboxylate, DIAST-2 | 0.028 | 0.002 | >30$^d$ | 33483 |
| 112 | (2R)-1,1,1-trifluoro-3-hydroxypropan-2-yl 3-[(cyclopentylsulfonyl)(methyl)amino]-1-oxa-8-azaspiro[4.5]decane-8-carboxylate | 0.064 | 0.007 | >30$^d$ | 14232 |
| 113 | (2R)-1,1,1-trifluoro-3-hydroxypropan-2-yl 3-[(cyclobutylsulfonyl)(methyl)amino]-1-oxa-8-azaspiro[4.5]decane-8-carboxylate | 0.139 | 0.010 | >25.5 | 6254 |
| 114 | (2R)-1,1,1-trifluoro-3-hydroxypropan-2-yl 3-[methyl(pyridin-3-ylsulfonyl)amino]-1-oxa-8-azaspiro[4.5]decane-8-carboxylate | 0.163 | 0.015 | >30$^d$ | 6263 |
| 115 | (2R)-1,1,1-trifluoro-3-hydroxypropan-2-yl 3-[methyl(pyrimidin-5-ylsulfonyl)amino]-1-oxa-8-azaspiro[4.5]decane-8-carboxylate | 0.341 | 0.027 | >30$^d$ | 2917 |
| 116 | (2R)-1,1,1-trifluoro-3-hydroxypropan-2-yl 3-[methyl(tetrahydro-2H-pyran-4-ylsulfonyl)amino]-1-oxa-8-azaspiro[4.5]decane-8-carboxylate [From DIAST-2 in footnote 43, Table 6] | 0.986 | 0.084 | N.D. | N.D. |
| 117 | (2R)-1,1,1-trifluoro-3-hydroxypropan-2-yl 3-[methyl(tetrahydro-2H-pyran-4-ylsulfonyl)amino]-1-oxa-8-azaspiro[4.5]decane-8-carboxylate [From DIAST-1 in footnote 43, Table 6] | 1.97 | 0.153 | N.D. | N.D. |
| 118 | (2R)-1,1,1-trifluoro-3-hydroxypropan-2-yl 3-[3-(trifluoromethoxy)phenyl]-1-oxa-8-azaspiro[4.5]decane-8-carboxylate | 0.002 | 0.0004 | >24.8 | 172844 |
| 119 | (2R)-1,1,1-trifluoro-3-hydroxypropan-2-yl 3-(3-chlorophenyl)-1-oxa-8-azaspiro[4.5]decane-8-carboxylate | 0.032 | 0.003 | 3.57 | 23176 |
| 120 | (2R)-1,1,1-trifluoro-3-hydroxypropan-2-yl 3-(6-fluoropyridin-3-yl)-1-oxa-8-azaspiro[4.5]decane-8-carboxylate | 0.166 | 0.021 | >30$^d$ | 1516 |
| 121 | (2R)-1,1,1-trifluoro-3-hydroxypropan-2-yl 3-(5-methoxypyridin-2-yl)-1-oxa-8-azaspiro[4.5]decane-8-carboxylate | 0.149 | 0.020 | 14.7 | 1207 |
| 122 | (2R)-1,1,1-trifluoro-3-hydroxypropan-2-yl 3-(pyridin-3-yl)-1-oxa-8-azaspiro[4.5]decane-8-carboxylate, trifluoroacetate salt | 0.385 | 0.032 | N.D. | N.D. |
| 123 | (2R)-1,1,1-trifluoro-3-hydroxypropan-2-yl 3-(6-methylpyridin-3-yl)-1-oxa-8-azaspiro[4.5]decane-8-carboxylate, trifluoroacetate salt | 0.349 | 0.030 | 24.6 | N.D. |

TABLE AA-1-continued

Biological Data (MAGL IC$_{50}$, FAAH IC$_{50}$, and MAGL k$_{inact}$/K$_I$) for Examples 1-150.

| Example Number | Compound Name | MAGL (T = 0 min) IC$_{50}$ (μM)$^a$ | MAGL (T = 30 min) IC$_{50}$ (μM)$^a$ | FAAH (T = 30 min) IC$_{50}$ (μM)$^a$ | MAGL k$_{inact}$/K$_I$ (1/s per M)$^a$ |
|---|---|---|---|---|---|
| 124 | (2R)-1,1,1-trifluoro-3-hydroxypropan-2-yl 2-(cyclopentylcarbonyl)-2,8-diazaspiro[4.5]decane-8-carboxylate | 0.092 | 0.010 | >30$^d$ | 6720 |
| 125 | (2R)-1,1,1-trifluoro-3-hydroxypropan-2-yl 2-(1,3-thiazol-2-ylcarbonyl)-2,8-diazaspiro[4.5]decane-8-carboxylate | 0.065 | 0.007 | >30$^d$ | 5464 |
| 126 | (2R)-1,1,1-trifluoro-3-hydroxypropan-2-yl 2-benzoyl-2,8-diazaspiro[4.5]decane-8-carboxylate | 0.112 | 0.012 | >30$^d$ | 3723 |
| 127 | (2R)-1,1,1-trifluoro-3-hydroxypropan-2-yl 2-[(4,4-difluorocyclohexyl)carbonyl]-2,8-diazaspiro[4.5]decane-8-carboxylate | 0.163 | 0.017 | >30$^d$ | 2067 |
| 128 | (2R)-1,1,1-trifluoro-3-hydroxypropan-2-yl 2-(pyridin-2-ylcarbonyl)-2,8-diazaspiro[4.5]decane-8-carboxylate | 0.423 | 0.050 | N.D. | N.D. |
| 129 | (2R)-1,1,1-trifluoro-3-hydroxypropan-2-yl 3-(pyridin-2-yloxy)-1-oxa-8-azaspiro[4.5]decane-8-carboxylate, DIAST-1 | >3$^d$ | 0.474 | N.D. | N.D. |
| 130 | (2R)-1,1,1-trifluoro-3-hydroxypropan-2-yl 3-(pyridin-2-yloxy)-1-oxa-8-azaspiro[4.5]decane-8-carboxylate, DIAST-2 | 0.076 | 0.006 | 25.7 | 12483 |
| 131 | (2R)-1,1,1-trifluoro-3-hydroxypropan-2-yl 3-(1,1-dioxido-3,4-dihydro-2H-1,2-benzothiazin-2-yl)-1-oxa-8-azaspiro[4.5]decane-8-carboxylate | 0.086 | 0.011 | 17.4 | 4241 |
| 132 | (2R)-1,1,1-trifluoro-3-hydroxypropan-2-yl 3-(benzyloxy)-1-oxa-8-azaspiro[4.5]decane-8-carboxylate | 0.130 | 0.012 | N.D. | 8426 |
| 133 | (2R)-1,1,1-trifluoro-3-hydroxypropan-2-yl 2-(pyrrolidin-1-ylcarbonyl)-2,8-diazaspiro[4.5]decane-8-carboxylate | 0.174 | 0.020 | 4.75 | 3614 |
| 134 | (2R)-1,1,1-trifluoro-3-hydroxypropan-2-yl 2-(1,3-thiazol-2-ylsulfonyl)-2,8-diazaspiro[4.5]decane-8-carboxylate | 0.096 | 0.007 | >23.4 | 9930 |
| 135 | (2R)-1,1,1-trifluoro-3-hydroxypropan-2-yl 2-(pyridin-3-ylsulfonyl)-2,8-diazaspiro[4.5]decane-8-carboxylate | 0.168 | 0.013 | >30$^d$ | 4723 |
| 136 | (2R)-1,1,1-trifluoro-3-hydroxypropan-2-yl (3R)-3-[methyl(1,3-thiazol-2-ylsulfonyl)amino]-1-oxa-8-azaspiro[4.5]decane-8-carboxylate | 0.052 | 0.005 | >30$^d$ | 15516 |
| 137 | (2R)-1,1,1-trifluoro-3-hydroxypropan-2-yl (3R)-3-{methyl[(2,2,2-trifluoroethyl)sulfonyl]amino}-1-oxa-8-azaspiro[4.5]decane-8-carboxylate | 0.126 | 0.011 | >30$^d$ | 7582 |
| 138 | (2R)-1,1,1-trifluoro-3-hydroxypropan-2-yl (3R)-3-{methyl[(1-methyl-1H-pyrazol-4-yl)sulfonyl]amino}-1-oxa-8-azaspiro[4.5]decane-8-carboxylate | 0.185 | 0.015 | 16.3 | 2154 |
| 139 | (2R)-1,1,1-trifluoro-3-hydroxypropan-2-yl (3R)-3-{methyl[(2-methylpropyl)sulfonyl]amino}-1-oxa-8-azaspiro[4.5]decane-8-carboxylate | 0.153 | 0.015 | >30$^d$ | 3058 |
| 140 | (2R)-1,1,1-trifluoro-3-hydroxypropan-2-yl (3R)-3-{[(cyclobutylmethyl)sulfonyl](methyl)amino}-1-oxa-8-azaspiro[4.5]decane-8-carboxylate | 0.094 | 0.009 | >30$^d$ | 4595 |
| 141 | (2R)-1,1,1-trifluoro-3-hydroxypropan-2-yl (3R)-3-[(3-fluorobenzoyl)(methyl)amino]-1-oxa-8-azaspiro[4.5]decane-8-carboxylate | 0.077 | 0.007 | >30$^d$ | 3519 |
| 142 | (2R)-1,1,1-trifluoro-3-hydroxypropan-2-yl (3R)-3-[(cyclobutylcarbonyl)(methyl)amino]-1-oxa-8-azaspiro[4.5]decane-8-carboxylate | 0.084 | 0.009 | >30$^d$ | 3961 |

TABLE AA-1-continued

Biological Data (MAGL $IC_{50}$, FAAH $IC_{50}$, and MAGL $k_{inact}/K_I$) for Examples 1-150.

| Example Number | Compound Name | MAGL (T = 0 min) $IC_{50}$ (μM)[a] | MAGL (T = 30 min) $IC_{50}$ (μM)[a] | FAAH (T = 30 min) $IC_{50}$ (μM)[a] | MAGL $k_{inact}/K_I$ (1/s per M)[a] |
|---|---|---|---|---|---|
| 143 | (2R)-1,1,1-trifluoro-3-hydroxypropan-2-yl (3R)-3-[(cyclobutylacetyl)(methyl)amino]-1-oxa-8-azaspiro[4.5]decane-8-carboxylate | 0.096 | 0.010 | >30[d] | 2585 |
| 144 | (2R)-1,1,1-trifluoro-3-hydroxypropan-2-yl (3R)-3-[methyl(3-methylbutanoyl)amino]-1-oxa-8-azaspiro[4.5]decane-8-carboxylate | 0.105 | 0.010 | >30[d] | 2802 |
| 145 | (2R)-1,1,1-trifluoro-3-hydroxypropan-2-yl (3R)-3-[(cyclopropylacetyl)(methyl)amino]-1-oxa-8-azaspiro[4.5]decane-8-carboxylate | 0.198 | 0.019 | >30[d] | 1476 |
| 146 | (2R)-1,1,1-trifluoro-3-hydroxypropan-2-yl (3R)-3-[methyl(pyridin-2-ylcarbonyl)amino]-1-oxa-8-azaspiro[4.5]decane-8-carboxylate, formate salt | 0.539 | 0.048 | N.D. | N.D. |
| 147 | (2R)-1,1,1-trifluoro-3-hydroxypropan-2-yl 3-(3-cyanophenyl)-1-oxa-8-azaspiro[4.5]decane-8-carboxylate | 0.060 | 0.006 | >26.4 | 5973 |
| 148 | (2R)-3,3,3-trifluoro-2-[({(3R)-3-[methyl(phenylsulfonyl)amino]-1-oxa-8-azaspiro[4.5]dec-8-yl}carbonyl)oxy]propyl phosphate, (bis)-L-lysine salt | >3[d] | >1.23 | N.D. | N.D. |
| 149 | (2R)-3,3,3-trifluoro-2-({[4-(phenylsulfonyl)-1-oxa-4,9-diazaspiro[5.5]undec-9-yl]carbonyl}oxy)propyl phosphate, (bis)-L-lysine salt | N.D. | N.D. | N.D. | N.D. |
| 150 | (2R)-3,3,3-trifluoro-2-({[(3R)-3-{[(4-fluorophenyl)sulfonyl](methyl)amino}-1-oxa-8-azaspiro[4.5]dec-8-yl]carbonyl}oxy)propyl phosphate, (bis)-L-lysine salt | N.D. | N.D. | N.D. | N.D. |

[a]Reported $IC_{50}$ values or $k_{inact}/K_I$ values are the geometric mean of 2-4 determinations, unless otherwise indicated.
[b]N.D. = not determined
[c]The reported $IC_{50}$ value or $k_{inact}/K_I$ value is the geometric mean of ≥5 determinations.
[d]The $IC_{50}$ value or $k_{inact}/K_I$ value is from a single determination.
[e]In this case, the corresponding phosphate itself was tested, rather than the salt.

Example BB: Prodrug In Vivo Data

Rats

Test compounds (Examples 31 and 32) were administered intravenously to groups of two rats. The characteristics of the experimental rats are given in Table BB-1.

TABLE BB-1

Characteristics of experimental rats used in study

| Species | Rats |
|---|---|
| Type | Wistar Hann |
| Number and sex | 2 males |
| Approximate age | 7-11 weeks |
| Approx. Body weight | 250-320 g at start of treatment |
| Source | Charles River Labs |

Blood samples were taken at various times after administration and submitted to analysis for the parent compound (Examples 9 or 6) and prodrug compound (Examples 31 or 32, respectively) using an LC-MS-MS assay. Pharmacokinetic parameters derived from the plasma analytical data were determined using Watson LIMS 7.2.003 (Thermo Fisher Scientific, Waltham, Mass.). The results are given in Tables BB-2 to BB-5.

TABLE BB-2

Pharmacokinetic Parameters of Example 31 in Wistar Hann Rats Following IV Administration at 1.48 mg/kg

| Parameter | Units | Subject Rat 01 | Subject Rat 02 | Mean | S.D |
|---|---|---|---|---|---|
| Original Dose (Example 31) | mg/kg | 1.48 | 1.48 | | |
| AUC Interval | | (0-0.5 Hours) | (0-0.25 Hours) | | |
| AUC | ng*Hours/mL | 43.1 | 42.9 | 43.0 | |
| AUC Extrap | ng*Hours/mL | 43.6 | 43.6 | 43.6 | |
| % AUC Extrap | % | 1.19 | 1.62 | 1.41 | |
| Co | ng/mL | 399 | 553 | 476 | |
| CL | mL/min/kg | 566 | 566 | 566 | |
| T½ | Hours | 0.0805 | 0.0445 | 0.0625 | |
| Vdss | L/kg | 2.86 | 1.59 | 2.23 | |
| Rate Constant | 1/Hours | 8.61 | 15.6 | 12.1 | |
| Regression Points | Hours | 0.083, 0.25, 0.5 | 0.083, 0.25 | | |

TABLE BB-3

Pharmacokinetic Parameters of Example 9 in Wistar Hann Rats Following IV Administration of Example 31 at 1.48 mg/kg

| Parameter | Units | Subject Rat 01 | Subject Rat 02 | Mean | S.D. |
|---|---|---|---|---|---|
| Original Dose (Example 31) | mg/kg | 1.48 | 1.48 | | |
| Cmax | ng/mL | 253 | 378 | 316 | |
| Tmax | Hours | 0.083 | 0.083 | 0.083 | |
| AUC | ng*Hours/mL | 118 | 173 | 146 | |
| AUC Extrap | ng*Hours/mL | 121 | 178 | 150 | |
| % AUC Extrap | % | 2.08 | 2.83 | 2.46 | |
| Rate Constant | 1/Hours | 0.560 | 0.440 | 0.500 | |
| T½ | Hours | 1.24 | 1.57 | 1.41 | |
| Regression Points | Hours | 4, 7 | 1, 2, 4, 7 | | |

TABLE BB-4

Pharmacokinetics of Example 32 in rats after IV administration of Example 32 (2 mg/kg active)

| Parameter | Units | Subject Rat 03 | Subject Rat 04 | Mean | S.D. |
|---|---|---|---|---|---|
| Original Dose (Example 32) | mg/kg | 2 | 2 | | |
| AUC Interval | | (0-1 Hours) | (0-0.5 Hours) | | |
| AUC | ng*Hours/mL | 185 | 133 | 159 | |
| AUC Extrap | ng*Hours/mL | 185 | 134 | 160 | |
| % AUC Extrap | % | 0.232 | 0.832 | 0.532 | |
| Co | ng/mL | 4480 | 3040 | 3760 | |
| CL | mL/min/kg | 180 | 249 | 215 | |
| T½ | Hours | 0.147 | 0.0971 | 0.122 | |
| Vdss | L/kg | 0.515 | 0.679 | 0.597 | |
| Rate Constant | 1/Hours | 4.73 | 7.14 | 5.94 | |
| Regression Points | Hours | 0.5, 1 | 0.25, 0.5 | | |

TABLE BB-5

Pharmacokinetic Parameters of Example 6 in Wistar Hann Rats Following IV Administration of Example 32 at 2 mg/kg

| Parameter | Units | Subject Rat 03 | Subject Rat 04 | Mean | S.D. |
|---|---|---|---|---|---|
| Original Dose (Example 32) | mg/kg | 2 | 2 | | |
| Cmax | ng/mL | 234 | 384 | 309 | |
| Tmax | Hours | 0.083 | 0.033 | 0.058 | |
| AUC | ng*Hours/mL | 102 | 213 | 158 | |
| AUC Extrap | ng*Hours/mL | 109 | 215 | 162 | |
| % AUC Extrap | % | 6.04 | 0.880 | 3.46 | |
| Rate Constant | 1/Hours | 2.86 | 1.57 | 2.22 | |
| T½ | Hours | 0.242 | 0.442 | 0.342 | |
| Regression Points | Hours | 0.25, 0.5, 1 | 0.5, 1, 3 | | |

Dogs

Test compounds (Examples 31 and 32) were administered intravenously to groups of two dogs. The characteristics of the experimental dogs are given in Table BB-6.

TABLE BB-6

Characteristics of experimental dogs used in study

| | |
|---|---|
| Species | Dogs |
| Type | Beagle |
| Number and sex | 2 males |
| Approximate age | 2-5 years |
| Approx. Body weight | 9-13 kg at start of treatment |
| Source | Marshall Farms |

Blood samples were taken at various times after administration and submitted to analysis for the parent compound (Example 9 or 6) and its prodrug compound (Example 31 or 32, respectively) using an LC-MS-MS assay. Pharmacokinetic parameters derived from the plasma analytical data were determined using Watson LIMS 7.2.003 (Thermo Fisher Scientific, Waltham, Mass.). The results are given in Tables BB-7 to BB-10.

TABLE BB-7

Pharmacokinetic Parameters of Example 31 in Beagle Dogs Following IV Administration at 0.7 mg/kg

| Parameter | Units | Subject Dog 01 | Subject Dog 02 | Mean | S.D. |
|---|---|---|---|---|---|
| Original Dose (Example 31) | mg/kg | 0.7 | 0.7 | | |
| AUC Interval | | (0-0.5 Hours) | (0-0.5 Hours) | | |
| AUC | ng*Hours/mL | 108 | 53.8 | 80.9 | |
| AUC Extrap | ng*Hours/mL | 108 | 53.9 | 81.0 | |
| % AUC Extrap | % | 0.181 | 0.103 | 0.142 | |
| Co | ng/mL | 1630 | 821 | 1230 | |
| CL | mL/min/kg | 108 | 216 | 162 | |
| T½ | Hours | 0.0614 | 0.0620 | 0.0617 | |
| Vdss | L/kg | 0.235 | 0.465 | 0.350 | |
| Rate Constant | 1/Hours | 11.3 | 11.2 | 11.3 | |
| Regression Points | Hours | 0.083, 0.25, 0.5 | 0.083, 0.25, 0.5 | | |

TABLE BB-8

Pharmacokinetic Parameters of Example 9 in Beagle Dogs Following IV Administration of Example 31 at 0.7 mg/kg

| Parameter | Units | Subject Dog 01 | Subject Dog 02 | Mean | S.D. |
|---|---|---|---|---|---|
| Original Dose (Example 31) | mg/kg | 0.7 | 0.7 | | |
| Cmax | ng/mL | 614 | 789 | 702 | |
| Tmax | Hours | 0.25 | 0.083 | 0.17 | |
| AUC | ng*Hours/mL | 1350 | 1460 | 1410 | |
| AUC Extrap | ng*Hours/mL | 1550 | 1560 | 1560 | |
| % AUC Extrap | % | 12.6 | 6.12 | 9.36 | |
| Rate Constant | 1/Hours | 0.0648 | 0.0863 | 0.0756 | |
| T½ | Hours | 10.7 | 8.03 | 9.37 | |
| Regression Points | Hours | 4, 7, 24 | 2, 4, 7, 24 | | |

TABLE BB-9

Pharmacokinetic Parameters of Example 32 in Beagle
Dogs Following IV Administration at 1 mg/kg

| Parameter | Units | Subject Dog 03 | Subject Dog 04 | Mean | S.D. |
|---|---|---|---|---|---|
| Original Dose (Example 32) | mg/kg | 1 | 1 | | |
| AUC Interval | | (0-1 Hours) | (0-1 Hours) | | |
| AUC | ng*Hours/mL | 146 | 229 | 188 | |
| AUC Extrap | ng*Hours/mL | 146 | 229 | 188 | |
| % AUC Extrap | % | 0.0443 | 0.150 | 0.0972 | |
| Co | ng/mL | 1220 | 2370 | 1800 | |
| CL | mL/min/kg | 114 | 72.8 | 93.4 | |
| T½ | Hours | 0.136 | 0.137 | 0.137 | |
| Vdss | L/kg | 0.751 | 0.357 | 0.554 | |
| Rate Constant | 1/Hours | 5.08 | 5.06 | 5.07 | |
| Regression Points | Hours | 0.25, 0.5, 1 | 0.25, 0.5, 1 | | |

TABLE BB-10

Pharmacokinetic Parameters of Example 6 in Beagle Dogs
Following IV Administration of Example 32 at 1 mg/kg

| Parameter | Units | Subject Dog 03 | Subject Dog 04 | Mean | S.D. |
|---|---|---|---|---|---|
| Original Dose (Example 32) | mg/kg | 1 | 1 | | |
| Cmax | ng/mL | 514 | 653 | 584 | |
| Tmax | Hours | 0.083 | 0.083 | 0.083 | |
| AUC | ng*Hours/mL | 591 | 705 | 648 | |
| AUC Extrap | ng*Hours/mL | 595 | 710 | 653 | |
| % AUC Extrap | % | 0.630 | 0.733 | 0.682 | |
| Rate Constant | 1/Hours | 0.169 | 0.129 | 0.149 | |
| T½ | Hours | 4.10 | 5.36 | 4.73 | |
| Regression Points | Hours | 4, 7, 24 | 7, 24 | | |

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A compound selected from the group consisting of:
   (2R)-1,1,1-trifluoro-3-hydroxypropan-2-yl 4-[(4-fluorophenyl)sulfonyl]-1-oxa-4,9-diazaspiro[5.5]undecane-9-carboxylate;
   (2R)-1,1,1-trifluoro-3-hydroxypropan-2-yl 4-(phenylsulfonyl)-1-oxa-4,9-diazaspiro[5.5]undecane-9-carboxylate;
   (2R)-1,1,1-trifluoro-3-hydroxypropan-2-yl (3R)-3-[methyl(phenylsulfonyl)amino]-1-oxa-8-azaspiro[4.5]decane-8-carboxylate;
   (2R)-3,3,3-trifluoro-2-[({(3R)-3-[methyl(phenylsulfonyl)amino]-1-oxa-8-azaspiro[4.5]dec-8-yl}carbonyl)oxy]propyl dihydrogen phosphate;
   (2R)-3,3,3-trifluoro-2-[({4-[(4-fluorophenyl)sulfonyl]-1-oxa-4,9-diazaspiro[5.5]undec-9-yl}carbonyl)oxy]propyl dihydrogen phosphate;
   (2R)-1,1,1-trifluoro-3-hydroxypropan-2-yl 3-{[(4-fluorophenyl)sulfonyl](methyl)amino}-1-oxa-8-azaspiro[4.5]decane-8-carboxylate, DIAST-1;
   (2R)-1,1,1-trifluoro-3-hydroxypropan-2-yl 3-{[(4-fluorophenyl)sulfonyl](methyl)amino}-1-oxa-8-azaspiro[4.5]decane-8-carboxylate, DIAST-2; and
   (2R)-3,3,3-trifluoro-2-({[(3R)-3-{[(4-fluorophenyl)sulfonyl](methyl)amino}-1-oxa-8-azaspiro[4.5]dec-8-yl]carbonyl}oxy)propyl dihydrogen phosphate,
   or a pharmaceutically acceptable salt thereof,
   or a pharmaceutically acceptable salt selected from the group consisting of:
   (2R)-3,3,3-trifluoro-2-[({(3R)-3-[methyl(phenylsulfonyl)amino]-1-oxa-8-azaspiro[4.5]dec-8-yl}carbonyl)oxy]propyl phosphate, disodium salt;
   (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, disodium salt;
   (2R)-3,3,3-trifluoro-2-[({4-[(4-fluorophenyl)sulfonyl]-1-oxa-4,9-diazaspiro[5.5]undec-9-yl}carbonyl)oxy]propyl phosphate, (bis)-L-lysine salt;
   (2R)-3,3,3-trifluoro-2-({[4-(phenylsulfonyl)-1-oxa-4,9-diazaspiro[5.5]undec-9-yl]carbonyl}oxy)propyl phosphate, disodium salt;
   (2R)-3,3,3-trifluoro-2-[({(3R)-3-[methyl(phenylsulfonyl)amino]-1-oxa-8-azaspiro[4.5]dec-8-yl}carbonyl)oxy]propyl phosphate, (bis)-L-lysine salt;
   (2R)-3,3,3-trifluoro-2-({[4-(phenylsulfonyl)-1-oxa-4,9-diazaspiro[5.5]undec-9-yl]carbonyl}oxy)propyl phosphate, (bis)-L-lysine salt, and
   (2R)-3,3,3-trifluoro-2-({[(3R)-3-{[(4-fluorophenyl)sulfonyl](methyl)amino}-1-oxa-8-azaspiro[4.5]dec-8-yl]carbonyl}oxy)propyl phosphate, (bis)-L-lysine salt.

2. A compound of claim 1 that is (2R)-1,1,1-trifluoro-3-hydroxypropan-2-yl 4-[(4-fluorophenyl)sulfonyl]-1-oxa-4,9-diazaspiro[5.5]undecane-9-carboxylate, or a pharmaceutically acceptable salt thereof.

3. A compound of claim 1 that is (2R)-1,1,1-trifluoro-3-hydroxypropan-2-yl 4-(phenylsulfonyl)-1-oxa-4,9-diazaspiro[5.5]undecane-9-carboxylate, or a pharmaceutically acceptable salt thereof.

4. A compound of claim 1 that is (2R)-1,1,1-trifluoro-3-hydroxypropan-2-yl(3R)-3-[methyl(phenylsulfonyl)amino]-1-oxa-8-azaspiro[4.5]decane-8-carboxylate, or a pharmaceutically acceptable salt thereof.

5. A compound of claim 1 that is (2R)-1,1,1-trifluoro-3-hydroxypropan-2-yl 3-{[(4-fluorophenyl)sulfonyl](methyl)amino}-1-oxa-8-azaspiro[4.5]decane-8-carboxylate, DIAST-1; or (2R)-1,1,1-trifluoro-3-hydroxypropan-2-yl 3-{[(4-fluorophenyl)sulfonyl](methyl)amino}-1-oxa-8-azaspiro[4.5]decane-8-carboxylate, DIAST-2; or a pharmaceutically acceptable salt thereof.

6. A compound of claim 1 that is (2R)-3,3,3-trifluoro-2-[({(3R)-3-[methyl(phenylsulfonyl)amino]-1-oxa-8-azaspiro[4.5]dec-8-yl}carbonyl)oxy]propyl dihydrogen phosphate, or a pharmaceutically acceptable salt thereof.

7. A compound of claim 1 that is (2R)-3,3,3-trifluoro-2-[({4-[(4-fluorophenyl)sulfonyl]-1-oxa-4,9-diazaspiro[5.5]undec-9-yl}carbonyl)oxy]propyl dihydrogen phosphate, or a pharmaceutically acceptable salt thereof.

8. A compound of claim 1 that is (2R)-3,3,3-trifluoro-2-({[(3R)-3-{[(4-fluorophenyl)sulfonyl](methyl)amino}-1-oxa-8-azaspiro[4.5]dec-8-yl]carbonyl}oxy)propyl dihydrogen phosphate, or a pharmaceutically acceptable salt thereof.

9. A pharmaceutical composition comprising a compound of claim 1 or pharmaceutically acceptable salt thereof, and a pharmaceutically acceptable carrier.

\* \* \* \* \*